United States Patent [19]

Bold et al.

[11] Patent Number: 5,663,200

[45] Date of Patent: Sep. 2, 1997

[54] ANTIVIRAL ETHERS OF ASPARTATE PROTEASE SUBSTRATE ISOSTERES

[75] Inventors: Guido Bold, Gipf-Oberfrick; Hans-Georg Capraro, Rheinfelden; Alexander Fässler, Oberwil, all of Switzerland; Marc Lang, Mulhouse, France; Shripad Subray Bhagwat, Libertyville, Ill.; Satish Chandra Khanna, Bottmingen; Janis Karlis Lazdins, Basel, both of Switzerland; Jürgen Mestan, Denzlingen, Germany

[73] Assignee: Ciba-Geigy Corporation, Tarrytown, N.Y.

[21] Appl. No.: 545,170

[22] Filed: Oct. 19, 1995

[30] Foreign Application Priority Data

Oct. 19, 1994 [CH] Switzerland .............. 3140/94
Aug. 21, 1995 [CH] Switzerland .............. 2382/95

[51] Int. Cl.⁶ .................. A61K 31/215; C07C 271/20
[52] U.S. Cl. .................. 514/487; 514/479; 544/168; 546/221; 548/200; 560/27
[58] Field of Search .................. 560/27; 514/487

[56] References Cited

U.S. PATENT DOCUMENTS

| 4,894,437 | 1/1990 | TenBrink . |
| 5,189,017 | 2/1993 | Lukas et al. . |

FOREIGN PATENT DOCUMENTS

| 0278158 | 8/1988 | European Pat. Off. . |
| 0311012 | 4/1989 | European Pat. Off. . |
| 0329609 | 8/1989 | European Pat. Off. . |
| 0337714 | 10/1989 | European Pat. Off. . |
| 0356223 | 2/1990 | European Pat. Off. . |
| 0374097 | 6/1990 | European Pat. Off. . |
| 0434365 | 6/1991 | European Pat. Off. . |
| 0487270 | 5/1992 | European Pat. Off. . |
| 0528661 | 2/1993 | European Pat. Off. . |
| 8802374 | 4/1988 | WIPO . |
| 9106561 | 5/1991 | WIPO . |
| 9110442 | 7/1991 | WIPO . |

OTHER PUBLICATIONS

Rich et al., J. Med. Chem. 34, 1225–1228 (1991).
de Solms et al, J. Med. Chem. 34, 2852–2857 (1991).

*Primary Examiner*—Robert W. Ramsuer
*Attorney, Agent, or Firm*—Marla J. Mathias

[57] ABSTRACT

Antiretroviral compounds (which are effective, for example, against HIV) of the formula I

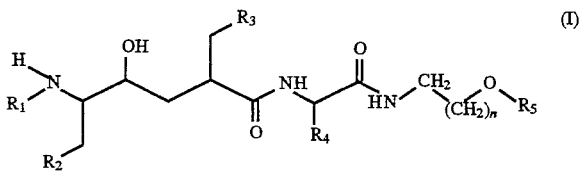

in which $R_1$ is an acyl radical lower-alkoxyl-lower-alkanoyl whose lower alkoxy radical is unsubstituted or is substituted by halogen, phenyl, lower alkoxy or a heterocyclic radical selected from piperidinyl, pyrrolidinyl, tetrahydropyranyl, tetrahydrofuranyl, thiazolidinyl, thiazolyl, indolyl or 4H-1-benzopyranyl which is unsubstituted or substituted by oxo, hydroxyl, amine, lower alkyl, lower-alkoxycarbonyl and/or phenyl-lower-alkoxycarbonyl; lower alkanoyl which is unsubstituted or is substituted by one of the said unsubstituted or substituted heterocyclic radicals; arylcarbonyl or heterocyclylcarbonyl which are substituted by heterocyclyl or heterocyclyl-lower-alkyl; phenyl-lower-alkanoyl which is substituted by hydroxyl and lower alkyl; or arylsulfonyl;

or the residue of an amino acid which is defined in accordance with the description (and which may be acylated on the amino nitrogen by one of the abovementioned acyl radicals);

$R_2$ and $R_3$ are in each case cyclohexyl, cyclohexenyl, phenyl, naphthyl or tetrahydronaphthyl which are unsubstituted or substituted by lower alkyl, phenyl, cyanophenyl, phenyl-lower-alkyl, halogen, halo-lower-alkyl, cyano, hydroxyl, lower alkoxy, phenyl-lower-alkoxyl, pyridyl-lower-alkoxy, lower-alkoxy-lower-alkoxy, lower-alkoxycarbonyl-lower-alkoxy, carboxyl-lower-alkoxy, hydroxyl-lower-alkoxy, carbamoyl-lower-alkoxy, cyano-lower-alkoxy, and phenyl-lower-alkanesulfonyl which is unsubstituted or substituted by halogen;

$R_4$ is lower alkyl, cyclohexyl or phenyl; and $R_5$ is lower alkyl; and n is 1 or 2, or salts thereof, are novel.

11 Claims, No Drawings

ANTIVIRAL ETHERS OF ASPARTATE PROTEASE SUBSTRATE ISOSTERES

RESUMÉ AND FIELD OF THE INVENTION

The invention relates to ethers of aspartate protease substrate isosteres and their salts, to processes for preparing these compounds and the salts thereof, to pharmaceutical preparations which comprise these compounds or the salts thereof, and to the use of these compounds or the salts thereof (either alone or in combination with other active compounds which are effective against retroviruses) for the therapeutic or diagnostic treatment of the human or animal body or for producing pharmaceutical preparations.

BACKGROUND OF THE INVENTION

According to WHO estimates, considerably more than 15 million people are currently infected with HIV-1 or HIV-2.

Inhibitors of reverse transcriptase, an enzyme which converts retroviral RNA into DNA, such as 3'-azido-3'-deoxythymidine (AZT) or dideoxyinosine (DDI), and also trisodium phosphonoformate, ammonium 21-tungsto-9-antimoniate, 1-β-D-ribofuranoxyl-1,2,4-triazole-3-carboxamide and dideoxycytidine, and also adriamycin, have primarily been used hitherto for treating retroviral diseases such as AIDS. Attempts are also being made to introduce the T4 cell receptor, which is present in the human body on certain cells of the immune system and which is responsible for anchoring infectious viral particles and introducing them into these cells, and is consequently responsible for their ability to infect, into the body, for example as a recombinant molecule or molecular fragment. This would have the effect of titrating out binding sites for the virus so that the virions would no longer be able to bind to the cells. Compounds which use other means to prevent the virus penetrating through the cell membrane, such as polymannoacetate, are also used.

In addition to this, the first clinical experiments in which a hydroxyethylene isostere, N-tert-butyldecahydro-2-[2(R)-hydroxy-4-phenyl-3(S)-[[N-2-quinolylcarbonyl-L-asparaginyl]amino]butyl]-(4aS,8aS)-isoquinoline-3(S)-carboxamide (Ro 31-8959) is used as an inhibitor of the HIV protease have been reported. This compound had an inhibitory effect on HIV protease in vitro and suppressed viral replication in cell experiments, and useful blood levels were achieved in rodents even with oral administration (see Roberts, N. A., et al., Biochemical Soc. Transactions 20, 513–516 (1992)); useful blood levels were also achieved in humans (see, for example, G. J. Muirhead et al., Brit. J. Clin. Pharmacol. 34, 170P–171P (1992)). A so-called "surrogate marker" (titre of the CD4 lymphocytes in the blood, whose decline in untreated patients represents a measure of the development of the AIDS disease) demonstrated the first positive effects in AIDS patients (see "Roche statement on HIV Proteinase Inhibitor (Ro 31-8959) European Trials Results", which was distributed to participants at the 9th International Congress on AIDS in Berlin, Jun. 7–11, 1993).

In the AIDS viruses, HIV-1 and HIV-2, and in other retroviruses, for example the corresponding viruses in cats (FIV) and monkeys (SIV), proteolytic maturation, for example of the core proteins of the virus, is effected by an aspartate protease, such as the HIV protease. No infectious viral particles can be produced without this proteolytic maturation. On the basis of the central role played by the said aspartate proteases, such as HIV-1 protease or HIV-2 protease, in viral maturation, and on the basis of experimental results, for example obtained with infected cell cultures, it is assumed that effective prevention in vivo of the maturation step which is brought about by this protease will prevent mature virions from being assembled. Consequently, appropriate inhibitors can be employed therapeutically.

It is the object of the present invention to prepare a novel class of compounds which also possess, in particular, favourable pharmacological properties, such as good pharmacokinetics, bioavailability and/or good tolerability.

DETAILED DESCRIPTION OF THE INVENTION

The novel ethers of aspartate protease substrate isosteres are compounds of the formula I,

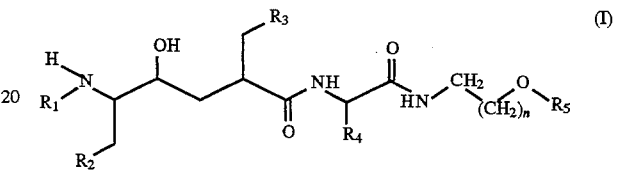

in which $R_1$ is an acyl radical which is selected from lower-alkoxyl-lower-alkanoyl (including lower-alkoxycarbonyl), in which the lower-alkoxy radical is unsubstituted or is substituted by one or more radicals selected, independently of each other, from halogen, phenyl and lower-alkoxy, or by a radical selected from piperidinyl, pyrrolidinyl, tetrahydropyranyl, tetrahydrofuranyl, thiazolidinyl, thiazolyl, indolyl or 4H-1-benzopyranyl which are unsubstituted or substituted by one or more radicals selected, independently of each other, from oxo, hydroxyl, amino, lower alkyl, lower alkoxycarbonyl and phenyl-lower-alkoxycarbonyl; lower alkanoyl which is unsubstituted or is substituted by piperidinyl, pyrrolidinyl, tetrahydropyranyl, tetrahydrofuranyl, thiazolidinyl, thiazolyl, indolyl, 4H-1-benzopyranyl, piperidinyloxy, pyrrolidinyloxy, tetrahydropyranyloxy, tetrahydrofuranyl, thiazolidinyloxy, thiazolyloxy, indolyloxy or 4H-1-benzopyranyloxy which are in each case unsubstituted or substituted by one or more substituents selected, independently of each other, from oxo, hydroxyl, amino, lower alkyl, lower-alkoxycarbonyl and phenyl-lower-alkoxycarbonyl; arylcarbonyl or heterocyclylcarbonyl which is substituted by heterocyclyl or heterocyclyl-lower-alkyl; phenyl-lower-alkanoyl which is substituted by hydroxyl and lower alkyl; and arylsulfonyl;

the residue, which is bonded via the carbonyl group, of an amino acid selected from glycine, alanine, 3-aminopropanoic acid, 2-aminobutyric acid, 3-aminobutyric acid, 4-aminobutyric acid, 3-aminopentanoic acid, 4-aminopentanoic acid, 5-aminopentanoic acid, 3-aminohexanoic acid, 4-aminohexanoic acid, 5-aminohexanoic acid, valine, norvaline, leucine, isoleucine, norleucine, serine, homoserine, threonine, methionine, cysteine, phenylalanine, tyrosine, 4-aminophenylalanine, 4-chlorophenylalanine, 4-carboxyphenylalanine, β-phenylserine, phenylglycine, α-naphthylalanine, cyclohexylalanine, cyclohexylglycine, tryptophan, asparatic acid, β-phenyl-lower-alkyl aspartate, asparagine, aminomalonic acid, aminomalonic acid monoamide, glutamic acid, γ-phenyl-lower-alkyl glutamate, glutamine, histidine, arginine, lysine, δ-hydroxylysine, ornithine, α,γ-diaminobutyric acid and α,β-diaminopropionic acid;
or the radical, which is bonded via the carbonyl group, of one of the later amino acids which is N-acylated on an amino nitrogen by one of the previously mentioned acyl radicals, $R_2$ and $R_3$ are, independently of each other, cyclohexyl, cyclohexenyl, phenyl, naphthyl or tetrahydronaphthyl which are unsubstituted or are substituted by one or more radicals selected, independently of each other, from lower alkyl, phenyl, cyanophenyl, phenyl-lower-alkyl, halogen, halo-lower-alkyl, cyano, hydroxyl, lower alkoxy, phenyl-lower-alkoxyl, pyridyl-lower-alkoxy, in which pyridyl is bonded via a ring carbon atom, lower-alkoxyl-lower-alkoxy, lower-alkoxycarbonyl-lower-alkoxy, carboxyl-lower-alkoxy, hydroxyl-lower-alkoxy having at least two carbon atoms, in which hydroxyl is not bonded in the 1 position, carbamoyl-lower-alkoxy, cyano-lower-alkoxy, lower-alkylenedioxy, and phenyl-lower-alkanesulfonyl which is unsubstituted or is substituted in the phenyl radical by one or more radicals selected, independently of each other, from halogen, $R_4$ is lower alkyl, cyclohexyl or phenyl, $R_5$ is lower alkyl, and n is 1 or 2, or salts thereof, provided at least one salt-forming group is present.

Within the scope of the present application, the general terms used above and below preferably have the following meanings unless otherwise indicated:

The prefix "lower" or the word component "lower", for example in lower alkyl, lower alkoxy, lower alkanoyl or phenyl-lower-alkyl, denote a radical having not more than 7, in particular not more than 4, carbon atoms, it being possible for the radicals concerned to be unbranched or to be branched once or more than once.

When compounds, salts, etc. are mentioned, these terms also mean a compound, a salt, etc.

Asymmetric carbon atoms which may be present, including those in the substituents $R_1$, $R_2$, $R_3$, $R_4$ and $R_5$, can be in the (R), (S) or (R,S) configurations, preferably in the (R) configuration or (S) configuration. The present compounds can consequently exist as isomeric mixtures or as pure isomers, in particular as diastereomeric mixtures, enantiomeric mixtures or, preferably, pure enantiomers.

The additional statement "alternatively or additionally" means either that the corresponding designated substituent meanings combined with the respective groups of substituent meanings which are not designated with this additional statement together form a group of substituents, or that the correspondingly designated substituent meanings form a group on their own, or that the meanings which are not designated with this additional statement also on their own form a group of substituent meanings.

Preferably, the compounds of the formula I have the formula I',

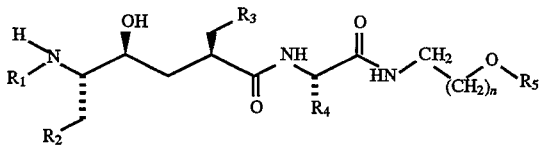

in which the radicals have the meanings given for compounds of the formula I.

In lower alkoxyl-lower-alkanoyl, $R_1$ is the lower-alkoxy radical, preferably methoxy, ethoxy, n-propoxy, iso-propoxy, n-butoxy, isobutoxy, sec-butoxy or tert-butoxy, while lower alkanoyl is preferably formyl (the corresponding radical is then a lower-alkoxycarbonyl radical, in particular methoxycarbonyl, ethoxycarbonyl or tert-butoxycarbonyl), acetyl or propionyl.

Piperidinyl, pyrrolidinyl, tetrahydropyranyl, tetrahydrofuranyl, thiazolidinyl, thiazolyl, indolyl or 4H-1-benzopyranyl are unsubstituted or substituted by one or more radicals selected, independently of each other, from oxo, hydroxyl, amino, lower alkyl, lower-alkoxycarbonyl and phenyl-lower-alkoxycarbonyl, in particular unsubstituted or substituted by one or two of the said radicals selected independently of each other.

Halogen is fluorine, chlorine, bromine or iodine, in particular fluorine or chlorine.

Piperidinyl is, in particular, piperidin-4-yl which is unsubstituted or is preferably substituted on the nitrogen atom by lower alkyl, such as methyl, or lower-alkoxycarbonyl, such as ethoxycarbonyl.

Pyrrolidinyl is, in particular, pyrrolidin-2-yl or -5-yl which is unsubstituted or preferably substituted by oxo or hydroxyl on a carbon atom and substituted by phenyl-lower-alkoxycarbonyl on the nitrogen, or is unsubstituted on the nitrogen, and is preferably in the (R) form, the (R,S) form or, in particular, the (S) form at the binding carbon atom, and is, in particular, 2-oxopyrrolidin-5(S)-yl, (L)-trans-4-hydroxyprolyl or (L)-N-benzyloxycarbonyl-trans-4-hydroxypropyl.

Tetrahydropyranyl is, in particular, tetrahydropyran-2-yl or -4-yl which is preferably unsubstituted and is preferably bonded in the (R) form, (S) form or, in particular, the (R,S) form, provided it is bonded via the 2 carbon atom.

Tetrahydrofuranyl is, in particular, tetrahydrofuran-3-yl which is preferably unsubstituted and is preferably bonded in the (R) form, the (R,S) form or, in particular, the (S) form.

Thiazolidinyl is, in particular, thiazolidin-4-yl which is preferably unsubstituted and is preferably in the (S) form, the (R,S) form or, in particular, the (R) form (=(L) form) at the binding carbon atom.

Thiazolyl is, in particular, thiazol-4-yl which is preferably substituted by amino, such as 2-amino-4-thiazolyl.

Indolyl is, in particular, indol-2-yl which is preferably unsubstituted.

4H-1-Benzopyranyl is, in particular, 4H-1-benzopyran-2-yl which is unsubstituted or preferably substituted by oxo, such as 4-oxo-4H-1-benzopyran-2-yl.

The oxo, hydroxyl and amino substituents of piperidinyl, pyrrolidinyl, tetrahydropyranyl, tetrahydrofuranyl, thiazolidinyl, thiazolyl, indolyl or 4H-1-benzopyranyl which may be present are preferably bonded to carbon, while the lower alkoxy, lower-alkoxycarbonyl and phenyl-lower-alkoxycarbonyl substituents are preferably bonded to nitrogen or carbon.

The lower-alkoxy radical in lower-alkoxyl-lower-alkanoyl $R_1$ is unsubstituted or substituted by one or more, in particular by from 1 up to and including 3, of the said radicals, in particular (preferably from one to, in particular, three times) by halogen, in particular fluorine; or (preferably once) by one of the remaining radicals mentioned, in particular (preferably once) by lower alkoxy, in particular methoxy, or (preferably once) by pyrrolidinyl, in particular pyrrolidin-2-yl or -5-yl which is unsubstituted or, in particular, substituted by oxo; or, in addition, by phenyl, as in benzyloxycarbonyl.

In lower alkanoyl $R_1$, which is unsubstituted or substituted by piperidinyl, pyrrolidinyl, tetrahydropyranyl, tetrahydrofuranyl, thiazolidinyl, thiazolyl, indolyl, 4H-1-benzopyranyl, piperidinyloxy, pyrrolidinyloxy, tetrahydropyranyloxy, tetrahydrofuranyloxy, thiazolidinyloxy, thiazolyloxy, indolyloxy or 4H-1-benzopyranyloxy, which are in each case unsubstituted or substituted by one or more (preferably one) substituents selected, independently of each other, from oxo, hydroxyl, amino, lower alkyl, lower-alkoxycarbonyl and phenyl-lower-alkoxycarbonyl; lower alkanoyl is, in particular, formyl (in each case yields with one of the said radicals the correspondingly substituted carbonyl radical), acetyl or 2- or 3-propionyl, with preferably the (R) form, (R,S) form or, in particular, the (S) form being present when the substituent is bonded in the 2 position, while the remaining radicals are defined as above. That which is preferred is N-lower-alkoxycarbonyl-piperidinyl-lower-alkanoyl, for example -carbonyl, such as N-ethoxycarbonyl-piperidin-4-ylcarbonyl, pyrrolidinyl-lower-alkanoyl, such as -carbonyl, which is substituted by hydroxyl on a carbon atom and/or by phenyl-lower-alkoxycarbonyl on the nitrogen atom and which is preferably in the (R) form, the (R,S) form or, in particular, the (S) form at the binding carbon atom, such as (L)-trans-4-hydroxyprolyl or (L)-N-benzyloxycarbonyl-trans-4-hydroxyprolyl, aminothiazolidinyl-lower-alkanoyl, for example-acetyl, such as 2-amino-4-thiazolyl-acetyl, thiazolyl-lower-alkanoyl, for example -carbonyl, such as thiazol-2-ylcarbonyl, indolyl-lower-alkanoyl, for example -carbonyl, such as indol-2-ylcarbonyl, 4H-1-benzopyranyl-lower-alkanoyl, for example -carbonyl, which is substituted by oxo, such as 4-oxo-4H-1-benzopyran-2-ylcarbonyl, N-lower-alkyl-piperidinyloxy-lower-alkanoyl, for example -carbonyl, such as N-methylpiperidin-4-yloxycarbonyl, tetrahydropyranyloxy-lower-alkanoyl, for example -propionyl or -carbonyl, such as 2(S)-(tetrahydropyran-4-yloxy)propionyl or tetrahydropyran-2(R,S)-yloxycarbonyl, or tetrahydrofuranyloxy-lower-alkanoyl, for example -carbonyl, such as tetrahydrofuran-3(S)-yloxycarbonyl.

Heterocyclyl is preferably an unsubstituted or substituted heterocyclic ring having from 5 to 7, preferably 5 or 6, ring atoms in which 1 or 2 ting carbon atoms are replaced by a hetero atom selected from O, N and S, is unsaturated or completely or partially saturated and can be a simple ring or be benzo-fused, cyclopenta-fused or cyclohexa-fused, where the substituents preferably are choosen, independently of each other, from one or more (preferably one or two) substituents selected from oxo, hydroxyl, amino, lower alkyl, lower-alkoxycarbonyl and phenyl-lower-alkoxycarbonyl; and is, in particular, selected from morpholinyl, piperazinyl, for example piperazin-1-yl, pyridinyl, for example pyridin-3-yl, piperidinyl, pyrrolidinyl, tetrahydropyranyl, tetrahydrofuranyl, thiazolidinyl, thiazolyl, indolyl and 4H-1-benzopyranyl which are in each case unsubstituted or substituted by one or more radicals selected, independently of each other, from oxo, hydroxyl, amino, lower alkyl, lower-alkoxycarbonyl and phenyl-lower-alkoxycarbonyl, preferably unsubstituted or substituted by one or, in addition, two of the said radicals; and is primarily morpholinyl, such as morpholin-4-yl, lower-alkylpiperazinyl, in particular N-lower-alkyl-piperazinyl, for example 4-lower-alkyl-piperazin-1-yl, such as 4-methybpiperazin-1-yl, or pyridinyl, such as pyridin-3-yl.

Ary is preferably $C_6$–$C_{14}$aryl, for example phenyl, naphthyl, such as 1- or 2-naphthyl, or, in addition, fluorenyl, such as fluoren-9-yl, and is unsubstituted or substituted by one or more (preferably from one to three) radicals which are selected, independently of each other, from lower alkyl, phenyl-lower-alkyl, halogen, cyano, hydroxyl, lower alkoxy, phenyl-lower-alkoxy, lower-alkoxyl-lower-alkoxy, lower-alkylenedioxy (bonded to two adjacent carbon atoms of the respective aryl ring), pyridyl-lower-alkoxy and phenyl-lower-alkanesulfonyl which is unsubstituted or is substituted in the phenyl radical by one or more radicals selected, independently of each other, from halogen, such as chlorine; and (alternatively or in addition) from nitro; and is, in particular, phenyl.

In arylcarbonyl which is substituted by heterocyclyl or heterocyclyl-lower alkyl, such as, in particular, -methyl, or in heterocyclylcarbonyl which is substituted (likewise by one or more of these radicals), aryl and heterocyclyl are as defined immediately above, preferably as indicated there as being preferred; preferably, only one heterocyclyl or heterocyclyl-lower alkyl substituent is present.

Of these radicals, arylcarbonyl which is substituted once by heterocyclyl-lower-alkyl, and heterocyclylcarbonyl which is substituted once by heterocyclyl are preferred.

Arylcarbonyl which is substituted by heterocyclyl-lower alkyl is, in particular, morpholinyl-lower-alkyl-benzoyl, such as 4-(morpholin-4-ylmethyl)benzoyl.

Heterocyclylcarbonyl which is substituted by heterocyclyl is, in particular, lower-alkylpiperazinyl-pyridylcarbonyl, such as N-lower-alkylpiperazinyl-pyridylcarbonyl, in particular 4-lower-alkyl-piperazin-1-yl-pyridylcarbonyl, for example 2- or 3-(4-lower-alkyl[such as methyl]-piperazin-1-yl)pyridin-2-ylcarbonyl or -3-ylcarbonyl.

Phenyl-lower-alkanoyl (in this context, the term "phenyl-lower-alkanoyl" also includes benzoyl=phenylcarbonyl) which is substituted by hydroxyl and lower alkyl preferably has, in each case, a hydroxyl and a lower alkyl substituent, in particular hydroxyl and methyl or ethyl, on the phenyl ring and is, in particular, correspondingly substituted benzoyl, such as 3-hydroxy-2-methylbenzoyl.

Arylsulfonyl (=aryl-$SO_2$—) preferably contains, as aryl, a radical as defined above, in particular phenyl which is substituted by amino, nitro, amino and lower alkyl or nitro and lower alkyl, and is primarily 4-nitrobenzenesulfonyl, 4-aminobenzenesulfonyl, 2-lower-alkyl(in particular 2-methyl)-4-nitrobenzenesulfonyl or 4-amino-2-lower-alkyl (in particular 2-methyl)-benzenesulfonyl.

The respective radicals which come within the definition of "phenyl-lower-alkanoyl which is substituted by hydroxyl and lower alkyl" and "arylsulfonyl" $R_1$ can both above and below, at all levels of definition of $R_1$, also stand alone or be omitted.

A residue of an amino acid, which residue is bonded via the carbonyl group (of its carboxyl group, which is present in the corresponding free amino acid), to the binding nitrogen, i.e. can be obtained by removing the OH group in the carboxyl group (—COOH), is selected from glycine (H-Gly-OH), alanine (H-Ala-OH), 2-aminobutyric acid, 3-amino-butyric acid, 4-aminobutyric acid, 3-aminopentanoic acid, 4-aminopentanoic acid, 5-aminopentanoic acid, 3-aminohexanoic acid, 4-aminohexanoic acid or 5-aminohexanoic acid, valine (H-Val-OH), norvaline (α-aminovaleric acid), leucine (H-Leu-OH), isoleucine (H-Ile-OH), norleucine (α-aminohexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH), phenylalanine (H-Phe-OH), tyrosine (H-Tyr-OH), 4-aminophenylalanine, 4-chlorophenylalanine, 4-carboxyphenylalanine, β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), aspartic acid (H-Asp-OH), β-phenyl-lower-alkyl aspartate, such as β-benzyl aspartate, asparagine (H-Ash-OH), aminomalonic acid, aminomalonic acid monoamide, glutamic acid (H-Glu-OH), glutamine (H-Gln-OH), histidine (H-His-OH), arginine (H-Arg-OH), lysine (H-Lys-OH); δ-hydroxylysine, ornithine (α,δ-diaminovaleric acid), 3-aminopropanoic acid, α,γ-diaminobutyric acid and α,β-diaminopropionic acid; and preferably selected from valine, norvaline, leucine, isoleucine and norleucine, and, in addition, from serine, homoserine, threonine, methionine, cysteine, phenylalanine, tyrosine, 4-aminophenylalanine, 4-chlorophenylalanine, 4-carboxyphenylalanine, β-phenylserine, phenylglycine, α-naphthylalanine, cyclohexylalanine, cyclohexylglycine, tryptophan, asparatic acid, β-phenyl-lower-alkyl aspartate, suaminomalonicenzyl aspartate, asparagine, aminomalonic acid monoamide, glutamic acid, γ-phenyl-lower-alkyl glutamate, such as γ-benzyl glutamate, glutamine, histidine, arginine, lysine, δ-hydroxylysine and ornithine; with β-benzyl aspartate, aspartic acid, asparagine or in particular, valine being particularly preferred; with the respective amino group(s) and other functional groups being free or (if possible) in salt form; and with the said amino acid radicals having asymmetric carbon atoms being in the (D) form, the (L) form or the (D,L) form, preferably in the (L) form.

In a residue of one of the latter amino acids which is bonded via the carbonyl group and which is N-acylated on the amino nitrogen by one of the previously mentioned acyl radicals, the acyl radicals are selected from lower alkoxyl-lower-alkanoyl, in which the lower-alkoxy radical is unsubstituted or is substituted by one or more radicals selected, independently of each other, from halogen and lower alkoxy, and, in addition, phenyl, or by a radical selected from piperidinyl, pyrrolidinyl, tetrahydropyranyl, tetrahydrofuranyl, thiazolidinyl, thiazolyl, indolyl or 4H-1-benzopyranyl which are unsubstituted or substituted by one or more radicals selected, independently of each other, from oxo, hydroxyl, amino, lower alkyl, lower-alkoxycarbonyl and phenyl-lower-alkoxycarbonyl; lower alkanoyl which is unsubstituted or is substituted by piperidinyl, pyrrolidinyl, tetrahydropyranyl, tetrahydrofuranyl, thiazolidinyl, thiazolyl, indolyl, 4H-1-benzopyranyl, piperidinyloxy, pyrrolidinyloxy, tetrahydropyranyloxy, tetrahydrofuranyloxy, thiazolidinyloxy, thiazolyloxy, indolyloxy or 4H-1-benzopyranyloxy which are in each case unsubstituted or substituted by one or more substituents selected, independently of each other, from oxo, hydroxyl, amino, lower alkyl, lower-alkoxycarbonyl and phenyl-lower-alkoxycarbonyl; arylcarbonyl or heterocyclylcarbonyl which is substituted by heterocyclyl or heterocyclyl-lower alkyl; (alternatively or additionally) phenyl-lower-alkanoyl which is substituted by hydroxyl and lower alkyl; and (alternatively or additionally) arylsulfonyl; where the said acyl radicals are preferably defined as above; while the amino acid residue is selected from the residues mentioned above for residues of an amino acid which are bonded via the carbonyl group, in particular from the residues mentioned there as being preferred. That which is particularly preferred is lower-alkoxyl-lower-alkanoyl-valyl, such as lower-alkoxycarbonyl-valyl, for example methoxycarbonyl-valyl, or thiazolidinyl-valyl, in particular thiazolidin-4-yl-valyl, which is preferably in the (S) form, the (R,S) form or, in particular the (R) form (=(L) form) it the 4-carbon atom of the thiazolidine ring; with the valyl residue in each case preferably being in the (L) form; or, in addition, aspartyl, N-phenyl-lower-alkoxycarbonyl-(L)-β-(O-phenyl-lower-alkyl)aspartyl, such as N-benzyloxycarbonyl-(L)-β-(O-benzyl)-aspartyl, asparaginyl or N-phenyl-lower-alkoxycarbonyl-asparaginyl, such as N-benzyloxycarbonyl-asparaginyl.

$R_1$ is primarily selected from tert-butoxycarbonyl, 2,2,2-trifluoroethoxy-carbonyl, 2-(methoxy)ethoxy-carbonyl, 5(S)-2-oxo-pyrrolidinyl-methoxycarbonyl, 1-ethoxycarbonyl-piperidin-4-ylcarbonyl, trans-(L)-4-hydroxyprolyl, N-(benzyloxycarbonyl)-trans-(L)-4-hydroxyprolyl, (L)-thiazolidin-4-ylcarbonyl, indol-2-ylcarbonyl, 4H-1-benzopyran-2-ylcarbonyl, N-methyl-piperidinyloxycarbonyl, tetrahydropyran-2(R,S)-ylcarbonyl, O-(tetrahydropyran-4-yl)-(L)-lactoyl (=2(S)-(tetrahydropyran-4-yloxy)propionyl), 3(S)-tetrahydrofuranyloxycarbonyl, 2-amino-thiazol-4-ylacetyl, 6-(4-methyl-piperazin-1-yl)-pyridin-3-ylcarbonyl, 4-(morpholin-4-ylmethyl)-benzoyl, N-methoxycarbonyl-(L)-valyl and N-[(L)-thiazolidin-4-ylcarbonyl]-(L)-valyl, and, in addition, from (L)-asparaginyl, N-benzyloxycarbonyl-(L)-asparaginyl, (L)-aspartyl and N-benzyloxycarbonyl-(L)-β-(O-benzyl)-aspanyl, or is (alternatively or additionally) selected from methoxycarbonyl, 2-methoxy-1(R,S)-methyl-ethoxycarbonyl, 1,1-dimethyl-2-methoxyethoxycarbonyl and 3-hydroxy-2-methylbenzoyl.

Cyclohexyl, cyclohexenyl, phenyl, naphthyl (such as 1- or 2-naphthyl) or tetrahydronaphthyl $R_2$ and $R_3$ are, independently of each other, unsubstituted or substituted, as indicated, with the substituents phenyl or cyanophenyl being alternative or additional with respect to the group of the other substituents mentioned; and with lower-alkylenedioxy being linked to 2, preferably adjacent, carbon atoms of the respective ring. Preferably, cyclohexenyl and tetrahydronaphthyl are unsubstituted, while cyclohexyl and, in particular, phenyl and naphthyl are unsubstituted or substituted by one, two or three radicals which are selected, independently of each other, from lower alkyl, in particular methyl; phenyl (alternatively or additionally); cyanophenyl, in particular 2-cyanophenyl (alternatively or additionally); phenyl-lower-alkyl, in particular 2-phenylethyl, halogen, in particular fluorine, cyano, hydroxyl, lower alkoxy, in particular methoxy or, in addition, iso-butoxy, lower-alkoxyl-lower-alkoxy, in particular 2-methoxyethoxy, lower-alkylenedioxy, in particular ethylene-1,2-dioxy or, in particular, methylenedioxy, which is linked to 2 adjacent carbon atoms of the respective ring, phenyl-lower-alkoxy, in particular benzyloxy, pyridyl-lower-alkoxy, in which pyridyl is bonded via a ring carbon atom, such as pyridin-2-, pyridin-3- or, in addition, pyridin-4-ylmethoxy, and phenyl-lower-alkanesulfonyl (=phenyl-lower-alkyl-S(=O)$_2$—) which is unsubstituted or is substituted, in particular in the phenyl radical, by one or more, in particular 2, radicals selected from halogen, in particular chlorine, in particular dichlorophenyl-lower-alkanesulfonyl, such as 2,6-dichlorobenzylsulfonyl (=2,6-dichlorophenylmethanesulfonyl), and, in addition, from halo-lower-alkyl, preferably having not more than 3 halogen atoms, in particular fluorine atoms, for example trifluoromethyl, lower-alkoxycarbonyl-lower alkoxy, such as ethoxycarbonylmethoxy, carboxyl-lower-alkoxy, such as carboxymethoxy, hydroxyl-lower-alkoxy having at least two carbon atoms, in which hydroxyl is not bonded in the 1 position, such as 2-hydroxyethoxy, carbamoyl-lower-alkoxy, such as carbamoylmethoxy ($H_2N$—C(=O)—$CH_2O$—), and cyano-lower-alkoxy, such as cyanomethoxy.

Preferably, $R_2$ and $R_3$ are selected from cyclohexyl, cyclohexenyl, such as cyclohexen-1-yl, phenyl, phenyl-lower-alkoxy-phenyl, in particular 4-phenyl-lower-alkoxyphenyl, such as 4-(benzyloxy)phenyl, difluorophenyl, in particular 2,4-difluorophenyl, cyanophenyl, in particular 4-cyanophenyl, lower-alkoxyphenyl, such as 2-, 3- or 4-lower-alkoxyphenyl, for example 4-isobutyloxyphenyl and, in particular, 2-, 3- and, in particular, 4-methoxyphenyl, tri-lower-alkoxy-phenyl, in particular trimethoxyphenyl, for example having the lower-alkoxy substituents in the 3,4,5 positions, as in 3,4,5-trimethoxyphenyl, in the 2,4,5 positions, as in 2,4,5-trimethoxyphenyl, in 2,4,6 positions, as in 2,4,6-trimethoxyphenyl, where the tri-lower alkoxy radicals or methoxy radicals preferably being bonded asymmetrically on the phenyl ring, primarily in the 2,3,4 positions, for example in 2,3,4-trimethoxyphenyl, lower-alkoxyl-lower-alkoxy-phenyl, such as 4-(lower-alkoxy-lower-alkoxy)phenyl, especially 4-)2-methoxy-ethoxy) phenyl, lower-alkylenedioxyphenyl, in which the lower-alkylenedioxy radical is bonded via its two oxygen atoms to two adjacent carbon atoms of the phenyl ring, for example methylenedioxyphenyl, such as 3,4-methylenedioxyphenyl, and pyrictyl-lower-alkoxy-phenyl, such as 4-(pyridin-2- or pyridin-3-yl-lower-alkoxy)phenyl, in particular pyridin-3-yl-loweralkoxyphenyl, for example pyridin-3-yl-methoxyphenyl; and, in addition, from 4-lower-alkoxy-2-fluorophenyl, such as 4-methoxy-2-fluorophenyl, 4-fluoro-2-lower-alkoxyphenyl, such as 4-fluoro-2-methoxyphenyl, 4-lower-alkoxy-2-hydroxyphenyl, such as 4-methoxy-2-hydroxyphenyl, phenyl which is substituted not more than three times by lower alkyl, such as methyl, and lower alkoxy, such as methoxy, such as 4-lower-alkoxy-2,3-di-lower-alkylphenyl, for example 4-methoxy-2,3-dimethylphenyl, phenyl-lower-alkylphenyl, such as 4-phenyl-lower-alkylphenyl, for example 4-(2-phenyl-ethyl)-phenyl, fluorophenyl, such as 2-fluorophenyl, hydroxyphenyl, such as 4-hydroxyphenyl, di-lower-alkoxyphenyl, in particular dimethoxyphenyl, for example 2,4-di-lower-alkoxyphenyl, such as 2,4-dimethoxyphenyl, 3,4-di-lower-alkoxyphenyl, such as 3,4-dimethoxyphenyl, 2,5-di-lower-alkoxyphenyl, such as 2,5-dimethoxyphenyl, or 2,6-di-lower-alkoxyphenyl, such as 2,6-dimethoxyphenyl, tetrahydronaphthyl, in particular 5,6,7,8-tetrahydro-1-naphthyl, halonaphthyl, such as fluoronaphthyl, in particular 4-fluoronaphthyl, cyanonaphthyl, in particular 4-cyanonaphthyl, lower-alkoxynaphthyl, in particular 4-lower-alkoxynaphthyl, such as 4-methoxy-1-naphthyl, and dihalophenyl-lower-alkanesulfonylphenyl, in particular dichlorophenyl-lower-alkanesulfonylphenyl, such as 4-(2,6-dichlorobenzylsulfonyl)phenyl; or, alternatively or additionally to the previously mentioned radicals, selected from biphenylyl, such as 4-biphenylyl, and (cyanophenyl) phenyl, such as 2'-cyanobiphenyl-4-yl.

Compounds of the formula I are particularly preferred in which $R_3$ is 2,3,4-tri-lower-alkoxyphenyl, in particular 2,3,4-trimethoxyphenyl, while the remaining radicals $R_1$, $R_2$, $R_4$, $R_5$ and n are as defined above or below.

Compounds of the formula I are preferred in which the following combinations of $R_2$ and $R_3$ are present:

| Radical R2 | Radical R3 |
|---|---|
| 1) 4-(Phenyl-lower-alkoxy)-phenyl, in particular 4-(benzyloxy)phenyl | 4-(Phenyl-lower-alkoxy)-phenyl, in particular 4-(benzyloxy)phenyl |
| 2) Phenyl | Cyanophenyl, in particular 4-cyanophenyl |
| 3) Phenyl | 2-Fluorophenyl |
| 4) Phenyl | 2,4-Difluorophenyl |
| 5) Phenyl | 4-Phenyl-lower-alkylphenyl, in particular 4-(2-phenylethyl)phenyl |
| 6) Phenyl | 4-Lower-alkoxyphenyl, in particular 4-methoxyphenyl or, in addition, 4-isobutoxyphenyl |
| 7) Phenyl | Dichlorophenyl-lower-alkanesulfonylphenyl, in particular 4-(2,6-dichlorobenzyl-sulfonyl)phenyl |
| 8) 4-(Lower alkoxy-lower-alkoxy)phenyl, in particular 4-(2-methoxy-ethoxy)phenyl | 4-(Phenyl-lower-alkoxy phenyl, in particular 4-(benzyloxy)phenyl |
| 9) 4-(Lower-alkoxy-lower-alkoxy)phenyl, in particular 4-(2-methoxy-ethoxy)phenyl | Hydroxyphenyl, in particular 4-hydroxyphenyl |
| 10) 4-(Lower-alkoxy-lower-alkoxy)phenyl, in particular 4-(2-methoxy-ethoxy)phenyl | 4-(Lower alkoxy)phenyl, in particular 4-methoxyphenyl |
| 11) 4-(Lower-alkoxy-lower-alkoxy)phenyl, in particular 4-(2-methoxy-ethoxy)phenyl | 4-(Lower-alkoxy-lower-alkoxy)-phenyl, in particular 4-(2-methoxyethoxy)phenyl |
| 12) 4-(Phenyl-lower-alkoxy)-phenyl, in particular 4-(benzyloxy)phenyl | 4-(Lower alkoxy)phenyl, in particular 4-methoxyphenyl |
| 13) 4-Hydroxyphenyl | 4-(Lower alkoxy)-phenyl, in particular 4-methoxyphenyl |
| 14) 4-(Lower alkoxy)phenyl, in particular 4-methoxyphenyl or 4-isobutoxyphenyl | 4-Lower alkoxyphenyl, in particular 4-methoxyphenyl |
| 15) 4-(Lower alkoxy)phenyl, | Phenyl in particular 4-methoxy |

-continued

| Radical R2 | Radical R3 |
| --- | --- |
| 16) Cyclohexyl | phenyl<br>4-Lower-alkoxyphenyl,<br>in particular<br>4-methoxyphenyl |
| 17) Phenyl | 4-Lower-alkoxy-2-fluorophenyl,<br>in particular 4-methoxy-<br>2-fluorophenyl |
| 18) Phenyl | 4-Fluoro-2-lower-alkoxyphenyl,<br>in particular 4-fluoro-2-methoxyphenyl |
| 19) Phenyl | 4-Lower-alkoxy-2-hydroxyphenyl,<br>in particular 4-methoxy-<br>2-hydroxyphenyl |
| 20) 4-Lower-alkoxyphenyl, | Cyclohexyl |
| in particular | |
| 4-methoxyphenyl | |
| 21) 4-Lower-alkoxy<br>phenyl,<br>in particular<br>4-methoxyphenyl | Cyclohexen-1-yl |
| 22) Cyclohexyl | 4-(Phenyl-lower-alkoxy)phenyl,<br>in particular<br>4-(benzyloxy)phenyl |
| 23) Cyclohexyl | 4-Hydroxyphenyl |
| 24) Phenyl | Phenyl |
| 25) Phenyl | 4-(Phenyl-lower-alkoxy)phenyl,<br>in particular<br>4-(benzyloxy)phenyl |
| 26) Phenyl | 4-((Pyridin-2-yl- or<br>pyridin-3-yl)lower alkoxy)-<br>phenyl, in particular<br>4-(pyridin-2-yl- or, especially,<br>pyridin-3-yl)methoxyphenyl |
| 27) Phenyl | 3,4-Lower-alkylenedioxyphenyl,<br>in particular<br>3,4-methylenedioxyphenyl |
| 28) Phenyl | 3,4-Di-lower-alkoxyphenyl,<br>in particular<br>3,4-dimethoxyphenyl |
| 29) Phenyl | 3-Lower-alkoxyphenyl,<br>in particular<br>3-methoxyphenyl |
| 30) Phenyl | 2,3,4-Tri-lower-alkoxyphenyl,<br>in particular<br>2,3,4-trimethoxyphenyl |
| 31) Phenyl | 3,4,5-Tri-lower-alkoxyphenyl,<br>in particular<br>3,4,5-trimethoxyphenyl |
| 32) Phenyl | 2,4-Di-lower-alkoxyphenyl,<br>in particular<br>2,4-dimethoxyphenyl |
| 33) Phenyl | 2-(Lower alkoxy)phenyl,<br>in particular<br>2-methoxy phenyl |
| 34) Phenyl | 4-Lower-alkoxy-2,3-di-<br>lower-alkylphenyl,<br>in particular 4-methoxy-2,3-<br>dimethylphenyl |
| 35) Phenyl | 2,4,5-Tri-lower-alkoxyphenyl,<br>in particular<br>2,4,5-trimethoxyphenyl |
| 36) Phenyl | 2,4,6-Tri-lower-alkoxyphenyl,<br>in particular<br>2,4,6-trimethox,yphenyl |
| 37) Phenyl | 5,6,7,8-Tetrahydro-1-naphthyl- |
| 38) Phenyl | 2,5-Di-lower-alkoxyphenyl,<br>in particular<br>2,5-dimethoxyphenyl |
| 39) Phenyl | 2,6-Di-lower-alkoxyphenyl,<br>in particular<br>2,6-dimethoxyphenyl |
| 40) Phenyl | Lower-alkoxy-naphthyl,<br>in particular<br>4-methoxy-1-naphthyl |
| 41) Phenyl | Cyano-naphthyl, in particular<br>4-cyano-1-naphthyl |
| 42) Phenyl | Fluoronaphthyl, in particular<br>4-fluoro-1-naphthyl |
| 43) Cyclohexyl | 2,3,4-Tri-lower-alkoxyphenyl, |

-continued

| Radical R2 | Radical R3 |
|---|---|
| 44) Cyclohexyl | in particular 2,3,4-trimethoxyphenyl 4-(Lower-alkoxy-lower-alkoxy)-phenyl, in particular 4-(2-methoxyethoxy)phenyl |
| 45) Cyclohexyl | 3,4-Lower-alkylenedioxyphenyl, in particular 3,4-methylenedioxyphenyl |
| 46) Cyclohexyl | 3,4-Di-lower-alkoxyphenyl, in particular 3,4-dimethoxyphenyl |
| 47) Cyclohexyl | 3-Lower-alkoxyphenyl, in particular 3-methoxyphenyl |
| 48) Cyclohexyl | 3,4,5-Tri-lower-alkoxyphenyl, in particular 3,4,5-trimethoxyphenyl |
| 49) Cyclohexyl | 2,4-Di-lower-alkoxyphenyl, in particular 2,4-dimethoxyphenyl |
| 50) Cyclohexyl | 2-(Lower alkoxy)phenyl, in particular 2-methoxyphenyl |
| 51) Cyclohexyl | 4-Lower-alkoxy-2,3-&-lower-alkylphenyl, in particular 4-methoxy-2,3-dimethylphenyl |
| 52) Cyclohexyl | 2,4,5-Tri-lower-alkoxyphenyl, in particular 2,4,5-trimethoxyphenyl |
| 53) Cyclohexyl | 2,4,6-Tri-lower-alkoxyphenyl, in particular 2,4,6-trimethoxyphenyl |
| 54) Cyclohexyl | 5,6,7,8-Tetrahydro-1-naphthyl- |
| 55) Cyclohexyl | 2,5-Di-lower-alkoxyphenyl., in particular 2,5-dimethoxyphenyl |
| 56) Cyclohexyl | 2,6-Di-lower-alkoxyphenyl, in particular 2,6-dimethoxyphenyl |
| 57) Cyclohexyl | Lower-alkoxy-naphthyl, in particular 4-methoxy-1-naphthyl |
| 58) Cyclohexyl | Cyano-naphthyl, in particular 4-cyano-1-naphthyl |
| 59) Cyclohexyl | Fluoronaphthyl, in particular 4-fluoro-1-naphthyl |
| or alternatively or additionally: | |
| 60) Phenyl | Biphenylyl, in particular 4-biphenylyl |
| 61) 4-(Phenyl-lower-alkoxy)-phenyl, in particular 4-benzyloxyphenyl | Biphenylyl, in particular 4-biphenylyl |
| 62) 4-Hydroxyphenyl | Biphenylyl, in particular 4-biphenylyl |
| 63) 4-Lower-alkoxyphenyl, in particular 4-methoxyphenyl | Biphenylyl, in particular 4-biphenylyl |
| 64) Phenyl | (Cyanophenyl)phenyl, in particular 2'-cyanobiphenyl-4-yl |
| 65) 4-(Phenyl-lower-alkoxy)-phenyl, in particular 4-benzyloxyphenyl | (Cyanophenyl)phenyl, in particular 2'-cyanobiphenyl-4-yl |
| 66) 4-Hydroxyphenyl | (Cyanophenyl)phenyl, in particular 2'-cyanobiphenyl-4-yl |
| 67) 4-Lower-alkoxyphenyl, in particular 4-methoxyphenyl | (Cyanophenyl)phenyl, in particular 2'-cyanobiphenyl-4-yl |
| 68) Cyclohexyl | (Cyanophenyl)phenyl, in particular 2'-cyanobiphenyl-4-yl |
| 69) Cyclohexyl | 4-Lower-alkoxyphenyl, in particular 4-methoxyphenyl |
| 70) Phenyl | 4-Hydroxyphenyl |

The combinations $R_2$ and $R_3$ which are very particularly preferred are those mentioned immediately above under numbers 2), 4), 6), 8), 16), 24), 26), 27), 30) and 44), especially those mentioned under 6) and, in particular, under 30).

$R_4$ is preferably lower alkyl, in particular methyl or isopropyl, or else sec-butyl (=1-methylpropyl).

Lower alkyl $R_5$ is preferably methyl or else ethyl.

The variable n is preferably 1.

Salts of compounds of the formula I are, in particular (when basic groups are present in compounds of the formula I), acid addition salts, salts with bases (when acidic groups are present in compounds of the formula I) or else possibly mixed salts or internal salts when several salt-forming groups are present.

Salts are primarily the pharmaceutically utilizable, non-toxic salts of compounds of the formula I.

Such salts are formed, for example, from compounds of the formula I having an acidic group, for example a carboxyl group, a sulfo group or a phosphoryl group which is substituted by one or two hydroxyl groups, and are, for example, their salts with suitable bases, such as non-toxic metal salts derived from metals of groups Ia, Ib, IIa and IIb of the periodic system of the elements, primarily suitable alkali metal salts, for example lithium, sodium or potassium salts, or alkaline earth metal salts, for example magnesium or calcium salts, and also zinc salts or ammonium salts, and also those salts which are formed with organic amines, such as mono-, di- or n-trialkylamines, in particular mono-, di- or tri-lower-alkylamines, which are unsubstituted or substituted by hydroxyl, or with quaternary ammonium compounds, for example with N-methyl-N-ethylamine, diethylamine, triethylamine, mono-, bis- or tris-(2-hydroxyl-lower-alkyl)amines, such as mono-, bis- or tris-(2-hydroxyethyl)amine, 2-hydroxy-tert-butylamine or tris-(hydroxymethyl)methylamine, N,N-di-lower-alkyl-N-(hydroxyl-lower-alkyl)amines, such as N,N-dimethyl-N-(2-hydroxyethyl)amine or tri-(2-hydroxyethyl)amine, N-methyl-D-glucamine or quaternary ammonium salts, such as tetrabutylammonium salts. The compounds of the formula I which have a basic group, for example an amino group, can form acid addition salts, for example with inorganic acids, for example hydrohalic acid, such as hydrochloric acid, sulfuric acid or phosphoric acid, or with organic carboxylic, sulfonic, sulfate (—O—SO$_3$H) or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example the α-amino acids mentioned above, in particular glutamic acid and aspartic acid, and also with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose-6-phosphate or N-cyclohexylsulfamic acid (with the formation of cyclamates), or with other acidic organic compounds, such as ascorbic acid. Compounds of the formula I which possess acidic and basic groups can also form internal salts.

Pharmaceutically unsuitable salts, for example perchlorates or picrates, may also be used for isolation or purification. Only the pharmaceutically utilizable salts, which are non-toxic when properly used, are suitable for therapeutic use, and are, therefore, preferred.

The compounds of the formula I have valuable pharmacological properties. They possess anti-retroviral activity, particularly against the HIV-1 and HIV-2 viruses, which are considered to be causative agents of AIDS, and surprisingly have synergistic effects when used in combination with other compounds which possess activity against retroviral aspartate proteases. The compounds of the formula I are inhibitors of retroviral aspartate proteases, in particular inhibitors of the aspartate protease of HIV-1 or HIV-2, and are therefore suitable for treating retroviral diseases, such as AIDS or its preliminary stages (e.g. ARDS). Compounds of the formula I also have an effect against corresponding animal retroviruses, such as SIV (in monkeys) or FIV (in cats).

In this context, compounds of the formula I have particularly advantageous pharmacodynamic properties, for example good pharmacodynamics, such as a high bioavailability and/or high blood levels (especially when administered orally), and/or good tolerability.

The inhibitory effect of the compounds of the formula I on the proteolytic activity of HIV-1 protease can be demonstrated, for example, using a method analogous to that described by A. D. Richards et al., J. Biol. Chem. 2.65(14), 7733–7736 (1990). In this case, inhibition of the action of the HIV-1 protease (prepared in accordance with S. Billich et al., J. Biol. Chem. 263(34), 17905–17908 (1990)) is measured in the presence of the icosapeptide RRSN-QVSQNYPIVQNIQGRR (an artificial substrate of HIV-1 protease, prepared by peptide synthesis using known methods, see J. Schneider et al., Cell 54, 363–368 (1988)), which, as a substrate analogue, comprises one of the cleavage sites of the gag precursor protein (natural substrate of the HIV-1 protease). This substrate and its cleavage products are analysed by high performance liquid chromatography (HPLC).

The active compound to be tested is dissolved in dimethyl sulfoxide. The enzymic test is carried out by adding suitable dilutions of the inhibitor in 20 mM β-morpholinoethanesulfonic acid (MES) buffer pH 6.0, to the test mixture. The latter consists of the abovementioned icosapeptide (122 μM) in 20 mM MES buffer, pH 6.0. 100 μl are employed per test mixture. The reaction is started by adding 10 μl of HIV-1 protease solution, and is ended after one hour of incubation at 37° C. by adding 10 μl of 0.3M HClO$_4$. After the sample has been centrifuged at 10,000×g for 5 min, 20 μl of the resulting supernatant are loaded onto a 125×4.6 mm ®Nucleosil C18-5μ HPLC column (reverse-phase material from Macherey & Nagel, Düren, FRG, based on silica gel which is coated with $C_{18}$alkyl chains). The uncleaved icosapeptide and its cleavage products are eluted from the column using the following gradient: 100 % eluent 1→50% eluent 1+50% eluent 2 (eluent 1: 10% acetonitrile, 90 % H$_2$O, 0.1% trifluoroacetic acid (TFA); eluent 2:75 % acetonitrile, 25 % H$_2$O, 0.08 % TFA) over 15 min, flow rate 1 ml/min The eluted peptide fragments are quantified by measuring the peak height of the cleavage product at 215 nm.

Compounds of the formula I have inhibitory effects in the range from $10^{-5}$ to $10^{-9}$M. In this context, IC$_{50}$ values (IC$_{50}$=that concentration which decreases the activity of the HIV-1 protease by 50% as compared with the activity of a control without inhibitor) of from about $5×10^{-5}$ to $10^{-9}$M are preferably obtained.

In a further test, it can be shown that compounds of the formula I either protect cells which are normally infected by HIV from such an infection or at least retard such an infection. This test uses the human T cell leukaemia cell line MT-2 (Science 229, 563 (1985)), which is extremely sensitive to the cytopathic effect of HIV since it continually produces HTLV-1 (a virus which causes leukaemia). The MT-2 cells are grown in RPMI 1640 medium (Gibco, Scotland; RPMI comprises an amino acid mixture lacking glutamine) which is supplemented with 10% heat-inactivated fetal calf serum, glutamine and standard antibiotics. The cells are always free of mycoplasmas. The HIV-1 virus (strain LAV) is cultured in A 3.01 cells (NIH, Bethesda, U.S.A.), a cell line which is used for culturing HIV-1 and which derives from the CEM cell line. Measuring by the test for reverse transcriptase (see below) indicates that the titre of the virus preparation is $2 \times 10^7$ IU/ml.

In order to measure the infection-inhibiting effect of the test compounds, 50 µl of the respective test substance in culture medium and 100 µl of HIV-1 in culture medium (800 TCID50/ml, TCID50=tissue culture infective dose=dose, which infects 50% of the MT-2 cells) are added to $10 \times 10^4$ exponentially growing MT-2 cells which are initially introduced in 50 µl of culture medium on 96-well microtitre plates. After 4 days of incubation, a sample consisting of 10 µl of the supernatant is removed from each well for measuring the reverse transcriptase activity. The titre of the reverse transcriptase enzyme, which is specific for retroviruses, is used as a measure of the virus titre. For determining the titre, the samples which have been removed are first added to another 96-well microtitre plate and stored at $-20°$ C. until measured.

When carrying out the measurement, 30 µl of reverse transcriptase cocktail are added to each well. The reverse transcriptase cocktail consists of 50 mM Tris ($\alpha,\alpha,\alpha$-tris(hydroxymethyl)methylamine, Ultra pur, Merck, Germany), pH 7.8; 75 mM KCl, 2 mM dithiothreitol, 5 mM $MgCl_2$; 0.1% Nonidet P-40 (detergent; Sigma, Switzerland), 0.8 mM EDTA, 10 µg/ml poly-A (Pharmacia, Uppsala, Sweden) and 0.16 µg/ml oligo(T) (=pdT(12–18), Pharmacia, Uppsala, Sweden) as template primer. The mixture is filtered through a 0.45 µm Acrodisc filter (Gelman Sciences Inc., Ann Arbor, U.S.A.) and stored at $-20°$ C. Prior to the test, 0.1% (v/v) of [alpha-$^{32}$P]dTTP is added to aliquots of the solution to produce a final radioactivity of 10 µCi/ml.

After mixing has taken place, the plate is incubated at $37°$ C. for 2 h. 5 µl of the reaction mixture are then transferred to DE81 paper (Whatman, one filter per well). The dried filters are washed three times for 5 min with 300 mM NaCl/25 mM trisodium citrate and then once with ethanol, and air-dried once again. The radioactivity on the filters is measured in a Packard Matrix 96-well counter (Packard, Zürich, Switzerland). The ED90 values are calculated and are defined as the concentrations of the test compounds which reduce the RT activity by 90% as compared with that of a control without test compound.

In this test, the compounds of the formula I preferably inhibit virus replication at concentrations of from $5 \times 10^{-5}$ to $10^{-8}$M.

Thus, the compounds of the formula I are suitable for actively retarding the replication of HIV-1 in cell cultures.

It is also possible to measure the blood levels of compounds of the formula I.

For this purpose, the compounds of the formula I which are to be investigated are dissolved, for example, in dimethyl sulfoxide (DMSO) at a concentration of 240 mg/ml. The resulting solutions are diluted with 20% (w/v) hydroxypropyl-β-cyclodextrin (HPβCD) in order to obtain a concentration of the test substance of 12 mg/ml. This solution is administered orally to mice, by means of artificial feeding by garage, at a dose of 120 mg/kg. The animals are sacrificed at 30, 60, 90 and 120 min after the administration, and blood is removed. From three to four animals are examined at each time point. The blood is heparinized and worked up for the analysis as follows: an internal standard is added to the heparinized blood to give a final concentration of 4 µM. The blood is centrifuged. 0.25 ml of plasma are taken off and deproteinized with an equal volume of acetonitrile. After centrifugation, the supernatant is dried in vacuo and the residue is suspended in 20 µl of a 3M solution of NaCl and 100 µl of 0.05M phthalate buffer having a pH of 3.0. The suspension is extracted firstly with 1 ml, and then with 0.2 ml, of diisopropyl ether. The diisopropyl ether solution is evaporated to dryness and the residue is dissolved in 50% (v/v) of aqueous acetonitrile. This solution is examined by reversed-phase HPLC.

The reversed-phase HPLC analysis is carried out using a $125 \times 4.6$ mm Nucleosil® $C_{18}$ column (reversed-phase material from Macherey-Nagel, Düren, Federal Republic of Germany, based on silica gel which has been derivatized with hydrocarbon residues of 18 carbon atoms), which is equilibrated with a mobile phase of 50% acetonitrile in water/0.1% trifluoroacetic acid. The flow rate is 1 ml/min. Detection takes place at 215 nm. Standards for the compounds in blood are worked up in analogy with the blood samples and are used for constructing standard curves which are then employed for determining the in-vivo concentrations.

These and related experiments, and also experiments involving parenteral administration, demonstrate that using the compounds of the formula I, blood levels can be obtained which are greater than the $ED_{90}$ in the abovementioned cell assay. For this reason, compounds of this nature are also suitable for preventing virus growth in vivo.

The combination of aspartate protease inhibition in vitro, inhibition of viral replication in cell culture and measurement of the blood levels in rodents, such as rat or mouse, is used for determining the clinical potential of aspartate protease inhibitors (see, for example, Roberts, N. A., et al., Biochemical Soc. Transaction 20, 513–515 (1992)).

Blood levels which are greater than the $ED_{90}$ in the abovementioned cell assay can also be observed when compounds of the formula I are administered (for example orally) to dogs. Consequently, the combination of the data from the cell experiment, the blood levels in rodents and the blood levels in dogs also renders plausible the possibility of using the compounds to treat retroviral diseases, in particular the said diseases, in other mammals, such as humans.

The compounds of the formula I can also be used for the prevention, control and therapy of infections due to retroviruses, in particular HIV, such as HIV-1 or HIV-2, in cell cultures, in particular cell cultures of lymphocyte cell lines from mammals, which is particularly advantageous in the case of very valuable cell cultures which, for example, produce specific antibodies, vaccines or messenger substances, such as interleukins etc., and are therefore of great commercial value.

Finally, the compounds of the formula I can be used as standards in experiments, for example as HPLC standards or as standards for comparing animal models, in relation to different aspartate protease inhibitors, for example in regard to the blood levels which can be achieved.

The compounds of the formula I can be administered alone or else in combination (as a fixed combination of appropriate preparations or as a combination of individual active compounds or individual preparations administered in chronologically staggered sequence) with other substances which are active against retroviruses, in particular HIV, such as HIV-1 or HIV-2, or salts thereof, provided at least one salt-forming group is present; in particular together with inhibitors of reverse transcriptase, especially nucleoside analogues, in particular 3'-azido-3'-deoxythyimidine (=zidovudine=®RETROVIR, Burroughs-Wellcome), 2', 3'-dideoxycytidine (=zalcitabine=®HIVID, Hoffmann-LaRoche), 2',3'-clideoxyinosine (=didanosine=®VIDEX, Bristol-Myers-Squibb) or (2R,cis)-4-amino-1-(2-hydroxymethyl-1,3-oxathiolan-5-yl)-(1H)-pyrimidin-2-one (=lamivindine, Glaxo) or non-nucleoside analogues, such as 11-cyclopropyl-5,11 -dihydro-4-methyl-(6H)-dipyrido[3,2-b;2',3'-e]-[1,4]diazepin-6-one; and in the first place with one or more (in particular one or else two) other inhibitors of retroviral aspartate proteases, in particular the aspartate proteases from HIV, such as HIV-1 and HIV-2, in particular one or more (preferably one or two), in particular a) one of the inhibitors named in EP 0 346 847 (published on 20.12.1989) and EP 0 432 695 (published on 10.06.1991; corresponds to U.S. Pat. No. 5,196,438, published on 23.03.1993), in particular the compound with the designation Ro 31-8959 (=saquinavir; Hoffmann-LaRoche) of the formula (saquinavir)

b) one of the inhibitors named in EP 0 541 168 (published on 12.05.1993; corresponds to U.S. Pat. No. 5,413, 999), in particular the compound with the designation L-735,524 (=indinavir=®CRIXIVAN; Merck & Co., Inc.) of the formula (indinavir)

c) one of the inhibitors named in EP 0486 948 (published on 27.05.1992; corresponds to U.S. Pat. No. 5,354, 866), in particular the compound with the designation ABT-538 (Abbott) of the formula

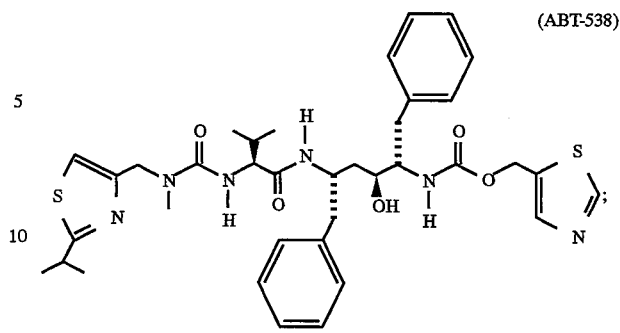

d) the compound with the designation KVX-478 (or VX-478 or 141W94; Glaxo Wellcome, Vertex and Kissei Pharmaceuticals) of the formula

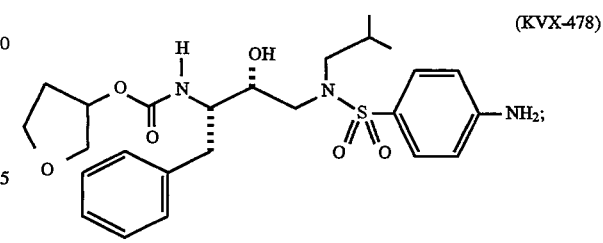

e) the compound with the designation AG-1343 (Agouron) of the formula

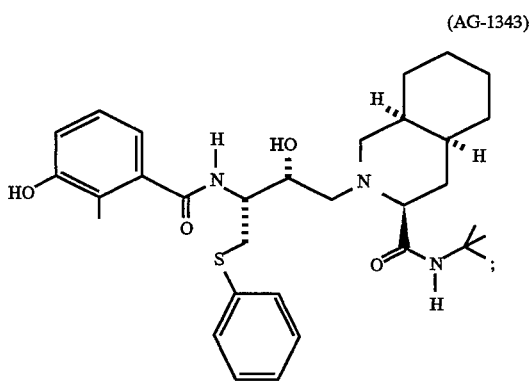

f) the compound with the designation KNI-272 (Nippon Mining) of the formula

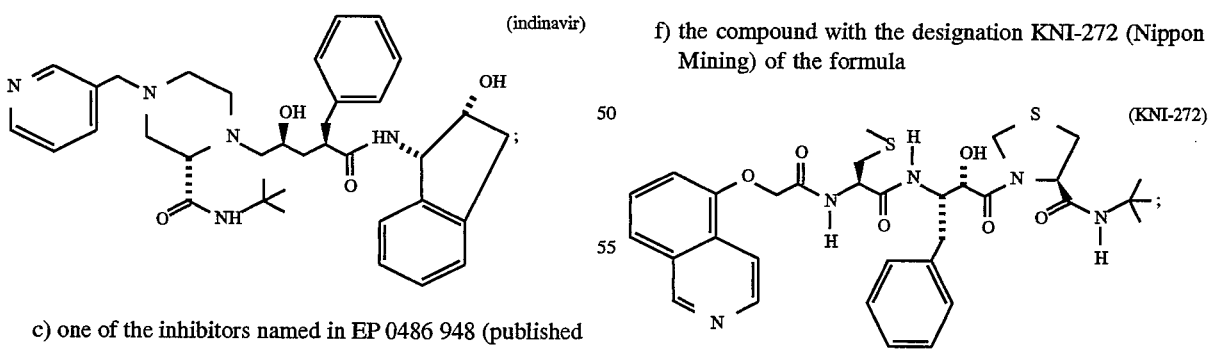

g) the compound with the designation U-96988 (Upjohn) of the formula

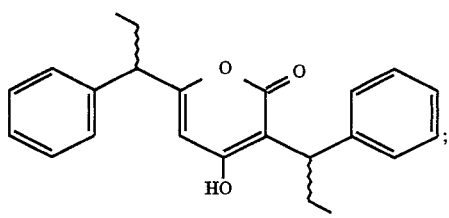
(U-96988)

and/or h) the compound with the designation BILA-2011 BS (=palinavir; Boehringer-Ingelheim) of the formula

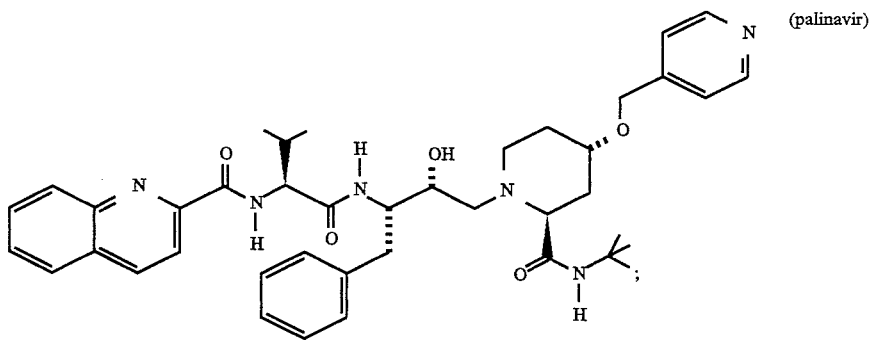
(palinavir)

or in each case a salt thereof, provided salt-forming groups are present.

Particularly when a compound of the formula I is combined with one or more of the said inhibitors of retroviral aspartate proteases, synergistic effects can actually be observed, which is surprising since the inhibitors act on the same enzyme. The particular advantage of such combinations then resides in the decrease in the dosage quantities which are required and in the more powerful anti-retroviral activity, which can simultaneously be achieved, of the active compounds when used in combination as compared with that which can be achieved using the individual active compounds. This yields advantages with regard to possible side effects of the individual compounds and results in a lower number of viruses in the organism, so that the frequency of mutation can also be lowered and hence the possibility of the development of resistance can be reduced.

The activity of the combinations, and, in particular, the synergistic effects, can be verified, for example, by means of experiments using cell lines and peripheral mononuclear blood cells (lymphocytes and monocytes).

CEM-SS cells (see Nara, P. L., et al., AIDS Res. Human Retroviruses 3, 283–302 (1987), or Nara, P. L., et al., Nature 332, 469–70 (1988)) and the permanently infected cell line H9/HTLV-IIIB NIH 1983 (H9/HIV-1/IIIB cells) of Gallo (see Popovic, M., et al., Science 224, 497–500 (1984); Popovic, M., et al., Lancet (1984) ii, 1472–3; or Ratner, L., et al., Nature 313, 277–84 (1985)), for example, are employed for the experiments using cell lines.

For the experiments using peripheral mononuclear blood cells, the cells are isolated from the blood of healthy HIV-seronegative human subjects using a combination of leukaphoresis and counter-current centrifugal elutriation in accordance with known methods (see Alteri, E., et al., Antimicrob. Agent Chemother. 37(10), 2087–92 (1993)).

The lymphocytotrophic isolate HIV-1/LAV (LAV.04/A.301), for example, is used as the virus (see Science 220, 868–71 (1983)).

The compounds to be tested, for example a compound of the formula I and one of the other inhibitors of retroviral aspartate proteases mentioned above, for example saquinavir or indinavir, are dissolved in dimethyl sulfoxide (=DMSO; 2 mM), with further dilutions being made using complete tissue culture medium (see below). The final concentration of free DMSO is less than 0.5%.

The experiments for testing antiviral activity are carried out as follows:

When using cell lines:

The cell lines are maintained in complete culture medium of the following composition: RPMI 1640 (GIBCO, Paisley, Scotland), supplemented with 10% fetal calf serum (SEROMED, Berlin, Germany), 10 mM 4-(2-hydroxyethyl) piperazine-1-ethanesulfonic acid (=HEPES) and 2 mM L-glutamine (AMIMED, Muttenz, Switzerland). The antiviral activity of the compounds is tested in a coculture system using CEM-SS cells and permanently infected H9/HIV-1/IIIB cells. The test compounds are tested as individual substances or as a combination of two active substances in defined concentration milos. H9/HIV-1/IIIB cells are mixed, after having been washed twice and having been suspended in fresh medium, with CEM-SS cells in a ratio of 1:50. 100 μl of the cell mixture are dispensed into each well of 96-well containing culture plates with the wells in each case containing 400 H9/HIV-1/IIIB cells and 2×10⁴ CEM-SS cells. Immediately after the cells have been dispensed, two-fold serial dilutions of the test compounds are added (100 μl per well) in each case in sets of six. Instead of this, 100 μl of medium are added to each well for the virus control (VC); CEM-SS cells on their own (without H9/HIV-1/IIIB cells) are used as the control (CC). The final volume is 200 μl/well. After a 24 h incubation at 37° C. and in 5% CO₂, 150 μl of each supernatant is removed, without removing any cells, and replaced by 150 μl of fresh medium which contains (or, in the case of the VC does not contain) fresh test substance or fresh test substances. 10 μl samples of the culture supernatants are collected on day 4 and added to another 96-well microtitre plate which, if required, is stored at −20° C. The virus production is determined as the virus-associated activity of the reverse transcriptase (RT) in accordance with the following method, which has already been described above (see Alteri, E., et al., Antimicrob. Agent Chemother. 37(10), 2087–92 (1993)):

When carrying out the measurement, 30 μl of reverse transcriptase cocktail are added to each well. The reverse transcriptase cocktail consists of 50 mM Tris (α,α,α-tris (hydroxymethyl)methylamine, Ultra pur, Merck, Germany), pH 7.8; 75 mM KCl, 2 mM dithiothreitol, 5 mM MgCl₂; 0.1% Nonidet P-40 (detergent; Sigma, Switzerland), 0.8 mM EDTA, 10 μg/ml poly-A (Pharmacia, Uppsala, Sweden) and 0.16 μg/ml oligo(T) (=pdT(12–18), Pharmacia, Uppsala, Sweden) as template primer. The mixture is filtered through a 0.45 μm Acrodisc filter (Gelman Sciences Inc., Ann Arbor, U.S.A.) and stored at −20° C. Prior to the test, 0.1% (v/v)

[alpha-$^{32}$P]dTTP is added to aliquots of the solution in order to achieve a final radioactivity of 10 μCi/ml.

After mixing, the plate is incubated at 37° C. for 1.5 h. 5 μl of the reaction mixture are transferred to DE81 paper (Whatman, one filter per well). The dried filters are washed three times for 5 min with 300 mM NaCl/25 mM trisodium citrate and then once with ethanol, and air-dried once again. The radioactivity on the filters is measured in a Packard Matrix 96-well counter (Packard, Zurich, Switzerland). The antiretroviral effect is given as the % reduction in RT activity as compared with the VC values.

When peripheral mononuclear blood cells are used:

The mixture of mononuclear cells (lymphocytes and monocytes); which is obtained as described above, is cultured, in the presence of 0.25 μg/ml phytohaemagglutinin (Wellcome Diagnostics, Temple Hill, Dartford, England), for two days in RPMI-1640 (GIBCO, Paisley, Scotland), 50 mU/ml penicillin, 50 μg/ml streptomycin (ANIMED, Muttenz, Switzerland), 2 mM L-glutamine (AMIMED, Muttenz, Switzerland) and 10 mM HEPES buffer (GIBCO, Paisley, Scotland). Successful activation is monitored by measuring the increase in cell size (scattergram, FCM analysis). The cells are resuspended in complete medium containing 10% human AB serum (Sigma, St. Louis, U.S.A.) and infected with HIV-1 for 6 h. After the viral adsorption, the cells are washed and resuspended in complete medium which is supplemented with 100 U/ml human recombinant IL-2 (Genzyme, Cambridge, U.S.A.). 9×10$^4$ cells are plated out per well (0.3 ml) in 96-well plates having U-shaped well bottoms. The antiviral compounds are added either alone or in combination to sets of five cell cultures in each case (pentaplicates) directly following the infection. Two thirds of the culture medium with or without antiviral compound(s) are replaced every three days. The test is concluded on day 13 after infection. The progress of the vital infection is measured by determining the RT activity as described above for the cell lines.

In the groups of preferred compounds of the formula I which are mentioned below, definitions of substituents from the abovementioned general definitions can be employed in a meaningful manner, for example to replace more general definitions by more specific definitions or in particular those definitions characterized as being preferred; in each case, those definitions are preferred which are characterized above as being preferred or as being examples.

A compound of the formula I (in particular of the formula I') is preferred in which:

$R_1$ is an acyl radical selected from lower-alkoxyl-lower-alkanoyl, such as, in particular, lower-alkoxycarbonyl, especially tert-butoxycarbonyl, ethoxycarbonyl or methoxycarbonyl; lower-alkoxyl-lower-alkanoyl (in particular correspondingly substituted lower-alkoxycarbonyl) which is substituted in the lower-alkoxy radical, once or more than once, by halogen, in particular fluorine, by lower alkoxy or by pyrrolidinyl which is unsubstituted or substituted by oxo, such as 2,2,2-trifluoroethoxycarbonyl, 2-methoxyethoxycarbonyl, 2-methoxy-1 (R,S)-methylethoxycarbonyl, 1,1-dimethyl-2-methoxyethoxycarbonyl or 2-oxopyrrolidin-5(S)-ylmethoxycarbonyl; N-lower-alkoxycarbonyl-piperidinyl-lower-alkanoyl, for example -carbonyl, such as N-ethoxycarbonyl-piperidin-4-ylcarbonyl; pyrrolidinyl-lower-alkanoyl, such as -carbonyl, which is substituted by hydroxyl on a carbon atom and/or by phenyl-lower-alkoxycarbonyl on the nitrogen atom and which is preferably in the (R) form, the (R,S) form or, in particular, the (S) form on the binding carbon atom, such as (L)-trans-4-hydroxyprolyl or (L)-N-benzyloxycarbonyl-trans-4-hydroxyprolyl; aminothiazolidinyl-lower-alkanoyl, for example -acetyl, such as 2-amino-4-thiazolyl-acetyl; thiazolyl-lower alkanoyl, for example -carbonyl, such as thiazol-2-ylcarbonyl; indolyl-lower-alkanoyl, for example -carbonyl, such as indol-2-ylcarbonyl; 4H-1-benzopyranyl-lower-alkanoyl, for example -carbonyl, which is substituted by oxo, such as 4-oxo-4H-1-benzopyran-2-ylcarbonyl; N-lower-alkyl-piperidinyloxy-lower-alkanoyl, for example -carbonyl, such as N-methyl-piperidin-4-yloxycarbonyl; tetrahydropyranyloxy-lower-alkanoyl, for example -propionyl or -carbonyl, such as 2(S)-(tetrahydropyran-4-yloxy)propionyl or tetrahydropyran-2(R,S)-yloxycarbonyl; tetrahydrofuranyloxy-lower-alkanoyl, for example -carbonyl, such as tetrahydrofuran-3(S)-yloxycarbonyl; morpholinyl-lower-alkyl-benzoyl, such as 4-(morpholin-4-ylmethyl)benzoyl; lower-alkylpiperazinyl-pyridylcarbonyl, such as N-lower-alkylpiperazinyl-pyridylcarbonyl, in particular 4-lower-alkyl-piperazin-1-yl-pyridylcarbonyl, for example 2- or 3-(4-lower-alkyl[such as methyl]-piperazin-1-yl)-pyridin-2-ylcarbonyl or -3-ylcarbonyl; phenyl-lower alkanoyl which is substituted by hydroxyl or lower alkyl, in particular methyl, preferably having in each case a hydroxyl substituent and a lower alkyl substituent, in particular hydroxyl and methyl, on the phenyl ring, in particular corresponding substituted benzoyl, such as 3-hydroxy-2-methyl-benzoyl; and phenylsulfonyl which is substituted by amino, nitro, amino and lower alkyl, such as methyl, or nitro and lower alkyl, such as methyl, such as 4-nitrobenzenesulfonyl, 4-aminobenzenesulfonyl, 2-lower-alkyl(in particular 2-methyl)-4-nitrobenzenesulfonyl or 4-amino-2-lower-alkyl (in particular 2-methyl)-benzenesulfonyl;

is the residue, which is bonded via the carboxyl group, of an amino acid selected from valine, norvaline, leucine, isoleucine and norleucine and, in addition, from serine, homoserine, threonine, methionine, cysteine, phenylalanine, tyrosine, 4-aminophenylalanine, 4-chlorophenylalanine, 4-carboxyphenylalanine, β-phenylsefine, phenylglycine, α-naphthylalanine, cyclohexylalanine, cyclohexylglycine, tryptophan, asparagine, aminomalonic acid monoamide, glutamic acid, glutamine, histidine, arginine, lysine, δ-hydroxylysine and ornithine; with valine being particularly preferred; with the respective amino group(s) and other functional groups being free or (if possible) in salt form; and with the said amino acid residues having asymmetric carbon atoms being in the (D) form, the (L) form or the (D,L) form, preferably in the (L) form;

or is the residue, which is bonded via the carbonyl group, of one of the amino acids mentioned immediately above, which residue is N-acylated on the amino nitrogen by one of the previously mentioned acyl radicals, in particular a valine residue which is bonded via the carbonyl group and which is N-acylated by one of the previously mentioned acyl radicals, in particular lower-alkoxyl-lower-alkanoyl-valyl, such as lower-alkoxycarbonyl-valyl, for example methoxycarbonyl-valyl, or thiazolidinyl-valyl, in particular thiazolidin-4-yl-valyl which is preferably in the (S) form, the (R,S) form or, in particular, the (R) form (=(L) form) at the 4 carbon atom of the thiazolidine ring; with the valyl residue in each case preferably being in the (L) form;

$R_2$ and $R_3$ are selected, independently of each other, from cyclohexyl, cyclohexenyl, such as cyclohexen-1-yl, phenyl, biphenylyl, such as 4-biphenylyl, (cyanophenyl)phenyl, such as 2'-cyanobiphenyl-4-yl, phenyl-lower-alkoxy-phenyl, in particular 4-phenyl-lower-alkoxy-phenyl, such as 4-(benzyloxy)-phenyl, difluorophenyl, in particular 2,4-difluorophenyl, cyanophenyl, in particular 4-cyanophenyl, lower-alkoxyphenyl, such as 2-, 3- or 4-lower-alkoxyphenyl; for example 4-isobutyloxyphenyl and, in particular, 2-, 3- and, especially, 4-methoxyphenyl, tri-lower-alkoxyphenyl, in particular trimethoxyphenyl, for example having the lower-alkoxy substituents in the 3,4,5 positions, such as in 3,4,5-trimethoxyphenyl, in the 2,4,5 positions, such as in 2,4,5-trimethoxyphenyl, or in the 2,4,6 positions, such as in 2,4,6-trimethoxyphenyl, where the tri-lower-alkoxy- or methoxy radicals are preferably asymmetrically bonded on the phenyl ring, primarily in the 2,3,4 positions, for example in 2,3,4-trimethoxyphenyl, lower-alkoxyl-lower-alkoxyphenyl, such as 4-lower-alkoxyl-lower-alkoxyphenyl, especially 4-(2-methoxyethoxy)-phenyl, lower-alkylenedioxyphenyl, in which the lower-alkylenedioxy radical is bonded via its two oxygen atoms to two adjacent carbon atoms of the phenyl ring, for example methylenedioxyphenyl, such as 3,4-methylenedioxyphenyl, and pyridyl-lower-alkoxyphenyl, in which pyridyl is bonded via a ring carbon atom, such as 4-(pyridin-2- or pyridin-3-yl-lower alkoxy) phenyl, in particular pyridin-3-yl-lower-alkoxyphenyl, for example pyridin-3-ylmethoxyphenyl; and, in addition, from 4-lower-alkoxy-2-fluorophenyl, such as 4-methoxy-2-fluorophenyl, 4-fluoro-2-lower-alkoxyphenyl, such as 4-fluoro-2-methoxyphenyl, 4-lower-alkoxy-2-hydroxyphenyl, such as 4-methoxy-2-hydroxyphenyl, phenyl which is substituted not more than three times by lower alkyl, such as methyl, and lower alkoxy, such as methoxy, such as 4-lower-alkoxy-2,3-di-lower-alkylphenyl, for example 4-methoxy-2,3-dimethylphenyl, phenyl-lower-alkylphenyl, such as 4-phenyl-lower-alkylphenyl, for example 4-(2-phenylethyl)-phenyl, fluorophenyl, such as 2-fluorophenyl, hydroxyphenyl, such as 4-hydroxyphenyl, di-lower-alkoxyphenyl, in particular dimethoxyphenyl, for example 2,4-di-lower-alkoxyphenyl, such as 2,4-dimethoxyphenyl, 3,4-di-lower-alkoxyphenyl, such as 3,4-dimethoxyphenyl, 2,5-di-lower-alkoxyphenyl, such as 2,5-dimethoxyphenyl, or 2,6-di-lower-alkoxyphenyl, such as 2,6-dimethoxyphenyl, tetrahydronaphthyl, in particular 5,6,7,8-tetrahydro-1-naphthyl, halonaphthyl, such as fluoronaphthyl, in particular 4-fluoronaphthyl, cyanonaphthyl, in particular 4-cyanonaphthyl, lower-alkoxynaphthyl, in particular 4-lower-alkoxynaphthyl, such as 4-methoxy-1-naphthyl, and dihalophenyl-lower-alkanesulfonylphenyl, in particular dichlorophenyl-lower-alkanesulfonylphenyl, such as 4-(2,6-dichlorobenzylsulfonyl)phenyl; with the corresponding radicals preferably being present in the combinations specified above as being preferred; in particular in one of the combinations specified above under numbers 2), 4), 6), 8), 16), 24), 26), 27), 30) and 44), i.e. $R_2$=phenyl and $R_3$=cyanophenyl (in particular 4-cyanophenyl); $R_2$=phenyl and $R_3$=2,4-difluorophenyl; $R_2$=phenyl and $R_3$=4-lower-alkoxyphenyl, in particular 4-methoxyphenyl; $R_2$=4-(lower-alkoxyl-lower-alkoxy)phenyl, in particular 4-(2-methoxyethoxy)phenyl and $R_3$=4-(phenyl-lower-alkoxy)phenyl, in particular 4-(benzyloxy)phenyl; $R_2$=cyclohexyl and $R_3$=4-lower-alkoxyphenyl, in particular 4-methoxyphenyl; $R_2$=phenyl and $R_3$=phenyl; $R_2$=phenyl and $R_3$=4-((pyridin-2-yl- or, in particular, pyridin-3-yl)-lower alkoxy)phenyl, such as -methoxyphenyl; $R_2$=phenyl and $R_3$=3,4-lower-alkylenedioxyphenyl, in particular 3,4-methylenedioxyphenyl; $R_2$=cyclohexyl and $R_3$=4-(lower-alkoxyl-lower-alkoxy)phenyl, in particular 4-(2-methoxyethoxy)phenyl; or, in a particularly preferred manner, $R_2$=phenyl and $R_3$=2,3,4-tri-lower-alkoxyphenyl, in particular 2,3,4-trimethoxyphenyl;

$R_4$ is lower alkyl, preferably isopropyl, or, in addition, cyclohexyl or phenyl;

$R_5$ is lower alkyl, especially methyl or, in addition, ethyl or n-propyl; and n is 2 or, preferably, is 1, or a salt thereof, provided at least one salt-forming group is present.

A compound of the formula I is more strongly preferred in which $R_1$ is an acyl radical selected from lower-alkoxyl-lower-alkanoyl, such as, in particular, lower-alkoxycarbonyl, especially tert-butoxycarbonyl, ethoxycarbonyl or methoxycarbonyl; lower-alkoxyl-lower-alkanoyl (in particular correspondingly substituted lower-alkoxycarbonyl) which is substituted in the lower-alkoxy radical once or more than once by halogen, in particular fluorine, by lower alkoxy or by pyrrolidinyl which is unsubstituted or substituted by oxo, such as 2,2,2-trifluoroethoxycarbonyl, 2-methoxyethoxycarbonyl or 2-oxopyrrolidin-5(S)-ylmethoxycarbonyl; N-lower-alkoxy-carbonyl-piperidinyl-lower-alkanoyl, for example -carbonyl, such as N-ethoxycarbonyl-piperidin-4-ylcarbonyl; pyrrolidinyl-lower-alkanoyl, such as -carbonyl, which is substituted by hydroxyl on a carbon atom and/or by phenyl-lower-alkoxycarbonyl on the nitrogen atom and which is preferably in the (R) form, the (R,S) form or, in particular, the (S) form at the binding carbon atom, such as (L)-trans-4-hydroxyprolyl or (L)-N-benzyloxycarbonyl-trans-4-hydroxyprolyl; aminothiazolidinyl-lower-alkanoyl, for example -acetyl, such as 2-amino-4-thiazolyl-acetyl; thiazolyl-lower-alkanoyl, for example -carbonyl, such as thiazol-2-ylcarbonyl; indolyl-lower-alkanoyl, for example -carbonyl, such as indol-2-ylcarbonyl; 4H-1-benzopyranyl-lower-alkanoyl, for example -carbonyl, which is substituted by oxo, such as 4-oxo-4H-1-benzopyran-2-ylcarbonyl; N-lower-alkyl-piperidinyloxy-lower-alkanoyl, for example -carbonyl, such as N-methylpiperidin-4-yloxycarbonyl; tetrahydropyranyloxy-lower-alkanoyl, for example -propionyl or -carbonyl, such as 2(S)-(tetrahydropyran-4-yloxy)propionyl or tetrahydropyran-2(R,S)-yloxycarbonyl; tetrahydrofuranyloxy-lower-alkanoyl, for example -carbonyl, such as tetrahydrofuran-3(S)-yloxycarbonyl; morpholinyl-lower-alkyl-benzoyl, such as 4-(morpholin-4-ylmethyl)-benzoyl; and lower-alkylpiperazinyl-pyridylcarbonyl, such as N-lower-alkylpiperazinyl-pyridylcarbonyl, in particular 4-lower-alkyl-piperazin-1-yl-pyridylcarbonyl, for example 2- or 3-(4-lower-alkyl[such as methyl]-piperazin-1-yl-)-pyridin-2-ylcarbonyl or -3-ylcarbonyl;

is the residue, which is bonded via the carboxyl group, of an amino acid selected from valine, norvaline, leucine, isoleucine and norleucine and, in addition, from serine, homoserine, threonine, methionine, cysteine, phenylalanine, tyrosine, 4-aminophenylalanine, 4-chlorophenylalanine, 4-carboxyphenylalanine, β-phenylserine, phenylglycine, α-naphthylalanine, cyclohexylalanine, cyclohexylglycine, tryptophane, asparagine, aminomalonic acid monoamide, glutamic acid, glutamine, histidine, arginine, lysine, δ-hydroxylysine and ornithine; with valine being particularly preferred with the respective amino group(s) and other functional groups being free or (if possible) in salt form; and with the said amino acid residues having asymmetric carbon atoms being in the (D) form, the (L) form or the (D,L) form, preferably in the (L) form;

or is the residue, which is bonded via the carbonyl group, of one of the amino acids mentioned immediately above, which residue is N-acylated on the amino nitrogen by one of the previously mentioned acyl radicals, in particular a valine residue which is bonded via the carbonyl group and is N-acylated by one of the previously mentioned acyl radicals, in particular lower-alkoxyl-lower-alkanoyl-valyl, such as lower-alkoxycarbonyl-valyl, for example methoxycarbonyl-valyl, or thiazolidinyl-valyl, in particular thiazolidin-4-yl-valyl, which is preferably in the (S) form, the (R,S) form or, in particular, the (R) form (=(L) form) at the 4 carbon atom of the thiazolidine ring; with the valyl residue in each case preferably being in the (L) form;

$R_2$ and $R_3$ are selected, independently of each other, from cyclohexyl, cyclohexenyl, such as cyclohexen-1-yl, phenyl, phenyl-lower-alkoxy-phenyl, in particular 4-phenyl-lower-alkoxyphenyl, such as 4-(benzyloxy)-phenyl, difluorophenyl, in particular 2,4-difluorophenyl, cyanophenyl, in particular 4-cyanophenyl, lower-alkoxyphenyl, such as 2-, 3- or 4-lower-alkoxyphenyl, for example 4-isobutyloxyphenyl and in particular 2-, 3- and, especially, 4-methoxyphenyl, tri-lower-alkoxy-phenyl, in particular trimethoxyphenyl, for example with the lower-alkoxy substituents in the 3,4,5 positions, as in 3,4,5-trimethoxyphenyl, in the 2,4,5 positions, as in 2,4,5-trimethoxyphenyl, or in the 2,4,6 positions, as in 2,4,6-trimethoxyphenyl, where the tri-lower-alkoxy or methoxy radicals are preferably bonded asymmetrically on the phenyl ring, primarily in the 2,3,4 positions, for example in 2,3,4-trimethoxyphenyl, lower-alkoxyl-lower-alkoxyphenyl, such as 4-lower-alkoxyl-lower-alkoxyphenyl, especially 4-(2-methoxyethoxy)-phenyl, lower-alklenedioxyphenyl, in which the lower-alkylenedioxy radical is bonded via its two oxygen atoms to two adjacent carbon atoms on the phenyl ring, for example methylenedioxyphenyl, such as 3,4-methylenedioxyphenyl, and pyridyl-lower-alkoxyphenyl, in which pyridyl is bonded via a ring carbon atom, such as 4-(pyridin-2- or pyridin-3-yl-lower-alkoxy)phenyl, in particular pyridin-3-yl-lower-alkoxyphenyl, for example pyridin-3-yl-methoxyphenyl; and, in addition, from 4-lower-alkoxy-2-fluorophenyl, such as 4-methoxy-2-fluorophenyl, 4-fluoro-2-lower-alkoxyphenyl, such as 4-fluoro-2-methoxyphenyl, 4-lower-alkoxy-2-hydroxyphenyl, such as 4-methoxy-2-hydroxyphenyl, phenyl which is substituted not more than three times by lower alkyl, such as methyl, and lower alkoxy, such as methoxy, such as 4-lower-alkoxy-2,3-di-lower-alkylphenyl, for example 4-methoxy-2,3-dimethylphenyl, phenyl-lower-alkylphenyl, such as 4-phenyl-lower-alkylphenyl, for example 4-(2-phenylethyl)phenyl, fluorophenyl, such as 2-fluorophenyl, hydroxyphenyl, such as 4-hydroxyphenyl, di-lower-alkoxyphenyl, in particular dimethoxyphenyl, for example 2,4-di-lower-alkoxyphenyl, such as 2,4-dimethoxyphenyl, 3,4-di-lower-alkoxyphenyl, such as 3,4-dimethoxyphenyl, 2,5-di-lower-alkoxyphenyl, such as 2,5-dimethoxyphenyl, or 2,6-di-lower-alkoxyphenyl, such as 2,6-dimethoxyphenyl, tetrahydronaphthyl, in particular 5,6,7,8-tetrahydro-1-naphthyl, halonaphthyl, such as fluoronaphthyl, in particular 4-fluoronaphthyl, cyanonaphthyl, in particular 4-cyanonaphthyl, lower-alkoxynaphthyl, in particular 4-lower-alkoxynaphthyl, such as 4-methoxy-1-naphthyl, and dihalophenyl-lower-alkanesulfonylphenyl, in particular dichlorophenyl-lower-alkanesulfonylphenyl, such as 4-(2,6-dichlorobenzylsulfonyl)phenyl; with the corresponding radicals preferably being present in the combinations indicated above as being preferred; in particular in one of the combinations specified above under numbers 2), 4), 6), 8), 16), 24), 26), 27), 30) a i.e. $R_2$=phenyl and $R_3$=cyanophenyl (in particular 4-cyanophenyl); $R_2$=phenyl and $R_3$=2,4-difluorophenyl; $R_1$=phenyl and $R_3$=4-lower-alkoxyphenyl, in particular 4-methoxyphenyl; $R_2$=4-(lower-alkoxyl-lower-alkoxy)phenyl, in particular 4-(2-methoxyethoxy)phenyl, and $R_3$=4-(phenyl-lower-alkoxy)phenyl, in particular 4-(benzyloxy)phenyl; $R_2$=cyclohexyl and $R_3$=4-lower-alkoxyphenyl, in particular 4-methoxyphenyl; $R_2$=phenyl and $R_3$=phenyl; $R_2$=phenyl and $R_3$=4-((pyridin-2-yl- or, in particular pyridin-3-yl)-lower-alkoxy)phenyl, such as -methoxyphenyl; $R_2$=phenyl and $R_3$=3,4-lower-alkylenedioxyphenyl, in particular 3,4-methylenedioxyphenyl; $R_2$=cyclohexyl and $R_3$=4-(lower-alkoxyl-lower-alkoxy)phenyl, in particular 4-(2-methoxyethoxy)phenyl; or, in particularly preferred manner, $R_2$=phenyl and $R_3$=2,3,4-tri-lower-alkoxyphenyl, in particular 2,3,4-trimethoxyphenyl;

$R_4$ is lower alkyl, preferably isopropyl, or, in addition, cyclohexyl or phenyl;

$R_5$ is lower alkyl, in particular methyl; and n is 2 or, preferably is 1, or a salt thereof, provided at least one salt-forming group is present.

A compound of the formula I (in particular I') is still more strongly preferred in which $R_1$ is selected from ethoxycarbonyl, tert-butoxycarbonyl, 2,2,2-trifluoroethoxycarbonyl, 2-(methoxy)ethoxycarbonyl, 2-methoxy-1(R,S)-methylethoxycarbonyl, 1,1-dimethyl-2-methoxyethoxycarbonyl, 5(S)-2-oxopyrrolidinylmethoxycarbonyl, 1-ethoxycarbonylpiperidin-4-ylcarbonyl, trans-(L)-4-hydroxyprolyl, N-(benzyloxycarbonyl)-trans-(L)-4-hydroxyprolyl, (L)-thiazolidin-4-ylcarbonyl, indol-2-ylcarbonyl, 4H-1-benzopyran-2-ylcarbonyl, N-methylpiperidinyloxycarbonyl, tetrahydropyran-2(R,S)-ylcarbonyl, O-(tetrahydropyran-4-yl)-(L)-lactoyl (=2(S)-(tetrahydropyran-4-yloxy)propionyl), 3(S)-tetrahydrofuranyloxycarbonyl, 2-aminothiazol-4-ylacetyl, 6-(4-methyl-piperazin-1-yl)pyridin-3-ylcarbonyl, 4-(morpholin-4-ylmethyl)benzoyl, N-methoxycarbonyl-(L)-valyl, N-[(L)-thiazolidin-4-ylcarbonyl]-(L)-valyl, 3-hydroxy-2-methylbenzoyl, 4-nitrobenzenesulfonyl, 4-aminobenzenesulfonyl, 2-methyl-4-nitrobenzenesulfonyl and 4-amino-2-methylbenzenesulfonyl; with tert-butoxycarbonyl being particularly preferred;

$R_2$ and $R_3$ are selected from cyclohexyl, cyclohexen-1-yl, phenyl, 4-biphenylyl, 2'-cyanobiphenyl-4-yl, 4-(benzyloxy)-phenyl, 2,4-difluorophenyl, 4-cyanophenyl, 2-, 3- or 4-methoxyphenyl, 4-isobutyloxyphenyl, trimethoxyphenyl, for example having the methoxy substituents in the 3,4,5 positions, as in 3,4,5-trimethoxyphenyl, in the 2,4,5 positions, as in 2,4,5-tri-methoxyphenyl or in the 2,4,6 positions, as in 2,4,6-trimethoxyphenyl, where the methoxy radicals are preferably bonded asymmetrically on the phenyl ring, primarily in the 2,3,4 positions, for example in 2,3,4-trimethoxyphenyl, 4-(2-methoxy-ethoxy)-phenyl, 3,4-methylenedioxyphenyl, and 4-(pyridin-2-or, in particular, pyridin-3-yl-methoxy)phenyl; and, in addition, from 4-methoxy-2-fluorophenyl, 4-fluoro-2-methoxyphenyl, 4-methoxy-2-hydroxyphenyl, 4-methoxy-2,3-dimethylphenyl, 4-(2-phenylethyl) phenyl, 2-fluorophenyl, 4-hydroxyphenyl, dimethoxyphenyl, 2,4-dimethoxyphenyl, 3,4-dimethoxyphenyl, 2,5-dimethoxyphenyl or 2,6-dimethoxyphenyl, 5,6,7,8-tetrahydro-1-naphthyl, 4-fluoronaphthyl, 4-cyanonaphthyl, 4-lower-alkoxynaphthyl and 4-(2,6-dichlorobenzylsulfonyl) phenyl, with $R_2$ and $R_3$ preferably being present in the following combinations: $R_2$=4-benzyloxyphenyl and $R_3$=4-benzyloxyphenyl; $R_2$=phenyl and $R_3$=4-cyanophenyl; $R_2$=phenyl and $R_3$=2-fluorophenyl; $R_2$=phenyl and $R_3$=2,4-difluorophenyl; $R_2$=phenyl and $R_3$=4-(2-phenylethyl)phenyl; $R_2$=phenyl and $R_3$=4-(2,6-dichlorobenzylsulfonyl)phenyl; $R_2$=4-(2-methoxyethoxy)phenyl and $R_3$=4-benzyloxyphenyl; $R_2$=4-(2-methoxyethoxy)phenyl and $R_3$=4-hydroxyphenyl; $R_2$=4-(2-methoxyethoxy)phenyl and $R_3$=4-methoxyphenyl; $R_2$=4-(2-methoxyethoxy) phenyl and $R_3$=4-(2-methoxyethoxy)phenyl; $R_2$=4-benzyloxyphenyl and $R_3$=4-methoxyphenyl; $R_2$=4-hydroxyphenyl and $R_3$=4-methoxyphenyl; $R_2$=4-methoxyphenyl and $R_3$=4-methoxyphenyl; $R_2$=4-isobutyloxyphenyl and $R_3$=4-methoxyphenyl; $R_2$=4-methoxyphenyl and $R_3$=phenyl; $R_2$=cyclohexyl and $R_3$=4-methoxyphenyl; $R_2$=phenyl and $R_3$=4-methoxy-2-fluorophenyl; $R_2$=phenyl and $R_3$=4-fluoro-2-methoxyphenyl; $R_2$=phenyl and $R_3$=4-methoxy-2-hydroxyphenyl; $R_2$=4-methoxyphenyl and $R_3$=cyclohexyl; $R_2$=4-methoxyphenyl and $R_3$=cyclohexen-1-yl; $R_2$=cyclohexyl and $R_3$=4-benzyloxyphenyl; $R_2$=cyclohexyl and $R_3$=4-hydroxyphenyl; $R_2$=cyclohexyl and $R_3$=4-methoxyphenyl; $R_2$=cyclohexyl and $R_3$=4-(2-methoxyethoxy)phenyl; $R_2$=phenyl and $R_3$=phenyl; $R_2$=phenyl and $R_3$=4-benzyloxyphenyl; $R_2$=phenyl and $R_3$=4-hydroxyphenyl; R2=phenyl and $R_3$=4-isobutoxyphenyl; $R_2$=phenyl and $R_3$=4-(pyridin-2-ylmethoxy)phenyl; $R_2$=phenyl and $R_3$=4-(pyridin-3-ylmethoxy)phenyl; $R_2$=phenyl and $R_3$=4-methoxyphenyl; $R_2$=phenyl and $R_3$=3,4-methylenedioxyphenyl; $R_2$=phenyl and $R_3$=3,4-dimethoxyphenyl; $R_2$=phenyl and $R_3$=3-methoxyphenyl; $R_2$=phenyl and $R_3$=2,3,4-trimethoxyphenyl; $R_2$=phenyl and $R_3$=3,4,5-trimethoxyphenyl; $R_2$=phenyl and $R_3$=2,4-dimethoxyphenyl; $R_2$=phenyl and $R_3$=2-methoxyphenyl; $R_2$=phenyl and $R_3$=2,3-dimethyl-4-methoxyphenyl; $R_2$=phenyl and $R_3$=2,4,5-trimethoxyphenyl; $R_2$=phenyl and $R_3$=2,4,6-trimethoxyphenyl; $R_2$=phenyl and $R_3$=5,6,7,8-tetrahydro-1-naphthyl; $R_2$=phenyl and $R_3$=2,5-dimethoxyphenyl; $R_2$=phenyl and $R_3$=2,6-dimethoxyphenyl; $R_2$=phenyl and $R_3$=4-methoxy-1-naphthyl; $R_2$=and $R_3$=4-cyano-1-naphthyl; $R_2$=phenyl and $R_3$=4-fluoro-1-naphthyl; $R_2$=cyclohexyl and $R_3$=2,3,4-trimethoxyphenyl; $R_2$=cyclohexyl and $R_3$=3,4-methylenedioxyphenyl; $R_2$=cyclohexyl and $R_3$=3,4-dimethoxyphenyl; $R_2$=cyclohexyl and $R_3$=3-methoxyphenyl; $R_2$=cyclohexyl and $R_3$=3,4,5-trimethoxyphenyl; $R_2$=cyclohexyl and $R_3$=2,4-dimethoxyphenyl; $R_2$=cyclohexyl and $R_3$=2-methoxyphenyl; $R_2$=cyclohexyl and $R_3$=4-methoxy-2,3-dimethylphenyl; $R_2$=cyclohexyl and $R_3$=2,4,5-trimethoxyphenyl; $R_2$=cyclohexyl and $R_3$=2,4,6-trimethoxyphenyl; $R_2$=cyclohexyl and $R_3$=5,6,7,8-tetrahydro-1-naphthyl; $R_2$=cyclohexyl and $R_3$=2,5-dimethoxyphenyl; $R_2$=cyclohexyl and $R_3$=2,6-dimethoxyphenyl; $R_2$=cyclohexyl and $R_3$=4-methoxy-1-naphthyl; $R_2$=cyclohexyl and $R_3$=4-cyano-1-naphthyl; $R_2$=cyclohexyl and $R_3$=4-fluoro-1-naphthyl; or (alternatively or additionally) $R_2$=phenyl and $R_3$=4-biphenylyl; $R_2$=4-benzyloxyphenyl and $R_3$=4-biphenylyl; $R_2$=4-hydroxyphenyl and $R_3$=4-biphenylyl; $R_2$=4-methoxyphenyl and $R_3$=4-biphenylyl; $R_2$=phenyl and $R_3$=2'-cyanobiphenyl-4-yl; $R_2$=4-benzyloxyphenyl and $R_3$=2'-cyanobiphenyl-4-yl; $R_2$=4-hydroxyphenyl and $R_3$=2'-cyanobiphenyl-4-yl; $R_2$=4-methoxyphenyl and $R_3$=2'-cyanobiphenyl-4-yl; or $R_2$=cyclohexyl and $R_3$=2'-cyanobiphenyl-4-yl; with the following of these combinations being very particularly preferred: $R_2$=phenyl and $R_3$=2,3,4-trimethoxyphenyl; $R_2$=cyclohexyl and $R_3$=2,3,4-trimethoxyphenyl; and, in addition, $R_2$=phenyl and $R_3$=4-methoxyphenyl; or $R_2$=cyclohexyl and $R_3$=4-methoxyphenyl;

$R_4$ is isopropyl or, in addition, cyclohexyl or phenyl;

$R_5$ is methyl or, in addition, ethyl or n-propyl; and n is 2 or, in particular, is 1;

or a salt thereof, provided at least one salt-forming group is present.

A compound of the formula I is much more strongly preferred in which $R_1$ is selected from tert-butoxycarbonyl, 2,2,2-trifluoroethoxy-carbonyl, 2-(methoxy)ethoxycarbonyl, 5(S)-2-oxo-pyrrolidinylmethoxycarbonyl, 1-ethoxycarbonyl-piperidin-4-ylcarbonyl, trans-(L)-4-hydroxyprolyl, N-(benzyloxycarbonyl)-trans-(L)-4-hydroxyprolyl, (L)-thiazolidin-4-ylcarbonyl, indol-2-ylcarbonyl, 4H-1-benzopyran-2-ylcarbonyl, N-methyl-piperidinyloxycarbonyl, tetrahydropyran-2(R,S)-ylcarbonyl, O-(tetrahydropyran-4-yl)-(L)-lactoyl (=2(S)-(tetrahydropyran-4-yloxy)propionyl), 3(S)-tetrahydrofuranyloxycarbonyl, 2-amino-thiazol-4-ylacetyl, 6-(4-methyl-piperazin-1-yl)-pyridin-3-ylcarbonyl, 4-(morpholin-4-ylmethyl)-benzoyl, N-methoxycarbonyl-(L)-valyl and N-[(L)-thiazolidin-4-yl-carbonyl]-(L)-valyl; with tert-butoxycarbonyl being particularly preferred;

$R_2$ and $R_3$ are selected from cyclohexyl, cyclohexen-1-yl, phenyl, 4-(benzyloxy)-phenyl, 2,4-difluorophenyl, 4-cyanophenyl, 2-, 3- or 4-methoxyphenyl, 4-isobutyloxyphenyl, trimethoxyphenyl, for example with the methoxy substituents in the 3,4,5 positions, as in 3,4,5-trimethoxyphenyl, in the 2,4,5 positions, as in 2,4,5-trimethoxyphenyl or in the 2,4,6 positions, as in 2,4,6-trimethoxyphenyl, where the methoxy radicals are preferably bonded asymmetrically on the phenyl ring, primarily in the 2,3,4 positions, for example in 2,3,4-trimethoxyphenyl, 4-(2-methoxyethoxy)phenyl, 3,4-methylenedioxyphenyl, and 4-(pyridin-2- or, in particular, pyridin-3-yl-methoxy)phenyl; and, in addition, from 4-methoxy-2-fluorophenyl, 4-fluoro-2-methoxyphenyl, 4-methoxy-2-hydroxyphenyl, 4-methoxy-2,3-dimethylphenyl, 4-(2-phenylethyl) phenyl, 2-fluorophenyl, 4-hydroxyphenyl, dimethoxyphenyl, such as 2,4-dimethoxyphenyl, 3,4-dimethoxyphenyl, 2,5-dimethoxyphenyl or 2,6-dimethoxyphenyl, 5,6,7,8-tetrahydro-1-naphthyl, 4-fluoronaphthyl, 4-cyanonaphthyl, 4-lower-alkoxynaphthyl and 4-(2,6-dichlorobenzylsulfonyl) phenyl, with $R_2$ and $R_3$ preferably being present in the following combinations: $R_2$=4-benzyloxyphenyl and $R_3$=4-benzyloxyphenyl; $R_2$=phenyl and $R_3$=4-cyanophenyl; $R_2$=phenyl and $R_3$=2-fluorophenyl; $R_2$=phenyl and $R_3$=2,4-difluorophenyl; $R_2$=phenyl and $R_3$=4-(2-phenylethyl)phenyl; $R_2$=phenyl and $R_3$=4-(2,6-dichlorobenzylsulfonyl)phenyl; $R_2$=4-(2-methoxyethoxy)phenyl and $R_3$=4-benzyloxyphenyl; $R_2$=4-(2-methoxyethoxy)phenyl and $R_3$=4-hydroxyphenyl; $R_2$=4-(2-methoxyethoxy)phenyl and $R_3$=4-methoxyphenyl; $R_2$=4-(2-methoxyethoxy) phenyl and $R_3$=4-(2-methoxyethoxy)phenyl; $R_2$=4-benzyloxyphenyl and $R_3$=4-methoxyphenyl; $R_2$=4-hydroxyphenyl and and $R_3$=4-methoxyphenyl; $R_2$=4-methoxyphenyl and $R_3$=4-methoxyphenyl; $R_2$=4-isobutyloxyphenyl and $R_3$=4-methoxyphenyl; $R_2$=4-methoxyphenyl and $R_3$=phenyl; $R_2$=cyclohexyl and $R_3$=4-methoxyphenyl; $R_2$=phenyl and $R_3$=4-methoxy-2-fluorphenyl; $R_2$=phenyl and $R_3$=4-fluoro-2-methoxyphenyl; $R_2$=phenyl and $R_3$=4-methoxy-2-hydroxyphenyl; $R_2$=4-methoxyphenyl and $R_3$=cyclohexyl; $R_2$=4-methoxyphenyl and $R_3$=cyclohexen-1-yl; $R_2$=cyclohexyl and $R_3$=4-benzyloxyphenyl; $R_2$=cyclohexyl and $R_3$=4-hydroxyphenyl; $R_2$=cyclohexyl and $R_3$=4-methoxyphenyl; $R_2$=cyclohexyl and $R_3$=4-(2-methoxyethoxy)phenyl; $R_2$=phenyl and $R_3$=phenyl; $R_2$=phenyl and $R_3$=4-benzyloxyphenyl; $R_2$=phenyl and $R_3$=4-hydroxyphenyl; $R_2$=phenyl and $R_3$=4-isobutoxyphenyl; $R_2$=phenyl and $R_3$=4-(pyridin-2-ylmethoxy)phenyl; $R_2$=phenyl and $R_3$=4-(pyridin-3-ylmethoxy)phenyl; $R_2$=phenyl and $R_3$=4-methoxyphenyl; $R_2$=phenyl and $R_3$=3,4-methylenedioxyphenyl; $R_2$=phenyl and $R_3$=3,4-dimethoxyphenyl; $R_2$=phenyl and $R_3$=3-methoxyphenyl; $R_2$=phenyl and $R_3$=2,3,4-trimethoxyphenyl; $R_2$=phenyl and $R_3$=3,4,5-trimethoxyphenyl; $R_2$=phenyl and $R_3$=2,4-dimethoxyphenyl; $R_2$=phenyl and $R_3$=2-methoxyphenyl; $R_2$=phenyl and $R_3$=2,3-dimethyl-4-methoxyphenyl; $R_2$=phenyl and $R_3$=2,4,5-trimethoxyphenyl; $R_2$=phenyl and $R_3$=2,4,6-trimethoxyphenyl; $R_2$=phenyl and $R_3$=5,6,7,8-tetrahydro1-naphthyl; $R_2$=phenyl and $R_3$=2,5-dimethoxyphenyl; $R_2$=phenyl and $R_3$=2,6-dimethoxyphenyl; $R_2$=phenyl and $R_3$=4-methoxy-1-naphthyl; $R_2$=phenyl and $R_3$=4-cyano-1-naphthyl; $R_2$=phenyl and $R_3$=4-fluoro-1-naphthyl; $R_2$=cyclohexyl and $R_3$=3,4-methylenedioxyphenyl; $R_2$=cyclohexyl and $R_3$=3,4-dimethoxyphenyl; $R_2$=cyclohexyl and $R_3$=3-methoxyphenyl; $R_2$=cyclohexyl and $R_3$=3,4,5-trimethoxyphenyl; $R_2$=cyclohexyl and $R_3$=2,4-dimethoxyphenyl; $R_2$=cyclohexyl and $R_3$=2-methoxyphenyl; $R_2$=cyclohexyl and $R_3$=2,3,4-trimethoxyphenyl; $R_2$=cyclohexyl and $R_3$=2,4,6-trimethoxyphenyl; $R_2$=cyclohexyl and $R_3$=5,6,7,8-tetrahydro-1-naphthyl; $R_2$=cyclohexyl and $R_3$=2,5-dimethoxyphenyl; $R_2$=cyclohexyl and $R_3$=2,6-dimethoxyphenyl; $R_2$=cyclohexyl and $R_3$=4-methoxy-1-naphthyl; $R_2$=cyclohexyl and $R_3$=4-cyano-1-naphthyl; or $R_2$=cyclohexyl and $R_3$=4-fluoro-1-naphthyl; with the following of these combinations being very particularly preferred: $R_2$=phenyl and $R_3$=2,3,4-trimethoxyphenyl; $R_2$=cyclohexyl and $R_3$=2,3,4-trimethoxyphenyl; $R_2$=phenyl and $R_3$=4-methoxyphenyl; or $R_2$=cyclohexyl and $R_3$=4-methoxyphenyl; and, very particularly, the combinations $R_2$=phenyl and $R_3$=2,3,4-trimethoxyphenyl; and, in addition, $R_2$=cyclohexyl and $R_3$=2,3,4-trimethoxyphenyl;

$R_4$ is isopropyl or, in addition, cyclohexyl or phenyl;

$R_5$ is ethyl or, in particular, methyl; and n is 2 or, in particular, is 1;

or a salt thereof, provided at least one salt-forming group is present.

A compound of the formula I (in particular of the formula I') is very much preferred in which $R_1$ is lower-alkoxycarbonyl or lower-alkoxycarbonyl which is substituted not more than three times by halogen, in particular fluorine, and is, in particular, tert-butoxycarbonyl or 2,2,2-trifluoroethoxycarbonyl;

$R_2$ and $R_3$ occur in the following combinations:
  $R_2$=phenyl and $R_3$=cyanophenyl, in particular 4-cyanophenyl;
  $R_2$=phenyl and $R_3$=difluorophenyl, in particular 2,4-difluorophenyl;
  $R_2$=phenyl and $R_3$=4-lower-alkoxyphenyl, in particular 4-methoxyphenyl;
  $R_2$=4-(lower-alkoxyl-lower-alkoxy)phenyl, in particular 4-(2-methoxyethoxy)phenyl, and
  $R_3$=4-phenyl-lower-alkoxyphenyl, in particular 4-benzyloxyphenyl;
  $R_2$=cyclohexyl and $R_3$=4-lower-alkoxyphenyl, in particular 4-methoxyphenyl;
  $R_2$=phenyl and $R_3$=phenyl; $R_2$=phenyl and $R_3$=4-phenyl-lower-alkoxyphenyl, in particular 4-benzyloxyphenyl;
  $R_2$=phenyl and $R_3$=4-(pyridin-3-yl-lower-alkoxy)phenyl, in particular 4-(pyridin-3-ylmethoxy) phenyl;
  $R_2$=phenyl and $R_3$=3,4-lower-alkylenedioxyphenyl, in particular 3,4-methylenedioxyphenyl;
  $R_2$=phenyl and $R_3$=2,3,4-tri-lower-alkoxyphenyl (particularly preferred), in particular 2,3,4-trimethoxyphenyl (very particularly preferred); or, in addition,
  $R_2$=cyclohexyl and $R_3$=4-(lower-alkoxyl-lower-alkoxy)phenyl, in particular 4-(2-methoxyethoxy) phenyl;

$R_4$ is isopropyl;

$R_5$ is methyl; and n is 1.

A compound of the formula I' is very particularly preferred in which $R_1$ is lower-alkoxycarbonyl, in particular tert-butoxycarbonyl;

$R_2$=phenyl and $R_3$=4-lower-alkoxyphenyl, in particular 4-methoxyphenyl, or, preferably, 2,3,4-tri-lower-alkoxyphenyl, in particular 2,3,4-trimethoxycarbonyl;

$R_4$ is isopropyl;

$R_5$ is methyl;
and n is 1.

Compounds of the formula I which are named in the examples, or pharmaceutically acceptable salts thereof, provided at least one salt-forming group is present, are the most strongly preferred.

The compounds of the formula I, or salts of such compounds having at least one salt-forming group, are obtained by processes which are known per se, for example by a) condensing an acid of the formula

  (II)

or a reactive acid derivative thereof, in which $R_1$ has the same meanings as $R_1$ in compounds of the formula I, with an amino compound of the formula

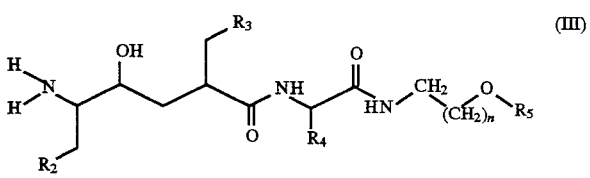  (III)

(in particular of the formula

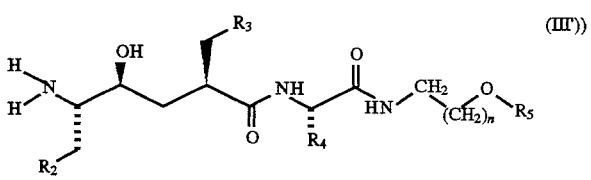  (III'))

or a reactive derivative thereof, in which n and the radicals have the meanings specified for compounds of the formula I, with free functional groups, with the exception of those participating in the reaction, being present, if necessary, in protected form in the starting materials of the formulae II and III (or III'), and eliminating protective groups which are present, or b) for preparing a compound of the formula

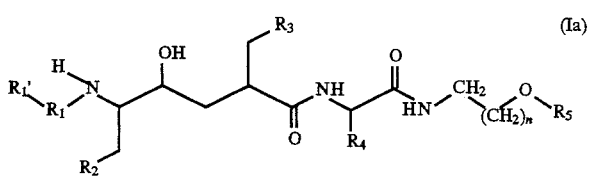  (Ia)

(in particular of the formula

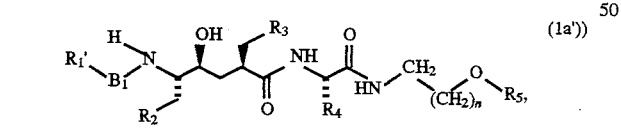  (Ia'))

in which $B_1$ is a bivalent residue of an amino acid, as defined under formula I, which is bonded via the carbonyl group (to the binding nitrogen atom shown in formula Ia') and the amino group (to $R_1'$), and $R_1'$ is one of the radicals defined for $R_1$ under formula I, apart from an unacylated or N-acylated amino acid residue as defined under formula I, so that $B_1$ and $R_1'$, together, are a residue, which is bonded via its carbonyl group, of a N-acylated amino acid, as defined for $R_1$ under formula I, and n and the remaining radicals have the meanings specified for compounds of the formula I, condensing a carboxylic acid of the formula

  (IV)

or a reactive acid derivative thereof, in which $R_1'$ can be a radical as defined for $R_1$ in compounds of the formula I apart from a residue of an unacylated or N-acylated amino acid which is bonded via its carbonyl group, with an amino compound of the formula

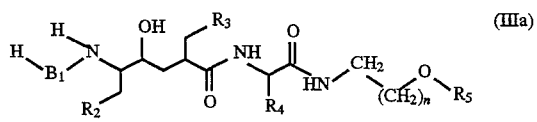  (IIIa)

(in particular of the formula

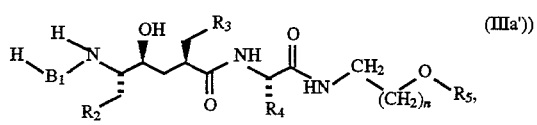  (IIIa'))

or a reactive derivative thereof, in which $B_1$ has the meanings specified immediately above and n and the remaining radicals have the meanings specified for compounds of the formula I, with free functional groups, with the exception of those participating in the reaction, being present, if necessary, in protected form in the starting materials of the formulae IIIa (or IIIa') and IV, and protective groups which are present being eliminated, or c) condensing a carboxylic acid of the formula

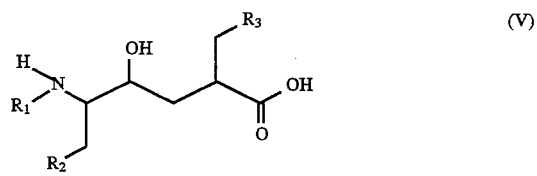  (V)

(in particular of the formula

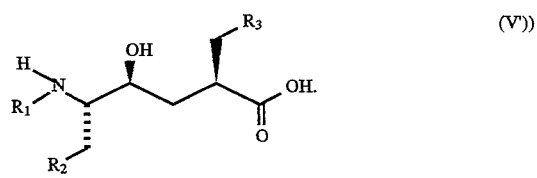  (V'))

or a reactive derivative thereof, in which the radicals have the meanings specified for compounds of the formula I, with an amino compound of the formula

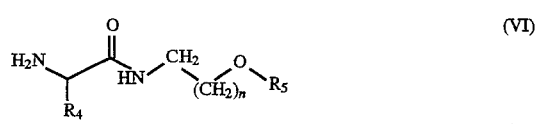  (VI)

(in particular of the formula

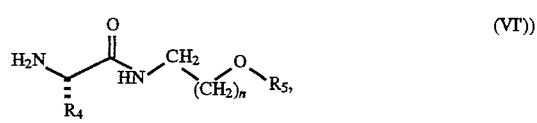  (VI'))

or a reactive derivative thereof, in which n and the radicals have the meanings specified for compounds of the formula I, with free functional groups, with the exception of those participating in the reaction, being present, if necessary, in protected form in the starting materials of the formulae V (or V') and VI (or VI'), and protective groups which are present being eliminated, or d) condensing a carboxylic acid of the formula

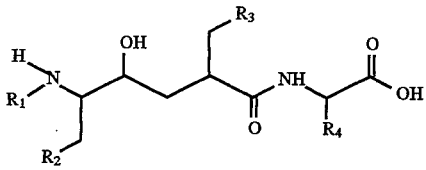     (VII)

(in particular of the formula

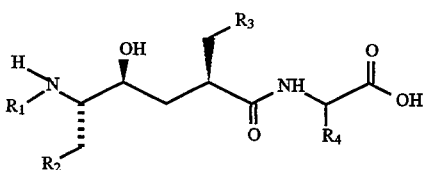     (VII'))

or a reactive derivative thereof, in which the radicals have the meanings specified for compounds of the formula I, with an amino compound of the formula

     (VIII)

or a reactive derivative thereof, in which n and $R_5$ have the meanings specified for compounds of the formula I, with free functional groups, with the exception of those participating in the reaction, being present, if required, in protected form in the starting materials of the formulae VII (or VII') and VIII, and protective groups which are present being eliminated if desired, or e) either (i) etherifying a hydroxy compound of the formula

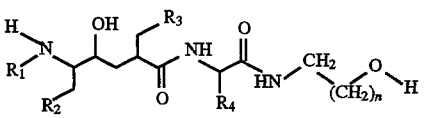     (IX)

(in particular of the formula

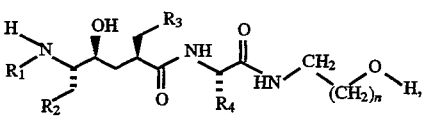     (IX'))

or its alcoholate salt, in which n and the radicals have the meanings specified for compounds of the formula I, with a compound of the formula

—$R_6$     (X), in which $R_6$ has the meanings specified for compounds of the formula I and $W_1$ is a leaving group, or (ii) etherifying a reactive derivative of the hydroxy compound of the formula IX (or IX') with a compound of the formula HO—$R_6$     (Xa), or its alcoholate salt, in which $R_6$ is defined as immediately above, with free functional groups, with the exception of those participating in the reaction, being present, if necessary, in protected form in the starting materials of the formulae IX (or IX'), X and Xa, and protective groups which are present being eliminated, or f) eliminating protective groups which are present in a compound of the formula I (in particular I'), in which the substituents are as defined above, with the proviso that in the compound of the formula I concerned at least one functional group is protected by protective groups, with it being possible, in the specified process steps a) to f), if not already specifically mentioned, for starting materials also to be employed in the form of salts, provided salt-forming groups are present, and/or, if desired, a compound of the formula I (or I'), which is obtained by one of the abovementioned processes a) to f) and which has at least one salt-forming group, into its salt, and/or converting an obtainable salt into the free compound or into another salt, and/or resolving isomeric mixtures, which may be obtainable, of compounds of the formula I (or I'), and/or transforming a novel compound of the formula I (or I') into another novel compound of the formula I (or I').

The above-defined processes are described in more detail below:

In the description of the respective process steps, the radicals $R_1$, $R_2$, $R_3$, $R_4$ and $R_5$, and n have, both above and below, the meanings specified for compounds of the formula I, unless otherwise indicated.

In each case, the preparation of compounds of the formula

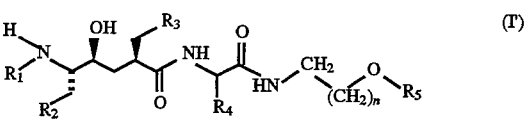     (I')

in which n and the radicals have the meanings specified for compounds of the formula I, is preferred when preparing compounds of the formula I.

In the respective processes, the compounds of the apostrophe-labelled formulae I', Ia', III', IIIa', V', VI', VII' and IX', having the stereospecificity indicated, are particularly preferred as compared with the corresponding compounds without an indicated stereospecificity and with the formulae I, Ia, III, IIIa, V, VI, VII and IX; the corresponding compound mixtures, in which the carbon atoms (in the given sequence C(5), C(2) and C(4)) carrying the radical $R_2$—$CH_2$—, the radical $R_3$—$CH_2$— and the OH located between them are in the (2R,4S,5S) configuration and the (2S,4R,5R) configuration and are in each case less preferred than the compounds labelled with an apostrophe but more strongly preferred than the corresponding compounds without any indicated stereospecificity.

In that which follows, preferably the corresponding compound mixtures having the (2R,4S,5S) configuration and the (2S,4R,5R) configuration or, in particular the compounds of the formulae which in each case correspond and which are labelled with an apostrophe can in each case be employed in place of the compounds of the formulae I, Ia, III, IIIa, V, VI, VII and IX, provided this is chemically meaningful; this also applies to the section on additional process measures and starting materials.

Process a) (preparation of an amide bond)

In starting materials of the formulae II and III, functional groups, with the exception of the groups which are to take part in the reaction or do not react under the reaction conditions, are, independently of each other, protected by protective groups.

Protective groups for functional groups in starting materials whose reaction is to be avoided, in particular carboxyl, amino, hydroxyl and mercapto groups, include, in particular, those protective groups (conventional protecting groups) which are customarily used in the synthesis of peptide compounds or else of cephalosporins and penicillins, and also nucleic acid derivatives and sugars. These protective groups can already be present in the precursors and are intended to protect the functional groups concerned against unwanted side reactions such as acylations, etherifications, esterifications, oxidations, solvolysis, etc. In certain cases, the protective groups can, in addition to this, have the effect of making the course of reactions selective, for example stereoselective. It is characteristic of protective groups that they are easily detachable, i.e. without undesirable side reactions, for example solvolytically, reductively, photolytically or else enzymically, for example under physiological conditions as well, and that they are not present in the end products. Compounds of the formula I which possess protected functional groups, whose protective groups are detachable under physiological conditions, can have a higher degree of metabolic stability, or pharmacodynamic properties which are otherwise improved, as compared with the corresponding compounds having free functional groups.

The protection of functional groups by such protective groups, the protective groups themselves, and also the reactions for eliminating them, are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides"; Volume 3 (E. Gross and J. Meienhofer, editors), Academic Press, London and New York 1981, in "Methoden der organischen Chemie" (Methods of Organic Chemistry), Houben Weyl, 4th Edition, Volume 15/I, Georg Thieme Verlag, Stuttgart 1974, in H.-D. Jakubke and H. Jescheit, "Aminosäuren, Peptide, Proteine" (Amino Acids, Peptides and Proteins), Verlag Chemie, Weinheim, Deerfield Beach and Basel 1982, and in Joehen Lehmann, "Chemie der Kohlenhydrate: Monosaccharide und Derivate" (Chemistry of the Carbohydrates: Monosaccharides and Derivatives), Georg Thieme Verlag, Stuttgart 1974.

A carboxyl group is, for example, protected as an ester group which can be selectively cleaved under mild conditions. A carboxyl group which is protected in esterified form is primarily esterified with a lower alkyl group which is preferably branched in the 1 position of the lower alkyl group or is substituted by suitable substituents in the 1 or 2 position of the lower alkyl group.

A protected carboxyl group which is esterified with a lower alkyl group is, for example, methoxycarbonyl or ethoxycarbonyl.

A protected carboxyl group which is esterified with a lower alkyl group which is branched in the 1 position of the lower alkyl group is, for example, tert-lower-alkoxycarbonyl, for example tert-butoxycarbonyl.

A protected carboxyl group which is esterified with a lower alkyl group which is substituted in the 1 or 2 position of the lower alkyl group by suitable substituents is, for example, 1-aryl-1-lower-alkoxycarbonyl, such as arylmethoxycarbonyl, having one or two aryl radicals, in which aryl is phenyl which is unsubstituted or is substituted once, twice or three times by, for example, lower alkyl, for example tert-lower-alkyl, such as tert-butyl, lower alkoxy, for example methoxy, hydroxyl, halogen, for example chlorine, and/or nitro, for example benzyloxycarbonyl, benzyloxycarbonyl which is substituted by the said substituents, for example 4-nitrobenzyloxycarbonyl or 4-methoxybenzyloxycarbonyl, diphenylmethoxycarbonyl or diphenylmethoxycarbonyl which is substituted by the said substituents, for example di-(4-methoxyphenyl) methoxycarbonyl, and, in addition, carboxyl which is esterified with a lower alkyl group, where the lower alkyl group is substituted in the 1 or 2 position by suitable substituents, such as 1-lower-alkoxyl-lower-alkoxycarbonyl, for example methoxymethoxycarbonyl, 1-methoxyethoxycarbonyl or 1-ethoxyethoxycarbonyl, 1-lower-alkylthio-lower-alkoxycarbonyl, for example 1-methylthiomethoxycarbonyl or 1-ethylthioethoxycarbonyl, aroylmethoxycarbonyl, in which the aroyl group is benzoyl which is unsubstituted or substituted, for example, by halogen, such as bromine, for example phenacyloxycarbonyl, 2-halo-lower-alkoxycarbonyl, for example 2,2,2-trichloroethoxycarbonyl, 2-bromoethoxycarbonyl or 2-iodethoxycarbonyl, and also 2-(trisubstituted silyl)-lower-alkoxycarbonyl, in which the substituents, independently of each other, are in each case an aliphatic, araliphatic, cycloaliphatic or aromatic hydrocarbon radical which is unsubstituted or substituted, for example, by lower alkyl, lower alkoxy, aryl, halogen and/or nitro, for example lower alkyl which is unsubstituted or substituted as above, pheny-lower alkyl, cycloalkyl or phenyl, for example 2-tri-lower-alkylsilyl-lower-alkoxycarbonyl, such as 2-tri-lower-alkylsilylethoxycarbonyl, for example 2-trimethylsilylethoxycarbonyl or 2-(di-n-butylmethylsilyl) ethoxycarbonyl, or 2-triarylsilylethoxycarbonyl, such as triphenylsilylethoxycarbonyl.

A carboxyl group can also be protected as an organic silyloxycarbonyl group. An organic silyloxycarbonyl group is, for example, a tri-lower-alkylsilyloxycarbonyl group, for example trimethylsilyloxycarbonyl. The silicon atom of the silyloxycarbonyl group can also be substituted by two lower alkyl, for example methyl, groups, and an amino or carboxyl group of a second molecule of the formula I. Compounds possessing such protective groups can be prepared, for example, using corresponding tri-lower-alkylhalosilanes, such as tert-butyldimethylchlorosilane, as silylating agents.

A carboxyl group is also protected in the form of an internal ester with a hydroxyl group which is present in the molecule at a suitable distance, for example in the γ position with regard to the carboxyl group, i.e. in the form of a lactone, preferably a γ-lactone.

A protected carboxyl group is preferably tert-lower-alkoxycarbonyl, for example tert-butoxycarbonyl, benzyloxycarbonyl, 4-nitrobenzyloxycarbonyl, 9-fluorenylmethoxycarbonyl or diphenylmethoxycarbonyl, or a protected carboxyl group in the form of a lactone, in particular a γ-lactone.

A protected amino group is protected by an amino protecting group, for example in the form of an acylamino, arylmethylamino, etherified mercaptoamino, 2-acyl-lower-alk-1-enylamino or silylamino group, or as an azido group.

In an acylamino group, acyl is, for example, the acyl radical of an organic carboxylic acid having, for example, up to 18 carbon atoms, in particular of a lower-alkanecarboxylic acid which is unsubstituted or substituted, for example, by halogen or aryl, or of benzoic acid which is unsubstituted or substituted, for example, by halogen, lower alkoxy or nitro, or, preferably, of a carbonic acid semiester. Such acyl groups are, preferably, lower alkanoyl, such as formyl, acetyl, propionyl or pivaloyl, halo-lower-alkanoyl, for example 2-haloacetyl, such as 2-chloro-, 2-bromo-, 2-iodo-, 2,2,2-trifluoro- or 2,2,2-trichloroacetyl, benzoyl which is unsubstituted or substituted, for example, by halogen, lower alkoxy or nitro, such as benzoyl, 4-chlorobenzoyl, 4-methoxybenzoyl or 4-nitrobenzoyl, lower-alkoxycarbonyl, lower-alkoxycarbonyl which is preferably branched in the 1 position of the lower-alkyl radical or is suitably substituted in the 1 or 2 position, for example tert-lower-alkoxycarbonyl, such as tert-butoxycarbonyl, 1-aryl-lower-alkoxycarbonyl, such as arylmethoxycarbonyl, having one, two or three aryl radicals which are phenyl which is unsubstituted or substituted once or more than once by, for example, lower alkyl, in particular tert-lower-alkyl, such as tert-butyl, lower alkoxy, such as methoxy, hydroxyl, halogen, such as chlorine, and/or nitro, for example benzyloxycarbonyl, 4-nitrobenzyloxycarbonyl, diphenylmethoxycarbonyl, 9-fluorenylmethoxycarbonyl or di-(4-methoxyphenyl)methoxycarbonyl, aroylmethoxycarbonyl, in which the aroyl group is benzoyl which is unsubstituted or preferably substituted, for example, by halogen, such as bromine, for example phenacyloxycarbonyl, 2-halo-lower-alkoxycarbonyl, for example 2,2,2-trichloroethoxycarbonyl, 2-bromoethoxycarbonyl or 2-iodoethoxycarbonyl, 2-(tri-substituted silyl)-lower-alkoxycarbonyl, for example 2-tri-lower-alkylsilyl-lower-alkoxycarbonyl such as 2-trimethylsilylethoxycarbonyl or 2-(di-n-butylmethylsilyl)ethoxycarbonyl, or triarylsilyl-lower-alkoxycarbonyl, for example 2-triphenylsilylethoxycarbonyl.

In an arylmethylamino group, for example a mono-, di- or, in particular, tri-arylmethylamino group, the aryl radicals are, in particular, phenyl radicals which are unsubstituted or substituted. Examples of such groups are benzyl-, diphenylmethyl- or, in particular, trityl-amino.

In an etherified mercaptoamino group, the mercapto group is primarily present as substituted arylthio or aryl-lower-alkylthio in which aryl is, for example, phenyl which is unsubstituted or substituted, for example, by lower alkyl, such as methyl or tert-butyl, lower alkoxy, such as methoxy, halogen, such as chlorine, and/or nitro, for example 4-nitrophenylthio.

In a 2-acyl-lower-alk-1-enyl radical which can be used as an amino protective group, acyl is, for example, the corresponding radical of a lower-alkanecarboxylic acid, of a benzoic acid which is unsubstituted or substituted, for example, by lower alkyl, such as methyl or tert-butyl, lower alkoxy, such as methoxy, halogen, such as chlorine, and/or nitro, or, in particular, of a carbonic acid semiester, such as a carbonic acid lower-alkyl semiester. Corresponding protective groups are, primarily, 1-lower-alkanoyl-lower-alk-1-en-2-yl, for example 1-lower-alkanoyl-prop-1-en-2-yl, such as 1-acetyl-prop-1-en-2-yl, or lower-alkoxycarbonyl-lower-alk-1-en-2-yl, for example lower-alkoxycarbonyl-prop-1-en-2-yl, such as 1-ethoxycarbonyl-prop-1-en-2-yl.

A silylamino group is, for example, a tri-lower-alkylsilylamino group, for example trimethylsilylamino or tert-butyldimethylsilylamino. The silicon atom of the silylamino group can also only be substituted by two lower alkyl groups, for example methyl groups, and the amino group or carboxyl group of a second molecule of the formula I. Compounds having such protective groups can be prepared, for example, using the corresponding chlorosilanes, such as tert-butyldimethylchlorosilane, as silating agents.

An amino group can also be protected by conversion into the protonated form; suitable corresponding anions are primarily those of strong inorganic acids, such as of sulfuric acid, phosphoric acid or hydrohalic acids, for example the chlorine or bromine anion, or of organic sulfonic acids, such as p-toluenesulfonic acid.

Preferred amino protective groups are lower-alkoxycarbonyl, phenyl-lower-alkoxycarbonyl, fluorenyl-lower-alkoxycarbonyl, 2-lower-alkanoyl-lower-alk-1-en-2-yl or lower-alkoxycarbonyl-lower-alk-1-en-2-yl, especially tert-butoxycarbonyl or benzyloxycarbonyl.

A hydroxyl group can, for example, be protected by an acyl group, for example lower alkanoyl which is unsubstituted or substituted by halogen, such as chlorine, such as acetyl or 2,2-dichloroacetyl, or, in particular, by an acyl radical, which is specified for protected amino groups, of a carbonic acid semiester. A hydroxyl group can also be protected by tri-lower-alkylsilyl, for example trimethylsilyl, triisopropylsilyl or tert-butyldimethylsilyl, a readily detachable etherifying group, for example an alkyl group, such as tert-lower-alkyl, for example tert-butyl, an oxa- or a thia-aliphatic or -cycloaliphatic, in particular 2-oxa- or 2-thia-aliphatic or -cycloaliphatic, hydrocarbon radical, for example 1-lower-alkoxyl-lower-alkyl or 1-lower-alkylthio-lower-alkyl, such as methoxymethyl, 1-methoxymethyl, 1-ethoxymethyl, methylthiomethyl, 1-methylthioethyl or 1-ethylthioethyl, or 2-oxa- or 2-thia-cycloalkyl having 5–7 ring atoms, such as 2-tetrahydrofuryl or 2-tetrahydropyranyl, or a corresponding thia analogue, and also by 1-phenyl-lower-alkyl, such as benzyl, diphenylmethyl or trityl, with it being possible for the phenyl radicals to be substituted for example, by halogen, for example chlorine, lower alkoxy, for example methoxy, and/or nitro. A preferred hydroxyl protective group is, for example, 2,2,2-trichloroethoxycarbonyl, 4-nitrobenzyloxycarbonyl, diphenylmethoxycarbonyl, benzyl or trityl.

Two hydroxyl groups, in particular adjacent hydroxyl groups, which are present in a molecule, or an adjacent hydroxyl group and amino group, can, for example, be protected by bivalent protective groups, such as a methylene group which is preferably substituted, for example by one or two lower alkyl radicals or oxo, for example by unsubstituted or substituted alkylidene, for example lower alkylidene, such as isopropylidene, cycloalkylidene, such as cyclohexylidene, a carbonyl group or benzylidene.

A hydroxyl group which is located adjacent to a carboxyl group can be protected by the formation of an internal ester (lactone), in particular of a γ-lactone.

Preferably, a protected hydroxyl group is protected by tri-lower-alkylsilyl or as a lactone, in particular by tert-butyldimethylsilyl or as a γ-lactone.

A mercapto group, for example in cysteine, can be protected, in particular, by S-alkylation with unsubstituted or substituted alkyl radicals, silylation, thioacetal formation, S-acylation or by the formation of asymmetric disulfide groups. Preferred mercapto protective groups are, for example, benzyl which is unsubstituted or substituted in the phenyl radical, for example by methoxy or nitro, such as 4-methoxybenzyl, diphenylmethyl which is unsubstituted or substituted in the phenyl radical, for example by methoxy, such as di-(4-methoxyphenyl)methyl, Triphenylmethyl, Pyridyldiphenylmethyl, trimethylsilyl, benzylthiomethyl, tetrahydropyranyl, acylaminomethyl, such as acetamidomethyl, iso-butyrylacetamidomethyl or 2-chloroacetamidomethyl, benzoyl, benzyloxycarbonyl or alkyl-, in particular lower-alkylaminocarbonyl, such as ethylaminocarbonyl, and also lower-alkylthio, such as S-ethylthio or S-tert-butylthio, or S-sulfo.

Within the meaning of this application, a polymeric support, as is suitable, for example, for the Merrifield synthesis, and which is bound in an easily detachable manner to the functional group to be protected, for example a carboxyl group, is also expressly understood to be a protective group, for example a carboxyl protective group. A suitable polymeric support of this nature is, in particular, a polystyrene resin which is weakly cross-connected by copolymerization with divinylbenzene and which carries suitable bridge members for the reversible binding.

The acids of the formula II are carboxylic acids or sulfonic acids and either have a free carboxylic group or free sulfo group or are present as a reactive derivative thereof, for example as an activated ester which is derived from the free carboxy or sulfo compound, as a reactive anhydride, or, in addition, as a reactive cyclic amide. The reactive derivatives can also be formed in situ.

Activated esters of compounds of the formula II having a carboxyl group are, in particular, esters which are unsaturated at the linking carbon atom of the esterifying radical, for example of the vinyl ester type, such as vinyl ester (obtainable, for example, by transesterifying a corresponding ester with vinyl acetate; method of the activated vinyl ester), carbamoyl esters (obtainable, for example, by treating the corresponding acid with an isoxazolium reagent; 1,2-oxazolium method or Woodward method), or 1-lower-alkoxyvinyl ester (obtainable, for example, by treating the corresponding acid with a lower-alkoxyacetylene; ethoxyacetylene method), or esters of amidino type, such as N,N'-disubstituted amidinoesters (obtainable, for example, by treating the corresponding acid with a suitable N,N'-disubstituted carbodiimide, for example N,N'-dicyclohexylcarbodiimide; carbodiimide method), or N,N-disubstituted amidinoesters (obtainable, for example, by treating the corresponding acid with a N,N-disubstituted cyanamide; cyanamide method), suitable aryl esters, in particular phenyl esters which are substituted by electron-attracting substituents (obtainable, for example, by treating the corresponding acids with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensing agent, such as N,N'-dicyclohexylcarbodiimide; method of the activated aryl esters), cyanomethyl esters (obtainable, for example, by treating the corresponding acid with chloroacetonitrile in the presence of a base; cyanomethyl ester method), thioesters, in particular phenylthioesters, which are unsubstituted or substituted, for example, by nitro (obtainable, for example, by treating the corresponding acid with thiophenols which are unsubstituted or substituted, for example, by nitro, inter alia using the anhydride method or carbodiimide method; method of the activated thiol esters), or, in particular, amino esters or amido esters (obtainable, for example, by treating the corresponding acid with a N-hydroxyamino compound or N-hydroxyamido compound, for example N-hydroxy-succinimide, N-hydroxypiperidine, N-hydroxyphthalimide, N-hydroxy-5-norbornene-2,3-dicarboximide, 1-hydroxybenzotriazole or 3-hydroxy-3,4-dihydro-1,2,3-benzotriazin-4-one, for example in accordance with the anhydride method or carbodiimide method; method of the activated N-hydroxy esters). Internal esters, for example γ-lactones, can also be employed.

Anhydrides of acids can be symmetrical or, preferably, mixed anhydrides of these acids, for example anhydrides with inorganic acids, such as acid halides, in particular acid chlorides (obtainable, for example, by treating the corresponding acid with thionyl chloride, phosphorus pentachloride or oxalyl chloride; acid chloride method), azides (obtainable, for example, from a corresponding acid ester via the corresponding hydrazide and its treatment with nitrous acid; azide method), anhydrides with carbonic acid semiesters, for example carbonic acid lower-alkyl semiesters (obtainable, for example, by treating the corresponding acid with lower-alkyl chloroformates, for example isobutyl chloroformate, or with a 1-lower-alkoxycarbonyl-2-lower-alkoxy-1,2-dihydroquinoline; method of mixed O-alkylcarbonic acid anhydrides) or trichloromethyl carbonates (obtainable, for example, by treating the corresponding acid with bis(trichloromethyl)carbonate in ether/pyridine); anhydrides with dihalogenated, in particular dichlorinated, phosphoric acid (obtainable, for example, by treating the corresponding acid with phosphorus oxychloride; phosphorus oxychloride method), anhydrides with other phosphoric acid derivatives (for example those which can be obtained with phenyl N-phenylphosphoramidochloridate or by reaction of alkylphosphoric acid amides in the presence of sulfonic anhydrides and/or racemization-lowering additives, such as N-hydroxybenzotriazole, or in the presence of diethyl cyanophosphonates) or with phosphoric acid derivatives, or anhydrides with organic acids, such as mixed anhydrides with organic carboxylic acids (obtainable, for example, by treating the corresponding acid with a lower-alkane- or phenyl-lower-alkanecarbonyl halide which is unsubstituted or substituted, for example phenyl acetyl chloride, pivaloyl chloride or trifluoroacetyl chloride; method of the mixed carboxylic anhydrides) or with organic sulfonic acids (obtainable, for example, by treating a salt, such as an alkali metal salt, of the corresponding acid with a suitable organic sulfonyl halide, such as lower-alkane- or aryl-, for example methane- or p-toluene-sulfonyl chloride; method of the mixed sulfonic anhydrides) and also symmetrical anhydrides (obtainable, for example, by condensing the corresponding acid in the presence of a carbodiimide or of 1-diethylaminopropyne; method of the symmetrical anhydrides).

Suitable cyclic amides are, in particular, amides with five-membered diazacycles of aromatic character, such as amides with imidazoles, for example imidazole (obtainable, for example, by treating the corresponding acid with N,N'-carbonyldiimidazole; imidazole method), or pyrazole, for example 3,5-dimethylpyrazole (obtainable, for example, via the acid hydrazide by treating with acetylacetone; pyrazolide method).

As mentioned, derivatives of carboxylic acids which are used as acylating agents can also be formed in situ. Thus, N,N'-disubstituted amidinoesters can be formed in situ by causing the mixture of the starting material of the formula III and the acid of the formula II used as acylating agent, in the presence of a suitable N,N'-disubstituted carbodiimide, for example N,N'-dicyclohexylcarbodiimide, to react, for example in the presence of a suitable base, such as triethylamine, and/or a racemization-lowering additive, such as N-hydroxybenzotriazole. In addition, aminoesters or amidoesters of the acids used as acylating agents can be formed in the presence of the starting material of the formula III which is to be acylated by reacting the mixture of the corresponding acid and amino starting materials in the presence of a N,N'-disubstituted carbodiimide, for example N,N'-dicyclohexylcarbodiimide, and a N-hydroxyamine or N-hydroxyamide, for example N-hydroxysuccinimide, in the presence or absence of a suitable base, for example 4-dimethylaminopyridine. In addition, activation can be achieved in situ by reacting with N,N,N',N'-tetraalkyluronium compounds, such as O-benzotriazol-1-yl-N,N,N',N'-tetramethyluronium hexafluorophosphate (preferably in the presence of a tertiary nitrogen base, in particular N-methylmorpholine). Phosphoric anhydrides of the carboxylic acids of the formula II can also be prepared in situ by reacting an alkylphosphoric acid amide, such as hexamethylphosphoric triamide, in the presence of a sulfonic anhydride, such as 4-toluenesulfonic anhydride, with a salt, such as a tetrafluoroborate, for example sodium tetrafluoroborate, or with another derivative of hexamethylphosphoric triamide, such as benzotriazol-1-yloxytris (dimethylamino)phosphonium hexafluoride, preferably in the presence of a racemization-lowering additive, such as N-hydroxybenzotriazole, and with or without a tertiary nitrogen base, such as N-methylmorpholine. It is also possible to carry out the reaction with di-lower-alkyl cyanophosphonates, such as diethyl cyanophosphonate, in the presence of a tertiary nitrogen base, such as triethylamine. Finally, chlorocarbonic acid derivatives of the carboxylic acids of the formula II can be prepared directly in situ by the reaction of a corresponding alcohol with phosgene or an analogue thereof, such as triphosgene (=bis (trichloromethyl)carbonate) in the presence or absence of a tertiary nitrogen base, such as triethylamine, and subsequently reacted with a compound of the formula III.

The amino group of compounds of the formula III, which participates in the reaction, preferably carries at least one reactive hydrogen atom, in particular when the carboxyl group reacting with it is present in reactive form; however, it can itself also be derivatized, for example by reaction with a phosphite, such as diethyl chlorophosphite, 1,2-phenylene chlorophosphite, ethyl dichlorophosphite, ethylene chlorophosphite or tetraethyl pyrophosphite. A derivative of such a compound with an amino group is also, for example, a carbamoyl halide, with the amino group participating in the reaction being substituted by halocarbonyl, for example chlorocarbonyl.

The condensation for preparing an amide bond can be carried out in a manner known per se, for example as described in standard works such as "Houben-Weyl, Methoden der organischen Chemie" (Methods of Organic Chemistry), 4th Edition, Volume 15/II (1974), Volume IX (1955) Volume E 11 (1985), Georg Thieme Verlag, Stuttgart, "The Peptides" (E. Gross and J. Meienhofer, editors), Volumes 1 and 2, Academic Press, London and New York, 1979/1980, or M. Bodansky, "Principles of Peptide Synthesis", Springer-Verlag, Berlin 1984.

The condensation of a free carboxylic acid with the corresponding amine can preferably be carried out in the presence of one of the customary condensing agents. Examples of customary condensing agents are carbodiimides, for example diethyl-, dipropyl-, N-ethyl-N'-(3-dimethylaminopropyl)carbodiimide or, in particular, dicyclohexylcarbodiimide, and, in addition, suitable carbonyl compounds, for example carbonylimidazole, 1,2-oxazolium compounds, for example 2-ethyl-5-phenyl-1,2-oxazolium-3'-sulfonate and 2-tert-butyl-5-methylisoxazolium perchlorate, or a suitable acylamino compound, for example 2-ethoxy-1-ethoxycarbonyl-1,2-dihydroquinoline, N,N,N',N'-tetraalkyluronium compounds, such as O-benzotriazol-1-yl-N,N,N',N'-tetramethyluronium hexafluorophosphate, and, in addition, activated phosphoric acid derivatives, for example diphenylphosphoryl azide, diethylphosphoryl cyanide (=diethyl cyanophosphonate), phenyl-N-phenylphosphoroamidochloridate, bis(2-oxo-3-oxazolidinyl)phosphinic chloride or 1-benzotriazolyloxytris (dimethylamino)phosphonium hexafluorophosphate.

If necessary or desired, an organic base is added, preferably a tri-substituted nitrogen base, for example a tri-lower-alkylamine, for example with bulky radicals, for example ethyl diisopropylamine, or with unbranched radicals, such as, in particular, triethylamine, and/or a heterocyclic base, for example pyridine, 4-dimethylaminopyridine or, preferably N-methylmorpholine. The base can also be bonded to a polymeric support, for example polystyrene, for example as a "polyhünig base" (=diisopropylaminomethylpolystyrene).

Racemization-lowering reagents, such as N-hydroxybenzotriazole, can also be added, possibly also in combination with organic bases, as defined immediately above.

The condensation of activated esters, reactive anhydrides or reactive cyclic amides with the corresponding amines is customarily carried out in the presence of an organic base, for example simple tri-lower-alkylamines, for example triethylamine or tributylamine, polyhünig base or one of the abovementioned organic bases. It is possible, if desired, additionally to use a condensing agent as well, as described for free carboxylic acids.

The condensation of acid anhydrides with amines can, for example, also be effected in the presence of inorganic carbonates, for example ammonium or alkali metal carbonates or hydrogen carbonates, such as sodium or potassium carbonate or hydrogen carbonate (customarily together with a sulfate).

Carbonyl chlorides or 4-nitrophenyl carbonates, and also the chlorocarbonic acid derivatives derived from the acid of the formula II, are preferably condensed with the corresponding amines in the presence of an organic amine, for example the abovementioned tri-lower-alkylamines or heterocyclic bases, in the presence or absence of a hydrogen sulfate.

The condensation is preferably carried out in inert, aprotic, preferably anhydrous, solvents or solvent mixtures, for example in a carboxamide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, if desired at decreased or increased temperature, for example in a temperature range of from about −40° C. up to about +1 00° C., preferably from about −20° C. to about +50° C., and without inert gas (=protective gas) or under an inert gas, for example nitrogen or argon, atmosphere.

Aqueous, for example alcoholic, solvents or solvent mixtures, for example ethanol, or aromatic solvents, for example benzene or toluene, are also possible. A lower-alkanone, such as acetone, can also, if desired, be added in the presence of alkali metal hydroxides as bases.

The condensation can also be effected in accordance with the technique known as solid-phase synthesis which goes back to R. Merrifield and is described, for example, in Angew. Chem. 97, 801–812 (1985), Naturwissenschaften 71, 252–258 (1984) or in R. A. Houghten, Proc. Natl. Acad. Sci. U.S.A. 82, 5131–5135 (1985).

Many of the reaction types listed above for carboxylic acids of the formula II and analogous reactive sulfonic acid derivatives, also in the case of compounds of the formula II having a sulfo group to be linked, can be used in an analogous manner for preparing sulfonamide compounds of the formula I, in particular I'.

Thus, activated sulfonic esters, for example, can be employed, for example the corresponding aryl esters which are substituted, in particular, by nitro groups, such as 4-nitrophenyl esters, with it being possible also to employ the amine component of the formula III as an alkali metal amide, for example alkali metal arylamide, such as sodium anilineamide, or as an alkali metal salt of nitrogen-containing heterocycles, for example potassium pyrrolide.

Reactive anhydrides can also be employed, such as, for example, the corresponding symmetrical (which can be prepared, for example, by reacting the alkanesulfonic silver salts with alkanesulfonyl chlorides) or, preferably, asymmetrical acid anhydrides, for example anhydrides with inorganic acids, such as sulfonyl halides, in particular sulfonyl chlorides (obtainable, for example, by teaching the corresponding sulfonic acid of the formula II with inorganic acid chlorides, for example thionyl chloride or phosphorus pentachloride), with organic carboxylic acids (obtainable, for example, by treating a sulfonyl halide with the salt of a carboxylic acid, such as an alkali metal salt, in an analogous manner to the abovementioned method of mixed carboxylic anhydrides), or azides (obtainable, for example, from a corresponding sulfonyl chloride and sodium azide or via the corresponding hydrazide and its treatment with nitrous acid in analogy with the abovementioned azide method).

The release of functional groups which are protected by protective groups in the resulting compounds of the formula I having protected functions is effected using one or more of the methods specified under process f).

Process b) (preparation of an amide bond)

In starting materials of the formulae IIIa and IV, functional groups, with the exception of the groups which are to participate in the reaction or which do not react under the reaction conditions, are protected, independently of each other, by protective groups.

The protective groups, the free carboxylic acids and their reactive derivatives, the free amines and their reactive derivatives and the processes used for the condensation are completely analogous to those described under process a) for the preparation of an amide bond proceeding from compounds of the formulae II and III, if the carboxylic acids of the formula IV are employed there in place of those of the formula II and the amino compounds of the formula IIIa are employed in place of those of the formula III.

The release of functional groups which are protected by protective groups in the resulting compounds of the formula I having protected functions is effected using one or more of the methods specified under process f).

Process c) (preparation of an amide bond)

In starting materials of the formulae V and VI, functional groups, with the exception of the groups which are to participate in the reaction or which do not react under the reaction conditions, are protected, independently of each other, by protective groups.

The protective groups, the free carboxylic acids and their reactive derivatives, the free amines and their reactive derivatives and the processes used for the condensation are completely analogous to those described under process a) for the preparation of an amide bond proceeding from compounds of the formulae II and III, if the carboxylic acids of the formula V are employed there in place of those of the formula II and the amino compounds of the formula VI are employed in place of those of the formula III.

In addition to the reactive derivatives in analogy with process a), a reactive derivative of a carboxylic acid of the formula V can also be the corresponding γ-lactone of the formula XXA

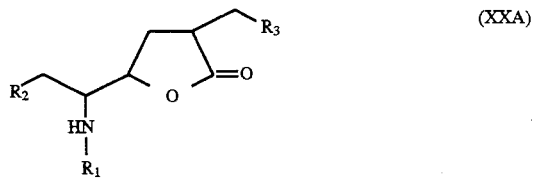

(in particular of the formula XXA')

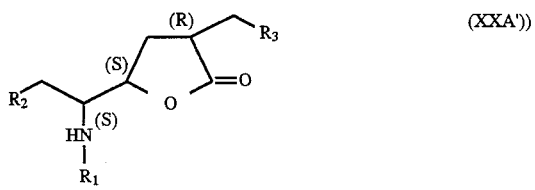

in which the radicals $R_1$, $R_2$ and $R_3$ have the meanings specified for compounds of the formula I. The reaction then proceeds directly to yield the end product in the presence of an organic acid which is, if anything, mild, for example a substituted or (preferably) unsubstituted lower-alkanoic acid, such as trihaloacetic acid, for example trichloroacetic acid, or, in particular, acetic acid, or other organic acids of similar acidity, for example 2-hydroxypyridine, at preferred temperatures of between 10° and 100° C., in particular of between 60° and 100° C., in the presence or, preferably, in the absence of solvents, preferably while excluding the atmosphere, for example in bomb tubes. Preferably, the compound of the formula VI, in particular VI', is then employed in a slight excess, for example in from 1.01-fold to 4-fold molar excess, in relation to the compound of the formula XXA, in particular XXA', with the, if anything, mild organic acid on the other hand preferably being employed in slight excess, in equimolar quantity or in slight deficit in relation to the compound of the formula VI, in particular VI', for example in a 0.3-fold to 2-fold molar ratio.

The release of functional groups which are protected by protective groups in the resulting compounds of the formula I having protected functions is effected using one or more of the methods specified under process f).

Process d) (preparation of an amide bond)

In starting materials of the formulae VII and VIII, functional groups, with the exception of the groups which are to participate in the reaction or which do not react under the reaction conditions, are protected, independently of each other, by protective groups.

The protective groups, the free carboxylic acids and their reactive derivatives, the free amines and their reactive derivatives and the processes used for the condensation are completely analogous to those described under process a) for the preparation of an amide bond proceeding from compounds of the formulae II and III, if the carboxylic acids of the formula VII are employed there in place of those of the formula II and the amino compounds of the formula VIII are employed in place of those of the formula III.

The release of functional groups which are protected by protective groups in the resulting compounds of the formula I having protected functions is effected using one or more of the methods specified under process f).

Process e) (preparation of an ether bond-nucleophilic substitution)

In starting materials of the formulae IX, X and Xa, functional groups, with the exception of the groups which are to parreaction an the reaction or which do not react under the reaction conditions, are protected, independently of each other, by protective groups.

The protective groups, and the methods for introducing them, correspond to those specified under process a).

In the nucleophilic substitution, ether, in case (i), the compound of the formula IX has a free hydroxyl group which is to be etherified and $W_1$ in the compound of the formula X is a leaving group, or, in case (ii), the compound of the formula IX is in the form of a reactive derivative and is reacted with the hydroxyl group which is to be etherified.

In this context, the hydroxyl group, which is to be reacted, of the respective hydroxyl compound is converted into its alcoholate salt either in situ or in a previous, independent reaction. In an alcoholate salt, the hydroxyl group (—OH) is present in anionic form (as —O$^\ominus$), with a suitable counterion principally being a metal cation, such as an alkali metal cation, for example K$^\oplus$, Cs$^\oplus$ or, in particular, Na$^{61}$.

A leaving group W$_1$ is, in particular, a nucleofugic leaving group selected from hydroxyl which is esterified with a strong inorganic or organic acid, such as hydroxyl which is esterified with a mineral acid, for example hydrophilic acid, such as hydrochloric, hydrobromic or hydriodic acid, or with a strong organic sulfonic acid such as a lower-alkanesulfonic acid which is unsubstituted or substituted, for example, by halogen, such as fluorine, or an aromatic sulfonic acid, for example a benzenesulfonic acid which is unsubstituted or substituted by lower alkyl, such as methyl, halogen, such as bromine, and/or nitro, for example a methanesulfonic, p-bromotoluenesulfonic or p-toluenesulfonic acid, or hydroxyl which is esterified with hydriodic acid. It is also possible to prepare the compound concerned in situ by substituting another corresponding radical W$_1$, for example of Cl, by another radical W$_1$, for example I (preferably using an alkali metal iodide, such as NaI) and subsequently continuing with the reaction in the resulting reaction mixture.

In a reactive derivative of a compound of the formula IX, a leaving group, such as described immediately above for W$_1$, is present in place of the hydroxyl group.

The etherification preferably takes place in the presence of a relatively mild base, such as an alkali metal carbonate, for example sodium or potassium carbonate, of a strong base, for example a hydroxide-containing base, such as a metal hydroxide, for example an alkali metal hydroxide, such as sodium or potassium hydroxide, or, in particular, using a metal alcoholate of the respective hydroxy compound or its preparation in situ in the presence of a strong base, for example of an alkali metal hydride, such as sodium hydride, or in the presence of an alkali metal, such as sodium, in the absence or presence of suitable solvents or solvent mixtures, in particular aprotic solvents, for example of DMPU, an ether, such as diethyl ether, dioxane or tetrahydrofuran, of a carboxamide, such as dimethylformamide, or of a mixture of two or more of these solvents, at temperatures of between 0° C. and reflux temperature, in particular between 20° C. and reflux temperature, if necessary under protective gas, such as nitrogen or argon.

Depending on the reaction conditions, the substitution can proceed as a nucleophilic substitution of the first or second order.

Since a series of side reactions (for example racemization by the formation of carbanions etc.) are possible in the reaction according to process e), this process can sometimes only be carried out under very precisely controlled reaction conditions (for example careful metering-in of the base which is employed or of the respective alcoholate, etc.). Possible interfering reactions and suitable reaction conditions are immediately apparent to the person skilled in the art. In a preferred variant of the process according to the invention for preparing compounds of the formula I, process e) is excluded for this reason.

The release of functional groups which are protected by protective groups in the resulting compounds of the formula I having protected functions is effected using one or more of the methods specified under process f).

Process f) (protective group detachment)

Detachment of the protective groups which are not components of the desired end product of the formula I, for example the carboxyl, amino, hydroxyl and/or mercapto protective groups, is effected in a manner known per se, for example using solvolysis, in particular hydrolysis, alcoholysis or acidolysis, or by means of reduction, in particular hydrogenolysis, or by means of other reducing agents, and also photolysis, as desired stepwise or simultaneously, with it also being possible to use enzymic methods. Detachment of the protective groups is described, for example, in the standard works which are mentioned above in the section on "protective groups".

Thus, a protected carboxyl, for example, for example lower-alkoxycarbonyl (which is preferably branched in the 1 position), such as tert-lower-alkoxycarbonyl, lower-alkoxycarbonyl which is substituted in the 2 position by a tri-substituted silyl group or in the 1 position by lower alkoxy or lower-alkylthio, or diphenylmethoxycarbonyl which is unsubstituted or substituted, can be converted into free carboxyl by treatment with a suitable acid, such as formic acid, acetic acid, hydrochloric acid or trifluoroacetic acid, if desired while adding a nucleophilic compound, such as phenol or anisole. Benzyloxycarbonyl which is unsubstituted or substituted can, for example, be set free by means of hydrogenolysis, i.e. by treatment with hydrogen in the presence of a metallic hydrogenation catalyst, such as a palladium catalyst. In addition, suitably substituted benzyloxycarbonyl, such as 4-nitrobenzyloxycarbonyl, can also be converted into free carboxyl by reduction, for example by treatment with an alkali metal dithionite, such as sodium dithionite, or with a reducing metal, for example zinc, or a reducing metal salt, such as a chromium(II) salt, for example chromium(II) chloride customarily in the presence of a hydrogen-releasing agent which, together with metal, can produce nascent hydrogen, such as an acid, primarily a suitable carboxylic acid, such as a lower-alkanecarboxylic acid which is unsubstituted or substituted, for example, by hydroxyl, for example acetic acid, formic acid, glycolic acid, diphenylglycolic acid, lactic acid, mandelic acid, 4-chloromandelic acid or tartaric acid, or an alcohol or thiol, with water preferably being added. By means of treating with a reducing metal or metal salt, as described above, 2-halo-lower-alkoxycarbonyl (if desired after converting a 2-bromo-lower-alkoxycarbonyl group into a corresponding 2-iodo-lower-alkoxycarbonyl group) or aroylmethoxycarbonyl can also be converted into free carboxyl. Aroylmethoxycarbonyl can be cleaved by treating with a nucleophilic, preferably salt-forming reagent, such as sodium thiophenoxide or sodium iodide. The carboxyl group can also be set free from 1-aryl-lower-alkoxycarbonyl, for example arylmethoxycarbonyl, such as benzyloxycarbonyl, by hydrolysing in the presence of a base such as an alkali metal hydroxide, for example sodium or potassium hydroxide. 2-(Tri-substituted silyl)-lower-alkoxycarbonyl, such as 2-tri-lower-alkylsilyl-lower-alkoxycarbonyl, can also be converted into free carboxyl by treating with a salt of hydrofluoric acid which provides the fluoride anion, such as an alkali metal fluoride, for example sodium or potassium fluoride, in the absence or presence of a macrocyclic polyether ("crown ether"), or with a fluoride of an organic quaternary base, such as tetra-lower-alkylammonium fluoride or tri-lower-alkylaryl-lower-alkylammonium fluoride, for example tetraethylammonium fluoride or tetrabutylammonium fluoride, in the presence of an aprotic, polar solvent, such as dimethyl sulfoxide, N,N-dimethylformamide or N,N-dimethylacetamide. Carboxyl which is protected as organic silyloxycarbonyl, such as tri-lower-alkylsilyloxycarbonyl, for example trimethylsilyloxycarbonyl, can be released solvolytically in a customary manner, for example by treating with water, an alcohol or acid, or, in addition, fluoride, as described above. Esterified carboxyl can also be set free enzymically, for example using esterases or suitable peptidases, for example esterified arginine or lysine, such as lysine methyl ester, using trypsin. Carboxyl which is protected as an internal ester, such as a γ-lactone, can be released by hydrolysis in the presence of a hydroxide-containing base, such as an alkaline earth metal hydroxide or, in particular, an alkali metal hydroxide, for example NaOH, KOH or LiOH, in particular LiOH, with the corresponding protected hydroxyl group being set free simultaneously.

A protected amino group is set free in a manner which is known per se and which differs depending on the nature of the protective groups, preferably using solvolysis or reduction. Lower-alkoxycarbonylamino, such as tert-butoxycarbonylamino, can be cleaved in the presence of acids, for example mineral acids, for example hydrohalic acid, such as hydrochloric acid or hydrobromic acid, in particular hydrobromic acid, or of sulfuric acid or phosphoric acid, preferably of hydrochloric acid, or of relatively strong organic acids, such as formic acid, trichloroacetic acid or trifluoroacetic acid, in polar solvents, for example water or a carboxylic acid, such as acetic acid or formic acid, halohydrocarbons, such as chlorinated lower-alkanes, for example dichloromethane or chloroform, or ethers, preferably cyclic ethers, such as dioxane, or in organic carboxylic acids which are liquid at the reaction temperature, without solvent, for example in formic acid. 2-Halo-lower-alkoxycarbonylamino (if desired, after converting a 2-bromo-lower-alkoxycarbonylamino group into a 2-iodo-lower-alkoxycarbonylamino group), aroylmethoxycarbonylamino or 4-nitrobenzyloxycarbonylamino can, for example, be cleaved by treating with a suitable reducing agent, such as zinc in the presence of a suitable carboxylic acid, such as aqueous acetic acid. Aroylmethoxycarbonylamino can also be cleaved by treating with a nucleophilic, preferably salt-forming, reagent such as sodium thiophenoxide, and 4-nitrobenzyloxycarbonylamino also by treating with an alkali metal dithionite, for example sodium dithionite. Substituted or unsubstituted diphenylmethoxycarbonylamino, tert-lower-alkoxycarbonylamino or 2-(trisubstituted silyl)-lower-alkoxycarbonylamino, such as 2-tri-lower-alkylsilyl-lower-alkoxycarbonylamino, can be cleaved by treating with a suitable acid, for example formic or trifluoroacetic acid, for example in a halogenated hydrocarbon, such as methylene chloride or chloroform (in particular, if hydroxyl which is simultaneously protected with benzyl is not to be set free), 1-aryl-lower-alkoxycarbonylamino, such as substituted or unsubstituted benzyloxycarbonylamino, can, for example, be cleaved by means of hydrogenolysis, i.e. by treating with hydrogen in the presence of a suitable hydrogenation catalyst, such as a palladium catalyst, for example bound to a support material, such as carbon, preferably in polar solvents, such as di-lower-alkyl-lower-alkanoylamides, for example dimethylformamide, ethers, such as cyclic ethers, for example dioxane, esters, such as lower-alkyl lower-alkanoates, for example ethyl acetate, or alcohols, such as methanol, ethanol or propanel, with methanol being particularly preferred, preferably, for example, at room temperature, substituted or unsubstituted triarylmethylamino or formylamino can be cleaved, for example, by treating with an acid, such as a mineral acid, for example hydrochloric acid, or an organic acid, for example formic, acetic or trifluoroacetic acid, if desired in the presence of water, and triphenylaminomethyl can be cleaved, in particular, by hydrogenolysis using a precious metal or precious metal oxide as catalyst, such as platinum, palladium or, in particular, palladium hydroxide, with the catalyst preferably being bonded to a support material, such as carbon, silica gel or aluminium oxide, in inert solvents, such as an ester, or preferably a lower-alkyl lower-alkanoate, such as ethyl acetate, at temperatures of from 20° to 80° C., in particular of from 50° to 70° C., if required under elevated pressure, for example between about 1 and 10 bar, and an amino group which is protected as silylamino can be set free, for example, by means of hydrolysis or alcoholysis. An amino group which is protected by 2-haloacetyl, for example 2-chloroacetyl, can be set free by treating with thiourea in the presence of a base, or with a thiolate salt, such as an alkali metal thiolate of the thiourea, and subsequent solvolysis, such as alcoholysis or hydrolysis, of the resulting substitution product. An amino group which is protected by 2-(trisubstituted silyl)-lower-alkoxycarbonyl, such as 2-tri-lower-alkylsilyl-lower-alkoxycarbonyl, can also be converted into the free amino group by treating with a fluoride anion-providing salt of the hydrofluoric acid, as indicated above in connection with the release of a correspondingly protected carboxyl group. Silyl, such as trimethylsilyl or tert-butyldimethylsilyl, which is bonded directly to a heteroatom, such as nitrogen, can likewise be detached with fluoride ions, preferably using a fluoride of an organic, quaternary nitrogen base, such as tetra-lower-alkylammonium fluoride or tri-lower-alkylaryl-lower-alkylammonium fluoride, for example tetraethylammonium fluoride or tetrabutylammonium fluoride, in the presence of an aprotic, polar solvent, such as dimethyl sulfoxide or N,N-dimethylacetamide, or, in particular, of an ether, such as tetrahydrofuran, at temperatures between 0° and 50° C., in particular, for example, at room temperature.

Amino which is protected in the form of an azido group is converted into free amino, for example, by means of reduction for example by means of catalytic hydrogenation with hydrogen in the presence of a hydrogenation catalyst, such as platinum oxide, palladium or Raney nickel, by means of reduction with mercapto compounds, such as dithiothreitol or mercaptoethanol, or by treating with zinc in the presence of an acid, such as acetic acid. The catalytic hydrogenation is preferably carried out in an inert solvent, such as a halogenated hydrocarbon, for example methylene chloride, or else in water or a mixture of water and an organic solvent, such as an alcohol or dioxane, at from approximately 20° C. to 25° C., or else while cooling or heating.

A hydroxyl group or mercapto group which is protected by a suitable acyl group, a tri-lower-alkylsilyl group or by substituted or unsubstituted 1-aryl(such as 1-phenyl)-lower-alkyl is set free in an analogous manner to a correspondingly protected amino group. A hydroxyl group or mercapto group which is protected by 2,2-dichloroacetyl is set free, for example, by basic hydrolysis, while a hydroxyl group or mercapto group which is protected by tert-lower-alkyl or by a 2-oxa- or 2-thia-aliphatic or -cycloaliphatic hydrocarbon radical is set free by acidolysis, for example by treating with a mineral acid or a strong carboxylic acid, for example trifluoroacetic acid. A hydroxyl group which is protected by benzyloxy is set free, for example, by means of hydrogenolysis, i.e. by treating with hydrogen in the presence of a suitable hydrogenation catalyst, such as a palladium catalyst, for example bound to a support material, such as charcoal, preferably in polar solvents, such as di-loweralkyl-lower-alkanoylamides, for example dimethylformamide, ethers, such as cyclic ethers, for example dioxane, esters, such as lower-alkylalkanoates, for example ethyl acetate, chlorinated hydrocarbons, such as dichloromethane, or alcohols, such as methanol, ethanol or propanol, with methanol being particularly preferred, or mixtures of two or more of these solvents, preferably, for example, at room temperature. Mercapto which is protected by pyridyldiphenylmethyl can, for example, be set free by mercury(II) salts at pH 2–6 or by zinc/acetic acid or electrolytic reduction, acetamidomethyl and isobutyrylamidomethyl, for example, by reaction with mercury (II) salts at pH 2–6, 2-chloroacetamidomethyl, for example, by 1-piperidinothiocarboxamide, S-ethylthio, S-tert-butylthio and S-sulfo, for example, by means of thiolysis with thiophenol, thioglycolic acid, sodium thiophenoxide or 1,4-dithiothreitol. Two hydroxyl groups, or an adjacent amino group and hydroxyl group, which are together protected by means of a bivalent protective group, preferably, for example, a methylene group which is substituted once or twice by lower alkyl, such as by lower alkylidene, for example isopropylidene, cycloalkylidene, for example cyclohexylidene, or benzylidene, can be set free by acidic solvolysis, particularly in the presence of a mineral acid or a strong organic acid. A tri-lower-alkylsilyl group is likewise detached by means of acidolysis, for example by mineral acid, preferably hydrofluoric acid, or a strong carboxylic acid. Hydroxyl can also preferably be set free from tri-lower-alkylsilyloxy by treating with a fluoride anion-providing salt of hydrofluoric acid, such as an alkali metal fluoride, for example sodium or potassium fluoride, in the absence or presence of a macrocyclic polyether ("crown ether"), or with a fluoride of an organic quaternary base, such as tetra-lower-alkylammonium fluoride or tri-lower-alkylaryl-lower-alkylammonium fluoride, for example tetraethylammonium fluoride or tetrabutylammonium fluoride, in the presence of an aprotic, polar solvent, such as dimethyl sulfoxide or N,N-dimethylacetamide. 2-Halo-lower-alkoxycarbonyl is removed by the abovementioned reducing agents, for example reducing metal, such as zinc, reducing metal salts, such as chromium(II) salts, or by sulfur compounds, for example sodium dithionite or, preferably, sodium sulfide and carbon disulfide. Esterified hydroxyl groups, for example lower-alkanoyloxy, such as acetyloxy, can also be set free with esterases, while acylated amino can, for example, be set free using suitable peptidases.

The temperature for the release of the protected functional groups are preferably between –80° C. and the boiling temperature of the reaction mixture, in particular between –80° and 110° C.; particularly preferably between –20° and 50° C., for example between 10° and 35° C., such as, for example, at room temperature, or at from 80° C. up to the boiling temperature of the reaction mixture concerned, for example at approximately 100° C.

When several protected functional groups are present, the protective groups are, if desired, selected such that more than one such group can be detached simultaneously, for example acidolytically, as by means of treating with trifluoroacetic acid, or with hydrogen and a hydrogenation catalyst, such as a palladium charcoal catalyst. Conversely, the groups can also be selected such that they cannot all be detached simultaneously but, instead, in a desired sequence, with the corresponding intermediates being obtained.

Additional process measures

In the additional process measures, which are carried out if desired, functional groups of the starting compounds which are not to participate in the reaction can be unprotected or in protected form, for example protected by one or more of the protective groups specified under process a). The protective groups can be detached, in their entirety or in part, using one of the methods specified under process f).

Salts of compounds of the formula I having at least one salt-forming group can be prepared in a manner known per se. Thus, salts of compounds of the formula I having acidic groups can be formed, for example, by treating with metal compounds, such as alkali metal salts of suitable organic carboxylic acids, for example the sodium salt of 2-ethylhexanoic acid, with inorganic alkali metal or alkaline earth metal compounds, such as the corresponding hydroxides, carbonates or hydrogen carbonates, such as sodium and potassium hydroxide, carbonate or hydrogen carbonate, with corresponding calcium compounds or with ammonia, or with a suitable organic amine, with stoichiometric quantities, or only a small excess of the salt-forming agent, preferably being used. Acid addition salts of compounds of the formula I are obtained in a customary manner, for example by treating with an acid or a suitable anion exchange reagent. Internal salts of compounds of the formula I which contain acidic and basic salt-forming groups, for example a free carboxylic group and a free amino group, can be formed, for example, by neutralizing salts, such as acid addition salts, to the isoelectric point, for example using weak bases, or by treating with ion exchangers.

Salts can be converted into the free compounds in a customary manner, metal salts and ammonium salts can be converted, for example, by treating with suitable acids or acidic ion exchangers, and acid addition salts can be converted, for example, by treating with a suitable basic agent, in particular with inorganic alkali metal or alkaline earth metal compounds, such as the corresponding hydroxides, carbonates or hydrogen-carbonates, such as sodium and potassium hydroxide, carbonate or hydrogen-carbonate, with corresponding calcium compounds or with ammonia or a suitable organic amine, with stoichiometric quantities or only a small excess of the salt-forming agent preferably being used, in suitable solvents, for example halohydrocarbons, such as dichloromethane, in the presence or absence of water, or by means of treating with basic ion exchangers.

Stereoisomeric mixtures of compounds of the formula I, that is mixtures of diastereomers and/or enantiomers, for example racemic mixtures, can be resolved into the corresponding isomers in a manner known per se using suitable separation methods. Thus, diastereomeric mixtures, for example, can be resolved into the individual diastereomers by fractional crystallization, chromatography, solvent partition or other suitable methods. Racemates can be separated from each other after converting the optical antipodes into diastereomers, for example by reacting with optically active compounds, for example optically active acids or bases, by chromatography on column materials coated with optically active compounds, or by enzymic methods, for example by the selective reaction of only one of the two enantiomers. This separation can be effected either at the level of one of the starting products or at that of the compounds of the formula I.

In a compound of the formula I, in which one of the radicals $R_1$, $R_2$ or $R_3$, or several of these radicals, are substituted by 1-phenyl-lower-alkoxy, such as benzyloxy, the 1-phenyl-lower-alkoxy radical can be detached as described under process f). The corresponding compounds of the formula I are obtained in which hydroxyl is present in place of 1-phenyl-lower-alkoxy.

In an obtainable compound of the formula I, a carboxyl group which is present in free form or in reactive form can be esterified, or an esterified carboxyl group can be converted into a free carboxyl group.

In order to esterify a carboxyl group in a compound of the formula I, the free acid, if desired, can be used, or the free acid can be converted into one of the reactive derivatives specified above under process a) and can be reacted with a corresponding alcohol, or, for the esterification, the free acid or a reactive salt, for example the caesium salt, can be reacted with a reactive derivative of an alcohol. For example, the caesium salt of a carboxylic acid can be reacted with a halide or organic sulfonic acid ester corresponding to the alcohol (with halogen or the radical of an organic sulfonic acid, such as toluenesulfonic acid, in place of the hydroxyl group). The esterification of the carboxyl group can also be effected using other customary alkylating agents, for example using diazomethane, lower-alkyl halides, sulfonic acid esters, Meerwein salts or 1-substituted 3-aryltriazenes.

In order to convert an esterified carboxyl group into the free carboxyl group, use can be made of one of the methods described above in association with the detachment of the carboxyl protective groups or, if desired, of an alkaline hydrolysis under customary conditions, such as those specified under process f), preferably in the presence of an alkali metal hydroxide, such as LiOH, in suitable solvents, such as alcohols, for example methanol or ethanol, water or mixtures thereof.

A lower-alkoxycarbonyl-lower-alkoxy group which is present as a substituent, for example of phenyl or naphthyl $R_2$ and/or $R_3$, can be converted reductively into a hydroxyl-lower-alkoxy group (in which the lower alkyl radical has at least 2 carbon atoms) by, for example, reducing with complex hydrides which selectively reduce the carbonyl ester group under suitable reaction conditions, for example using $LiBH_4$ in 1,2-dimethoxyethane at temperatures of from 0° C. up to the reflux temperature, preferably from about 15° to 30° C.

In a compound of the formula I, a free amino or imino group which is present can be acylated, for example, for introducing a lower-alkoxycarbonyl radical on the nitrogen of piperidinylcarbonyl $R_1$. The acylation is effected in analogy with the methods specified above under process a) or in analogy with one of the methods specified for protective groups.

In an obtainable compound of the formula I, in which the substituents have the said meanings and there is at least one free hydroxyl group, and additional functional groups are, if necessary, present in protected form, the free hydroxyl group, for example the hydroxyl group on the phenyl or naphthyl $R_2$ and/or phenyl or naphthyl $R_3$, can be etherified, which hydroxyl group can be etherified with the radical of a lower-alkanol, of a phenyl-lower-alkanol, of a lower-alkoxy-carbonyl-lower-alkanol, of a carbamoyl-lower-alkanol, of a pyridyl-lower-alkanol, of a cyano-lower-alkanol or of a lower-alkoxyl-lower-alkanol, with the said alcohols preferably being employed in a form in which a nucleofugic leaving group is present in place of the hydroxyl group, for example as defined for $W_1$ in compounds of the formula X.

The etherification can be carded out in analogy with the process conditions according to process e) and is preferably effected using diazomethane or lower-alkyl-, phenyl-lower-alkyl-, lower-alkoxyl-lower-alkyl-, carbamoyl-lower-alkyl-, pyridyl-lower-alkyl-, cyano-lower-alkyl- or lower-alkoxyl-lower-alkyl-halides or -sulfonic acid esters. The reaction is preferably carried out using appropriate lower-alkyl-, phenyl-lower-alkyl-, lower-alkoxyl-lower-alkyl-, carbamoyl-lower-alkyl-, pyridyl-lower-alkyl-, cyano-lower-alkyl- or lower-alkoxyl-lower-alkyl-halides, such as -iodides, -bromides or -chlorides, in the presence of bases, preferably of a hydroxyl base, in particular a basic metal hyroxide, such as sodium or potassium hydroxide, or, especially, of a metal carbonate or metal hydrogen carbonate, such as sodium, potassium or, primarily, caesium carbonate in suitable solvents or solvent mixtures, for example in N,N-di-lower-alkyl-lower-alkanoylamides, such as dimethylformamide or dimethylacetamide, ketones, such as lower-alkanones, for example acetone, or ethers, such as dioxane, or mixtures thereof, at temperatures of between −10° C. up to the reflux temperature, preferably at from 0° to 60° C., for example at from about 0° to 50° C.

In a compound of the formula I, groups which are present and which correspond to protective groups, or, in addition, suitable $R_1$ radicals, apart from hydrogen, can be detached using one of the methods specified under process f), in particular by hydrolysis, for example in the presence of bases, such as alkali metal or alkaline earth metal hydroxides, for example sodium hydroxide, or acids, such as organic acids or mineral acids, for example hydrohalic acid, such as hydrochloric acid. The hydrolysis is effected under the customary conditions, for example in aqueous solution or in anhydrous solvents, in particular in ethers, such as dioxane, at temperatures of between −50° C. and the reflux temperature of the corresponding reaction mixtures, for example between 0° C. and 50° C., preferably in the presence of a protective gas, such as argon or nitrogen, or by means of hydrogenolysis (for example in the case of benzyloxycarbonyl radicals), preferably in polar solvents, such as alcohols, for example methanol or ethanol, or of esters, such as lower-alkyl-lower-alkanoates, for example ethyl acetate, at the abovementioned temperatures and in the presence of suitable hydrogenation catalysts, such as a palladium catalyst, which is preferably bound to a support, such as charcoal.

In a compound of the formula I, in which at least one of the radicals $R_2$ or $R_3$ is a phenyl group and/or one or more additional phenyl rings are present, with it also being possible for the phenyl radicals to be in each case substituted, as described above, the corresponding phenyl radical(s) can be hydrogenated selectively to form corresponding cyclohexyl radicals. The hydrogenation is preferably effected in the presence of a catalyst which permits selective hydrogenation of double bonds in the presence of amide bonds, in particular of a catalyst composed of heavy metal oxides such as an Rh(III)/Pt(VI) oxide catalyst in accordance with Nishimura (S. Nishimura, Bull. Chem. Soc. Japan 33, 566 (1960), in suitable solvents, in particular water, alcohols, such as methanol or ethanol, esters, such as ethyl acetate, or ethers, such as dioxane, for example in methanol, at temperatures of from 0° to 150° C., preferably of from 10° to 50° C., for example at room temperature; at hydrogen pressures of from 0.01 to 50 bar, for example under standard pressure or low pressure.

In a compound of the formula I, in which at least one of the radicals $R_2$ or $R_3$ is cyclohexenyl, the corresponding cyclohexenyl radical can be selectively hydrogenated to give the corresponding cyclohexyl radical, in suitable solvents or solvent mixtures, preferably dissolved in an alcohol, such as methanol or ethanol, an ester, for example lower-alkyl lower-alkanoate, such as ethyl acetate, or a mixture of these solvents, in the presence of a catalyst, for example palladium which is preferably bound to a support, such as charcoal, preferably active charcoal, at preferred temperatures of between 10° and 50° C., preferably at room temperature, under slightly elevated or reduced pressure or, preferably, standard pressure.

In a compound of the formula I, in which nitro groups are bonded to aromatic radicals (aryl), in particular if $R_1$ is arylsulfonyl having one or more nitro substituents, such as 4-nitrobenzenesulfonyl, nitro can be reduced to amino by, in particular, hydrogenating in suitable solvents or solvent mixtures, preferably dissolved in an alcohol, such as methanol or ethanol, an ester, for example lower-alkyl lower-alkanoate, such as ethyl acetate, or a mixture of these solvents, in the presence of a catalyst, for example of a skeleton catalyst, such as Raney nickel, at preferred temperatures of between 10° and 50° C., in particular room temperature, under slightly increased or reduced pressure or, preferably, standard pressure.

Pharmaceutical preparations and methods

The invention also relates to pharmaceutical preparations which comprise compounds of the formula I, in particular of the formula I.

The pharmacologically utilizable compounds of the present invention can be used, for example, for producing pharmaceutical preparations which comprise an effective quantity of the active compound together, or in a mixture, with a significant quantity of inorganic or organic, solid or liquid, pharmaceutically utilizable carrier substances.

The pharmaceutical preparations according to the invention are those for enteral, such as nasal, buccal, rectal or oral, or parenteral, such as intramuscular or intravenous, administration to mammals (humans and animals) and comprise an effective dose of the pharmacological active compound on its own or together with a significant quantity of a pharmaceutically utilizable carrier material.

The dose of the active compound depends on the mammalian species, the body weight, the age and the individual condition, the individual pharmacokinetic circumstances, the disease to be treated and the mode of administration.

The invention also relates to pharmaceutical preparations and to a method for treating diseases caused by retroviruses, for example AIDS or its preliminary stages, in particular when HIV-2 or, especially, HIV-1 causes the disease, or, in addition, for treating analogous diseases, or their preliminary stages, in non-human mammals which are caused, for example, by SIV in monkeys or FIV in cats, preferably wherein a quantity, which is therapeutically effective against retroviral diseases, such as AIDS or its preliminary stages, or analogous diseases in non-human mammals, of a novel compound of the formula I or, in particular, I' is included in a pharmaceutical preparation which is suitable for administration to a mammal, in particular humans, for treating a retroviral disease, such as, preferably, AIDS or, in addition, analogous diseases in non-human mammals, or wherein a therapeutically effective quantity of a novel compound of the formula I or, in particular I' is administered, in association with the treatment method, to a mammal, for example humans, which, on account of one of the said diseases, in particular AIDS or its preliminary stages, or, in addition, corresponding diseases in non-human mammals, requires a treatment of this nature, in a quantity which is therapeutically effective against retroviral diseases, such as AIDS or its preliminary stages, or, in addition, corresponding diseases in non-human mammals. The dose quantities to be administered to mammals, for example humans of about 70 kg body weight, are between about 3 mg and about 10 g, preferably between about 20 mg and about 4 g, for example approximately 100 mg to 2.5 g per person and day, distributed, preferably, between 1 to 3 individual doses which can, for example, be of equal size. Customarily, children are given half the dose given to adults. "Therapeutically effective" means, in particular, that the onset of the particular disease can be retarded when compared with the untreated patient, that at least one symptom can be delayed or attenuated, that at least one cell type (for example human CD4 cells) can be fully or partially protected from the disease, or that the disease can even be completely cured.

The pharmaceutical preparations comprise from about 1% to about 95%, preferably from about 20% to about 90%, of the active compound. Pharmaceutical preparations according to the invention can, for example, be present in unit dose form, such as ampoules, vials, suppositories, coated tablets, tablets or capsules.

The pharmaceutical preparations of the present invention are produced in a manner known per se, for example using conventional solubilizing, lyophilizing, mixing, granulating or coating methods.

Use is preferably made of solutions of the active compound, and in addition also suspensions or dispersions, specifically, and in particular, isotonic aqueous solutions, dispersions or suspensions, with it being possible for these, for example in the case of lyophilized preparations, which comprise the active substance alone or together with a carrier material, for example mannitol, to be prepared prior to use. The pharmaceutical preparations can be sterilized and/or comprise auxiliary substances, for example preservatives, stabilizers, crosslinking agents and/or emulsifiers, solubilizers, salts for regulating the osmotic pressure and/or buffers, and are produced in a manner known per se, for example using conventional solubilizing or lyophilizing methods. The said solutions or suspensions can comprise viscosity-increasing substances, such as sodium carboxymethylcellulose, carboxymethylcellulose, dextran, polyvinylpyrrolidone or gelatin.

Suspensions in oil contain, as the oily component, the vegetable, synthetic or semi-synthetic oils which are customary for injection purposes. Oils of this nature which are to be mentioned are, in particular, liquid fatty acid esters which, as acid component, contain a long-chain fatty acid having 8–22, in particular 12–22, carbon atoms, for example lauric acid, tridecanoic acid, myristic acid, pentadecanoic acid, palmitic acid, margaric acid, stearic acid, arachidonic acid, behenic acid, or corresponding unsaturated acids, for example oleic acid, elaidic acid, erucic acid, brassidic acid or linoleic acid, with or without the addition of antioxidants, for example vitamin E, β-carotene or 3,5-di-tert-butyl-4-hydroxytoluene. The alcohol component of these fatty acid esters has at most 6 carbon atoms and is a mono- or poly-hydric, for example monohydric, dihydric or trihydric alcohol, for example methanol, ethanol, propanol, butanol or pentanol, or their isomers, especially, however, glycol and glycerol. Fatty acids which are, therefore, to be mentioned by way of example are: ethyl oleate, isopropyl myristate, isopropyl palmitate, "Labrafil M 2375" (polyoxyethyleneglycerol trioleate from Gattefossé, Paris), "Miglyol 812" (triglyceride of saturated fatty acids of $C_8$ to $C_{12}$ chain length from Hüls AG, Germany), particularly, however, vegetable oils such as cottonseed oil, almond oil, olive oil, castor oil, sesame oil, soya bean oil and, especially, groundnut oil.

The production of the injection preparations is effected in a customary manner under sterile conditions, as is their filling into ampoules or vials, and the sealing of the containers.

Pharmaceutical preparations for oral use can be obtained by combining the active compound with solid carrier substances, if desired granulating a mixture which is obtained and, if desired or necessary, after having added suitable auxiliary substances, processing into tablets, coated tablet cores or capsules, or else by preparing dispersions, preferably with phospholipids, which are filled into glass vials. At the same time, the active compounds can also be incorporated into synthetic supports which release them in a metered manner or else allow them to diffuse.

Suitable carrier substances are, in particular, fillers, such as sugars, for example lactose, sucrose, mannitol or sorbitol, cellulose preparations, and/or calcium phosphates, for example tricalcium phosphate or calcium hydrogen phosphate and, in addition, binders, such as starch pastes using, for example, corn starch, wheat starch, rice starch or potato starch, gelatin, tragacanth, methylcellulose, hydroxypropylmethylcellulose, sodium carboxymethylcellulose and/or polyvinylpyrrolidone, and/or, if desired, disintegrants, such as the abovementioned starches, and, in addition, carboxymethyl starch, crosslinked polyvinylpyrrolidone, agar, alginic acid or a salt thereof, such as sodium alginate. Adjuvants are primarily flow regulators and lubricants, for example silicic acid, talc, stearic acid or salts thereof, such as magnesium or calcium stearate, and/or poyethylene glycol. Coated tablet cores are provided with suitable coatings which are or are not resistant to gastric juices, with, inter alia, concentrated sugar solutions, which do or do not contain gum arabic, talc, polyvinylpyrrolidone, polyethylene glycol and/or titanium dioxide, lacquer solutions in suitable organic solvents or, for preparing gastric juice-resistant coatings, solutions of suitable cellulose preparations, such as ethylcellulose phthalate or hydroxypropylmethylcellulose phthalate, being used.

Capsules are hard gelatin capsules and also soft, closed capsules made of gelatin and an emollient, such as glycerol or sorbitol. The hard capsules can contain the active compound in the form of a granulate, for example containing fillers, such as lactose, binders, such as starches, and/or glidants, such as talc or magnesium stearate, and, if desired, containing stabilizers. In capsules, the active compound is preferably suspended or dissolved in suitable, oily auxiliary substances, such as customary vegetable, synthetic or semi-synthetic oils. Oils of this nature which are to be mentioned, in particular are liquid fatty esters which contain, as the acid component, a long-chain fatty acid, for example having 8–22, in particular 12–22, carbon atoms, for example lauric acid, tridecanoic acid, myristic acid, pentadecanoic acid, palmitic acid, margaric acid, stearic acid, arachidonic acid, behenic acid, or corresponding unsaturated acids, for example oleic acid, elaidic acid, erucic acid, brassidic acid or linoleic acid, with or without the addition of antioxidants, for example, vitamin E, β-carotene or 3,5-di-tert-butyl-4-hydroxytoluene. The alcohol component of these fatty acid esters has at most 6 carbon atoms and is a mono- or poly-hydric, for example monohydric, dihydric or trihydric alcohol, for example methanol, ethanol, propanol, butanol or pentanol or their isomers, especially, however, ethylene glycol or propylene glycol and glycerol. Fatty acid esters which are to be mentioned therefore, by way of example, are: ethyl oleate, isopropyl myristate, isopropyl palmitate, "Labrafil M 2375" (polyoxyethyleneglycerol trioleate from Gattefossé, Paris), "Miglyol 812" (triglyceride of saturated fatty acids of $C_8$ to $C_{12}$ chain length from Hüls AG, Germany), particularly, however, vegetable oils, such as cottonseed oil, almond oil, olive oil, castor oil, groundnut oil, soya bean oil and, especially, sesame oil. Paraffin oil is also possible. Stabilizers, such as emulsifiers, wetting agents or surfactants, binders, such as starch pastes using, for example, corn starch, wheat starch, rice starch or potato starch, gelatin, tragacanth, methylcellulose, hydroxypropylmethylcellulose (preferably), sodium carboxymethylcellulose, cyclodextrin(s) and/or polyvinylpyrrolidone, and/or anti-bacterial agents, can be added. Suitable emulsifiers are, in particular, oleic acid, non-ionic surfactants of the fatty acid polyhydroxyalcohol ester type, such as sorbitan monolaurate, -oleate, -stearate or -palmitate, sorbitan tristearate or -trioleate, polyoxyethylene adducts of fatty acid polyhydroxyalcohol esters, such as polyoxyethylenesorbitan monolaurate, -oleate, -stearate, -palmitate, -tristearate or -trioleate, polyethylene glycol fatty acid esters, such as polyoxyethyl stearate, polyoxyethylene glycol-(300 or 400)-stearate, polyethylene glycol-2000-stearate, in particular ethylene oxide-propylene oxide block polymers of the ®Pluronic (Wyandotte Chem. Corp.; trademark of BASF, FRG) or ®Synperonic (ICI) type. If it is not soluble in the said oils, the active substance is preferably present in suspension form, for example with the active substance having a particle size of between about 1 and 100 μm.

Dyes or pigments can be added to the tablets or coated tablet coatings and to the capsule shells, for example for identifying or for labelling different doses of active compound.

The compounds of the formula I can be present either alone or in combination with other compounds which are effective against retroviruses, and used as mentioned above.

The invention also relates, correspondingly, to a process or a method for treating diseases caused by retroviruses, for example AIDS or its preliminary stages, in particular when HIV-2 or, especially, HIV-1 is causing the disease, or, in addition, analogous diseases, or their preliminary stages, in non-human mammals, for example those caused by SIV in monkeys or FIV in cats, which comprises administering a combination, which is therapeutically effective against retroviral diseases, such as AIDS or its preliminary stages, or analogous diseases in non-human mammals, of a) a novel compound of the formula I or, in particular, I' (or else several of these compounds) and b) another compound, or two or more thereof, which is/are effective against renoviruses, in particular several or, preferably, one of the inhibitors, mentioned above as being preferred, of reverse transcriptase or, in particular, retroviral aspartate proteases (which, for example, is included in a pharmaceutical product or preparation which is suitable for administering to a mammal, in particular humans, which are in need of such treatment, for treating a retroviral disease, such as, preferably, AIDS or else analogous diseases in non-human mammals) in a quantity which is therapeutically effective against retroviral diseases, such as AIDS or its preliminary stages, or else corresponding diseases in non-human mammals. The dose quantities of the combined individual active compounds which are to be administered to mammals, for example humans, of about 70 kg body weight are between about 3 mg and about 10 g, preferably between about 20 mg and about 4 g, for example from approximately 50 mg to 2.5 g per person and day, preferably divided between 1 to 3 individual doses which can, for example, be of equal size. Customarily, children are given half the dose given to adults. "Therapeutically effective" means, in particular, that the onset of the respective disease can be retarded as compared with the untreated patient, that at least one symptom can be delayed or attenuated, that at least one cell type (for example human CD4 cells) can be fully or partially protected from the disease, or that the disease can even be completely cured.

The invention also relates to products which comprise a) at least, and preferably, one compound of the formula I, or a salt thereof, providing a salt-forming group is present, and b) one, two (preferred) or more other active compounds which are effective against retroviruses, in particular HIV, such as HIV-1 or HIV-2, selected, in particular, from the abovementioned inhibitors of reverse transcriptase or, especially, from the abovementioned other inhibitors of retroviral aspartate proteases (in particular the inhibitors described above in each case as being preferred), in the presence or absence of one or more pharmaceutically acceptable carrier materials, as combination preparations for simultaneous or chronologically staggered use within a time span which is small enough for the active compounds both of the component a) and of the component b) to be present simultaneously in the patient (for example in blood), for treating a retroviral disease which responds to active compounds of this type. The underlying concept is that synergisms can occur in this way.

The invention also relates to pharmaceutical preparations which comprise a (preferably jointly) antiretrovirally active quantity of a) at least (and preferably) one compound of the formula I and b) one or more of the said active compounds which are effective against retroviruses, with or without one or more pharmaceutically acceptable carrier material(s), with the active compounds described above in each case as being preferred being preferred.

The invention furthermore relates to the use of a combination of a) a compound of the formula I and b) one or more of the abovementioned active compounds which are effective against retroviruses (in particular HIV, such as HIV-1 or HIV-2) for producing pharmaceutical preparations to be used as compositions against retroviral infections, in particular caused by HIV, such as HIV-1 or HIV-2; with the compounds mentioned in each case as being preferred being preferred.

The invention also relates to the provision of the abovementioned product or compound mixture for use in a process for the therapeutic treatment of the human or animal body.

In this context, the composition and production of the pharmaceutical preparations for the individual components of a product for staggered or simultaneous administration, or for the compound mixtures, are analogous to those of the abovementioned pharmaceutical preparations for active compounds of the formula I.

In each case, a combination of a) the compound of the formula I having the designation 5(S)-(Boc-amino)-4(S)-hydroxy-6-phenyl-2(R)-[(2,3,4-trimethoxyphenyl)methyl] hexanoyl-(L)-Val-N-(2-methoxyethyl)amide and b) one or two of the active compounds saquinavir or indinavir is particularly preferred.

The active compounds of the formula I and/or the other active compounds which are effective against retroviruses can in each case be replaced by their pharmaceutically utilizable salts.

Starting materials:

Novel starting materials and/or intermediates, and also methods for their preparation, are likewise the subject-matter of the present invention. Preferably, those starting compounds are used, and reaction conditions chosen, such that the compounds listed as being preferred are obtained.

All starting materials can preferably be prepared in analogy with the methods specified in the examples or else, for example, as described in EP 0 532 466 (published on 17 Mar. 1993) or EP 0 618 222 (published on 5 Oct. 1994); these applications are incorporated into the present text by reference.

In the preparation of all the starting materials, free functional groups which are not to participate in the respective reaction can be unprotected or, if necessary, be in protected form, for example protected by the protective groups mentioned above under process a), which groups can be introduced at appropriate stages in analogy with the methods mentioned there. Protective groups, or the protected groups, can be set free at suitable time points in analogy with the methods described under process f). Starting materials and intermediates having salt-forming groups can in each case be used as free compounds or as salts, and salts can, at every stage, be prepared or converted once again into the free compounds.

In analogy with the process steps described above for the additional process measures, hydroxyl-substituted phenyl $R_2$ and/or phenyl $R_3$ radicals in intermediates can be etherified, at appropriate reaction stages, with the radical of a lower alkanol, a phenyl-lower-alkanol, a lower-alkoxycarbonyl-lower-alkanol, a carbamoyl-lower-alkanol, a pyridyl-lower-alkanol, a cyano-lower-alkanol or a lower-alkoxyl-lower-alkanol. The etherification is preferably effected using diazomethane, or lower-alkyl-, phenyl-lower-alkyl-, lower-alkoxycarbonyl-lower-alkyl-, carbamoyl-lower-alkyl, pyridiyl-lower-alkyl-, cyano-lower-alkyl- or lower-alkoxyl-lower-alkyl-halides or -sulfonic acid esters. Preference is given to the reaction with corresponding lower-alkyl-, phenyl-lower-alkyl-, lower-alkoxycarbonyl-lower-alkyl-, carbamoyl-lower-alkyl-, pyridyl-lower-alkyl-, cyano-lower-alkyl- or lower-alkoxyl-lower-alkyl-halides, such as -iodides, -bromides or -chlorides, in the presence of bases, preferably of a hydroxyl base, in particular a basic metal hydroxide, such as sodium or potassium hydroxide, or, especially, of a metal carbonate or hydrogen carbonate, such as sodium, potassium or, primarily, caesium carbonate, in suitable solvents or solvent mixtures, for example in N,N-di-lower-alkyl-lower-alkanoylamides, such as dimethylformamide or -acetamide, ketones, such as lower alkanones, for example acetone, or ethers, such as dioxane, or mixtures thereof, at temperatures of from −10° C. up to the reflux temperature, preferably at from 0° to 60° C., for example from about 0° to 50° C.

In intermediates in which at least one of the radicals $R_2$ or $R_3$ is a phenyl group and/or one or more additional phenyl rings are present, with it also being possible for the phenyl radicals in each case to be substituted, as described above, an appropriate phenyl radical can, at suitable reaction stages, in analogy with the process steps described above for the additional process measures, be selectively reduced, i.e. hydrogenated, to corresponding cyclohexyl radicals. The hydrogenation is preferably effected in the presence of a catalyst which permits the selective hydrogenation of double bonds in the presence of peptide bonds, in particular of a catalyst consisting of heavy metal oxides, such as a Rh(III)/Pt(VI) oxide catalyst in accordance with Nishimura (S. Nishimura, Bull. Chem. Soc. Japan 33, 566 (1960), in suitable solvents, in particular water, alcohols, such as methanol or ethanol, esters, such as ethyl acetate, or ethers, such as dioxane, for example in methanol, at temperatures of from 0° to 150° C., preferably of from 10° to 50° C., for example at room temperature, and under hydrogen pressures of from 0.01 to 50 bar, for example under standard pressure or under low pressure.

In intermediates in which at least one of the radicals $R_2$ or $R_3$ is cyclohexenyl, an appropriate cyclohexenyl radical can, at suitable reaction stages, in analogy with the process steps described above for the additional process measures, be selectively hydrogenated to the corresponding cyclohexyl radical, for example in suitable solvents or solvent mixtures, preferably dissolved in an alcohol, such as methanol or ethanol, an ester, for example lower-alkyl lower-alkanolate, such as ethyl acetate, or a mixture of these solvents, in the presence of a catalyst, for example palladium which is preferably bound to a support, such as charcoal, preferably active charcoal, at preferred temperatures of between 10° and 50° C., preferably at room temperature under slightly elevated or reduced pressure or, in particular, under standard pressure.

Provided the stereochemistry of asymmetric carbon atoms is not defined directly by the choice of corresponding bond symbols, the configuration of asymmetric carbon atoms which is in each case preferred is designated in the formulae by the configuration designation, selected from (S), (R) and (S,R), which is in each case given in brackets. In addition, other isomers or isomeric mixtures can also be present in place of these.

The carboxylic acids of the formulae II and IV, or reactive derivatives thereof, are known, are commercially available or can be prepared by methods which are known per se.

The compounds of the formula III and III' are known or can be prepared by methods which are known per se. For example, they can be obtained from compounds of the formula

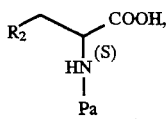

(XI)

in which $R_2$ has the meanings given for compounds of the formula I, and Pa is an amino protective group, in particular lower-alkoxycarbonyl, such as tert-butoxycarbonyl, or 1-phenyl-lower-alkoxycarbonyl, such as benzyloxycarbonyl (or analogues thereof in which hydrogen replaces Pa, which analogues can then be protected subsequently), which are in a first step converted by reduction into the corresponding compounds of the formula

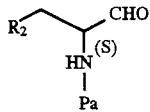

(XII)

(or the analogue having hydrogen in place of Pa), in which the radicals are as described above.

The reduction of amino acid derivatives of the formula XI to give the corresponding aldehydes XII is effected, for example, by reducing them to the corresponding alcohols and then oxidizing the latter to form the aldehydes of the formula XII.

The reduction to the alcohols is effected, in particular, by hydrogenation of the corresponding acid halides or other activated carboxylic acid derivatives which are specified under process a), or by reacting activated carboxylic acid derivatives of the compounds of the formula XI, in particular anhydrides with organic carboxylic acids, preferably those which are obtained with haloformic acid esters, for example isobutyl chloroformate (which are preferably obtained by reacting the compounds of the formula XI in the presence of basic amines, for example tri-lower-alkylamines, such as triethylamine, in organic solvents, such as cyclic ethers, for example dioxane, at temperatures of between −50° and 80° C., preferably of between 0° and 50° C.) with complex hydrides, such as alkali metal borohydrides, for example sodium borohydride, in aqueous solution in the presence or absence of the last organic solvents to be used, at temperatures of between −50° and 80° C., preferably of between 0° and 50° C. The subsequent oxidation of the resulting alcohols is preferably effected using those oxidizing agents which selectively convert the hydroxyl group into an aldehyde group, for example chromic acid or its derivatives, such as pyridinium chromate or tert-butyl chromate, dichromate/sulfuric acid, sulfur trioxide in the presence of heterocyclic bases, such as pyridine/$SO_3$ (preferably dissolved in di-lower-alkyl sulfoxides, such as dimethyl sulfoxide, aromatic solvents, such as toluene, or mixtures of these solvents), and also nitric acid, manganese dioxide or selenium dioxide, in water, aqueous or organic solvents, such as halogenated solvents, for example methylene chloride, carboxamides, such as dimethylformamide, and/or cyclic ethers, such as tetrahydrofuran, in the presence or absence of basic amines, for example tri-lower-alkylamines, such as triethylamine, at temperatures of from −70° to 100° C., preferably of from −70° to 50° C., or from −10° to 50° C., for example as described in European Patent Application EP-A-0 236 734, or by reaction with dicarbonyl halides, such as oxalyl chloride, and di-lower-alkyl sulfoxides, such as dimethyl sulfoxide, in a halogenated hydrocarbon, such as dichloromethylene, in the presence of a tertiary nitrogen base, such as triethylamine, at preferred temperatures of from about −70° to 0° C., for example at about −60° C.

It is also possible directly to reduce the compounds of the formula XI to the aldehydes, for example by hydrogenation in the presence of a partially poisoned palladium catalyst, or by reducing the corresponding amino acid esters, for example the lower-alkyl esters, such as ethyl esters, with complex hydrides, for example borohydrides, such as sodium borohydride or, preferably, aluminium hydrides, for example lithium aluminium hydride, lithium tri-(tert-butoxy)aluminium hydride or, in particular, diisobutylaluminium hydride, in apolar solvents, for example in hydrocarbons or aromatic solvents, such as toluene, at from −100° to 0° C., preferably from −70° to −30° C., and first subsequently converting the products into the corresponding semicarbazones, for example using the corresponding acid salts of semicarbazones, such as semicarbazide hydrochloride, in aqueous solvent systems, such as alcohol/water, for example ethanol/water, at temperatures of between −20° and 60° C., preferably from 10° to 30° C., and then reacting the resulting semicarbazone with a reactive aldehyde, for example formaldehyde, in an inert solvent, for example a polar organic solvent, for example a carboxamide, such as dimethylformamide, at temperatures of between −30° and 60° C., preferably from 0° to 30° C., and then reacting with an acid, for example a strong mineral acid, such as hydrohalic acid, in aqueous solution, in the absence or presence of the solvent which was previously used, at temperatures of between −40° and 50° C., preferably between −10° and 30° C. The corresponding esters are obtained by reacting the amino acids with the corresponding alcohols, for example ethanol, in analogy with the conditions used in the condensation under process b), for example by reacting with inorganic acid halides, such as thionyl chloride, in organic solvent mixtures, such as mixtures of aromatic and alcoholic solvents, for example toluene and ethanol, at temperatures of between −50° and 50° C., preferably of between −10° and 20° C.

In order to synthesize the compounds of the formula III or III', the compounds of the formula XII are then reacted with a reactive tetraalkylsilane, preferably a halomethyltri-lower-alkylsilane, such as chloromethyltrimethylsilane, in an inert solvent, for example an ether, such as diethyl ether, a cyclic ether, such as dioxane, or an ester, such as ethyl acetate, at temperatures of between −100° and 50° C., preferably of between −65° and 40° C., with compounds of the formula

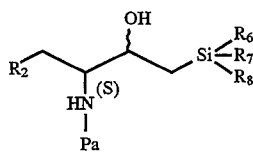
(XIII)

being obtained, in which $R_6$, $R_7$ and $R_8$ are lower alkyl, for example methyl, and the remaining radicals are as defined above, the resulting compounds are converted, in the presence of a Lewis acid, such as boron trifluoride ethyl etherate, in an inert solvent, in particular a halogenated hydrocarbon, such as methylene chloride or chloroform, with subsequent aftertreatment with an aqueous base, for example sodium hydroxide solution, at temperatures of between −30° and 80° C., in particular of between 0° and 50° C., with elimination and protective group detachment, into olefinic compounds of the formula

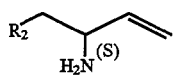
(XIV)

in which $R_2$ has the meanings specified for compounds of the formula I, an amino protective group Pa, for example tert-butoxycarbonyl, is once again introduced into the corresponding olefin, as described under process a) for the introduction of amino protective groups, in particular using an acid anhydride in a chlorinated hydrocarbon, such as methylene chloride or chloroform, at temperatures of between −50° and 80° C., in particular of between 0° and 35° C., with a protected amino-olefin of the formula

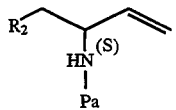
(XV)

being obtained in which the radicals are as defined above, the double bond is converted into an oxirane, preferably stereoselectively using peroxides, in particular peroxycarboxylic acids, for example haloperbenzoic acid, such as m-chloroperbenzoic acid, in an inert organic solvent, preferably a halogenated hydrocarbon, such as methylene chloride or chloroform, at temperatures of between −50° and 60° C., in particular of between −10° and 25° C., and, if required, a diastereomer resolution is undertaken, with epoxides of the formula

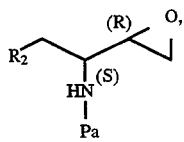
(XVI)

in which the radicals are as defined above, being obtained, a suitable malonic acid diester, for example dimethyl malonate or diethyl malonate, is added to the olefins concerned, for example by activating the methylene group of the malonic acid diester by means of an alkali metal, for example sodium, in a polar, anhydrous solvent, such as an alcohol, for example methanol or ethanol, at temperatures of between −50° and 80° C., in particular between 0° and 35° C., and the solution is treated with an acid, for example carboxylic acid, such as citric acid, with a lactone of the formula

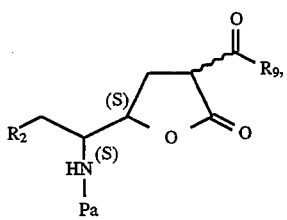
(XVII)

in which $R_9$ is lower alkoxy, for example methoxy or ethoxy, and the remaining radicals are as defined above, being obtained, if desired $R_2$ is reduced to cyclohexyl in those compounds in which this radical is phenyl which is unsubstituted or is substituted as described for compounds of the formula I, in particular by hydrogenation, preferably in the presence of catalysts, such as precious metal oxides, for example mixtures of Rh(III)/Pt(VI) oxides (in accordance with Nishimura), preferably in polar solvents, such as alcohols, for example methanol, under standard pressure or up to 5 bar, preferably under standard pressure, at temperatures of from −20° to 50° C., preferably from 10° to 35° C., the compounds of the formula XVII which are obtained directly or after the hydrogenation are reacted with a reagent which introduces the $R_3$—$CH_2$— radical, for example of the formula $$R_3-CH_2-W \quad (XVIII),$$

in which $R_3$ has the meanings specified for compounds of the formula I and W is a nucleofugic leaving group, preferably selected from hydroxyl which is esterified with a strong inorganic or organic acid, such as hydroxyl which is esterified with a mineral acid, for example hydrohalic acid, such as hydrochloric acid, hydrobromic acid or hydriodic acid, with a strong organic sulfonic acid, such as a lower-alkanesulfonic acid which is unsubstituted or substituted, for example, by halogen, such as fluorine, or an aromatic sulfonic acid, for example a benzenesulfonic acid which is unsubstituted or substituted by lower alkyl, such as methyl, halogen, such as bromine, and/or nitro, for example a methanesulfonic, trimethanesulfonic or p-toluenesulfonic acid, and hydroxyl which is esterified with hydrazole acid, in particular bromide, in an anhydrous polar solvent, for example an alcohol, such as ethanol, in the presence of an alkali metal, for example sodium, at temperatures of between −50° and 80° C., preferably of between 0° and 35° C., to form compounds of the formula

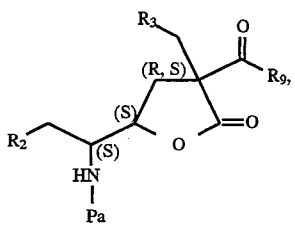
(XIX)

in which the radicals are as defined above, the compounds of the formula XIX are hydrolysed and decarboxylated, for example by hydrolysis with a base, such as an alkali metal hydroxide, for example lithium hydroxide or NaOH, at temperatures of between −50° and 80° C., preferably of between about 0° and 35° C., in an organic solvent, for example an ether, such as 1,2-dimethoxyethane, or an alcohol, such as ethanol, and subsequent decarboxylation by heating in an inert solvent, preferably a hydrocarbon, for example an aromatic hydrocarbon, such as toluene, at temperatures of between 40° and 120° C., preferably of between 70° and 120° C., with a compound of the formula

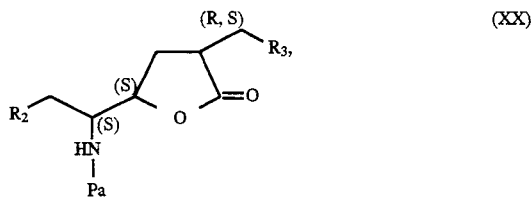
(XX)

in which the radicals are as defined above, being obtained, the resulting (R,S,S) and (S,S,S) isomers are resolved by column chromatography, the (R,S,S) isomer is reused and, for opening the lactone ring, is reacted with a base, such as an alkali metal hydroxide, for example lithium hydroxide or sodium hydroxide, in an inert solvent, such as an ether, for example dimethoxyethane, or an alcohol, such as ethanol, to form a compound of the formula

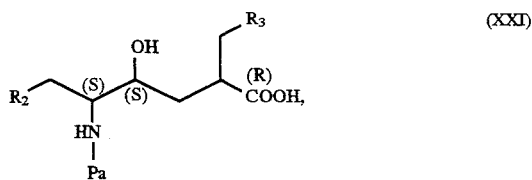
(XXI)

in which the radicals are as defined above, an hydroxyl protective group Py, for example one of the hydroxyl protective groups specified under process a), in particular a tri-lower-alkylsilyl group, is introduced, under the conditions specified there, into the resulting compound using the corresponding halo-tri-lower-alkylsilane, for example tert-butyldimethylchlorosilane, in a polar solvent, such as a di-lower-alkyl-lower-alkanoylamide, such as dimethylformamide, in the presence of a sterically hindered amino compound, such as a cyclic amine, for example imidazole, at temperatures of from −50° to 80° , preferably from 0° to 35° C., and the carboxyl group which is also silylated at the same time is set free once again by reaction with a basic metal salt, in particular an alkali metal hydroxide or alkali metal hydrogen carbonate or, preferably, an alkali metal carbonate, such as potassium carbonate, preferably in an alcohol, such as methanol or ethanol, a cyclic ether, such as tetrahydrofuran, in water or, in particular, a mixture of 2 or 3 of these solvents, at preferred temperatures of between 0° and 50° C., in particular of from 10° to 35° C., with a compound of the formula

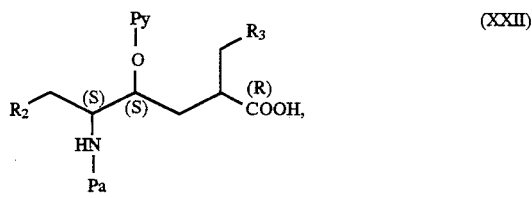
(XXII)

being obtained, in which the radicals are as defined above, and the compounds of the formula III or III' having the radicals given under process a) are prepared, for example, from one of the compounds of the formula XXII by condensation with a compound of the formula VI, in which the radicals have the meanings given under process c), under conditions which are analogous to those given for process a), in particular by in-situ reaction in the presence of a condensing agent, such as N,N-dicyclohexylcarbodiimide, ethyl cyanophosphonate, benzotriazol-1-yloxytris (dimethylamino)phosphonium hexafluorophosphate or O-benzotriazol-1-yl-N,N,N',N'-tetramethyluronium hexafluorophosphate, a sterically hindered amine, such as triethylamine or N-methylmorpholine, and, if desired, a racemization-preventing compound, such as 1-hydroxybenzotriazole, in a polar solvent, preferably an acid amide, for example a di-lower-alkylamino-lower-alkanoylamide, such as dimethylformamide, a cyclic ether, such as tetrahydrofuran, or a nitrile, such as acetonitrile, at preferred temperatures of between −50° and 80° C., in particular of between 0° and 35° C., if desired under protective gas, such as argon or nitrogen, and by the subsequent detachment of the protective group Pa under analogous conditions, as described under process f), (provided Pa is not a radical which corresponds to the radical $R_1$ having the meanings presented above for compounds of the formula I, which would lead directly to compounds of the formula I) and finally, if desired, the detachment of Py and/or further protective groups under analogous conditions to those described under process f). In order to prepare the compounds of the formula or III', it is also possible successively to condense the compounds of the formula XXII with compounds which introduce the radicals —HN—(CHR$_4$)—CO— (starting material: the corresponding amine acids $H_2N$—(CHR$_4$)—COOH) and —NH—CH$_2$—(CH$_2$)$_n$—O—R$_5$ (starting material: the corresponding amino compound $H_2N$—CH$_2$—(CH$_2$)$_n$—O—R$_5$) of the compound of the formula III or III', under conditions which are analogous to those specified for process a), preferably by reacting a compound which is analogous to the compound of the formula (i) V or V', (ii) VII or VII' or (iii) IX or IX', in which hydrogen is present in place of $R_1$, with a compound of the formula (i) VI or VI' (corresponds to a compound of the formula XXII in which Pa=hydrogen), (ii) VIII or (iii) X, where the remaining radicals in each case have the specified meanings and the starting materials can also be present as the reactive derivatives, in analogy with the conditions specified under (i) process c), (ii) process d) or (iii) process e), with it being possible to detach the protective group Py from compounds of the formula III or III' using one of the methods described under process f).

The following route can also be taken for preparing a compound of the formula XX from an abovementioned compound of the formula XVII:

Hydrolysis of a racemic compound of the formula XVII (which can be prepared from the racemate of a compound of the formula XV via the corresponding racemate of a compound of the formula XVI) and decarboxylation under conditions analogous to those for the hydrolysis and decarboxylation of compounds of the formula XIX leads to a compound which is analogous to the compound of the formula XIX in which, however, the radicals $R_3$—CH$_2$— and $R_9$—(C=O)— are missing (in both cases, a hydrogen atom is present instead) and which is present as a racemate (or as a diastereomer mixture providing an additional centre of asymmetry is present in $R_3$ and/or $R_9$); this latter compound is subsequently reacted with a compound of the formula XVIII, as defined above, in which W is one of the abovementioned nucleofugic leaving groups, in particular halo, such as iodine or, preferably, bromine or chlorine, by first deprotonating it in the presence of a strong base, such as an alkali metal bis(tri-lower-alkylsilyl)amide, for example lithium bis(trimethylsilyl)amide, and then alkylating it with the compound of the formula $R_3$—CH$_2$—W (preferably obtaining the [1'(S),3(R)-($R_3$—CH$_2$—),5(S)]- and the [1'(R),3(S)-($R_3$—CH$_2$—),5(R)] compounds of the formula XX, i.e. a racemate as regards the said asymmetric carbon atoms).

The abovementioned compounds of the formula XIV can also be present in the (R,S) configuration instead of the indicated (S) configuration at the carbon atom carrying the —NH₂ radical, while the compounds of the formulae XI, XII and XIII and, in particular, those of the formulae XV, XVI, XVII, XIX, XX, XXI and/or XXII can also be present in the (R,S) configuration instead of the (S) configuration at the carbon atom carrying the Pa—NH— radical. The above-mentioned compounds of the formulae XV, XVI and XVII can also be present as racemates. Other mixtures of the optical antipodes of the indicated formulae are also possible. Corresponding compounds of the formula V, for example, can be obtained from these racemates or mixtures (for example racemates or antipode mixtures if $R_1$ does not contain any centres of assymetry), so that, in this way, compounds of the formula I or I' are accessible in which either the carbon atom carrying $R_2$—CH₁— is in the (S) configuration, the carbon atom carrying HO— is in the (S) configuration and the carbon atom carrying $R_3$—CH₂— is in the (R) configuration (2R,4S,5S), or the said carbon atoms have the opposite configuration (2S,4R,5R); or else mixtures of compounds of the formula V or I are present which have both these configurations. Corresponding racemic mixtures or diastereomer mixtures can be dissolved at suitable stages (preferably) into individual isomers.

Compounds of the formula XX, in which the radicals have the said meanings, are prepared from compounds of the formula XII, in which the radicals have the said meanings, by reacting the aldehydes of the formula XII with 2-halopropionic acid esters, in particular lower-alkyl 2-iodopropionates, such as ethyl 2-iodopropionate, with the compounds of the formula

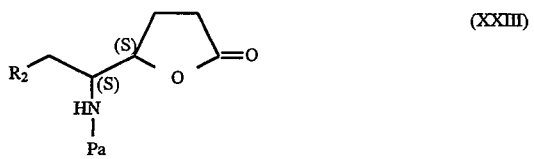

(XXIII)

being obtained, in which the radicals have the said meanings and in which the carbon atom carrying the Pa—NH— radical can also, alternatively, be present, for example, in the (R,S) configuration.

The reaction initially takes place with the formation of the homoenolate of the 2-halopropionic acid-lower-alkyl(such as ethyl) ester in the presence of a mixture of Zn/Cu in a di-lower-alkyl-lower-alkanoylamide, such as dimethylacetamide, or of an aromatic hydrocarbon, such as toluene, or mixtures thereof, at temperatures of between 0° and 100° C., in particular of between 20° and 80° C., if desired under protective gas, such as argon or $N_2$. In a subsequent reaction mixture, a suitable tetra-lower-alkyl orthotitanate, such as tetraisopropyl orthotitanate, is treated, preferably under a protective gas, such as nitrogen or argon, in an aromatic solvent, such as toluene or xylene, in the presence of a halohydrocarbon, such as methylene chloride, with a titanium tetrahalide, such as titanium tetrachloride, at from −50° to 50° C., preferably at from −40° to 25° C., and the mixture is stirred, with the corresponding dihalo-titanium-di-lower-alkylate or, preferably, the trihalo-titanium-lower-alkylate, in particular trichlorotitanium diisopropylate, being formed. The Zn-homoenolate solution is added dropwise to the latter at temperatures of between −50° and 0° C., in particular of from −40° to −25° C., and the aldehyde of the formula XII in a halohydrocarbon, for example methylene chloride, is subsequently added dropwise, with the reaction taking place at from −50° to 30° C., preferably at from about −40° to 5° C., with the formation of the lower-alkyl-(in particular ethyl) ester precursor, in particular the ethyl ester, of the compound of the formula XXIII. This ester is then hydrolysed and cyclized with the formation of the compound of the formula XXIII, as defined above, preferably in an organic solvent, such as an aromatic compound, for example in toluene or xylene, in the presence of an acid, such as a carboxylic acid, for example acetic acid, at temperatures of between 20° C. and the boiling point of the reaction mixture, in particular between 70° and 100° C. If necessary, the diastereomers are separated, for example by means of chromatography, for example on silica gel using an organic solvent mixture, such as a mixture of alkane and ester, such as lower alkane and lower-alkyl-lower-alkanoyl ester, such as hexane/ethyl acetate.

The corresponding compound of the formula XX is then obtained from the compound of the formula XXIII by deprotonation with a strong base, with the formation of the carbanion at the α-carbon next to the oxo group of the lactone, and subsequent nucleophilic substitution of the W radical of a compound of the formula XVIII, in which $R_3$ and W are defined as above in association with the preparation of compounds of the formula XIX (W is, in particular, bromo), with the reaction preferably leading stereoselectively to the (R) configuration at the carbon atom in the compound of the formula XX which carries the $R_3$—CH₂— radical. The reaction with the strong base, in particular with an alkali metal-organosilicon amide compound, for example an alkali metal bis(tri-lower-alkylsilyl)amide, such as lithium bis(trimethylsilyl)amide, or else an alkali metal di-lower-alkylamide, such as lithium diisopropylamide, is preferably carried out in an inert organic solvent, in particular an ether, for example a cyclic ether, such as tetrahydrofuran, or 1,3-dimethyl-3,4,5,6-tetrahydro-2(1H)-pyrimidinone (DMPU), or mixtures of these solvents, at temperatures of between −100° and 0° C., preferably of between −78° and −50° C., while the nucleophilic substitution is carried out in situ by adding the compound of the formula $R_3$—CH₂—W in the same solvent and at temperatures of between −100° and 0° C., preferably of between −60° and −40° C.

A compound of the formula XIV, in which the radicals have the said meanings, and in which the carbon atom carrying the —NH₂ group is preferably in the (R,S) configuration, can also be obtained by converting a formic acid ester, for example lower-alkyl formate, such as ethyl formate, into formic acid allylamide by reacting it with allylamine at temperatures of between 20° and 70° C., in particular of between 50° and 60° C. This amide is then dehydrated under a protective gas, such as nitrogen or argon, preferably using an acid halide, such as phosphorus oxychloride, phosgene or, in particular, an organic sulfonyl halide, for example an arylsulfonyl chloride, such as tolenesulfonyl chloride, in the presence of a base, for example a tri-lower-alkylamine, such as triethylamine, or, in particular, a mono- or bi-cyclic amine, such as pyridine or quinoline, at temperatures of between 50° and 100° C., in particular of between about 80° and about 100° C. This results in the formation of allyl isocyanide, which is converted into the corresponding lithium salt by reaction with an organolithium salt, for example lower-alkyllithium, such as n-butyllithium, with the reaction preferably being carried out in an inert organic solvent, in particular an ether, such as dioxane or diethyl ether, or an alkane, for example hexane, or a mixture of these solvents, at temperatures of from −120° to −50°, in particular of from about −100° to −70° C. The lithium salt which has been formed is then reacted in situ with a compound of the formula $R_2$—CH₂—W, in which $R_2$ has the meanings specified for compounds of the formula I and W has the meanings specified above for compounds of the formula XVIII, in particular bromine, preferably by adding R$_2$—CH$_2$—W dropwise in an organic solvent, for example an ether, such as tetrahydrofuran, at the temperatures mentioned immediately above, and then warming to from 0° to 50° C., preferably to from 20° to 30° C. This results in the formation of an isocyanide of the formula

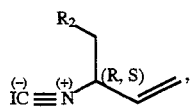
(XXIV)

in which the radicals have the said meanings. The compound of the formula XXIV is subsequently hydrolysed, preferably in aqueous solution to which an acid is added, for example in aqueous hydrohalic acid, such as hydrochloric acid, in particular in concentrated hydrochloric acid, at temperatures of between −20° and 30° C., in particular of between about 0° and 10° C., and the compound of the formula XIV is obtained, in which the radicals are defined as most recently above and in which the carbon atom carrying the —NH$_2$ group is preferably in the (R,S) configuration.

Amino compounds of the formula IIIa or IIIa', or their reactive derivatives, are known or can be prepared by methods which are known per se, for example by condensing amino acids of the formula H—B$_1$—OH, in which B$_1$ has the meanings specified for compounds of the formula III or III', or reactive derivatives thereof, with amino compounds of the formula III or III', or reactive derivatives thereof, with the reactive derivatives and the condensation conditions being analogous to those described under process a).

Compounds of the formula V or V' are prepared, for example, provided the protective group Pa in formula XXI or XXII does not correspond directly to an R$_1$ radical, from the amino compounds of the formula XXI or XXII, for example by introducing a carboxyl protective group, as described under process a), and detaching the protective group Pa, as described under process f), by condensation with a carboxylic acid of the formula R$_1$—OH, or a reactive derivative thereof, in which the radicals have the meanings specified for compounds of the formula I, under conditions which are analogous to the condensation conditions specified for process a).

Compounds of the formula XXA or XXA' are prepared, for example, provided the protective group Pa in the formula XX does not correspond directly to an R$_1$ radical, from the γ-lactone compounds of the formula XX (preferably from the (R,S,S) isomer), for example by detaching the protective group Pa, as described under process f), by condensation with a carboxylic acid of the formula R$_1$—OH, or a reactive derivative thereof, in which the radicals have the meanings specified for compounds of the formula I, under conditions which are analogous to the condensation conditions specified for process a).

Compounds of the formula VI (or VI') are prepared, for example, from the corresponding amino acids of the formula

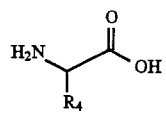
(XXV)

(in particular of the formula

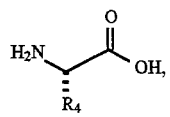
(XXV'))

in which the radicals have the said meanings, or reactive acid derivatives thereof, and the amino component of the formula VIII, in which the radicals are in each case defined as above, or reactive derivatives thereof, by condensation in analogy with the method described under process a) and, if desired, using analogous reactive derivatives.

Compounds of the formula VII (or VII') can be prepared, for example, from compounds of the formula V (or V') by condensation with an amino acid of the formula XXV (or XXV'), as defined immediately above, which introduces the radical —NH—CH(R$_4$)—COOH. The reaction is carried out in analogy with the conditions described under process a) using the corresponding free compounds or their reactive derivatives; or they can be prepared from compounds of the formula XXA (or XXA') by condensation with an amino acid of the formula XXV (or XXV'), as defined immediately above, which introduces the radical —NH—CH(R$_4$)—COOH. The reaction is carried out in analogy with the conditions described under process c) using the corresponding γ-lactones of the formula XXA, in particular XXA'.

The amino compound of the formula VIII is known or is prepared by methods which are known per se.

Compounds of the formula IX (or IX') are known or can be prepared by methods which are known per se, and are obtained, for example, by the condensation of a compound of the formula VII (or VII'), in which the radicals have the said meanings, and an (if necessary hydroxyl-protected) amine of the formula $$H_2N—CH_2—(CH_2)_n—OH \qquad (XXVI),$$

or a reactive derivative thereof, in which n has the meanings given for compounds of the formula I, under reaction conditions analogous to those described under process a).

Compounds of the formula X or Xa are known, are commercially available, or can be prepared by methods which are known per se.

Compounds of the formula XVIII and the formula R$_2$—CH$_2$—W are known or can be prepared by methods which are known per se, or they can be obtained commercially. As an example, mention may be made of the preparation of a compound of the formula XVIII or R$_2$—CH$_2$—W, in which W is Br or I, by reacting the corresponding precursor, in which W is Cl, with an alkali metal iodide or bromide, such as NaI, for example in ketones, such as a lower-alkanone, for example acetone, at temperatures of between 0° and 50° C., in particular room temperature, or with a phosphorus tri- or penta-iodide or -bromide, such as PBr$_3$, for example in hydrocarbons, for example an aromatic hydrocarbon, such as toluene, at preferred temperatures of between 0° and 40° C., for example at room temperature. The precursor (W=Cl) is commercially obtainable, is known or can prepared by methods which are known per se.

For example, a precursor, in which a hydroxyl group is present in place of the Cl (=W), can be converted into the corresponding chlorinated compound by reaction with PCl$_3$, PCl$_5$ or, in particular, SOCl$_2$, in the presence of a tertiary nitrogen base, for example polyhünig base or pyridine, in suitable solvents, for example an ether, such as diethyl ether, or a halohydrocarbon, such as methylene chloride or chloroform, at preferred temperatures of between −10° and 30° C., preferably of between 0° and 25° C. The precursors in which a hydroxyl group is present in place of W are known, can be prepared by methods which are known per se, or are commercially available.

The remaining starting compounds are known, are prepared by methods which are known per se, and/or are commercially available.

The following intermediates, which are specified under (i) to (iv) are also, in particular, a preferred subject-matter of the present invention:

(i) a compound of the formula XIXA,

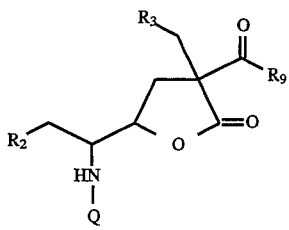

(in particular of the formula XIXA'

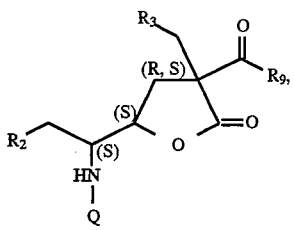

in which

Q is hydrogen; an amino protective group, preferably an amino protective group Pa, as defined for compounds of the formula XI (in particular one of the amino protective groups specified under process a)); or a radical $R_1$, as defined for compounds of the formula I, apart from those radicals which come within the definition of the protective group Pa;

$R_2$ has one of the meanings specified in the definition of compounds of the formula I;

$R_3$ is phenyl which is trisubstituted by radicals selected from lower alkyl, lower alkoxy and halogen, or is lower-alkylenedioxyphenyl, in particular 2,3,4-tri-lower-alkoxyphenyl, especially 2,3,4-trimethoxyphenyl; and $R_9$ is lower alkoxy, for example methoxy or ethoxy, or a salt them off provided salt-forming groups are present.

A compound of the formula XIXA, in particular XIXA', is particularly preferred in which Q is hydrogen or, in particular, is 1-phenyl-lower-alkoxycarbonyl, in particular benzyloxycarbonyl, 1-phenyl-lower-alkyl, in particular benzyl, or is primarily lower-alkoxycarbonyl, such as tert-butoxycarbonyl;

$R_2$ is cyclohexyl or, in particular, phenyl;

$R_3$ is 2,3,4-tri-lower-alkoxyphenyl, in particular 2,3,4-trimethoxyphenyl;

and $R_9$ is lower alkoxy, such as methoxy or ethoxy;

or a salt thereof, provided salt-forming groups are present.

The compounds of the formula XIXA or XIXA' either correspond directly to the compounds of the formula XIX, when Q is an amino protective group Pa, or they can be prepared from these compounds by protective group detachment in analogy with the conditions described under process f) (yields compounds of the formula XIXA or XIXA' in which Q=H) and, if desired, introduction of an $R_1$ radical with an acid of the formula II, as defined above for process a), under analogous conditions to those specified under process a).

(ii) A compound of the formula XXA

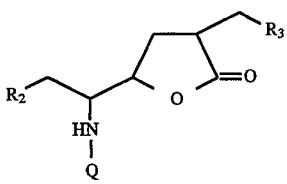

(in particular of the formula XXA'

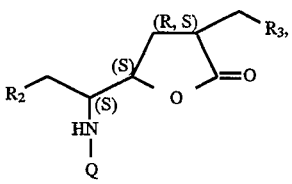

especially of the formula XXA"

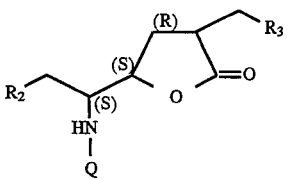

in which

Q is hydrogen; an amino protective group, preferably an amino protective group Pa, as defined for compounds of the formula XI (in particular one of the amino protective groups specified under process a)); or an $R_1$ radical, as defined for compounds of the formula I, apart from those radicals which come within the definition of the protective group Pa;

$R_2$ has one of the meanings specified in the definition of compounds of the formula I: and $R_3$ is phenyl which is trisubstituted by radicals selected from lower alkyl, lower alkoxy and halogen, or is lower-alkylenedioxyphenyl, in particular 2,3,4-tri-lower-alkoxyphenyl, especially 2,3,4-trimethoxyphenyl;

or a salt thereof, provided salt-forming groups are present.

A compound of the formula XXA, in particular XXA', especially XXA", is particularly preferred in which Q is hydrogen or, in particular, is 1-phenyl-lower-alkoxycarbonyl, in particular benzyloxycarbonyl, 1-phenyl-lower-alkyl, in particular benzyl, or is, primarily, lower-alkoxycarbonyl, such as tert-butoxycarbonyl;

$R_2$ is cyclohexyl or, in particular, phenyl; and $R_3$ is 2,3,4-tri-lower-alkoxyphenyl, in particular is 2,3,4-trimethoxyphenyl;

or a salt thereof, provided salt-forming groups are present.

A compound of the formula XXA" is preferred which has the designation 5(S)-[1(S)-(Boc-amino)-2-cyclohexylethyl]-3(R)-(2,3,4-trimethoxyphenylmethyl)dihydrofuran-2-(3H)-one.

A compound of the formula XXA" is very particularly preferred which has the designation 5(S)-[1(S)-(Boc-amino)-2-phenylethyl]-3(R)-(2,3,4-trimethoxyphenylmethyl)dihydrofuran-2-(3H)-one.

The compounds of the formula XXA or XXA' or XXA" can be prepared from the compounds of the formula XIX or XIXA in an analogous manner to that described above for the conversion of compounds of the formula XIX into those of the formula XX; or they correspond directly to the compounds of the formula XX when Q is an amino protective group Pa, or they can be prepared directly from these compounds by protective group detachment in analogy with the conditions specified under process f) (yields compounds of the formula XIXA or XIXA' in which Q=H) and, if desired, introduction of an $R_1$ radical with an acid of the formula II, as defined above for process a), under conditions which are analogous to those specified under process a).

iii) A compound of the formula VA

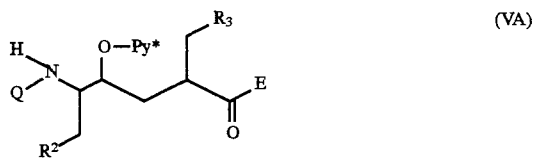

(in particular of the formula VA'

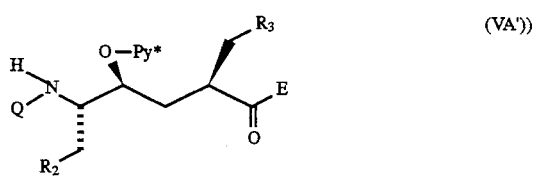

in which

Q is hydrogen; an amino protective group, preferably an amino protective group Pa, as defined for compounds of the formula XI (in particular one of the amino protective groups specified under process a)); or an $R_1$ radical, as defined for compounds of the formula I, apart from those radicals which come within the definition of the protective group Pa;

$R_2$ has one of the meanings specified in the definition of compounds of the formula I;

$R_3$ is phenyl which is trisubstituted by radicals selected from lower alkyl, lower alkoxy and halogen, or is lower-alkylenedioxyphenyl, in particular is 2,3,4-tri-lower-alkoxyphenyl, especially 2,3,4-trimethoxyphenyl;

Py* is hydrogen or a hydroxyl protective group, preferably one of the protective groups specified under process a), in particular tri-lower-alkylsilyl, such as tert-butyldimethylsilyl; and E is hydroxy or a carboxyl protective group, preferably as defined under process a), in particular lower-alkoxy, such as methoxy, ethoxy or tert-butoxy, or tri-lower-alkylsilyloxy, in particular tert-butyldimethylsilyloxy, or the radical —(C=O)—E is a reactive derivative of a carboxylic group, in particular is a carboxylic group in the form of an activated ester, of a reactive anhydride or else of a reactive cyclic amide, preferably in an analogous manner to that described for reactive derivatives of compounds of the formula II under process a);

or a salt thereof, provided salt-forming groups are present.

A compound of the formula XXA, in particular XXA', especially XXA", is particularly preferred in which Q is hydrogen or, in particular, is 1-phenyl-lower-alkoxycarbonyl, in particular benzyloxycarbonyl, 1-phenyl-lower-alkyl, in particular benzyl, or, primarily, is lower-alkoxycarbonyl, such as tert-butoxycarbonyl;

$R_2$ is cyclohexyl or, in particular, phenyl;

$R_3$ is 2,3,4-tri-lower-alkoxyphenyl, in particular 2,3,4-trimethoxyphenyl;

Py* is hydrogen or a hydroxyl protective group, preferably one of those protective groups specified under process a), in particular tri-lower-alkylsilyl, such as tert-butyldimethylsilyl; and E is hydroxyl or a carboxyl protective group, preferably as defined under process a), in particular lower alkoxy, such as methoxy, ethoxy or tert-butoxy, or tri-lower-alkylsilyloxy, in particular tert-butyldimethylsilyloxy, or the radical —(C=O)—E is a reactive derivative of a carboxyl group, in particular is a carboxyl group in the form of an activated ester, of a reactive anhydride or else of a reactive cyclic amide, preferably in an analogous manner to that described for reactive derivatives of compounds of the formula II under process a); in particular is hydroxyl and lower alkoxy;

or a salt thereof, provided salt-forming groups are present.

A compound of the formula VA' is preferred which has the designation 5(S)-(Boc-amino)-4(S)-hydroxy-6-cyclohexyl-2(R)-[(2,3,4-trimethexyphenyl)methyl]hexanoic acid, or a salt thereof.

A compound of the formula VA' is also preferred which has the designation 5(S)-(Boc-amino)-4(S)-(tert-butyldimethylsilyloxy)-6-cyclohexyl-2(R)-[2,3,4-trimethoxyphenyl)methyl]hexanoic acid or a salt thereof.

A compound of the formula VA' is very particularly preferred which has the designation 5(S)-(Boc-amino)-4(S)-hydroxy-6-phenyl-2(R)-[(2,3,4-trimethoxyphenyl)methyl]hexanoic acid, or a salt thereof (in particular an alkali metal salt, for example the sodium salt, which can be very efficiently crystallized).

A compound of the formula VA' is likewise very particularly preferred which has the designation 5(S)-(Boc-amino)-4(S)-(tert-butyldimethylsilyloxy)-6-phenyl-2(R)-[(2,3,4-trimethoxyphenyl)methyl]hexanoic acid, or a salt thereof.

Compounds of the formula VA and VA' correspond to compounds of the formula V and V', respectively, whose preparation has already been described above.

The compounds of the formula VA and VA' correspond directly to the compounds of the formula V and V', respectively, when Q is an amino protective group Pa, Py* is hydrogen and E is hydroxyl; the remaining corresponding compounds of the formula VA and VA', in which at least one of the radicals Py* or E has a meaning specified in the definition of compounds of the formula VA and VA' which is different from those mentioned above, can be obtained from these latter compounds by protective group introduction, for example as described in association with the introduction of Py in compounds of the formula XXI in order to prepare compounds of the formula XXII, or as described under process a), or by the preparation of reactive carboxylic acid derivatives, as described under process a). The corresponding compounds in which Q has a meaning other than Pa can be prepared from these compounds of the formula VA and VA', or those of the formula V and V', by protective group detachment in analogy with the conditions specified under process f) (yields compounds of the formula VA and VA' in which Q=H) and, if desired, introduction of an $R_1$ radical with an acid of the formula II, as defined above for process a), under conditions which are analogous to those specified under process a).

And/or:
(iv) A compound of the formula VIIA

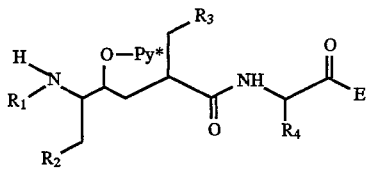
(VIIA)

(in particular of the formula VIIA')

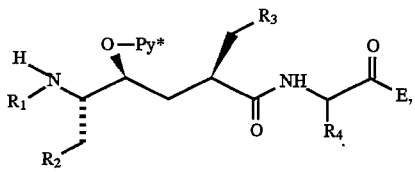
(VIIA'))

in which

R₁ has the meanings specified for compounds of the formula I,

R₂ has one of the meanings specified in association with the definition of compounds of the formula I;

R₃ is phenyl which is trisubstituted by radicals selected from lower alkyl, lower alkoxy and halogen, or is lower-alkylenedioxyphenyl, in particular is 2,3,4-tri-lower-alkoxyphenyl, especially 2,3,4-trimethoxyphenyl;

Py* is hydrogen or a hydroxyl protective group, preferably one of those specified under process a), in particular tri-lower-alkylsilyl, such as tert-butyldimethylsilyl; and E is hydroxyl or a carboxyl protective group, preferably as defined under process a), in particular lower alkoxy, such as methoxy, ethoxy or tert-butoxy, or tri-lower-alkylsilyloxy, in particular tert-butyldimethylsilyloxy, or the radical —(C═O)—E is a reactive derivative of a carboxylic group, in particular is a carboxylic group in the form of an activated ester, of a reactive anhydride or else of a reactive cyclic amide, preferably in an analogous manner to that described under process a) for reactive derivatives of compounds of the formula II;

or a salt thereof, provided salt-forming groups are present.

A compound of the formula VIIA, in particular VIIA', is particularly preferred in which R₁ is phenyl-lower-alkoxycarbonyl, in particular is lower-alkoxycarbonyl, such as tert-butoxycarbonyl;

R₂ is cyclohexyl or, in particular, phenyl;

R₃ is 2,3,4-tri-lower-alkoxyphenyl, in particular 2,3,4-trimethoxyphenyl;

Py* is hydrogen or a hydroxyl protective group, preferably one of those specified under process a), in particular tri-lower-alkylsilyl, such as tert-butyldimethylsilyl; and E is hydroxyl or a carboxyl protective group, preferably as defined under process a), in particular lower alkoxy, such as methoxy, ethoxy or tert-butoxy, or tri-lower-alkylsilyloxy, in particular tert-butyldimethylsilyloxy, or the radical —(C═O)—E is a reactive derivative of a carboxylic group, in particular is a carboxylic group in the form of an activated ester, of a reactive anhydride or else of a reactive cyclic amide, preferably in an analogous manner to that described under process a) for reactive derivatives of compounds of the formula II; in particular is hydroxyl and lower alkoxy;

or a salt thereof, provided salt-forming groups are present.

The compound of the formula VIIA' is particularly preferred which has the designation 5(S)-(Boc-amino)-4(S)-(tert-butyldimethylsilyloxy)-6-phenyl-2(R)-[(2,3,4-trimethoxyphenyl)methyl]hexanoic acid, or a salt thereof.

The compounds of the formula VIIA and VIIA' either correspond to compounds of the formula VII and VII', respectively, and can be prepared as described above (when Py*═H, and E═OH), or can be prepared (when Py* has one of the said meanings other than hydrogen and/or E has one of the said meanings other than hydroxyl) from compounds of the formula VII and VII', respectively, by protective group introduction, for example as described in association with the introduction of Py in compounds of the formula XXI in order to prepare compounds of the formula XXII, or as described under process a), or by the preparation of reactive carboxylic acid derivatives, as described under process a).

The following applies generally to all processes mentioned above and below:

As a consequence of the close relationship between the compounds of the formula I and their salts and starting materials (starting compounds and intermediates) in free form and in the form of their salts, the free compounds and/or their salts are to be understood both above and below, as meaning, analogously and expediently, where appropriate, the corresponding salts and/or the free compounds as well.

All the above-listed process steps can be carried out under reaction conditions which are known per se, preferably under those which have been specifically specified, in the absence or, customarily, the presence of solvents or diluents, preferably those which are inert towards the reagents employed and dissolve the latter, in the absence or presence of catalysts, condensing agents or neutralizing agents, for example ion exchangers, such as cation exchangers, for example in the H⁺ form, in each case depending on the nature of the reaction and/or of the reagent, at decreased, normal or increased temperature, for example in a temperature range of from about −100° C. to about 190° C., preferably from about −80° C. to about 150° C., for example at from −80° to −60 ° C., at room temperature, at from −20° to 40° C., or at reflux temperature, under atmospheric pressure or in a closed vessel, as desired under reduced or increased pressure, in an inert atmosphere, for example under an argon or nitrogen atmosphere, and/or with the exclusion of light.

If desired, isomeric mixtures which arise in any of the reaction stages can be resolved into the individual isomers, for example diastereomers or enantiomers, or into arbitrary mixtures of isomers, for example racemates or diastereomer mixtures, for example in analogy with the methods which are described under the "additional process measures".

In certain cases, for example in the case of hydrogenations, it is possible to achieve stereoselective reactions thereby, for example, facilitating the isolation of individual isomers.

The solvents from which those can be selected which are suitable for each respective reaction include, for example, water, esters, such as lower-alkyl-lower-alkanoates, for example diethyl acetate, ethers, such as aliphatic ethers, for example diethyl ether or 1,2-dimethoxyethane, or cyclic ethers, for example tetrahydrofuran, liquid aromatic hydrocarbons, such as benzene, toluene or o-, m- or p-xylene, liquid acyclic hydrocarbons, such as hexane or heptane, alcohols, such as methanol, ethanol or 1- or 2-propanol, nitriles, such as acetonitrile, halohydrocarbons, such as methylene chloride or chloroform, acid amides, such as dimethyl formamide or dimethylacetamide, ketones, such as lower-alkanones, for example acetone, heterocyclic solvents, for example bases, such as heterocyclic nitrogen bases, for example pyridine, or 1,3-dimethyl-3,4,5,6-tetrahydro-2(1H)-pyrimidone (DMPU), carboxylic acids, such as acetic acid or formic acid, carboxylic anhydrides, such as lower-alkanoic anhydrides, for example acetic anhydride, cyclic, linear or branched hydrocarbons, such as cyclohexane, hexane or isopentane, or mixtures of these solvents, for example aqueous solutions, unless otherwise indicated in the description of the processes. Solvent mixtures of this nature can also be used in the working-up, for example by chromatography or partition.

The compounds, including their salts, may also be obtained in the form of hydrates, or their crystals may, for example, include the solvent used for the crystallization.

The working-up after reactions is carried out in accordance with methods which are known per se, preferably in analogy with the methods described in the examples.

The invention also relates to those embodiments of the process in which a compound which is obtainable as an intermediate at an arbitrary process stage is used as the starting material, and the missing process steps are then carried out, or in which a starting compound is used which is formed under the reaction conditions or is in the form of a derivative, for example in protected form or as a salt, or a compound which can be obtained in accordance with the novel process is produced under the process conditions and subjected to further processing in situ. In the process of the present invention, those starting compounds are preferably employed which lead to the compounds which were described at the outset as being particularly valuable. Reaction conditions are primarily preferred which are analogous to those specified in the examples.

Insofar as necessary or desired, protected starting compounds can be employed at all process stages, and the protective groups can be removed at suitable reaction stages.

Protective groups, their introduction and their release are as described under processes a) and f).

EXAMPLES

The following examples serve to illustrate the invention but do not, in any way, restrict its scope.

Temperatures are given in degrees centigrade (°C.).

If no temperature is given, the reactions mentioned below take place at approximately room temperature. The $R_f$ values, which indicate the ratio of the distance migrated by the particular substance to the distance migrated by the eluent front, are determined by thin layer chromatography (TLC) on silica gel thin layer plates (Merck, Darmstadt, FRG) using the following solvent systems:

TLC eluent systems:

| | TLC eluent systems | |
|---|---|---|
| A | Ethyl acetate | |
| B | Methylene chloride/methanol | 9:1 |
| C | Hexane/ethyl acetate | 1:1 |
| D | Hexane/ethyl acetate | 2:1 |
| E | Hexane/ethyl acetate | 3:1 |
| F | Methylene chloride/methanol | 12:1 |
| G | Hexane/ethyl acetate | 6:1 |
| H | Methylene chloride/THF | 2:1 |
| I | Methylene chloride/ether | 25:1 |
| J | Hexane/ethyl acetate | 1:2 |
| K | Chloroform/methanol/water/acetic acid | 85:13:1.5:0.5 |

-continued

| | TLC eluent systems: | |
|---|---|---|
| L | Methylene chloride/methanol | 10:1 |
| M | Methylene chloride/methanol | 15:1 |
| N | Ethyl acetate/methanol | 9:1 |
| O | Methylene chloride/ethanol | 10:1 |
| P | Methylene chloride/ethyl acetate/ethanol | 30:20:1 |
| Q | Toluene/ethyl acetate | 9:1 |
| R | Methylene chloride/THF | 4:1 |

The abbreviation "$R_f(A)$" means, for example, that the $R_f$ value was determined in the solvent system A. The ratio of the quantities of solvents with respect to each other is always given in parts by volume (v/v). Quantity ratios are also given in parts by volume when defining the mobile solvent systems for the column chromatography.

Part of the abovementioned letter code for TLC eluents is also used, for example, for indicating eluents in column chromatography.

Medium pressure chromatography:

Phase: LiChroprep® Si 60 (Merck, Dietikon/Switzerland); pressure: 10–15 bar.

| HPLC gradients: | |
|---|---|
| I | 20% → 100% a) into b) over 35 min |
| II | 20% → 100% a) into b) over 20 min |
| III | 5% → 40% a) into b) over 15 min |

Eluent a): acetonitrile+0.05% TFA; eluent b): water+0.05% TFA. Column (250×4.6 mm) filled with $C_{18}$-Nucleosil® reversed-phase material (silica gel, of 5 μm average particle size, which is covalently derivatized with octadecylsilanes, Macherey & Nagel, Düren, FRG). Detection by UV absorption at 215 nm. The retention times ($t_{Ret}$) are given in minutes. Flow speed, 1 ml/min.

Mass spectroscopic measurements are as a rule obtained by the fast-atom bombardment method. Unless otherwise indicated, the mass values relate to the protonated molecule ion $(M+H)^+$.

The values for IR spectra are given in $cm^{-1}$, with the relevant solvent being given in round brackets.

The abbreviations which are customary in peptide chemistry are used to designate bivalent radicals of natural α-amino acids. Provided it is known, the configuration at the α-carbon atom is indicated by prefixing with (L)- or (D)-. Glycyl which is bonded to the remainder of the molecule via the amino nitrogen and the carboxyl carbon is indicated by -[(cyclohexyl)Gly]- when it is substituted at the α-carbon atom by a cyclohexyl radical and by -[(phenyl)Gly]- when it is substituted at the α-carbon atom by a phenyl radical.

| Abbreviations: | |
|---|---|
| abs. | absolute (indicates that the solvent is anhydrous) |
| anal. calc. | calculated value for elementary analysis (theoretical value) |
| anal. found | found value for elementary analysis (actual value) |
| atm | atmosphere (1 atm corresponds to 1.013 bar) |
| Boc | tert-butoxycarbonyl |
| BOP | benzotriazol-1-yloxytris(dimethylamino)phosphonium hexafluorophosphate |

| | |
|---|---|
| TLC | thin layer chromatography |
| DCC | dicyclohexylcarbodiimide |
| dimethoxyethane | 1,2-dimethoxyethane |
| DIPE | diisopropyl ether |
| DMF | dimethylformamide |
| DMPU | 1,3-dimethyl-3,4,5,6-tetrahydro-2(1H)-pyrimidinone |
| EDC | N-ethyl-N'-(3-dimethylaminopropyl)-carbo-diimide hydrochloride |
| ether | diethyl ether |
| sat | saturated |
| h | hour(s) |
| HBTU | O-benzotriazol-1-yl-N,N,N',N'-tetra-methyluronium hexafluorophosphate |
| HOBT | 1-hydroxybenzotriazole |
| HV | high vacuum |
| min | minute(s) |
| Ms | mass spectroscopy |
| sodium sulfate | indicates disodium sulfate ($Na_2SO_4$) |
| NMM | X-methylmorpholine |
| RT | room temperature |
| RE | rotary evaporator |
| saline | saturated solution of sodium chloride |
| TEF | tetrahydrofuran |
| TBAF | tetrabutylammonium fluoride trihydrate |
| Z | benzyloxycarbonyl |

Example 1

5(S)-(Boc-amino)-4(S)-hydroxy-6-(p-benzyloxyphenyl)-2(R)-[(p-benzyloxyphenyl) methyl]hexanoyl-(L)-Val-N-(2-methoxyethyl)amide 95 mg (0.301 mmol) of TBAF are added, under a $N_2$ atmosphere, to a solution of 135 mg (0.151 mmol) of 5(S)-(Boc-amino)-4(S)-(tert-butyldimethylsilyloxy)-6-(p-benzyloxyphenyl)-2(R)-[(p-benzyloxyphenyl)methyl]-hexanoyl-(L)-Val-N-(2-methoxyethyl)amide in 1.3 ml of DMF, and the mixture is stirred at RT for 16 h. The reaction mixture is poured onto water and this mixture is extracted with 4 portions of ethyl acetate. The organic phases are washed with sat. $NaHCO_3$ solution, water and saline, dried with $Na_2SO_4$ and evaporated. Digesting twice with DIPE yields the pure title compound: $t_{Ref}(II)$=18.5 min; FAB-MS $(M+H)^+$=782.

The starting material is prepared as follows:

1a) Z-(L)-Val-N-(2-methoxyethyl)amide 19.8 g (78.8 mmol) of Z-(L)-valine in 720 ml 0.25M $NMM/CH_3CN$ are treated, under protective gas, with 7.5 ml (87.3 mmol) of 2-methoxy-ethylamine (Fluka; Buchs/Switzerland). 32.3 g (85.2 mmol) of HBTU are added to the thick, white suspension, and this mixture is thoroughly stirred at RT for 24 h. The reaction mixture is evaporated under high vacuum and the residue is taken up in ethyl acetate; the solution is extracted with water, 2×10% citric acid solution, water, 2× sat. $NaHCO_3$ solution and saline. The aqueous phases are extracted twice more with ethyl acetate, and the organic phases are dried with $Na_2SO_4$ and evaporated. Crystallization from ethyl acetate/ hexane 1:1 leads to the title compound: TLC $R_f(G)$=0.6; $t_{Ref}(II)$=11.5 min.

1b) H-(L)-Val-N-(2-methoxyethyl)amide

Hydrogenating 22.8 g (74 mmol) of Z-(L)-Val-N-(2-methoxyethyl)amide in 496 ml of methanol, at RT under low pressure and in the presence of 2.3 g of 10% Pd/C, yields, after filtering off the catalyst, evaporating the filtrate and column chromatography ($SiO_2$, methylene chloride using 2.5→5→7.5→10% methanol), the pure title compound as an oil: TLC $R_f(B)$=0.3; FAB-MS $(M+H)^+$=175; $^1$H-NMR (360 MHz, $CD_3OD$): 0.90 and 0.95 (2d, J=7 Hz, $(H_3C)_2C$), 1.9 (m, HC—$Me_2$), 3.05 (d, J=6 Hz, $HC_\alpha$), 3.32 (s, $H_3C$—O), 3.37 (m, $H_2C$), 3.44 (m, $H_2C$).

1c) 5(S)-(Boc-amino)-4(S)-(tert-butyldimethylsilyloxy)-6-(p-benzyloxyphenyl)-2(R)-[(p-benzyloxyphenyl)methyl]-hexanoyl-(L)-Val-N-(2-methoxyethyl)amide Under an $N_2$ atmosphere, 100 mg (0.135 mmol) of 5(S)-(Boc-amino)-4(S)-(tert-butyldimethylsilyloxy)-6-(p-benzyloxyphenyl)-2(R)-[(p-benzyloxyphenyl)methyl] hexanoic acid [preparation, see Example 1j)] and 26 mg (0.148 mmol) of H-(L)-Val-N-(2-methoxyethyl)amide are dissolved in 1.2 ml of 0.25M $NMM/CH_3CN$, and the solution is treated with 56.3 mg (0.148 mmol) of HBTU. After 18 h at RT, the reaction mixture is evaporated and the residue is taken up in ethyl acetate; the solution is thoroughly washed with water, 2 portions of 10% citric acid solution, water, 2 portions of sat. $NaHCO_3$ solution and, finally, saline. The inorganic phases are extracted two more times with ethyl acetate and the organic phases are dried with $Na_2SO_4$ and evaporated to give the title compound: $t_{Ref}(II)$=24.4 min; FAB-MS $(M+H)^+$=896.

1d) p-Benzyloxybenzyl iodide

A solution of 1.0 g (4.3 mmol) of 4-benzyloxybenzyl chloride (Fluka; Buchs/Switzerland) in 8 ml of acetone is stirred at RT with 3.13 g (20.9 mmol) of sodium iodide. After 90 min, a gas chromatogram of the reaction mixture indicates that the reaction is complete; the reaction mixture is therefore poured onto ether, and this mixture is washed with 10% sodium thiosulfate solution and saline. Drying the organic phase with $Na_2SO_4$, and evaporating, yields the title compound: $^1$H-NMR (200 MHz, $CDCl_3$: 4.48 (s, 2H), 5.06 (s, 2H), 6.85–6.95 (m, 2H), 7.25–7.48 (m, 7H).

1e) (S)-N-Boc-(p-Benzyloxyphenylalaninol)

37.1 g (100 mmol) of Boc-(L)-(p-benzyloxy) phenylalanine (Bachem; Bubendorf/Switzerland) in 116 ml of THF are treated, at from −5° C. to −10° C., with 15.33 ml (110 mmol) of triethylamine, and a solution of 14.36 ml (110 mmol) of isobutyl chloroformate in 70 ml of THF is added to this mixture. After stirring at RT for 0.5 h, the precipitate which has formed is filtered off with suction. The filtered reaction mixture is added dropwise to 7.57 g (200 mmol) of sodium borohydride and 44 ml of $H_2O$ (approximately 10°–15° C.), and this mixture is thoroughly stirred at RT for 3.5 h. The pH of the mixture is adjusted to 2 by adding 10% citric acid solution, and the mixture is partially evaporated on an RE. The residue is extracted with 3 portions of ethyl acetate, and the organic phases are washed with 2×2N NaOH, saline, saturated $NaHCO_3$ solution and saline, dried with $Na_2SO_4$ and evaporated; the crude product is digested in hexane to give the title compound: TLC $R_f(C)$=0.50; FAB-MS $(M+H)^+$=358.

1f) (S)-N-Boc-(p-Benzyloxyphenylalaninal)

4.76 g (37.5 mmol) of oxalyl chloride in 33.6 ml of methylene chloride are treated dropwise, at −60° C. and under a $N_2$ atmosphere, with a solution of 3.5 ml (49 mmol) of DMSO in 60 ml of methylene chloride. After the mixture has been stirred for 15 min, 8.94 g (25 mmol) of (S)-N-Boc-(p-benzyloxyphenylalaninol) in 150 ml of methylene chloride are added, and this mixture is subsequently stirred for about 25 min. 14 ml (100 mmol) of triethylamine in 30 ml of methylene chloride are then added and the mixture is stirred for 30 min. 222 ml of a 20% of a $KHSO_4$ solution and 187 ml of hexane are added, and the mixture is warmed to 0° C. The aqueous phase is separated off and extracted 2× with ethyl acetate. The organic phases are washed with saturated $NaHCO_3$ solution and saline, dried with $Na_2SO_4$ and evaporated to give the title compound: TLC $R_f(C)$=0.71; $^1$H-NMR (200 MHz, $CDCl_3$): 1.44 (s, 9H), 3.06 (d, J=6 Hz, 2H), 4.39 (m, 1H), 5.03 (s+sb, $H_2C$—O+HN), 6.86–6.98 and 7.03–7.15 (2m, each 2H), 7.30–7.48 (m, 5H), 9.62 (s, 1H).

1g) 5(S)-[1(S)-(Boc-Amino)-2-(p-benzyloxyphenyl)ethyl] dihydrofuran-2-(3H)-one (see A. E. DeCamp et al., Tetrahedron Lett. 32, 1867 (1991))

6.0 g (91.8 mmol) of Zn/Cu (preparation: see R. D. Smith, H. E. Simmons, W. E. Parham, M. D. Bhavsar, Org. Synth., Coll. Vol 5, 855 (1973)) and 9.69 ml of dimethylacetamide are added, under an $N_2$ atmosphere, to a solution of 7.7 ml (57.1 mmol) of ethyl 2-iodopropionate (Example 1k)) in 100 ml of toluene, and this mixture is subsequently stirred vigorously at RT for 1 h and at 80° C. for 4 h (→Zn homoenolate solution). In a second apparatus, a solution of 4.17 ml (14.2 mmol) of tetraisopropyl orthotitanate in 12 ml of toluene and 69 ml of methylene chloride is treated, under an $N_2$ atmosphere and while cooling slightly, with 4.41 ml (40.2 mmol) of $TiCl_4$; this mixture is stirred at RT for 15 min (results in a yellow solution) and cooled down to –40° C., resulting in trichlorotitanium isopropoxide being obtained. The Zn homoenolate solution is decanted off from the metallic solid and transferred by means of a cannula to the trichlorotitanium isopropoxide, which has been cooled down to –40° C., with the temperature being maintained at from –40° to –30° C. (deep-red solution). The solution is warmed to –25° C. for 5 min and then cooled down once again to –40° C. A solution of 9.7 g (27 mmol) of (S)-N-Boc-(p-benzyloxyphenyl)alaninal in 24.5 ml of methylene chloride is then added dropwise and the mixture is subsequently stirred at approximately –20° C. for 15 h and finally at 0° C. for 1 h. The reaction mixture is poured onto 0.4 kg of ice-water and 0.5 l of ether, and this mixture is stirred vigorously for 10 min. The aqueous phase is separated off and extracted with 2 portions of ether; the organic phases are washed with water, sat. sodium hydrogen carbonate solution, water and saline, dried with sodium sulfate and evaporated (→crystalline ethyl 5(S)-(Boc-amino)-4(S)-hydroxy-6-(p-benzyloxyphenyl)hexanoate).

The intermediate mentioned immediately above is heated in 220 ml of toluene and 6.73 ml of acetic acid at 100° C. for 2.5 h. The cooled reaction mixture is treated with 0.5 l of water, and the aqueous phase is separated off and extracted with 2 portions of ether; the org. phases are washed with sat. sodium hydrogen carbonate solution, water and saline, dried with sodium sulfate and evaporated. Crystallization of the residue from ether/hexane yields the pure title compound: TLC $R_f(E)$=0.28; $t_{Ret}(I)$=23.5 min; $^1$H-NMR (200 MHz, $CDCl_3$): 1.40 (s, 9H), 2.03–2.2 and 2.44–2.64 and 2.73–2.98 (3m, each 2H), 3.95 and 4.48 (2m, each 1H), 4.62 (d, J=9 Hz, 1H), 6.87–6.97 and 7.09–7.21 (2m, each 2H), 7.27–7.48 (m, 5H).

1h) 5(S)-[1(S)-(Boc-Amino)-2-(p-benzyloxyphenyl)ethyl]-3(R)-[(p-benzyloxyohenyl)methyl]dihydrofuran-2-(3H)-one 2.47 g (6.0 mmol) of 5(S)-[1(S)-(Boc-amino)-2-(p-benzyloxyphenyl)ethyl]dihydrofuran-2-(3H)-one dissolved in 12 ml of THF and 1.2 ml of 1,3-dimethyl-3,4,5,6-tetrahydro-2(1H)-pyrimidinone are treated, at –70° C. and under a protective gas, with 11.73 ml of a 1M solution of lithium bis(trimethylsilyl)amide in THF, and this mixture is stirred for 15 min; it is then alkylated with 1.946 g (6.0 mmol) of p-benzyloxybenzyl iodide (Example 1d) in 3 ml of THF (60 min). For hydrolysing, 2.23 ml of propionic acid and 2.23 ml of water are added and the mixture is warmed to 0° C. The reaction mixture is poured onto 30 ml of 10% citric acid solution, and this mixture is extracted twice with ethyl acetate; the organic phases are washed twice with saturated $NaHCO_3$ solution and, finally, with saline. Drying the organic phases with $Na_2SO_4$ and evaporating them, and column chromatography ($SiO_2$, hexane/ethyl acetate 4:1) of the residue, and subsequent crystallization from ethyl acetate/hexane, affords the pure title compound: TLC $R_f(D)$ =0.45; $t_{Ret}(I)$=19.9 min; FAB-MS $(M+H)^+$=608.

1i) 5(S)-(Boc-Amino)-4(S)-hydroxy-6-(p-benzyloxyphenyl)-2(R)-[(p-benzyloxyphenyl)methyl] hexanoic acid 2.7 g (4.43 mmol) of 5(S)-[1(S)-(Boc-amino)-2-(p-benzyloxyphenyl)ethyl]-3(R)-[(p-benzyloxyphenyl)methyl] dihydrofuran-2-(3H)-one in 59 ml of dimethoxyethane and 31.8 ml of water are treated, while excluding air, with 14.8 ml of a 1M lithium hydroxide solution. The mixture is then stirred at RT for 3 h and partially evaporated. The residue is poured onto a mixture of ice, 181 ml of sat. $NH_4Cl$ solution, 16.2 ml of 10% citric acid solution and 400 ml of ethyl acetate, and THF is added until the precipitated solid dissolves. The aqueous phase is separated off and extracted with 2 portions of ethyl acetate, and the organic phases are washed with saline, dried with $Na_2SO_4$, evaporated and digested in hexane: TLC $R_f(C)$=0.07.

1j) 5(S)-(Boc-Amino)-4(S)-(tert-butyldimethylsilyloxy)-6-(p-benzyloxy-phenyl)-2(R)-[(p-benzyloxyphenyl)methyl] hexanoic acid 2.44 g (3.90 mmol) of 5(S)-(Boc-amino)-4(S)-hydroxy-6-(p-benzyloxyphenyl)-2(R)-[(p-benzyloxyphenyl)methyl]-hexanoic acid in 14 ml of DMF are stirred, under an $N_2$ atmosphere, together with 2.70 g (17.6 mmol) of tert-butyldimethylchlorosilane and 2.18 g (32 mmol) of imidazole at RT for 18 h. The reaction mixture is poured onto ice-water, and this mixture is extracted with 3 portions of ethyl acetate; the organic phases are washed with 10% citric acid solution, $H_2O$ and saline, dried with $Na_2SO_4$ and evaporated. The resulting oil is taken up in 30 ml of methanol/$THF/H_2O$ 3:1:1, and this solution is treated with 3.2 g of $K_2CO_3$ and stirred at RT for 1 h. The reaction mixture is partially evaporated, and the aqueous residue is poured onto 10% citric acid solution and ice, and this mixture is extracted 3× with ethyl acetate; the organic phases are washed twice with $H_2O$ and, finally, with saline, dried with $Na_2SO_4$ and evaporated. Column chromatography ($SiO_2$, hexane/ethyl acetate 2:1→1:1) of the crude product affords the title compound: TLC $R_f(C)$=0.53; FAB-MS $(M+H)^+$=740.

1k) Ethyl 2-iodopropionate

A suspension of 170 ml of ethyl 2-bromopropionate (Fluka; Buchs/Switzedand) and 950 g of sodium iodide in 1.8 l of acetone is stirred at 60° C. for 20 h. The reaction mixture is filtered, and the filtrate is partially evaporated, with the residue being poured onto approximately 2.5 l of ether; this mixture is washed with 1.0 l of 1% sodium thiosulfate solution and, finally, saline, dried with sodium sulfate and evaporated. Distillation (83° C., 20 mbar) affords the pure title compound: MS $(M)^+$=228; $^1$H-NMR (200 MHz, $CDCl_3$): 4.17 (q, 7 Hz, 2H), 3.34 and 2.97 (2t, 7 Hz, 2× 2H), 1.28 (t, 7 Hz, 3H).

Example 2

5(S)-(Boc-Amino)-4(S)-hydroxy-6-phenyl-2(R)-[(p-cyanophenyl)methyl]-hexanoyl-(L)-Val-N-(2-methoxyethyl)amide In analogy with Example 1), 2.73 g (3.85 mmol) of 5(S)-(Boc-amino)-4(S)-(tert-butyl-dimethylsilyloxy)-6-phenyl-2(R)-[(p-cyanophenyl)methyl]-hexanoyl-(L)-Val-N-(2-methoxyethyl)amide in 90.4 ml of DMF are desilylated with 3.65 g (11.6 mmol) of TBAF, and worked up. Crystallization from methylene chloride/hexane results in the title compound: $t_{Ret}(II)$=14.0 min; FAB-MS $(M+H)^+$=595.

The starting material is prepared as follows:

2a) 5(S)-(Boc-Amino)-4(S)-(tert-butyldimethylsilyloxy)-6-phenyl-2(R)-[(p-cyanophenyl)methyl]hexanoyl-(L)-Val-N-(2-methoxyethyl)amide 2.173 g (3.93 mmol) of 5(S)-(Boc-amino)-4(S)-(tert-butyldimethylsilyloxy)-6-phenyl-2(R)-[(p-cyanophenyl)methyl]hexanoic acid [preparation, see Example 2e)], 839 mg (4.07 mmol) of DCC and 596 mg (4.41 mmol) of HOBT are added, while excluding air, to the solution of 753.2 mg (4.32 mmol) of H-(L)-Val-N-(2-methoxy-ethyl)amide (Example 1b) in 47 ml of THF. After 24 h at RT, the reaction mixture is filtered and the filtrate is evaporated. The residue is partitioned betheen 3 portions of ethyl acetate, 10% citric acid solution, sat. NaHCO$_3$ solution and saline. Drying the organic phases with Na$_2$SO$_4$, evaporating them, and stirring up the residue in DIPE yields the title compound: $t_{Ret}(II)$=20.8 min.

2b) 5(S)-[1(S)-(Boc-Amino)-2-phenylethyl]dihydrofuran-2-(3H)-one (see, also, A. E. DeCamp, A. T. Kawaguchi, R. P. Volante, and I. Shinkai, Tetrahedron Lett. 32, 1867 (1991)).

8.03 g of Zn/Cu (preparation: R. D. Smith, H. E. Simmons, W. E. Parham, M.D. Bhavsar, Org. Synth., Coll. Vol 5, 855 (1973)) and 12.96 ml of dimethylacetamide are added, under a N$_2$ atmosphere, to a solution of 17.4 g of ethyl 2-iodopropionate (Example 1k)) in 130 ml of toluene, and the mixture is subsequently stirred vigorously at RT for 1 h and at 80° C. for 4 h (→Zn homoenolate solution). In a second apparatus (N$_2$ atmosphere), a solution of 5.58 ml (18.9 mmol) of tetraisopropyl orthotitanate in 16.4 ml of toluene and 91.8 ml of methylene chloride is treated, while cooling slightly, with 5.90 ml (53.8 mmol) of titanium tetrachloride, and this mixture is stirred at RT for 15 min (→yellow solution) and cooled down to −40° C. (→partial crystallization of the trichlorotitanium isopropoxide). Using a cannula, the Zn homoenolate solution, which has been cooled down to RT, is decanted off from the metallic solid and added dropwise to the trichlorotitanium isopropoxide, with the temperature being maintained at from −400° C. to −30° C. (→deep-red solution); the mixture is warmed to −25° C. for 5 min and then cooled down once again to −40° C. A solution of 9.0 g of (S)-N-Boc-phenylalaninal (preparation: see D. J. Kempf, J. Org. Chem. 51, 3921 (1986)) in 32.8 ml of methylene chloride is subsequently added dropwise, and this mixture is stirred at approximately −20° C. for 15 h and, finally, at 0° C. for 1 h. The reaction mixture is poured onto 0.5 kg of ice-water and 0.5 l of ether, and this mixture is stirred vigorously for 10 min. The aqueous phase is separated off and extracted with 2 portions of ether, the organic phases are washed with 2 portions of water, saturated sodium hydrogen carbonate solution and saline, dried with sodium sulfate and evaporated. Crystalline ethyl 5(S)-(Boc-amino)-4(S)-hydroxy-6-phenyl hexanoate is obtained as an intermediate. This intermediate is heated at 80° C. for 2.5 h in 295 ml of toluene and 9 ml of acetic acid. The reaction mixture is treated with 0.5 l of water, and the aqueous phase is separated off and extracted with 2 portions of ether; the org. phases are washed with saturated sodium hydrogen carbonate solution, water and saline, and dried with sodium sulfate. Partial evaporation of the organic phases, and treatment with hexane, affords the crystalline title compound, approximately 10% of which consists, according to analysis, of the (5R) epimer (TLC R$_f$(E)=0.08). Cohmn chromatography (SiO$_2$, hexane/ethyl acetate 2:1) yields the pure title compound: TLC R$_f$(E)=0.14; $[\alpha]^D$=17.7° (c=1; ethanol).

2c) 5(S)-[1(S)-(Boc-Amino)-2-phenylethyl]-3(R)-[(p-cyano-phenyl)methyl]dihydrofuran-2-(3H)-one In analogy with Example 1b), 1.5 g of 5(S)-[1(S)-(Boc-amino)-2-phenylethyl]dihydrofuran-2-(3H)-one, dissolved in 32 ml of THF, are deprotonated with 9.8 ml of a 1M solution of lithium bis(trimethylsilyl)amide in THF, and alkylated with 1.0 g of 4-bromomethylbenzonitrile (Fluka; Buchs/Switzerland) dissolved in 3 ml of THF. Column chromatography (SiO$_2$, hexane/ethyl acetate 1:1) affords the pure title compound: TLC R$_f$(D)=0.33.

2d) 5(S)-(Boc-Amino)-4(S)-hydroxy-6-phenyl-2(R)-[(p-cyanophenyl)methyl]hexanoic acid In analogy with Example 1i), 0.50 g of 5(S)-[1(S)-(Boc-amino)-2-phenylethyl]-3(R)-[(p-cyanophenyl)methyl] dihydrofuran-2-(3H)-one in 19 ml of dimethoxyethane and 10 ml of water is hydrolysed with 4.8 ml of a 1M lithium hydroxide solution to form the title compound: TLC R$_f$(B)=0.3.

2e) 5(S)-(Boc-Amino)-4(S)-(tert-butyldimethylsilyloxy)-6-phenyl-2(R)-[(p-cyano-phenyl)methyl]hexanoic acid In analogy with Example 1j), 0.62 g of 5(S)-(Boc-amino)-4(S)-hydroxy-6-phenyl-2(R)-[(p-cyano-phenyl)methyl] hexanoic acid in 6.2 ml of DMF is silylated with 0.98 g of tert-butyldimethylchlorosilane and 0.79 g of imidazole. Hydrolysis of the silyl ester function with 1.2 g of potassium carbonate in 31 ml of methanol/THF/water, 3:1:1, yields the title compound, after acidifying with citric acid solution and extracting with ethyl acetate: TLC R$_f$(D)=0.29; FAB-MS (M+H)$^+$=553.

Example 3

5(S)-(Boc-Amino)-4(S)-hydroxy-6-phenyl-2(R)-[(o-fluorophenyl)methyl]hexanoyl-(L)-Val-N-(2-methoxyethyl)amide In analogy with Example 1), 184.9 mg (0.263 mmol) of 5(S)-(Boc-amino)-4(S)-(tert-butyldimethylsilyloxy)-6-phenyl-2(R)-[(o-fluorophenyl)methyl]hexanoyl-(L)-Val-N-(2-methoxyethyl)amide in 5 ml of DMF are desilylated with 249.3 mg (0.79 mmol) of TBAF, and worked up. Stirring-up with DIPE affords the title compound: $t_{Ret}(II)$=14.8 min; FAB-MS (M+H)$^+$=588.

The starting material is prepared as follows:
3a) 5(S)-(Boc-Amino)-4(S)-(tert-butyldimethylsilyloxy)-6-phenyl-2(R)-[(o-fluorophenyl)methyl]hexanoyl-(L)-Val-N-(2-methoxyethyl)amide 168.9 mg (0.309 mmol) of 5(S)-(Boc-amino)-4(S)-(tert-butyldimethylsilyloxy)-6-phenyl-2(R)-[(o-fluorophenyl) methyl]-hexanoic acid [preparation, see Example 3d)], 77.1 mg (0.374 mmol) of DCC and 45.5 mg (0.337 mmol) of HOBT are added, under protective gas, to the solution of 59.3 mg (0.34 mmol) of H-(L)-Val-N-(2-methoxyethyl) amide (Example 1b) in 3.5 ml of THF. After 24 h at RT, the reaction mixture is filtered and the filtrate is evaporated. Partitioning the residue between 3 portions of ethyl acetate, 10% citric acid solution, sat. NaHCO$_3$ solution and saline, drying the organic phases with Na$_2$SO$_4$, and evaporating them, yields the title compound: $t_{Ret}(II)$=22.3 min.

3b) 5(S)-[1(S)-(Boc-Amino)-2-phenylethyl]-3(R)-[(o-fluorolphenyl)methyl]dihydrofuran-2-(3H)-one In analogy with Example 1h), 5.0 g (16.37 mmol) of 5(S)-[1(S)-(Boc-amino)-2-phenylethyl]dihydrofuran-2-(3H)-one [Example 2b)] dissolved in 75 ml of THF are deprotonated, at −75° C., with 32.7 ml of a 1M solution of lithium bis(trimethylsilyl)amide in THF, and alkylated with 2.1 ml (18.0 mmol) of o-fluorobenzyl bromide (Fluka; Buchs/Switzerland) at −75° C. initially (heating to a maximum of −60° C. over a period of 60 min). Column chromatography (SiO$_2$, hexane/ethyl acetate, 3:1) affords the title compound: TLC R$_f$(D)=0.61.

3c) 5(S)-(Boc-Amino)-4(S)-hydroxy-6-phenyl-2(R)-[(o-fluorophenyl)methyl]hexanoic acid In analogy with Example 1i), 4.5g (10.8 mmol) of 5(S)-[1(S)-(Boc-amino)-2-phenylethyl]-3(R)-[(o-fluorophenyl)methyl]dihydrofuran-2-(3H)-one in 170 ml of dimethoxyethane are hydrolysed with 43.5 ml of a 1M lithium hydroxide solution. The evaporation residue of the reaction mixture is poured onto a mixture of ice, 120 ml of sat. ammonium chloride solution and 240 ml of 10% citric acid solution, and this mixture is then extracted with 3 portions of methylene chloride. The organic phases are washed with water and saline, dried over $Na_2SO_4$ and evaporated: $t_{Ref}$(II)=14.5 min.

3d) 5(S)-(Boc-Amino)-4(S)-(tert-butyldimethylsilyloxy)-6-phenyl-2(R)-[(o-fluorophenyl)methyl]hexanoic acid In analogy with Example 1j), 1.5 g (3.47 mmol) of 5(S)-(Boc-amino)-4(S)-hydroxy-6-phenyl-2(R)-[(o-fluorophenyl)methyl]hexanoic acid in 15 ml of DMF are silylated with 2.4 g (16 mmol) of tert-butyldimethylchlorosilane and 1.95 g (28.5 mmol) of imidazole. Hydrolysis of the silyl ester function with 2.8 g of potassium carbonate in 50 ml of methanol/THF/water, 4:1:1, yields the title compound after column chromatography ($SiO_2$, hexane/ethyl acetate, 2:1): TLC $R_f$(D)=0.33; $t_{Ref}$(II)=20.7 min.

Example 4

5(S)-(Boc-Amino)-4(S)-hydroxy-6-phenyl-2(R)-[(2,4-difluorophenyl)methyl]hexanoyl-(L)-Val-N-(2-methoxyethyl)amide In analogy with Example 1), 197 mg (0.274 mmol) of 5(S)-(Boc-amino)-4(S)-(tert-butyldimethylsilyloxy)-6-phenyl-2(R)-[(2,4-difluorophenyl)methyl]hexanoyl-(L)-Val-N-(2-methoxyethyl)amide in 5 ml of DMF are desilylated with 173 mg (0.548 mmol) of TBAF, and worked up. Precipitating with DIPE from a concentrated solution in methylene chloride yields the title compound: TLC $R_f$(A)=0.71; $t_{Ref}$(II)=14.9 min; FAB-MS (M+H)$^+$=606.

The starting material is prepared as follows:

4a) 5(S)-(Boc-Amino)-4(S)-(tert-butyldimethylsilyloxy)-6-phenyl-2(R)-[(2,4-difluorophenyl)methyl]hexanoyl-(L)-Val-N-(2-methoxyethyl)amide 68 mg (0.39 mmol) of H-(L)-Val-N-(2-methoxyethyl)amide (Example 1b), 80.5 mg (0.39 mmol) of DCC and 57.5 mg (0.426 mmol) of HOBT are added, under an $N_2$ atmosphere, to 200 mg (0.354 mmol) of 5(S)-(Boc-amino)-4(S)-(tert-butyldimethylsilyloxy)-6-phenyl-2(R)-[(2,4-difluorophenyl)methyl]hexanoic acid [preparation, see Example 4d)] in 4.6 ml of THF. After 19 h at RT, the mixture is worked up, in analogy with Example 3a) to give the title compound: TLC $R_f$(D)=0.14; $t_{Ref}$(II)=21.7 min.

4b) 5(S)-[1(S)-(Boc-Amino)-2-phenylethyl]-3(R)-[(2,4-difluorophenyl)methyl]dihydrofuran-2-(3H)-one In analogy with Example 1h), 5.0 g (16.37 mmol) of 5(S)-[1(S)-(Boc-amino)-2-phenylethyl]dihydrofuran-2-(3H)-one [Example 2b)] dissolved in 100 ml of THF are deprotonated, at −75° C., with 32.7 ml of a 1M solution of lithium bis(trimethylsilyl)amide in THF, and alkylated with 2.51 ml (19.6 mmol) of 2,4-difluorobenzyl bromide (Aldrich; Milwaukee/U.S.A.) at −75° C. initially (heating to a maximum of −60° C. over a period of 2 h). Column chromatography ($SiO_2$, hexane/ethyl acetate, 2:1) affords the title compound: TLC $R_f$(D)=0.5; $t_{Ref}$(II)=17.2 min.

4c) 5(S)-(Boc-Amino)-4(S)-hydroxy-6-phenyl-2(R)-[(2,4-difluorophenyl)methyl]hexanoic acid In analogy with Example 1i), 3.1 g (7.18 mmol) 5(S)-[1(S)-(Boc-amino)-2-phenyl-ethyl]-3(R)-[(2,4-difluorophenyl)methyl]dihydrofuran-2-(3H)-one in 77 ml of dimethoxyethane and 19 ml of water are hydrolysed with 28.7 ml of a 1M lithium hydroxide solution (19 h at RT) to give the title compound: $t_{Ref}$(II)=14.7 min.

4d) 5(S)-(Boc-Amino)-4(S)-(tert-butyldimethylsilyloxy)-6-phenyl-2(R)-[(2,4-difluorophenyl)methyl]hexanoic acid In analogy with Example 1j), 3.2 g (7.12 mmol) of 5(S)-(Boc-amino)-4(S)-hydroxy-6-phenyl-2(R)-[(2,4-difluorophenyl)methyl]hexanoic acid in 67 ml of DMF are silylated with 4.93 g (32.7 mmol) of tert-butyldimethylchlorosilane and 3.97 g (58.4 mmol) of imidazole. Hydrolysis of the silyl ester function with 5.9 g of potassium carbonate in 77 ml of methanol, 20 ml of THF and 20 ml of water yields the title compound after column chromatography ($SiO_2$, hexane/ethyl acetate, 2:1): TLC $R_f$(D)=0.22; $t_{Ref}$(II)=20.8 min.

Example 5

5(S)-(Boc-Amino)-4(S)-hydroxy-6-phenyl-2(R)-{[p-(2-phenyl-ethyl)phenyl]methyl}-hexanoyl-(L)-Val-N-(2-methoxyethyl)amide In analogy with Example 1), 115 mg (0.146 mmol) of 5(S)-(Boc-amino)-4(S)-(tert-butyldimethylsilyloxy)-6-phenyl-2(R)-{[p-(2-phenylethyl)phenyl]-methyl}-hexanoyl-(L)-Val-N-(2-methoxyethyl)amide in 2.1 ml of DMF are desilylated with 92 mg (0.292 mmol) of TBAF, and extracted: TLC $R_f$(A)=0.58; $t_{Ref}$(II)=18.1 min.

The starting materials are prepared as follows:

5a) 5(S)-(Boc-Amino)-4(S)-(tert-butyldimethylsilyloxy)-6-phenyl-2(R)-{[p-(2-phenylethyl)phenyl]methyl}hexanoyl-(L)-Val-N-(2-methoxyethyl)amide Under an $N_2$ atmosphere, 100 mg (0.158 mmol) of 5(S)-(Boc-amino)-4(S)-(tert-butyldimethylsilyloxy)-6-phenyl-2(R)-{[p-(2-phenylethyl)phenyl]methyl}hexanoic acid (Example 5f) and 30 mg (0.174 mmol) of H-(L)-Val-N-(2-methoxyethyl)amide (Example 1b) are dissolved in 1.52 ml of 0.25M NMM/$CH_3CN$, and this solution is treated with 66 mg (0.174 mmol) of HBTU. After 18 h at RT, the reaction mixture is poured onto water, and this mixture is extracted with 3 portions of ethyl acetate. The organic phases are washed with 10% citric acid solution, water, sat. $NaHCO_3$ solution, water and saline, dried with $Na_2SO_4$ and evaporated: $t_{Ref}$(II)=24.4 min.

5b) p-(2-Phenylethyl)benzyl alcohol

Hydrogenating 10 g (48 mmol) of 4-stilbenemethanol (Aldrich; Milwankee/U.S.A.) in 100 ml of THF, in the presence of 0.5 g of 5% Pd/C under low pressure and at RT, filtering through ®Celite (filtering aid based on kieselguhr, Johns-Manville Corp., obtainable from Fluka, Buchs, Switzerland) and evaporating the filtrate affords the title compound, approximately 15% of which, according to the $^1$H-NMR spectrum, consists of p-(2-phenylethyl)toluene: TLC $R_f$(A)=0.62; $^1$H-NMR (200 MHz, $CDCl_3$): 2.92 (s, 4H), 4.68 (s, 2H), 7.15–7.35 (m, 9H).

5c) p-(2-Phenylethyl)benzyl bromide 3.14 ml (33.4 mmol) of phosphorus tribromide in 11 ml of toluene are added dropwise, while cooling and under an $N_2$ atmosphere, to 8.36 g (85%; 33.4 mmol) of p-(2-phenylethyl)benzyl alcohol in 100 ml of toluene. After 2 h at RT, the mixture is poured onto ice-water and the organic phase is separated off; it is washed with sat. $NaHCO_3$ solution, water and saline. The aqueous phases are extracted 2× with ether, and the combined organic phases are dried with $Na_2SO_4$ and evaporated: TLC $R_f$(A)=0.77; $^1$H-NMR (200 MHz, $CDCl_3$): 2.92 (s, 4H), 4.50 (s, 2H), 7.15–7.35 (m, 9H; additional signals of approximately 20% p-(2-phenylethyl)toluene.

5d) 5(S)-[1(S)-(Boc-Amino)-2-phenylethyl]-3(R)-{[p-(2-phenylethyl)phenyl]methyl}dihydrofuran-2-(3H)-one A solution of 4.4 g (14.53 mmol) of 5(S)-[1(S)-(Boc-amino)-2-phenylethyl]dihydrofuran-2-(3H)-one [preparation, see Example 2b)] in 21.4 ml of abs. THF and 2.4 ml of DMPU is treated, at −75° C. and under an $N_2$ atmosphere, with 28 ml of a 1M solution of lithium bis(trimethylsilyl)amide in THF (Aldrich, Steinheim, FRG), and the mixture is subsequently stirred at this temperature for 15 min. A solution of 6.0 g (approximately 80%, 17.5 mmol) of p-(2-phenylethyl)benzyl bromide in 5.4 ml of abs. THF is then added dropwise, and this mixture is thoroughly stirred at −70° C. for 30 min. 5.4 ml of propionic acid are then added at −75° C., followed by 5.4 ml of water. The mixture is warmed to 0° C. and diluted with 150 ml of ethyl acetate; this mixture is then washed with 80 ml of a 10% solution of citric acid, with sat. sodium bicarbonate solution and with saline. The aqueous phases are reextracted 2× with ethyl acetate, and the organic phases are dried over sodium sulfate and evaporated. Column chromatography ($SiO_2$, hexane/ethyl acetate, 3:1) yields the pure title compound: TLC $R_f(E)$=0.27; $t_{Ret}(II)$=20.8 min; FAB-MS (M−Buten+H)$^+$=444.

5e) 5(S)-(Boc-Amino)-4(S)-hydroxy-6-phenyl-2(R)-{[p-(2-phenylethyl)phenyl]methyl}hexanoic acid 5.15 g (10.31 mmol) of 5(S)-[1(S)-(Boc-amino)-2-phenylethyl]-3(R)-{[p-(2-phenylethyl)phenyl]methyl}dihydrofuran-2-(3H)-one in 166 ml of dimethoxyethane and 85 ml of water are hydrolysed, under protective gas, with 41 ml of a 1M lithium hydroxide solution. After 3 h, the dimethoxyethane is evaporated off on an RE, and the residue is treated with an ice-cold mixture of 506 ml of sat. $NH_4Cl$ solution, 42 ml of 10% citric acid solution and 207 ml of methylene chloride. Methanol is added to dissolve the product completely. The aqueous phase is separated off and extracted 2× with methylene chloride/methanol, 10:1. The organic phases are washed with saline, dried with $Na_2SO_4$ and evaporated: $t_{Ret}(II)$=17.8 min.

5f) 5(S)-(Boc-Amino)-4(S)-(tert-butyldimethylsilyloxy)-6-phenyl-2(R)-{[p-(2-phenylethyl)phenyl]methyl}hexanoic acid 5.08 g (9.81 mmol) of 5(S)-(Boc-Amino)-4(S)-hydroxy-6-phenyl-2(R)-{[p-(2-phenylethyl)phenyl]methyl}hexanoic acid in 22 ml of DMF are silylated, under a protective gas, with 6.80 g (45.1 mmol) of tert-butyldimethylchlorosilane and 5.48 g (80.4 mmol) of imidazole at RT for 20 h. The reaction mixture is poured onto 500 ml of ice-water, and this mixture is extracted 3× with ethyl acetate. The organic phases are washed with 10% citric acid solution, 2× water and saline, dried with $Na_2SO_4$ and evaporated. The residue is dissolved in 119 ml of methanol and 46 ml of THF, and this solution is treated with 8.1 g of potassium carbonate and 46 ml of water, and then stirred at RT for 17 h. The reaction mixture is subsequently poured onto ice-cold 10% citric acid solution, and this mixture is extracted 3× with ethyl acetate. The organic phases are washed with 2 portions of water and saline, dried with $Na_2SO_4$ and evaporated. Column chromatography ($SiO_2$, hexane/ethyl acetate 2:1→1:1→ethyl acetate) results in the pure title compound: TLC $R_f(D)$=0.22; $t_{Ret}(II)$=23.3 min.

Example 6

5(S)-(Boc-Amino)-4(S)-hydroxy-6-phenyl-2(R)-{[p-(2,6-dichlorobenzylsulfonyl)phenyl]methyl}hexanoyl-(L)-Val-N-(2-methoxyethyl)amide In analogy with Example 1), 241 mg (0.27 mmol) of 5(S)-(Boc-amino)-4(S)-(tert-butyldimethylsilyloxy)-6-phenyl-2(R)-{[p-(2,6-dichlorobenzylsulfonyl)phenyl]methyl}hexanoyl-(L)-Val-N-(2-methoxyethyl)amide are deprotected with 170 mg (0.54 mmol) of TBAF in 3.6 ml of DMF over a period of 17 h. Stirring up in a little ethyl acetate, adding DIPE and filtering off results in the pure title compound: TLC $R_f(B)$=0.67; $t_{Ret}(II)$=16.1 min; FAB-MS (M+H)$^+$=792.

The starting material is prepared as follows:

6a) 5(S)-[1(S)-(Boc-Amino)-2-phenylethyl]-3(R)-{[p-(2,6-dichlorobenzylsulfonyl)phenyl]methyl}dihydrofuran-2-(3H)-one In analogy with Example 5d), 5.0 g (16.34 mmol) of 5(S)-[1(S)-(Boc-amino)-2-phenylethyl]dihydrofuran-2-(3H)-one, dissolved in 24 ml of abs. THF and 2.7 ml of DMPU, are deprotonated, at −75° C., with 32.7 ml of a 1M solution of lithium bis(trimethylsilyl)amide in THF, and alkylated, at −75° C., with 9.67 g (24.5 mmol) of p-(2,6-dichlorobenzylsulfonyl)benzyl bromide (Maybridge; Tintagel/UK) in 50 ml of abs. THF. Protonation, at −75° C., with 6.1 ml (81.7 mmol) of propionic acid and 6.1 ml of water, extraction and column chromatography ($SiO_2$, hexane/ethyl acetate, 2:1) of the crude product, and crystallization from DIPE, affords the title compound: TLC $R_f(D)$=0.30; $t_{Ret}(II)$=17.3 min.

6b) 5(S)-(Boc-Amino)-4(S)-hydroxy-6-phenyl-2(R)-{[p-(2,6-dichlorobenzylsulfonyl)phenyl]methyl}hexanoic acid In analogy with Example 5e), 6.7 g (10.83 mmol) of 5(S)-[1(S)-(Boc-amino)-2-phenylethyl]-3(R)-{[p-(2,6-dichlorobenzylsulfonyl)phenyl]methyl}dihydrofuran-2-(3H)-one in 170 ml of dimethoxyethane are hydrolysed with 43.3 ml of a 1M lithium hydroxide solution (RT, 17 h). Partitioning between 3× methylene chloride, $NH_4Cl$/citric acid solution and saline, and stirring the crude product in ether, affords the title compound: $t_{Ret}(II)$=15.5 min.

6c) 5(S)-(Boc-Amino)-4(S)-(tert-butyldimethylsilyloxy)-6-phenyl-2(R)-{[p-(2,6-dichlorobenzylsulfonyl)phenyl]methyl}hexanoic acid In analogy with Example 5f), 5.0 g (7.85 mmol) of 5(S)-(Boc-amino)-4(S)-hydroxy-6-phenyl-2(R)-{[p-(2,6-dichlorobenzylsulfonyl)phenyl]methyl}hexanoic acid in 74 ml of DMF are silylated with 5.4 g (36.1 mmol) of tert-butyldimethylchlorosilane and 4.4 g (64.4 mmol) of imidazole. Hydrolysis of the silyl ester function with 6.5 g of potassium carbonate in 85 ml of methanol, 22 ml of THF and 22 ml of water yields the title compound after column chromatography ($SiO_2$, hexane/ethyl acetate, 1:1) and stirring-up with DIPE: TLC $R_f(C)$=0.5; $t_{Ret}(II)$=21.0 min.

6d) 5(S)-(Boc-Amino)-4(S)-(tert-butyldimethylsilyloxy)-6-phenyl-2(R)-{[p-(2,6-dichlorobenzylsulfonyl)phenyl]methyl}hexanoyl-(L)-Val-N-(2-methoxyethyl)amide 200 mg (0.27 mmol) of 5(S)-(Boc-amino)-4(S)-tert-butylidimethylsilyloxy)-6-phenyl-2(R)-{[p-(2,6-dichlorobenzylsulfonyl)phenyl]-methyl}hexanoic acid and 51.7 mg (0.297 mmol) of H-(L)-Val-N-(2-methoxyethyl)amide (Example 1b), dissolved in 2.6 ml of a 0.25M solution of NMM in $CH_3CN$, are reacted, at RT for 18 h under a nitrogen atmosphere, with 112.6 mg (0.297 mmol) of HBTU and subsequently worked up, in analogy with Example 5a), to give the title compound: TLC $t_{Ret}(D)$=0.21; $t_{Ret}(II)$=21.9 min.

Example 7

5(S)-(Boc-Amino)-4(S)-hydroxy-6-(p-benzyloxyphenyl)-2(R)-[(p-methoxyphenyl)methyl]hexanoyl-(L)-Val-N-(2-methoxyethyl)amide 1.11 g (1.35 mmol) of 5(S)-(Boc-amino)-4(S)-(tert-butyldimethylsilyloxy)-6-(p-benzyloxy-phenyl)-2(R)-[(p- methoxy-phenyl)methyl]hexanoyl-(L)-Val-N-(2-methoxyethyl)amide in 15 ml DMF are desilylated, under an N$_2$ atmosphere, with 0.85 g (2.70 mmol) of TBAF. After 18 h at RT, the reaction mixture is poured onto water, and this mixture is extracted with methylene chloride. The organic phases are washed with sat. NaHCO$_3$ solution and saline, dried with Na$_2$SO$_4$ and evaporated. Stirring-up in DIPE yields the tire compound: TLC R$_f$(B)=0.6; t$_{Ref}$(II)=16.6 min; FAB-MS (M+H)$^+$=706.

7a) 5(S)-[1(S)-(Boc-Amino)-2-(p-benzyloxyphenyl)ethyl]-3(R)-[(p-methoxyphenyl)methyl]dihydrofuran-2-(3H)-one In analogy with Example 5d), 2.9 g (7.04 mmol) of 5(S)-[1(S)-(Boc-amino)-2-(p-benzyloxy-phenyl)ethyl] dihydrofuran-2-(3H)-one [preparation, see Example 1g)], dissolved in 10.3 ml of THF and 1.2 ml of DMPU, are deprotonated, at −70° C., with 14.1 ml of a 1M solution of lithium bis(trimethylsilyl)amide in THF, and alkylated (at from −75° C. to −50° C.), with 2.6 g (10.57 mmol) of p-methoxybenzyl iodide [preparation, see Example 7e)] in 10 ml of THF. Protonation, at −75° C., with 2.6 ml (35.2 mmol) of propionic acid and 2.6 ml of water, extraction and column chromatography (SiO$_2$, hexane/ethyl acetate, 2:1) affords the title compound: TLC R$_f$(D)=0.48; t$_{Ref}$(II)=18.8 min.

7b) 5(S)-(Boc-Amino)-4(S)-hydroxy-6-(p-benzyloxyphenyl)-2(R)-[(p-methoxyphenyl)methyl] hexanoic acid 2.6 g (4.89 mmol) of 5(S)-[1(S)-(Boc-amino)-2-(p-benzyloxy-phenyl)-ethyl]-3(R)-[(p-methoxyphenyl)methyl] dihydrofuran-2-(3H)-one in 50 ml of dimethoxyethane are hydrolysed, under an N$_2$ atmosphere, with 19.6 ml of a 1M lithium hydroxide solution in water. After 25 h at RT, the dimethoxyethane is evaporated off on a RE, and the residue is treated with an ice-cold mixture of 150 ml of sat. NH$_4$Cl solution, 25 ml of 10% citric acid solution and methylene chloride. The aqueous phase is separated off and extracted 2× with methylene chloride. The organic phases are washed with saline, dried with Na$_2$SO$_4$ and evaporated to give the title compound: TLC R$_f$(B)=0.28; t$_{Ref}$(II)=16.4 min.

7c) 5(S)-(Boc-Amino)-4(S)-(tert-butyldimethylsilyloxy)-6-(p-benzyloxyphenyl)-2(R)-[(p-methoxyphenyl)methyl] hexanoic acid 2.5 g (4.54 mmol) of 5(S)-(Boc-amino)-4(S)-hydroxy-6-(p-benzyloxy-phenyl)-2(R)-[(p-methoxyphenyl)methyl] hexanoic acid in 42 ml of DMF are silylated, under a protective gas, with 3.15 g (20.9 mmol) of tert-butyldimethylchlorosilane and 2.53 g (37.3 mmol) of imidazole at RT for 20 h. The reaction mixture is diluted with ethyl acetate, and this mixture is washed with sat. NaHCO$_3$ solution, water and saline. The aqueous phases are exitacted 2× with ethyl acetate, and the organic phases are dried with Na$_2$SO$_4$ and evaporated. The residue is dissolved in 50 ml of methanol and 13 ml of THF, and this solution is treated with 3.8 g of potassium carbonate and 13 ml of water, and stirred at RT for 1 h. Subsequently, the reaction mixture is partially evaporated and the residue is diluted with ice-cold 10% citric acid solution; this mixture is then extracted 3× with ethyl acetate. The organic phases are washed with 2 portions of water and saline, dried with Na$_2$SO$_4$ and evaporated. Column chromatography (SiO$_2$, hexane/ethyl acetate, 2:1) results in the pure title compound: TLC R$_f$(C)=0.13; t$_{Ref}$(II)=21.7 min.

7d) 5(S)-(Boc-Amino)-4(S)-(tert-butyldimethylsilyloxy)-6-(p-benzyloxyphenyl)-2(R)-[(p-methoxyphenyl)methyl] hexanoyl-(L)-Val-N-(2-methoxyethyl)amide 960 mg (1.44 mmol) of 5(S)-(Boc-amino)-4(S)-(tert-butyldimethylsilyloxy)-6-(p-benzyloxy-phenyl)-2(R)-[(p-methoxy-phenyl)methyl]hexanoic acid and 290 mg (1.66 mmol) of H-(L)-Val-N-(2-methoxyethyl)amide (Example 1b) in 14.5 ml of 0.25M NMM/CH$_3$CN are reacted, at RT for 20 h and under an N$_2$ atmosphere, with 630 mg (1.66 mmol) of HBTU. The mixture is evaporated and the residue is taken up in ethyl acetate; the solution is washed in turn with water, 2× with 10% citric acid solution, once again with water, 2× with saturated NaHCO$_3$ solution, water and saline. The aqueous phases are extracted twice more with ethyl acetate, and the organic phases are dried with Na$_2$SO$_4$ and evaporated. Digesting the crude product in hexane results in the title compound: TLC R$_f$(B)=0.70; t$_{Ref}$(II)=22.5 min.

7e) p-Methoxybenzyl iodide

A solution of 1.7 ml (12.8 mmol) of 4-methoxybenzyl chloride (Fluka; Buchs/Switzerland) in 25 ml of acetone is stirred, at RT, together with 9.4 g (62.6 mmol) of sodium iodide. A gas chromatogram of the reaction mixture, carried out after 90 min, indicates that the reaction is complete; the reaction mixture is therefore poured onto ether and this mixture is washed with 10% sodium thiosulfate solution and saline. Drying the organic phase with Na$_2$SO$_4$, and evaporating it, affords the title compound: $^1$H-NMR (200 MHz, CD$_3$OD: 3.78 (s, 3H), 4.54 (s, 2H), 6.8–6.95 and 7.2–7.4 (2m, each 2H).

Example 8

5(S)-(Boc-Amino)-4(S)-hydroxy-6-(p-hydroxyphenyl)-2(R)-[(p-methoxyphenyl)methyl] hexanoyl-(L)-Val-N-(2-methoxyethyl)amide Hydrogenating 500 mg (0.703 mmol) of 5(S)-(Boc-amino)-4(S)-hydroxy-6-(p-benzyloxyphenyl)-2(R)-[(p-methoxyphenyl)methyl]hexanoyl-(L)-Val-N-(2-methoxyethyl)amide (Example 7) under low pressure in 33 ml of methanol in the presence of 0.11 g of 10% Pd/C yields the title compound, after filtration, evaporation of the filtrate and digestion with DIPE: TLC R$_f$(B)=0.53; t$_{Ref}$(II)=12.2 min; FAB-MS (M+H)$^+$=616.

Example 9

5(S)-(Boc-Amino)-4(S)-hydroxy-6-(p-methoxyphenyl)-2(R)-[(p-methoxyphenyl)methyl] hexanoyl-(L)-Val-N-(2-methoxyethyl)amide 100 mg (0.162 mmol) of 5(S)-(Boc-amino)-4(S)-hydroxy-6-(p-hydroxy-phenyl)-2(R)-[(p-methoxyphenyl) methyl]hexanoyl-(L)-Val-N-(2-methoxyethyl)amide (Example 8) in 3 ml of DMF/dioxane, 1:1, are treated, at 0° C. and under an N$_2$ atmosphere, with 105 mg (0.324 mmol) of Cs$_2$CO$_3$ and 10.1 μl (0.162 mmol) of methyl iodide, and the mixture is stirred at RT for 20 h. For the working-up, the reaction mixture is poured onto water, and this mixture is extracted with 3 portions of methylene chloride. The organic phases are washed with water and saline, dried with Na$_2$SO$_4$ and evaporated. Stirring up in DIPE in an ultrasonication bath yields the title compound: TLC R$_f$(B)=0.62; t$_{Ref}$(II)= 14.2 min; FAB-MS (M+H)$^+$=630.

Example 10

5(S)-(Boc-Amino)-4(S)-hydroxy-6-(p-(isobutoxy)-phenyl)-2(R)-[(p-methoxyphenyl)methyl]hexanoyl-(L)-Val-N-(2-methoxyethyl)amide 100 mg (0.162 mmol) of 5(S)-(Boc-amino)-4(S)-hydroxy-6-(p-hydroxyphenyl)-2(R)-[(p-methoxyphenyl) methyl]hexanoyl-(L)-Val-N-(2-methoxyethyl)amide (Example 8) in 3 ml of DMF/dioxane, 1:1, are treated, at 0° C. and under protective gas, with 105 mg (0.324 mmol) of $Cs_2CO_3$ and 18.7 μl (0.162 mmol) of isobutyl iodide, and this mixture is stirred at 50° C. for 16 h. Since HPLC indicates that starting material is still present, 5 equivalents of isobutyl iodide and 10 equivalents of $Cs_2CO_3$ are added in portions. After each portion, the mixture is stirred at 50° C. for 1 day until HPLC indicates that all the 5(S)-(Boc-amino)-4(S)-hydroxy-6-(p-hydroxyphenyl)-2(R)-[(p-methoxyphenyl)methyl]hexanoyl-(L)-Val-N-(2-methoxyethyl)amide has reacted. Working up in analogy with Example 9 affords the title compound: TLC $R_f(B)$= 0.76; $t_{Ret}(II)$=16.8 min; FAB-MS $(M+H)^+$=672.

Example 11

5(S)-(Boc-Amino)-4(S)-hydroxy-6-(p-methoxyphenyl)-2(R)-(phenylmethyl)hexanoyl-(L)-Val-N-(2-methoxyethyl)amide 2.07 g (2.90 mmol) of 5(S)-(Boc-amino)-4(S)-(tert-butyldimethylsilyloxy)-6-(p-methoxyphenyl)-2(R)-(phenylmethyl)hexanoyl-(L)-Val-N-(2-methoxyethyl)amide in 50 ml of DMF are desilylated, under an $N_2$ atmosphere, with 1.83 g (5.80 mmol) of TBAF. After 18 h, the reaction mixture is poured onto water, and this mixture is extracted with 4 portions of ethyl acetate. The organic phases are washed with sat. $NaHCO_3$ solution, water and saline, dried with $Na_2SO_4$ and evaporated. Digesting twice with DIPE yields the title compound: $t_{Ret}(II)$=14.2 min; FAB-MS $(M+H)^+$=600.

The starting material is prepared as follows:

11a) 5(S)-[1(S)-(Boc-Amino)-2-(p-methoxyphenyl)ethyl]dihydrofuran-2-(3H)-one

A suspension of 4.00 g (12.44 mmol) of 5(S)-[1(S)-(Boc-amino)-2-(p-hydroxyphenyl)ethyl]dihydrofuran-2-(3H)-one (Example 11f) in 240 ml of DMF/dioxane, 1:1, is reacted, under an $N_2$ atmosphere, with 8.1 g (24.88 mmol) of $Cs_2CO_3$ and 0.77 ml (12.44 mmol) of methyl iodide. After 18 h, the reaction mixture is poured onto 190 ml of ice-water, and this mixture is extracted 3× with methylene chloride. The organic phases are washed with water and saline, dried with $Na_2SO_4$ and evaporated. Stirring with hexane in an ultrasonication bath affords the title compound: TLC $R_f(C)$=0.43; $t_{Ret}(II)$=13.5 min; FAB-MS $(M+H)^+$=336.

11b) 5(S)-[1(S)-(Boc-Amino)-2-(p-methoxyphenyl)ethyl]-3(R)-(phenylmethyl)dihydrofuran-2-(3H)-one In analogy with Example 5d), 4.17 g (12.44 mmol) of 5(S)-[1(S)-(Boc-amino)-2-(p-methoxyphenyl)ethyl]dihydrofuran-2-(3H)-one, dissolved in 22.4 ml of THF and 2.5 ml of DMPU, are deprotonated, at −70° C., with 24 ml of a 1M solution of lithium bis(trimethylsilyl)amide in THF, and alkylated (−75° C., 1 h) with 1.5 ml (12.44 mmol) of benzyl bromide. Protonation, at −75° C., with 4.6 ml of propionic acid and 4.6 ml of water, extraction and column chromatography ($SiO_2$, methylene chloride/ether 25:1) yields the title compound: TLC $R_f(C)$=0,74; $t_{Ret}(II)$=16.6 min; FAB-MS $(M+H)^+$=426.

11c) 5(S)-(Boc-Amino)-4(S)-hydroxy-6-(p-methoxyphenyl)-2(R)-(phenylmethyl)hexanoic acid 3.00 g (7.05 mmol) of 5(S)-[1(S)-(Boc-amino)-2-(p-methoxy-phenyl)-ethyl]-3(R)-(phenylmethyl)dihydrofuran-2-(3H)-one in 112 ml of dimethoxyethane and 57 ml of water are hydrolysed, under protective gas, with 28 ml of 1M lithium hydroxide solution. After 20 h at RT, the reaction mixture is poured onto an ice-cold mixture of 340 ml of sat. $NH_4Cl$ solution, 28 ml of 10% citric acid solution and 140 ml of methylene chloride. Methanol is added in order to dissolve the product completely. The aqueous phase is separated off and extracted 2× with methylene chloride. The organic phases are washed with saline, dried with $Na_2SO_4$ and evaporated, with the title compound being obtained: $t_{Ret}(II)$=14.0 min; FAB-MS $(M+H)^+$=444.

11d) 5(S)-(Boc-Amino)-4(S)-(tert-butyldimethylsilyloxy)-6-(p-methoxyphenyl)-2(R)-(phenylmethyl)hexanoic acid 2.9 g (6.54 mmol) of 5(S)-(Boc-amino)-4(S)-hydroxy-6-(p-methoxyphenyl)-2(R)-(phenylmethyl)hexanoic acid in 7 ml of DMF are silylated, at RT for 20 h and under an $N_2$ atmosphere, with 4.5 g (30 mmol) of tert-butyldimethylchlorosilane and 3.65 g (53.6 mmol) of imidazole. The reaction mixture is poured onto 500 ml of ice-water, and this mixture is extracted 3× with ethyl acetate. The organic phases are washed with 10% citric acid solution, 2× water and saline, dried with $Na_2SO_4$ and evaporated. Hydrolysis of the residue in 80 ml of methanol and 30 ml of THF with 5.4 g of potassium carbonate and 30 ml of water, working up after 3 h in analogy with Example 7c), and column chromatography ($SiO_2$, hexane/ethyl acetate, 2:1), affords the title compound: TLC $R_f(D)$=0.13; $t_{Ret}(II)$=20.3 min.

11e) 5(S)-(Boc-Amino)-4(S)-(tert-butyldimethylsilyloxy)-6-(p-methoxyphenyl)-2(R)-(phenylmethyl)hexanoyl-(L)-Val-N-(2-methoxyethyl)amide 1.56 g (2.8 mmol) of 5(S)-(Boc-amino)-4(S)-(tert-butyldimethylsilyloxy)-6-(p-methoxyphenyl)-2(R)-(phenylmethyl)hexanoic acid and 538 mg (3.09 mmol) of H-(L)-Val-N-(2-methoxyethyl)amide (Example 1b) in 27 ml of 0.25M $NMM/CH_3CN$ are reacted, at RT for 20 h and under an $N_2$ atmosphere, with 1.17 g (3.09 mmol) of HBTU. Working up in analogy with Example 5a) results in the title compound: $t_{Ret}(II)$=21.1 min; FAB-MS $(M+H)^+$=714.

11f) 5(S)-[1(S)-(Boc-Amino)-2-(p-hydroxyphenyl)ethyl]dihydrofuran-2-(3H)-one

Hydrogenating 3.0 g (7.29 mmol) of 5(S)-[1(S)-(Boc-amino)-2-(p-benzyloxyphenyl)ethyl]dihydrofuran-2-(3H)-one [preparation, see Example 1g)] in 100 ml of methanol with 0.6 g of 10% Pd/C yields the title compound after filtering off the catalyst and evaporating the filtrate: $t_{Ret}(II)$=10.6 min.

Example 12

5(S)-(Boc-Amino)-4(S)-hydroxy-6-cyclohexyl-2(R)-[(p-methoxyphenyl)methyl]hexanoyl-(L)-Val-N-(2-methoxyethyl)amide Under an argon atmosphere, 115.6 g (160.5 mmol) of 5(S)-(Boc-amino)-4(S)-(tert-butyldimethylsilyloxy)-6-cyclohexyl-2(R)-[(p-methoxyphenyl)methyl]hexanoyl-(L)-Val-N-(2-methoxyethyl)amide are dissolved in 650 ml of DMF, and this solution is treated with 101.3 g (321 mmol) of TBAF. After 20 h at RT, the reaction mixture is poured onto 1 kg of ice and 500 ml of ethyl acetate, and the aqueous phase is separated off and extracted a further 2× with 500 ml of ethyl acetate on each occasion. The organic phases are washed with 2× 500 ml of water, 500 ml of sat. $NaHCO_3$ solution, 500 ml of water and 500 ml of saline. Drying with $Na_2SO_4$, evaporation, stirring up in 2 l of ether/hexane, 1:1, and filtering off, yields the title compound: TLC $R_f(A)$=0.35; $t_{Ret}(II)$=17.1 min; FAB-MS $(M+H)^+$=606; IR (KBr): inter alia, 3328s, 2922s, 1685s, 1650s, 1622s, 1531s, 1512s, 1448m, 1390m, 1365m, 1246s, 1174s.

The starting material is prepared as follows:

12a) 5(S)-[1(S)-(Boc-Amino)-2-cyclohexylethyl]dihydrofuran-2-(3H)-one

A solution of 122.2 g (400 mmol) of 5(S)-[1(S)-(Boc-amino)-2-phenylethyl]dihydrofuran-2-(3H)-one

[preparation, See Example 2b)] in 1500 ml of methanol is hydrogenated, at RT and under low pressure, in the presence of 4.0 g of Nishimura catalyst [Rh(III)- and Pt(IV)-oxide monohydrate, Degussa]. Filtering off the catalyst, and evaporating the filtrate, results in the title compound: TLC $R_f(D)$=0.54; FAB-MS (M+H)$^+$=312.

12b) 5(S)-[1(S)-(Boc-Amino)-2-cyclohexylethyl]-3(R)-[(p-methoxyphenyl)methyl]dihydrofuran-2-(3H)-one 880 ml of a 1M solution of lithium bis(trimethylsilyl) amide in THF are added dropwise, at −70° C., under an argon atmosphere and within the space of 20 min, to 130 g (400 mmol) of 5(S)-[1(S)-(Boc-amino)-2-cyclohexylethyl] dihydrofuran-2-(3H)-one which is dissolved in 1000 ml of abs. THF and 108 ml of DMPU. After 20 min, a solution of 110 g (443 mmol) of p-methoxybenzyl iodide [preparation, see Example 7e)] in 60 ml of abs. THF is added dropwise, and this mixture is thoroughly stirred at −75° C. for 2 h. The mixture is subsequently protonate at −70° C. with 152 ml of propionic acid followed by 250 ml of water (temperature rises to −20° C.); 1 l of ethyl acetate is then added and the reaction mixture is poured onto 2 l of 15% NaHCO$_3$ solution. The aqueous phase is separated off and extracted with 1 l of ethyl acetate. The organic phases are washed 2× with sat. NaHCO$_3$ solution, water and saline, dried with Na$_2$SO$_4$ and evaporated. Column chromatography (SiO$_2$, hexane/ethyl acetate, 9:1) and crystallization from hexane yields the pure title compound: TLC $R_f(E)$=0.45; $t_{Ret}$(II)= 18.6 min; FAB-MS (M+H)$^+$=432.

12c) 5(S)-(Boc-Amino)-4(S)-hydroxy-6-cyclohexyl-2(R)-[(p-methoxyphenyl)methyl]hexanoic acid 1000 ml of 1M aqueous LiOH solution are added, under a protective gas, to a solution of 103 g (239 mmol) of 5(S)-[1(S)-(Boc-amino)-2-cyclohexylethyl]-3(R)-[(p-methoxyphenyl)methyl]dihydrofuran-2-(3H)-one in 800 ml 1,2-dimethoxyethane. After 3 h at RT, the reaction solution is poured onto an ice-cold mixture of 1.5 l of sat. NH$_4$Cl solution, 1 l of 10% citric acid solution and 2 l of ether. The aqueous phase is separated off and extracted 2× with 1 l of ether on each occasion. The organic phases are washed 4× with ice-water and finally with saline. Drying with sodium sulfate and evaporating yields the title compound from the organic phases: $t_{Ret}$(II)=16.0 min; FAB-MS (M+H)$^+$=450.

12d) 5(S)-(Boc-Amino)-4(S)-(tert-butyldimethylsilyloxy)-6-cyclohexyl-2(R)-[(p-methoxyphenyl)methyl]hexanoic acid 133 g (1.95 mol) of imidazole and 164 g (1.09 mol) of tert-butyldimethylchlorosilane are added, under an argon atmosphere, to an ice-cold solution of 124 g (238 mmol) of 5(S)-(Boc-amino)-4(S)-hydroxy-6-cyclohexyl-2(R)-[(p-methoxyphenyl)methyl]hexanoic acid in 800 ml of DMF. After 17 h at RT, the reaction mixture is poured onto 1.9 l of ice-water and extracted 3× with 0.8 l of ethyl acetate on each occasion. The organic phases are washed with water, sat. NaHCO$_3$ solution, water, 10% citric acid solution, water and, finally, saline, dried with Na$_2$SO$_4$ and evaporated. The residue is dissolved in 700 ml of methanol and 175 ml of THF, and 175 g of K$_2$CO$_3$ in 820 ml of water are added to this solution, which is then stirred at RT for 1 h. The resulting emulsion is partially evaporated on an RE, and the residue is diluted with ice-water, and this mixture is acidified to pH 4 with 10% citric acid solution while stirring vigorously. The mixture is extracted 3× with ethyl acetate, and the organic phases are washed with water and saline, dried with Na$_2$SO$_4$ and evaporated. Column chromatography (SiO$_2$, hexane→hexane/ethyl acetate 95:5→9:1→2:1→1:1) results in the title compound: TLC $R_f(E)$=0.15; $t_{Ret}$(II)=22.7 min.

12e) 5(S)-(Boc-Amino)-4(S)-(tert-butyldimethylsilyloxy)-6-cyclohexyl-2(R)-[(p-methoxyphenyl)methyl]hexanoyl-(L)-Val-N-(2-methoxyethyl)amide 33.2 g (190 mmol) of H-(L)-Val-N-(2-methoxyethyl) amide (Example 1b) in 100 ml of DMF are added to a solution of 97.6 g (173.1 mmol) of 5(S)-(Boc-amino)-4(S)-(tert-butyldimethylsilyloxy)-6-cyclohexyl-2(R)-[(p-methoxyphenyl)methyl]hexanoic acid in 600 ml of DMF, and the mixture is cooled down to 10° C. 31.1 ml (93% pure, 190 mmol) of diethyl cyanophosphonate (Aldrich, Milwaukee/U.S.A.) and 60.4 ml (432 mmol) of triethylamine are then added. After 1 h at RT, the reaction mixture is poured onto 1.5 l of ice-water, and this mixture is extracted 3× with 0.5 l of ethyl acetate on each occasion. The ethyl acetate phases are washed 2× with water, 10% citric acid solution, water, sat. NaHCO$_3$ solution, water and saline, dried with Na$_2$SO$_4$ and evaporated. Stirring up in 2 l of hexane at 50° C., cooling down to 5° C. and filtering off yields the pure title compound: TLC $R_f(A)$=0.7; TLC $R_f(J)$ =0.2; $t_{Ret}$(II)=23.8 min; FAB-MS (M+H)$^+$=720.

Example 13

5(S)-{[(1-Ethoxycarbonylpiperidin-4-yl)carbonyl] amino}-4(S)-hydroxy-6-cyclohexyl-2(R)-[(p-methoxyphenyl)methyl]hexanoyl-(L)-Val-N-(2-methoxyethyl)amide An ice-cooled solution of 250 mg (0.461 mmol) of 5(S)-amino-4(S)-hydroxy-6-cyclohexyl-2(R)-[(p-methoxyphenyl)methyl]hexanoyl-(L)-Val-N-(2-methoxyethyl)amide (hydrochloride salt) in 3.5 ml of THF is treated, under an N$_2$ atmosphere, with 212 µl (1.15 mmol) of triethylamine and a solution of 101 mg (0.461 mmol) of (1-ethoxycarbonylpiperidin-4-yl)carbonyl chloride (see Example 13b), and this mixture is warmed to RT. After 2 h, the reaction mixture is poured onto water, and this mixture is extracted 3× with ethyl acetate. The organic phases are washed with water, sat. NaHCO$_3$ solution and saline, dried with Na$_2$SO$_4$ and evaporated; the residue is digested in DIPE to give the title compound: TLC $R_f(B)$=0.39; $t_{Ret}$(II) =14.4 min; FAB-MS (M+H)$^+$=689.

The starting material is prepared as follows:

13a) 5(S)-Amino-4(S)-hydroxy-6-cyclohexyl-2(R)-[(p-methoxyphenyl)methyl]hexanoyl-(L)-Val-N-(2-methoxyethyl)amide (hydrochloride salt)

43.8 g (72.3 mmol) of 5(S)-(Boc-amino)-4(S)-hydroxy)-6-cyclohexyl-2(R)-[(p-methoxyphenyl)methyl]hexanoyl-(L)-Val-N-(2-methoxyethyl)amide (Example 12) are treated, while excluding moisture and while cooling with ice, with 250 ml of 3.8M HCl/dioxane, and this mixture is stirred for 2 h. The reaction mixture is subsequently evaporated on a RE, and the residue is taken up in 600 ml of dioxane, and this solution is lyophilized. Stirring up the lyophilisate in 1 l of ether, filtering off, and stirring up once again in 0.7 l of ethyl acetate and filtering off, results in the title compound: $t_{Ret}$(II)=10.1 min; FAB-MS (M+H)$^+$=506; anal: calc. C 60.94%, H 8.96%, N 7.61%, Cl 6.42%, H$_2$O 1.76%; found C 60.7%, H 9.0%, N 7.7%, Cl 6.8%, H$_2$O 1.76%. The second filtrate (ethyl acetate) is evaporated and the residue is taken up in ethyl acetate; this solution is washed with sat. NaHCO$_3$ solution, water and saline, dried with Na$_2$SO$_4$ and evaporated. Column chromatography (SiO$_2$, ethyl acetate) of the residue affords 5(S)-[1(S)-amino-2-cyclohexylethyl] -3(R)-[(p-methoxyphenyl)methyl]dihydrofuran-2-(3H)-one: $t_{Ret}$(II)=11.3 min; FAB-MS (M+H)$^+$=332; IR (CH$_2$Cl$_2$): inter alia 3390wb, 2930s, 2855m, 1763s, 1612m, 1515s, 1245s, 1180s, 1037m.

13b) 4-Chlorocarbonyl-1-ethoxycarbonylpiperidine

A solution of 578.2 g of 4-carboxy-1-ethoxycarbonylpiperidine in 1200 ml of toluene is treated firstly with 1.0 g of N,N-dimethylformamide and then, at from 68° to 70° C. and within the space of 2 hours, with 369.0 g of thionyl chloride. The mixture is subsequently stirred at 70° C. for a further 30 min, after which the toluene is distilled off in vacuo and the residue is then degassed at RT for approximately 30 min under HV. This results in the title compound in the form of a weakly yellow oil [IR (Film): 2960, 2870, 1790, 1695, 1470, 1435, 1300, 1230, 1130, 960, 765 cm$^{-1}$]. The product distils without decomposition at a m.p. of 96°–98° C. (0.08–0.09 Torr).

13c) 4-Carboxy-1-ethoxycarbonylpiperidine

4-Carboxy-1-ethoxycarbonylpiperidine is prepared from piperidine-4-carboxylic acid (Aldrich, Steinheim, FRG), for example by reacting piperidine-4-carboxylic acid with ethyl chloroformate in aqueous sodium hydroxide solution for 2 h at from 0° to 5° C. The title compound is extracted from the aqueous phase by shaking with toluene. The toluene phase containing the dissolved title compound is dried over Na$_2$SO$_4$ and directly subjected to further use.

Example 14

The following compounds are prepared in analogy with one of the examples given above or below:

I) 5(S)-(Boc-Amino)-4(S)-hydroxy-6-phenyl-2(R)-[(o-fluoro-p-methoxyphenyl)methyl]hexanoyl-(L)-Val-N-(2-methoxyethyl)amide II) 5(S)-(Boc-Amino)-4(S)-hydroxy-6-phenyl-2(R)-[(p-fluoro-o-methoxyphenyl)methyl]hexanoyl-(L)-Val-N-(2-methoxyethyl)amide III) 5(S)-(Boc-Amino)-4(S)-hydroxy-6-phenyl-2(R)-[(o-hydroxy-p-methoxyphenyl)methyl]hexanoyl-(L)-Val-N-(2-methoxyethyl)amide IV) 5(S)-(Boc-Amino)-4(S)-hydroxy-6-(p-methoxyphenyl)-2(R)-(cyclohexylmethyl)hexanoyl-(L)-Val-N-(2-methoxyethyl)amide 80 mg (0.132 mmol) of 5(S)-(Boc-amino)-4(S)-hydroxy-6-(p-methoxyphenyl)-2(R)-[(cyclohexen-1-yl)-methyl]hexanoyl-(L)-Val-N-(2-methoxyethyl)amide (Example 14V)) in 4 ml of ethanol/ethyl acetate, 3:1, are hydrogenated in the presence of 40 mg of 5% Pd/C and under standard pressure. Filtering off the catalyst, washing the residue with methylene chloride/methanol and evaporating the filtrate yields a relatively large quantity of crystalline crude product. This is dissolved in methylene chloride/methanol, treated with silica gel and dried. Loading the powder onto a silica gel column and eluting with methylene chloride/ethyl acetate/ethanol, 30:20:1, affords the title compound: TLC R$_f$(P)=0.28; t$_{Ref}$(II)=15.9 min; FAB-MS (M+H)$^+$=606.

V) 5(S)-(Boc-Amino)-4(S)-hydroxy-6-(4-methoxyphenyl)-2(R)-[cyclohexen-1-ylmethyl]hexanoyl-(L)-Val-N-(2-methoxyethyl)amide Under a protective gas, 344 mg (0.479 mmol) of 5(S)-(Boc-amino)-4(S)-(tert-butyldimethylsilyloxy)-6-(p-methoxyphenyl)-2(R)-[(cyclohexen-1-yl)methyl]hexanoyl-(L)-Val-N-(2-methoxyethyl)amide are dissolved in 9.9 ml of DMF, and this solution is treated with 302 mg (0.958 mmol) of TBAF. After 15 h at RT, the reaction mixture is poured onto 160 ml of water, and this mixture is extracted with 3 portions of ethyl acetate. The organic phases are washed 2× with sat. NaHCO$_3$ solution and saline, dried with Na$_2$SO$_4$ and evaporated. Digestion with DIPE yields the title compound: TLC R$_f$(O)=0.56; TLC R$_f$(P)=0.28; t$_{Ref}$(II)=15.4 min; FAB-MS (M+H)$^+$=604.

The starting material is prepared as follows:

14Va) Cyclohexen-1-ylmethanol

Under protective gas, a solution of 8.0 g (55.3 mmol) of 1-cyclohexenecarbonyl chloride (Pfaltz & Bauer, Waterbury/U.S.A.) in 168 ml of ether is cooled down to –20° C. and treated with 2.35 g (62 mmol) of lithium aluminium hydride. After the mixture has been stirred at –16° C. for 1 h, 256 ml of ethyl acetate are added dropwise (exothermic), followed by 76 ml of a 2N solution of NaOH. The mixture is stirred at RT for 30 min, 160 g of Na$_2$SO$_4$ are added, and this mixture is then filtered. Na$_2$SO$_4$ is added once again to the filtrate, which is then filtered. Evaporating the filtrate under mild conditions (20 mbar, 35° C.) affords the title compound: $^1$H-NMR (200 MHz, CDCl$_3$): 1.60 (m, 5H), 2.00 (m, 2 H$_2$C$^{allyl.}$), 3.97 (s, H$_2$C—OH), 5.66 (m, HC$^{olefin}$).

14Vb) Cyclohexen-1-yl-methylbromide

A solution of 6.2 g (55.3 mmol) of cyclohexen-1-ylmethanol in 800 ml of methylene chloride is treated, at 0° C., with 27.5 g (83 mmol) of tetrabromomethane and 21.7 g (83 mmol) of triphenylphosphine. After 35 min the mixture is evaporated on a RE under mild conditions. The residue is washed with 5 portions of pentane of 40 ml each. The combined pentane phases yield the title compound, after evaporation and kugelrohr distillation (140°–160° C., ≈20 mbar): $^1$H-NMR (200 MHz, CDCl$_3$): 1.6 (m, 2 H$_2$C), 2.1 (m, 2 H$_2$C$^{allyl.}$), 3.93 (s, H$_2$C—Br), 5.88 (m, HC$^{olefin}$); $^{13}$C-NMR (CDCl$_3$): 22.3, 22.9, 25.9 26.8 (4 CH$_2$), 40.4 (CH$_2$—Br), 128.6, 135.1 (2 C$^{olefin}$).

14Vc) 5(S)-[1(S)-(Boc-Amino)-2-(p-methoxyphenyl)ethyl]-3(R)-[(cyclohexen-1-yl)methyl]dihydrofuran-2-(3H)-one A solution of 6.36 g (18.9 mmol) of 5(S)-[1(S)-(Boc-amino)-2-(p-methoxyphenyl)ethyl]dihydrofuran-2-(3H)-one (preparation, see Example 11a) in 34 ml of abs. THF and 3.8 ml of DMPU is treated, at –75° C. and under an N$_2$ atmosphere, with 36.5 ml of a 1M solution of lithium bis(trimethylsilyl)amide in THF (Aldrich). After 15 min, a solution of 3.3 g (18.9 mmol) of cyclohexen-1-ylmethyl bromide in a little abs. THF is added dropwise, and this mixture is then stirred thoroughly at –70° C. for 1 h. 7 ml of propionic acid, and then 7 ml of water, are subsequently added at –75° C. The reaction mixture is warmed to 0° C. and poured onto 190 ml of ethyl acetate and 100 ml of 10% citric acid solution, and this mixture is then stirred for 5 min; the organic phase is separated off and washed with sat. sodium bicarbonate solution and saline. The aqueous phases are reextracted 2× with ethyl acetate, and the organic phases are dried over sodium sulfate and evaporated. Column chromatography (SiO$_2$, hexane/ethyl acetate, 4:1→3:1) affords the pure title compound: TLC R$_f$(D)=0.54; t$_{Ref}$(II)= 18.7 min; FAB-MS (M-buten+H)$^+$=430.

14Vd) 5(S)-(Boc-Amino)-4(S)-hydroxy-6-(p-methoxyphenyl)-2(R)-[(cyclohexen1-yl)methyl]hexanoic acid 1.25 g (2.91 mmol) of 5(S)-[1(S)-(Boc-amino)-2-(p-methoxyphenyl)ethyl]-3(R)-[(cyclohexen-1-yl)methyl]dihydrofuran-2-(3H)-one in 43.4 ml of dimethoxyethane and 22.1 ml of water are hydrolysed, under a protective gas, with 10.8 ml of a 1M lithium hydroxide solution. After 15 h, the reaction mixture is poured onto an ice-cold mixture of 140 ml of sat. NH$_4$Cl solution, 12 ml of 10% citric acid solution and 58 ml of methylene chloride. The aqueous phase is separated off and extracted 2× with methylene chloride. The organic phases are washed with saline, dried with Na$_2$SO$_4$ and evaporated: t$_{Ref}$(II)=15.6 min; FAB-MS (M-buten+H)$^+$ =488.

14Ve) 5(S)-(Boc-Amino)-4(S)-(tert-butyldimethylsilyloxy)-6-(p-methoxyphenyl)-2(R)-[(cyclohexen-1-yl)-methyl]hexanoic acid Under a protective gas, 1.19 g (2.66 mmol) of 5(S)-(Boc-amino)-4(S)-hydroxy)-6-(p-methoxy-phenyl)-2(R)-[(cyclohexen-1-yl)methyl]hexanoic acid are dissolved in 2.9 ml of DMF, and this solution is treated with 1.84 g (12.2 mmol) of tert-butyldimethylchlorosilane and 1.48 g (21.8 mmol) of imidazole. After 16 h at RT, the reaction mixture is poured onto 200 ml of ice-water, and this mixture is extracted 3× with ethyl acetate. The organic phases are washed with 10% citric acid solution, 2× water and saline, dried with $Na_2SO_4$ and evaporated. The residue is taken up in 32 ml of methanol and 12 ml of THF, and this solution is treated with a solution of 2.2 g of potassium carbonate in 12 ml of water, and the mixture is stirred at RT for 3 h. The reaction mixture is subsequently partially evaporated on a RE, and the residue is poured onto ice-cold 10% citric acid solution, and this mixture is extracted 3× with ethyl acetate. Washing the organic phases with 2 portions of water and saline, drying with $Na_2SO_4$, and evaporating, affords the title compound: TLC $R_f(D)=0.37$; $t_{Ref}(II)=22.8$ min.

14Vf) 5(S)-(Boc-Amino)-4(S)-(tert-butyldimethylsilyloxy)-6-(p-methoxyphenyl)-2(R)-[(cyclohexen-1-yl)methyl]hexanoyl-(L)-Val-N-(2-methoxyethyl)amide Under an $N_2$ atmosphere, 300 mg (0.613 mmol) of 5(S)-(Boc-amino)-4(S)-(tert-butyldimethylsilyloxy)-6-(p-methoxyphenyl)-2(R)-[(cyclohexen-1-yl)methyl]hexanoic acid and 117 mg (0.674 mmol) of H-(L)-Val-N-(2-methoxyethyl)amide (Example 1b)) are dissolved in 6.0 ml of 0.25M $NMM/CH_3CN$ and 255.5 mg (0.674 mmol) of HBTU are added to this solution. After 17 h at RT, the reaction mixture is evaporated under HV and the residue is taken up in ethyl acetate; this solution is washed with water, 2× 10% citric acid solution, 2× sat. $NaHCO_3$ solution and saline. The aqueous phases are extracted a further 2× with ethyl acetate, and the combined organic phases are dried with $Na_2SO_4$ to give the title compound: $t_{Ref}(II)=23.3$ min.

Example 15

5(S)-(Boc-Amino)-4(S)-hydroxy-6-cyclohexyl-2(R)-[(4-benzyloxyphenyl)methyl]hexanoyl-(L)-Val-N-(2-methoxyethyl)amide In analogy with Example 1, 0.35 g (0.44 mmol) of 5(S)-(Boc-amino)-4(S)-(tert-butyldimethylsilyloxy)-6-cyclohexyl-2(R)-[(4-benzyloxy-phenyl)-methyl]-hexanoyl-(L)-Val-N-(2-methoxyethyl)amide in 3 ml DMF is reacted with 0.278 g (0.88 mmol) of TBAF trihydrate to give the title compound. Working up, stirring up with diethyl ether, and filtering, yields the pure title compound. TLC $R_f(B)=0.52$; $t_{Ref}(II)=18.06$ min; FAB-MS $(M+H^+)=682$.

15a) 3(R)-[(4-Benzyloxyphenyl)methyl]-5(S)-[1(S)-(Boc-amino)-2-cyclohexylethyl]dihydrofuran-2-one In analogy with Example 5d), 5.2 g (16.7 mmol) of 5(S)-[1(S)-(Boc-amino)-2-cyclohexylethyl]-dihydrofuran-2-one [(preparation, see Example 12a)], dissolved in 50 ml of THF, are deprotonated, at −70° C., with 33.4 ml of a 1M solution of lithium bis(trimethylsilyl)amide in THF, and alkylated, at −75° C. for 1 h, with 5.2 g (16.07 mmol) of 4-benzyloxybenzyl iodide [preparation, see Example 1d)] in 15 ml of THF. Treating, at −75° C., with 6.2 ml (83.02 mmol) of propionic acid and water, and further working up, affords the title compound after column chromatography ($SiO_2$, hexane/ethyl acetate: 4/1). TLC $R_f$ (hexane/ethyl acetate: 4/1)=0.27; $t_{Ref}(II)=20.41$ min.

15b) 5(S)-(Boc-Amino)-4(S)-hydroxy-6-cyclohexyl-2(R)-[(4-benzyloxyphenyl)methyl]hexanoic acid 2.4 g (4.728 mmol) of 3(R)-[(4-benzyloxyphenyl)methyl]-5(S)-[1(S)-(Boc-amino)-2-cyclohexylethyl]dihydrofuran-2-one in 10 ml of dimethoxyethane are hydrolysed, under a protective gas, with 9.45 ml of a 1M solution of lithium hydroxide. After 17 h at RT, the reaction mixture is treated with an ice-cold mixture of 324 ml of sat. $NH_4Cl$ solution, 27 ml of 10% citric acid solution and 134 ml of methylene chloride. Methanol is added in order to dissolve the product completely. The aqueous phase is separated off and extracted 2× with methylene chloride. The organic phases are washed with saline, dried with $Na_2SO_4$ and evaporated. The crude product is purified by column chromatography ($SiO_2$, eluent C), with the title compound being obtained. TLC $R_f$ (C)= 0.35; $t_{Ref}(II)=17.88$ min. FAB-MS $(M+H^+)=526$.

15c) 5(S)-(Boc-Amino)-4(S)-(tert-butyldimethylsilyloxy)-6-cyclohexyl-2(R)-[(4-benzyloxyphenyl)methyl]hexanoic acid In analogy with Example 5f), 28.8 g (54.8 mmol) of 5(S)-(Boc-amino)-4(S)-hydroxy-6-cyclohexyl-2(R)-[(4-benzyloxyphenyl)methyl]hexanoic acid in 288 ml of DMF are converted into the title compound using 35.8 g (237.6 mmol) of tert-butyldimethylchlorosilane and 30 g (440 mmol) of imidazole. The title compound is purified by column chromatography ($SiO_2$, hexane/ethyl acetate: 4/1 to 1/1); TLC $R_f$ (E)=0.34; $t_{Ref}$(gradient from 75 to 100% (a) in (b) over a period of 20 min)=25.06 min; FAB-MS $(M+H^+)=526$.

15d) 5(S)-(Boc-Amino)-4(S)-(tert-butyldimethylsilyloxy)-6-cyclohexyl-2(R)-[(4-benzyloxyphenyl)methyl]hexanoyl-(L)-Val-N-(2-methoxyethyl)amide In analogy with Example 12e, a solution of 3 g (18.7 mmol) of H-(L)-Val-N-(2-methoxyethyl)amide and 10 g (15.6 mmol) of 5(S)-(Boc-amino)-4(S)-(tert-butyldimethylsilyloxy)-6-cyclohexyl-2(R)-[(4-benzyloxy-phenyl)methyl]hexanoic acid in 50 ml of DMF is cooled down to 5° C. in an ice bath and treated with 2.9 ml (17.2 ml) of diethyl cyanophosphonate and, after that, with 5.5 ml of triethylamine. After having been stirred at RT, the mixture is poured onto water, and this mixture is extracted 3 times with ethyl acetate. The combined organic phases are washed with water, saturated sodium bicarbonate solution (twice) and saline, and are concentrated after having been dried over sodium sulfate under reduced pressure. The title compound is purified by column chromatography ($SiO_2$,C); TLC $R_f$ (A)=0.56; $t_{Ref}(B)=24.82$ min FAB-MS $(M+H^+)=796$.

Example 16

5(S)-(Boc-amino)-4(S)-(hydroxy)-6-cyclohexyl-2(R)-[(4-hydroxyphenyl)methyl]hexanoyl-(L)-Val-N-(2-methoxyethyl)amide In analogy with Example 1, 0.547 g (0.775 mmol) of 5(S)-(Boc-amino)-4(S)-(tert-butyldimethylsilyloxy)-6-cyclohexyl-2(R)-[(4-hydroxy-phenyl)methyl]hexanoyl-(L)-Val-N-(2-methoxyethyl)amide in 5 ml of DMF is reacted with 0.488 g (1.549 mmol) of TBAF trihydrate to give the title compound. The pure title compound is obtained after working up and after stirring up with diethyl ether and filtering. TLC $R_f$ (B)=0.37; $t_{Ref}(II)=14.44$ min; FAB-MS $(M+H^+)=592$.

The starting compound is obtained in the following manner:

16a) 5(S)-(Boc-amino)-4(S)-(tert-butyldimethylsilyloxy)-6-cyclohexyl-2(R)-[(4-hydroxyphenyl)methyl]hexanoyl-(L)-Val-N-(2-methoxyethyl)amide 0.64 g (0.804 mmol) of 5(S)-(Boc-amino)-4(S)-(tert-butyldimethylsilyloxy)-6-cyclohexyl-2(R)-[4-(benzyloxy)phenylmethyl]hexanoyl-(L)-Val-N-(2-methoxyethyl)amide in 20 ml of methanol is hydrogenated in the presence of 0.32 g of 10% Pd/C. The title compound, which is obtained after filtering off the catalyst and evaporating the filtrate, is subjected to further reaction without any additional purification; TLC $R_f$ (C)=0.18; $t_{Ref}(II)=21.81$ min; FAB-MS $(M+H^+)=706$.

Example 17

5(S)-(Boc-Amino)-4(S)-(hydroxy)-6-cyclohexyl-2 (R)-[(4-methoxyphenyl)methyl]hexanoyl-(L)-Val-N- (2-methoxyethyl)amide In analogy with Example 1, 0.6 g (0.833 mmol) of 5(S)-(Boc-amino)-4(S)-(tert-butyldimethylsilyloxy)-6-cyclohexyl-2(R)-[4-methoxyphenylmethyl]hexanoyl-(L)-Val-N-(2-methoxyethyl)amide in 5 ml of DMF is reacted with 0.526 g (1.67 mmol) of TBAF trihydrate to give the title compound. After working up, the pure title compound is obtained after stirring up with diethyl ether and filtering. TLC $R_f$ (A)=0.45; $t_{Ref}(II)$=16.14 min; FAB-MS $(M+H^+)$=606.

The starting compound is prepared in the following manner:

17a) 5(S)-(Boc-Amino)-4(S)-(tert-butyldimethylsilyloxy)-6-cyclohexyl-2(R)-[(4-methoxyphenyl)methyl]hexanoyl-(L)-Val-N-(2-methoxyethyl)amide A solution of 0.75 g (1.06 mmol) of 5(S)-(Boc-amino)-4(S)-(tert-butyldimethylsilyloxy)-6-cyclohexyl-2(R)-[(4-hydroxyphenyl)methyl]hexanoyl-(L)-Val-N-(2-methoxyethyl)amide in 25 ml of dioxane is treated with 1.384 g (4.25 mmol) of caesium carbonate and, after 1 h, with 2.07 ml (21.24 mmol) of methyl iodide. After stirring at RT for 16 h, the solid is filtered off and washed with ethyl acetate. The filtrate is washed, in succession, with water, saturated aqueous sodium bicarbonate solution and saline. After drying over sodium sulfate, and evaporating under reduced pressure, the resulting residue is stirred up with hexane and filtered off, with the title compound being obtained. TLC $R_f$ (J)=0.6; $t_{Ref}(II)$=23.65 min; FAB-MS $(M+H^+)$=720.

Example 18

5(S)-(2,2,2-Trifluoroethoxycarbonylamino)-4(S)- (hydroxy)-6-cyclohexyl-2(R)-[(4-methoxyphenyl) methyl]hexanoyl-(L)-Val-N-(2-methoxyethyl)amide 400 mg (0.791 mmol) of 5(S)-amino-4(S)-(hydroxy)-6-cyclohexyl-2-(R)-[4-methoxyphenylmethyl]hexanoyl-(L)-Val-N-(2-methoxyethyl)amide in 5 ml DMF are treated, at 0° C. and in succession, with 0.276 ml (1.97 mmol) of triethylamine and 0.193 g (1.186 mmol) of trifluoroethyl chloroformate (U.S. Pat. No. 3,852,464). After having been stirred for 10 min, the reaction mixture is poured onto water, and this mixture is extracted 3 times with ethyl acetate. The combined extracts are washed, in succession, with aqueous, saturated sodium bicarbonate solution and saline, and, after having been dried over sodium sulfate, are concentrated under reduced pressure. The residue is crystallized from ethyl acetate/diethyl ether, with the title compound being obtained. TLC $R_f$ (B)=0.78; $t_{Ref}(II)$=15.36 min; FAB-MS $(M+H^+)$=632.

The starting compound is prepared in the following manner:

18a) 5(S)-Amino-4(S)-(hydroxy)-6-cyclohexyl-2(R)-[(4-methoxyphenyl)methyl]hexanoyl-(L)-Val-N-(2-methoxyethyl)amide 2.27 g (3.747 mmol) of 5(S)-(Boc-amino)-4(S)-(hydroxy)-6-cyclohexyl-2(R)-[(4-methoxyphenyl)methyl]hexanoyl-(L)-Val-N-(2-methoxyethyl)amide (Example 17) in 20 ml of methylene chloride are treated with 20 ml of trifluoroacetic acid at 0° C. After having been stirred for 2 h at RT, the reaction mixture is evaporated and partitioned between saturated aqueous sodium bicarbonate solution and ethyl acetate. The organic phase is washed once again with saturated aqueous sodium bicarbonate solution and saline, and evaporated to dryness. The residue is digested with ether and subsequently chromatographed ($SiO_2$, methylene chloride/methanol: 9/1 to 1/1), with the title compound being obtained. TLC $R_f$ (B)=0.43; $t_{Ref}(II)$=10.23 min; FAB-MS $(M+H^+)$=506.

Example 19

5(S)-(Boc-Amino)-4(S)-hydroxy-6-phenyl-2(R)- (phenylmethyl)hexanoyl-(L)-Val-N-(2- methoxyethyl)amide In analogy with Example 1, 0.82 g (1.19 mmol) of 5(S)-(Boc-amino)-4(S)-(tert-butyldimethylsilyloxy)-6-phenyl-2(R)-phenylmethylhexanoyl-(L)-Val-N-(2-methloxyethyl)amide in 12 ml of DMF is reacted with 0.756 g (2.38 mnol) of TBAF trihydrate to give the title compound. After working up, the pure title compound is obtained after stirring up with diethyl ether and filtering. TLC $R_f$(A)=0.37; $t_{Ref}(II)$=14.58 min; FAB-MS $(M+H^+)$=570.

The starting compound is prepared in the following manner:

19a) 5(S)-[1(S)-(Boc-Amino)-2-phenylethyl]dihydrofuran-2-(3H)-one (see Ex. 2c)) (see, also, A. E. DeCamp, A. T. Kawaguchi, R. P. Volante, and I. Shinkai, Tetrahedron Lett. 32, 1867 (1991)). 173 g of Zn/Cu (preparation: see R. D. Smith, H. E. Simmons, W. E. Parham, M. D. Bhavsar, Org. Synth., Coll. Vol 5, 855 (1973)) and 280 ml of dimethylacetamide are added, under an $N_2$ atmosphere, to a solution of 375 g (1.65 mol) of ethyl 2-iodopropionate (Example 1k)) in 1700 ml of toluene and this mixture is subsequently stirred vigorously at RT for 1 h and at 80° C. for 4 h (→Zn-homoenolate solution). In a second apparatus ($N_2$ atmosphere), a solution of 122 ml (0.40 mol) of tetraisopropyl orthotitanate in 350 ml of toluene and 1900 ml of methylene chloride is treated, with slight cooling, at an internal temperature of from 15° to 25° C., with 127 ml (1.14 mol) of titanium tetrachloride, and this mixture is stirred at RT for 15 min (→yellow solution) and cooled down to −40° C. (→partial crystallization of the trichlorotitanium isopropoxide). The Zn-homoenolate solution, which has been cooled down to RT, is filtered, under an argon atmosphere, through a G3 glass frit and added dropwise to the trichlorotitanium isopropoxide, with the temperature being maintained at from −30° C. to −25° C. (→deep-red solution), after which the mixture is stirred at −25° C. for 5 min and then cooled down to −40° C. A solution of 233 g (0.85 mol) of (S)-N-Boc-phenylalaninal (preparation: see D. J. Kempf, J. Org. Chem. 51, 3921 (1986), then crystallization from hexane (0° C., approximately 18 h), washing with cold hexane, and drying) in 1500 ml of methylene chloride is subsequently added dropwise, and the mixture is then stirred at from −22° to −18° C. for 15 h and, finally, at 0° C. for 1 h. The reaction mixture is taken up in 10 l of ice-water and 12 l of tert-butyl methyl ether, and this mixture is stirred vigorously for 7–10 min. The aqueous phase is separated off; it is extracted 2× with 10 l of ether; the organic phases are washed with 8 l of water, 8 l of sat. sodium hydrocarbon carbonate solution, 8 l of water and 5 l of saline; they are dried with sodium sulfate and evaporated (→crystalline ethyl 5(S)-(Boc-amino)-4(S)-hydroxy-6-phenylhexanoate).

The above intermediate is heated, in 6500 ml of toluene and 230 ml of acetic acid and under an argon atmosphere, at 100° C. for 2.5 h. When it has cooled down, the reaction mixture is poured, with stirring, onto 6 l of ice-water, and the aqueous phase is separated off and extracted 2× with 2000 ml of toluene; the org. phases are washed with 5 l of sat. sodium hydrogen carbonate solution, 5 l of 40% sodium hydrogen sulfite solution, 4 l of water and 4 l of saline, and dried with sodium sulfate. Evaporating the org. phases down to a residue of approximately 300 g, and treating the latter with 800 ml of hexane (thorough stirring for several hours) affords crystalline lactone, which HPLC indicates contains approximately 10% of the (5R) epimer (TLC $R_f(E)$=0.08; $t_{Rel}(II)$=18.8 min). This material is employed in the next stage. The pure title compound can be obtained following column chromatography (SiO$_2$, hexane/ethyl acetate, 2:1): TLC $R_f(E)$=0.14; $t_{Rel}(II)$=19.2 min; $[\alpha]^D$=17.7° (c=1; ethanol).

19b) 5(S)-[1(S)-(Boc-Amino)-2-phenylethyl]-3(R)-phenylmethyldihydrofuran-2-(3H)-one (see, also, A. K. Ghosh, S. P. McKee, and W. J. Thompson, J. Org. Chem. 56, 6500 (1991)).

Under an N$_2$ atmosphere, a solution of 1943 g (6.32 mol) of 5(S)-[1(S)-(Boc-amino)-2-phenylethyl]dihydrofuran-2-(3H)-one in 12.0 l of THF and 1.9 l of 1,3-dimethyl-3,4,5,6-tetrahydro-2(1H)-pyrimidinone is cooled down to −75° C. and treated, at an internal temperature of below −70° C., with 14000 ml of a 1M solution of lithium bis(trimethylsilyl)amide in THF (Aldrich), and this mixture is subsequently stirred at −75° C. for 20 min. 835 ml (7.00 mol) of benzyl bromide are added dropwise to it over the space of 1 h, during which time the internal temperature is not allowed to exceed −70° C., and the mixture is then thoroughly stirred at −75° C. for 30 min. 2320 ml of propionic acid (90 min) and then 2320 ml of water (1 h) are subsequently added to the clear solution, with the temperature being allowed to rise to −10° C. The reaction mixture is poured onto 30 l of ethyl acetate and 35 l of 10% citric acid solution, and the aqueous phase is separated off and reextracted 2× with 10 l of ethyl acetate. The organic phases are washed with 3×12 l of sat. sodium bicarbonate solution, 20 l of saline and 2×20 l of water, and then concentrated. The oily residue is taken up in 10 l of toluene, and this mixture is evaporated down to a residue volume of approximately 5 l. Filtering the evaporation residue through 4 kg of Merck silica gel (0.063–0.200 mm), washing with toluene and crystallizing the crude product from hexane (4 l of hexane/kg of crude product) affords the title compound: TLC $R_f(D)$=0.54; FAB-MS (M+H)$^+$=414.

19c) 5(S)-(Boc-Amino)-4(S)-hydroxy-6-phenyl-2(R)-phenylmethylhexanoic acid

A solution of 17.6 g of 5(S)-[1(S)-(Boc-amino)-2-phenylethyl]-3(R)-phenylmethyldihydrofuran-2-(3H)one in 710 ml of ethylene glycol dimethyl ether and 352 ml of water is treated dropwise, at 20° C. and within the space of 10 min, with 176 ml of a 1M lithium hydroxide solution. After that, the reaction mixture is stirred at RT for 1.5 h, and the solvent is then evaporated off. The residue is poured onto 1 of cold 10% citric acid, and this acidic solution is extracted three times with 800 ml of ethyl acetate on each occasion. The combined extracts are washed first with 800 ml of water and then with 800 ml of saline. After the organic solution has been dried over sodium sulfate, the solvent is distilled off. The crude title compound is employed in the next stage without any further purification. FAB-MS (M+H)$^+$=414.

19d) 5(S)-(Boc-Amino)-4(S)-(tert-butyldimethylsilyloxy)-6-phenyl-2(R)-phenylmethylhexanoic acid A solution of 6.35 g of 5(S)-(Boc-amino)-4(S)-hydroxy-6-phenyl-2(R)-phenylmethylhexanoic acid in 90 ml of DMF is treated, while being stirred, with 8 g of imidazole and 10 g of t-butyldimethylchlorosilane. After having been stirred at RT for 18 h, the yellow, clear solution is poured onto ice-water, and this mixture is extracted three times with 250 ml of ethyl acetate on each occasion. The combined extracts are washed, in succession, three times with 10% citric acid, once with water, three times with aqueous, saturated sodium bicarbonate solution, once with water and, finally, with saline. After drying over sodium sulfate, the solvent is evaporated and the resulting tert-butyl dimethylsilyl ether (13.5 g) is dissolved in 53 ml of THF and treated with 53 ml of acetic acid and 20 ml of water. After having been stirred at RT for 3 h, the mixture is poured onto water, and this mixture is extracted three times with ether. The collected ether extracts are washed twice with water and once with saline and dried over sodium sulfate. After concentrating, the crude product is purified by column chromatography (SiO$_2$, hexane/ethyl acetate: 3.5/1.5), and the title compound is obtained. TLC $R_f(D)$=0.37; FAB-MS (M+H)$^+$=528.

19e) 5(S)-(Boc-Amino)-4(S)-(tert-butyldimethylsilyloxy)-6-phenyl-2(R)-(phenylmethyl)hexanoyl-(L)-Val-N-(2-methoxyethyl)amide A solution of 1.25 g (2 mmol) of 5(S)-(Boc-amino)-4(S)-(tert-butyldimethylsilyloxy)-6-phenyl-2(R)-(phenylmethyl)hexanoic acid, 0.98 g (2.21 mmol) of BOP, 0.3 g (2.21 mmol) of HOBT and 0.55 ml (4.98 mmol) of N-methylmorpholine in 15 ml of DMF is treated, after having been stirred at RT for 30 min, with 0.208 ml (2.42 mmol) of (L)-Val-N-(2-methoxyethyl)amide. After having been stirred at RT for 5.5 h, the mixture is poured onto 300 ml of water, and this mixture is extracted 3 times with ethyl acetate. The combined organic phases are washed with water, saturated sodium bicarbonate solution (twice) and saline, and, after drying over sodium sulfate, are concentrated under reduced pressure. The title compound is purified by column chromatography (SiO$_2$,D to A); TLC $R_f(C)$=0.23.

Example 20

5(S)-(Boc-Amino)-4(S)-hydroxy-6-phenyl-2(R)-(phenyl-methyl)hexanoyl-(L)-[(cyclohexyl)Gly]-N-(2-methoxyethyl)amide In analogy with Example 1, 0.96 g (1.33 mmol) of 5(S)-(Boc-amino)-4(S)-(tert-butyldimethylsilyloxy)-6-phenyl-2(R)-(phenylmethyl)hexanoyl-(L)-(cyclohexyl)Gly-N-(2-methoxyethyl)amide in 33 ml of DMF is reacted with 0.836 g (2.66 mmol) of TBAF trihydrate to give the title compound. The pure title compound is obtained after working up and column chromatography (SiO$_2$, D to A). TLC $R_f$ (A)=0.5; $t_{Rel}(II)$=15.92 min; FAB-MS (M+H$^+$)=610.

The starting compound is prepared in the following manner:

20a) N-Boc-(L)-(Cyclohexyl)glycine 2.51 g (10 mmol) of Boc-(L)-phenylglycine (Fluka, Buchs, Switzerland) are hydrogenated, at RT for 1 h under standard pressure, in 50 ml of methanol and in the presence of 250 mg of Nishimura catalyst. The catalyst is then filtered off and washed with methanol. The filtrate is evaporated and the resulting title product is employed in the next stage without further purification. TLC $R_f$ (A)=0.41.

20b) Boc-(L)-[(Cyclohexyl)Gly]-N-(2-methoxyethyl)amide

A solution of 0.515 g (2 mmol) of N-Boc-(L)-(cyclohexyl)glycine in 10 ml of methylene chloride is treated successively, after having been cooled down to 0° C., with 0.413 g (2 mmol) of DCC and 0.297 g (2.2 mmol) of HOBT. After 20 min, the mixture is treated over the space of 15 min with a solution of 0.172 ml (2 mmol) of 2-methoxyethylamine (Aldrich, Buchs, Switzerland) in 8 ml of methylene chloride. After the mixture has been thoroughly stirred at RT for 19.5 h, the solid is filtered off. The filtrate is washed in succession with water and saline and dried over sodium sulfate. After concentrating under reduced pressure, the crude product is purified by column chromatography (SiO₂, eluent J), with the title compound being obtained. TLC R_f (A)=0.56.

20c) H-(L)-[(Cyclohexyl)Gly]-N-(2-methoxyethyl)amide.

0.52 g (1.65 mmol) of Boc-(L)-[(cyclohexyl)Gly]-N-(2-methoxyethyl)amide is stirred for 2 h in 8.7 ml of formic acid. After that, the mixture is evaporated on a rotary evaporator, and the remaining formic acid is removed in vacuo. The residue is taken up in aqueous, saturated sodium bicarbonate solution, and this mixture is extracted 4 times with methylene chloride. The combined organic extracts are washed with water and saline, dried over sodium sulfate and concentrated. The crude title compound is purified by column chromatography (SiO₂, eluent B). TLC R_f (A)=0.6.

20d) 5(S)-(Boc-Amino)-4(S)-(tert-butyldimethylsilyloxy)-6-phenyl-2(R)-(phenylmethyl)hexanoyl-(L)-[(cyclohexyl)Gly]-N-(2-methoxyethyl)amide A solution of 0.817 g (1.55 mmol) of 5(S)-(Boc-amino)-4(S)-(tert-butyldimethylsilyl-oxy)-6-phenyl-2(R)-(phenylmethyl)]hexanoic acid (Example 19e)), 0.365 g (1.7 mmol) of H-(L)-[(cyclohexyl)Gly]-N-(2-methoxyethyl)amide, 0.645 g (1.7 mmol) of HBTU and 0.4 ml (3.72 mmol) of N-methylmorpholine in 15 ml of acetonitrile is stirred at RT for 16 h. The reaction mixture is then concentrated and the residue is taken up in ethyl acetate. After this solution has been washed with water, 10% citric acid, water, saturated aqueous sodium bicarbonate solution and saline, it is dried over sodium sulfate. After concentrating, the crude product is purified by column chromatography (SiO₂, C), with the title compound being obtained. TLC R_f (A)=0.53.

Example 21

5(S)-(Boc-Amino)-4(S)-hydroxy-6-phenyl-2(phenylmethylhexanoyl-(L)-[(phenyl)Gly]-N-(2-methoxyethyl)amide In analogy with Example 1, 1.15 g (1.6 mmol) of 5(S)-(Boc-amino)-4(S)-(tert-butyldimethylsilyloxy)-6-phenyl-2(R)-(phenylmethyl)hexanoyl-(L)-[(phenyl)Gly]-N-(2-methoxyethyl)amide in 37 ml of DMF are reacted with 1.01 g (3.2 mmol) of TBAF trihydrate to give the title compound. After working up, the pure title compound is obtained after column chromatography (SiO₂, D to A). TLC R_f (A)=0.47; t_Ret(II)=15.15 min; FAB-MS (M+H⁺)=604.

The starting compound is prepared in the following manner:

21a) Boc-(L)-(Phenyl)Gly-N-(2-methoxyethyl)amide

In analogy with Example 20b), a solution of 0.503 g (2 mmol) of N-Boc-(L)-(phenyl)glycine in 10 ml of methylene chloride is treated in succession, after having been cooled down to 0° C., with 0.413 g (2 mmol) of DCC and 0.297 g (2.2 mmol) of HOBT. After 20 min, the mixture is treated for 15 min with a solution of 0.172 ml (2 mmol) of 2-methoxyethylamine in 8 ml of methylene chloride. After thoroughly stirring at RT, and working up, the crude product is purified by being stirred up in ether. TLC R_f (A)=0.5.

2) H-(L)-[(Phenyl)Gly-]-N-(2-methoxyethyl)amide

In analogy with Example 20c), 0.61 g (1.98 mmol) of Boc-(L)-[(phenyl)Gly]-N-(2-methoxyethyl)amid is stirred in 10.4 ml of formic acid for 2 h. The title compound is obtained after working up and is subjected to further use without any additional purification. TLC R_f (B)=0.3.

21c) 5(S)-(Boc-Amino)-4(S)-(tert-butyldimethylsilyloxy)-6-phenyl-2(R)-(phenyl-methyl)hexanoyl-(L)-[(phenyl)Gly]-N-(2-methoxyethyl)amide In analogy with Example 20d), a solution of 0.921 g (1.75 mmol) of 5(S)-(Boc-amino)-4-(S)-(tert-butyldimethylsilyloxy)-6-phenyl-2(R)-(phenylmethyl)hexanoic acid, 0.4 g (1.92 mmol) of H-(L)-[(phenyl)Gly]-N-(2-methoxyethyl)amide, 0.728 g (1.92 mmol) of HBTU and 17.4 ml (4.2 mmol) of a 0.25M solution of N-methylmorpholine in acetonitrile is stirred at RT for 22 h. The working-up, and the subsequent column chromatography (SiO₂, ethyl acetate/hexane: 1/1 to 3/1) give the title compound. TLC R_f (A)=0.63.

Example 22

5(S)-[(1-Methyl-4-piperdinyloxycarbonyl)amino]-4(S)-hydroxy6-cyclohexyl-2(R)-[(p-methoxophenyl)methyl]hexanoyl-(L)-Val-N-(2-methoxyethyl)amide A solution of 346 mg (3 mmol) of 1-methyl-4-piperidinol (Fluka, Buchs, Switzerland) in 2 ml of THF is injected into a solution of 217 mg (0.73 mmol) of triphosgene in 20 ml of THF. The resulting suspension is cooled in an ice bath and then treated with 1.16 ml (8.3 mmol) of triethylamine, and the resulting mixture is subsequently stirred at RT for 30 min. This suspension is added to a slurry of 500 mg (0.92 mmol) of 5(S)-amino-4(S)-hydroxy-6-cyclohexyl-2(R)-[(p-methoxyphenyl)methyl]hexanoyl-(L)-Val-N-(2-methoxyethyl)amide in 20 ml of THF, and this mixture is stirred for 2 h under an argon atmosphere. The reaction mixture is poured onto ice water, and this mixture is extracted 2× with ethyl acetate. The organic extracts are washed, in succession, with water, sat. sodium bicarbonate solution, water and saline, and evaporated. The title compound is obtained after digesting the crude product with ether, filtering off the insoluble constituents with suction, and washing the residue with ether. TLC R_f(K)=0.60; t_ret(I) =10.8 min; FAB MS (M+H)⁺=647.

The starting material is prepared as follows:

22a) 5(S)-Amino-4(S)-hydroxy-6-cyclohexyl-2(R)-[(p-methoxyphenyl)methyl]-hexanoyl-(L)-Val-N-(2-methoxyethyl)amide A solution of 5 g (8.25 mmol) of 5(S)-(Boc-amino)-4(S)-hydroxy-6-cyclohexyl-2(R)-[(p-methoxyphenyl)methyl]hexanoyl-(L)-Val- N-(2-methoxyethyl)amide from Example 12 in 40 ml of 4N hydrochloric acid is stirred in dioxane for 2 h in an ice bath. The reaction mixture is subsequently evaporated in vacuo and the residue is lyophilized from dioxane, with the title compound being obtained. TLC R_f(B)=0.18; t_ret(I)=11.3 min; FAB MS (M+H)⁺506.

Example 23

5(S)-(3(S)-Tetrahydrofuryloxycarbonyl-amino)-4(S)-hydroxy-6-cyclohexyl-2(R)-[(p-methoxyphenyl)methyl]hexanoyl-(L)-Val-N-(2-methoxyethyl)amide A slurry of 1.0 g (1.84 mmol) of 5(S)-amino-4(S)-hydroxy-6-cyclohexyl-2(R)-[(p-methoxyphenyl)methyl]hexanoyl-(L)-Val-N-(2-methoxyethyl)amide from Example 22a) in 30 ml of THF is treated, at −5° C., with 1.28 ml of triethylamine and subsequently with 694 mg (4.61 mmol) of 3(S)-tetrahydrofuryloxycarbonyl chloride (see J. Chromatography 506, 598 (1990)) and this mixture is stirred at RT for 1 h under an argon atmosphere. The reaction mixture is poured onto ice-water, and this mixture is extracted 3× with ethyl acetate. The organic extracts are washed successively with water, sat. sodium bicarbonate solution, water and saline, and evaporated. The title compound is obtained after digesting the crude product with ethyl acetate, filtering off the insoluble constituents with suction, and washing the residue with ethyl acetate and ether. TLC $R_f(B)=0.74$; $t_{ret}(I)=14.0$ min; FAB MS $(M+H)^+=620$.

Example 24

5(S)-(2(R,S)-Tetrahydropyranylmethoxycarbonylamino)-4(S)-hydroxy-6-cyclohexyl-2(R)-[(p-methoxyphenyl)methyl]hexanoyl-(L)-Val-N-(2-methoxyethyl)amide In analogy with Example 23, the title compound is obtained as a mixture of 2 epimers, which cannot be resolved by HPLC, by proceeding from 1.0 g (1.84 mmol) of 5(S)-amino-4(S)-hydroxy-6-cyclohexyl-2(R)-[(p-methoxyphenyl)methyl]-hexanoyl-(L)-Val-N-(2-methoxyethyl)amide from Example 22a), 660 mg (3.68 mmol) of rac. tetrahydropyranylmethoxycarbonyl chloride (see Carbohydrate Res. 4(4), 343 (1967)) and 0.909 ml (6.45 mmol) of triethylamine. TLC $R_f(B)=0.69$; $t_{ret}(I)=15.5$ min; FAB MS $(M+H)^+=648$.

Example 25

5(S)-(5(S)-2-Oxopyrrolidinylmethoxycarbonylamino)-4(S)-hydroxy-6-cyclohexyl-2(R)-[(P-methoxyphenyl)methyl]hexanoyl-(L)-Val-N-(2-methoxyethyl)amide In analogy with Example 22, the title compound is obtained, after chromatographic purification on silica gel using the eluent system K, by proceeding from 542 mg (1.0 mmol) of 5(S)-amino-4(S)-hydroxy-6-cyclohexyl-2(R)-[(p-methoxyphenyl)methyl]-hexanoyl-(L)-Val-N-(2-methoxyethyl)amide from Example 22a), 345 mg (3 mmol) of 5-(S)-hydroxymethyl-2-pyrrolidone (=(L)-pyroglutaminol—Fluka, Buchs, Switzerland), 297 mg (1 mmol) of triphosgene and 1.25 ml (9 mmol) of triethylamine. TLC $R_f(K)=0.50$; $t_{ret}(I)=12.6$ min; FAB MS $(M+H)^+=647$.

Example 26

5(S)-(2-Methoxyethoxycarbonylamino)-4(S)-hydroxy-6-cyclohexyl-2(R)-[(p-methoxyphenyl)methyl]hexanoyl-(L)-Val-N-(2-methoxyethyl)amide In analogy with Example 23, the title compound is obtained by proceeding from 1.0 g (1.84 mmol) of 5(S)-amino-4(S)-hydroxy-6-cyclohexyl-2(R)-[(p-methoxyphenyl)methyl]-hexanoyl-(L)-Val-N-(2-methoxyethyl)amide from Example 22a), 511 mg (3.70 mmol) of 2-methoxyethoxycarbonyl chloride and 0.909 ml (6.45 mmol) of triethylamine. TLC $R_f(B)=0.63$; $t_{ret}(I)=13.9$ min; FAB MS $(M+H)^+=608$.

The starting material is prepared as follows:
26a) 2-Methoxyethoxycarbonyl chloride (=2-methoxyethyl chloroformate)

13.3 ml (168 mmol) of 2-methoxyethanol (Fluka, Buchs, Switzerland) are added dropwise, at from 0° to 5° C. and under a nitrogen atmosphere, to 100 ml (202 mmol) of a 20% solution of phosgene in toluene, and this mixture is thoroughly stirred at 0° C. for 90 min and at RT for 18 h. The reaction mixture is extracted with water, and the organic phase is filtered through wadding and evaporated: IR $(CH_2Cl_2)$: inter alia 3055w, 2995w, 2935w, 2895w, 2825w, 1775s, 1167s, 1127s; $^1$H-NMR (200 MHz, $CDCl_3$): 3.38 (s, 3H), 3.64 and 4.44 (2t, J=5 Hz, each 2H).

Example 27

5(S)-((L)-Thiazolidin-4-ylcarbonylamino)-4(S)-hydroxy-6-cyclohexyl-2(R)-[(n-methoxyphenyl)methyl]hexanoyl-(L)-Val-N-(2-methoxyethyl)amide A solution of 1.0 g (1.84 mmol) of 5(S)-amino-4(S)-hydroxy-6-cyclohexyl-2(R)-[(p-methoxy-phenyl)methyl] hexanoyl-(L)-Val-N-(2-methoxyethyl)amide from Example 22a) in 12 ml of DMF is treated, at RT, in succession, with 270 mg (2.02 mmol) of (L)-thiazolidine-4-carboxylic acid (=(L)-thiaproline; Sigma, Buchs, Switzerland), 0.33 ml (2.02 mmol) of diethyl cyanophosphonate and 0.91 ml (6.52 mmol) of triethylamine, and the resulting suspension is stirred under an argon atmosphere for 1 h. The suspension is diluted with 40 ml of ethyl acetate and filtered. The residue is dissolved in a 9:1 mixture of methylene chloride and methanol, and this mixture is then evaporated to dryness. The title compound is obtained as a white solid after digesting the residue with ethyl acetate. TLC $R_f(B)=0.72$; $t_{ret}(I)=10.5$ min; FAB MS $(M+H)^+=621$.

Example 28

5(S)-(4-Oxo-4H-1-benzopyran-2-ylcarbonylamino)-4(S)-hydroxy-6-cyclohexyl-2(R)-[(p-methoxyphenyl)methyl]hexanoyl-(L)-Val-N-(2-methoxyethyl)amide A solution of 1.0 g (1.84 mmol) of 5(S)-amino-4(S)-hydroxy-6-cyclohexyl-2(R)-[(p-methoxy-phenyl)methyl] hexanoyl-(L)-Val-N-(2-methoxyethyl)amide from Example 22a) in 18 ml of DMF is treated, at RT, and in succession, with 470 mg (2.40 mmol) of 4-oxo-4H-1-benzopyran-2-carboxylic acid (Aldrich, Steinheim, FRG), 0.59 ml (3.90 mmol) of diethyl cyanophosphonate and 0.90 ml (6.45 mmol) of triethylamine, and the mixture is stirred for 5 h under an argon atmosphere. For the working-up, the reaction mixture is poured onto ice-water, and this mixture is extracted 2× with ethyl acetate. The organic extracts are washed, in succession, with water, sat. sodium bicarbonate, water and saline, and then evaporated to dryness. The title compound is obtained as a white solid after chromatographic purification on silica gel using methylene chloride/methanol (98:2) and digesting with diethyl ether. TLC $R_f(B)=0.63$; $t_{ret}(I)=15.4$ min; FAB MS $(M+H)^+=678$.

Example 29

5(S)-(Indolyl-2-carbonylamino)-4(S)-hydroxy-6-cyclohexyl-2(R)-[(p-methoxyphenyl)methyl]hexanoyl-(L)-Val-N-(2-methoxyethyl)amide In analogy with Example 28, the title compound is obtained as a white solid, after digesting with diethyl ether, by proceeding from 1.0 g (1.84 mmol) of 5(S)-amino-4(S)-hydroxy-6-cyclohexyl-2(R)-[(p-methoxyphenyl)methyl] hexanoyl-(L)-Val-N-(2-methoxyethyl)amide from Example 22a), 331 mg (2.03 mmol) of indole-2-carboxylic acid (Fluka, Buchs, Switzerland), 0.331 ml (2.03 mmol) of diethyl cyanophosphonate and 0.90 ml (6.45 mmol) of triethylamine. TLC $R_f(B)=0.75$; $t_{ret}(I)=14.4$ min; FAB MS $(M+H)^+=651$.

Example 30

5(S)-(Methoxycarbonyl-(L)-Val-amino)-4(S)-hydroxy-6-cyclohexyl -2(R)-[(p-methoxy-phenyl)methyl]hexanoyl-(L)-Val-N-(2-methoxyethyl)amide In analogy with Example 28, the title compound is obtained as a white solid, after digesting with diethyl ether, by proceeding from 1.0 g (1.84 mmol) of 5(S)-amino-4(S)-hydroxy-6-cyclohexyl-2(R)-[(p-methoxyphenyl)methyl] hexanoyl-(L)-Val-N-(2-methoxyethyl)amide from Example 22a), 462 mg (2.63 mmol) of methoxycarbonyl-(L)-valine, 0.43 ml (2.83 mmol) of diethyl cyanophosphonate and 1.34 ml (9.61 mmol) of triethylamine. TLC $R_f(B)=0.61$; $t_{ret}(I)=$ 14.2 min; FAB MS $(M+H)^+=663$.

The starting material is prepared as follows:

30a) N-(Methoxycarbonyl)-(L)-valine 5.67 g (60 mmol) of methyl chloroformate (Fluka, Buchs, Switzerland) are added to 7.0 g (60 mmol) of L-valine in 100 ml of 2N NaOH and 30 ml of dioxane (→exothermic reaction), and this mixture is subsequently stirred at RT for 18 h. The reaction mixture is extracted with methylene chloride, and the aqueous phase is acidified with 27 ml of 4N HCl and once again extracted with methylene chloride. Drying and evaporating the latter methylene chloride phase affords the title compound: $t_{Ref}(I)=7.2$ min; $^1$H-NMR (200 MHz, CD$_3$OD): 0.96 (t, J=7 Hz, 6H), 2.16 (m, 1H), 3.67 (s, 3H), 4.06 (m, 1H), 7.07 (d, J=8 Hz, $HN_{partially\ exchanged}$).

Example 31

5(S)-([N-((L)-Thiazolidin-4-ylcarbonyl)-(L)-Val]-amino)-4(S)-hydroxy-6-cyclohexyl-2(R)-[(p-methoxyphenyl)methyl]hexanoyl-(L)-Val-N-(2-methoxyethyl)amide In analogy with Example 28, the title compound is obtained as a white solid, after digesting with diethyl ether, by proceeding from 0.60 g (1.11 mmol) of 5(S)-amino-4(S)-hydroxy-6-cyclo-hexyl-2(R)-[(p-methoxyphenyl)methyl]hexanoyl-(L)-Val-N-(2-methoxy-ethyl)amide from Example 22a), 311 mg (1.33 mmol) of N-[(L)-thiazolidin-4-yl-carbonyl]-(L)-valine (=(L)-thiaprolyl-(L)-valine), 0.25 ml (1.63 mmol) of diethyl cyanophosphonate and 0.55 ml (3.91 mmol) of triethylamine. TLC $R_f(K)=0.54$; $t_{ret}(I)=11.0$ min; FAB MS $(M+H)^+=720$.

31a) H-(L)-Thiaprolyl-(L)-valine

In analogy with Example 28, (L)-thiaprolyl-(L)-valine benzyl ester is obtained by proceeding from 3.99 g (10.5 mmol) of (L)-valine benzyl ester 4-toluenesulfonate (Fluka, Buchs, Switzerland), 1.33 g (10.0 mmol) of (L)-thiazolidine-4-carboxylic acid (=(L)-thiaproline; Sigma, Buchs, Switzerland), 1.8 ml (11.0 mmol) of diethyl cyanophosphonate and 5.6 ml (40.0 mmol) of triethylamine. A solution of 1.37 g of this crude product in 15 ml of methanol is treated with 8.5 ml of a 1N sodium hydroxide solution, and this mixture is stirred at RT for 2 h. The reaction solution is evaporated down to half its volume in vacuo, and washed with ethyl acetate. The aqueous phase is acidified with 1N hydrochloric acid, saturated with sodium chloride and extracted 4× with ethyl acetate. The title compound is obtained after evaporating the organic extracts and digesting the residue with ether. TLC $R_f(K)=0.54$; $t_{ret}(III)=12.2$ min; FAB MS $(M+H)^+=233$.

Example 32

5(S)-(Benzyloxycarbonyl-(L)-4-[trans-hydroxylprolyl]amino)-4(S)-hydroxy-6-cyclohexyl-2(R)-[(p-methoxylphenyl)methyl]hexanoyl-(L)-Val-N-(2-methoxyethyl)amide In analogy with Example 28, the title compound is obtained as a white solid, after chromatographic purification on silica gel using system K and digesting with diethyl ether, by proceeding from 0.84 g (1.55 mmol) of 5(S)-amino-4(S)-hydroxy-6-cyclohexyl-2(R)-[(p-methoxyphenyl)methyl]hexanoyl-(L)-Val-N-(2-methoxyethyl)amide from Example 22a, 412 mg (1.55 mmol) of trans-benzyloxycarbonyl-(L)-4-hydroxyproline (Bachem, Bubendorf, Switzerland), 0.26 ml (1.63 mmol) of diethyl cyanophosphonate and 0.5 ml (3.6 mmol) of triethylamine. TLC $R_f(K)=0.50$; $t_{ret}(I)=13.8$ min; FAB MS $(M+H)^+=753$.

Example 33

5(S)-((L)-[trans-4-Hydroxylprolyl]amino)-4(S)-hydroxy-6-cyclohexyl-2(R)-[(p-methoxyphenyl)methyl]hexanoyl-(L)-Val-N-(2-methoxyethyl)amide A solution of 700 mg (0.93 mmol) of 5(S)-(benzyloxycarbonyl-(L)-4-[trans-hydroxyprolyl]amino)-4(S)-hydroxy-6-cyclohexyl-2(R)-[(p-methoxyphenyl)methyl]hexanoyl-(L)-Val-N-(2-methoxyethyl)amide from Example 32 in 90 ml of methanol is hydrogenated, at RT for 2.5 h, in the presence of 140 mg of 10% palladium on charcoal under 1 atm hydrogen pressure. The catalyst is filtered off, the filtrate is evaporated to dryness, and the title compound is obtained as a white solid after digesting with diethyl ether. TLC $R_f(K)=0.18$; $t_{ret}(I)=9.9$ min; FAB MS $(M+H)^+=619$.

Example 34

5(S)-(2-Amino-4-thiazolylacetylamino)-4(S)-hydroxy-6-cyclohexyl-2(R)-[(p-methoxyphenyl)methyl]hexanoyl-(L)-Val-N-(2-methoxyethyl)amide In analogy with Example 28, the title compound is obtained as a white solid, after digesting with diethyl ether, by proceeding from 0.60 g (1.11 mmol) of 5(S)-amino-4(S)-hydroxy-6-cyclohexyl-2(R)-[(p-methoxyphenyl)methyl]hexanoyl-(L)-Val-N-(2-methoxyethyl)amide from Example 22a), 211 mg (1.33 mmol) of 2-amino-4-thiazoleacetic acid (Aldrich, Steinheim, FRG), 0.25 ml (1.63 mmol) of diethyl cyanophosphonate and 0.55 ml (3.91 mmol) of triethylamine. TLC $R_f(B)=0.50$; $t_{ret}(I)=10.8$ min; FAB MS $(M+H)^+=646$.

Example 35

5(S)-(6-(4-Methyl-1-piperazinyl)-3-pyridylcarbonylamino)-4(S)-hydroxy-6-cyclohexyl-2(R)-[(p-methoxyphenyl)methyl]hexanoyl-(L)-Val-N-(2-methoxyethyl)amide In analogy with Example 28, the title compound is obtained as a white solid, after digesting with ethyl acetate, by proceeding from 0.60 g (1.11 mmol) of 5(S)-amino-4(S)-hydroxy-6-cyclohexyl-2(R)-[(p-methoxyphenyl)methyl]hexanoyl-(L)-Val-N-(2-methoxyethyl)amide from Example 22a), 246 mg (1.12 mmol) of 6-(4-methyl-1-piperazinyl)-3-pyridinecarboxylic acid (preparation, see EP 0 385 351 A1), 0.2 ml (1.22 mmol) of diethyl cyanophosphonate and 0.55 ml (3.91 mmol) of triethylamine. TLC $R_f(B)=0.28$; $t_{ret}(I)=10.7$ min; FAB MS $(M+H)^+=709$.

Example 36

5(S)-(4-(4-Morpholinylmethyl)benzoylamino)-4(S)-hydroxy-6-cyclohexyl-2(R)-[(p-methoxyphenyl)methyl]hexanoyl-(L)-Val-N-(2-methoxyethyl)amide In analogy with Example 28, the title compound is obtained as a white solid, after digesting with diethyl ether, by proceeding from 1.0 g (1.84 mmol) of 5(S)-amino-4(S)-hydroxy-6-cyclohexyl-2(R)-[(p-methoxyphenyl)methyl]hexanoyl-(L)-Val-N-(2-methoxyethyl)amide from Example 22a), 523 mg (2.03 mmol) of 4-(4-morpholinylmethyl)benzoic acid hydrochloride (preparation, see Tet. Lett. 32, 7385 (1991)), 0.33 ml (2.02 mmol) of diethyl cyanophosphonate and 1.29 ml (9.22 mmol) of triethylamine. TLC R$_f$(B)=0.60; t$_{ret}$(I)=11.1 min; FAB MS (M+H)$^+$=709.

Example 37

5(S)-(O-[4-Tetrahydropyranyl]-(L)-lactoylamino)-4(S)-hydroxy-6-cyclohexyl-2(R)-[(p-methoxyphenyl)methyl]hexanoyl-(L)-Val-N-(2-methoxyethyl)amide In analogy with Example 28, the title compound is obtained as a white solid, after digesting with ethyl acetate, by proceeding from 1.0 g (1.84 mmol) of 5(S)-amino-4(S)-hydroxy-6-cyclohexyl-2(R)-[(p-methoxyphenyl)methyl]hexanoyl-(L)-Val-N-(2-methoxyethyl)amide from Example 22a), 321 mg (1.88 mmol) of O-[4-tetrahydropyranyl]-(L)-lactic acid, 0.33 ml (2.02 mmol) of diethyl cyanophosphonate and 1.03 ml (7.38 mmol) of triethylamine. TLC R$_f$(B)=0.72; t$_{ret}$(I)=14.0 min; FAB MS (M+H)$^+$=662.

The starting material is prepared in the following manner:

37a) O-[4-Tetrahydropyranyl]-(L)-lactic acid (=2(S)-(tetrahydropyran-4-yloxy)propanoic acid)

A solution of 1.021 g (0.951 ml, d=1.074; 10 mmol) of tetrahydro-2H-pyran-4-ol (Fluka, Buchs, Switzerland) in absolute 1,4-dioxane is treated, at 65° C., with 1.6 g (40 mmol) of 60% sodium hydride in oil (Fluka, Buchs, Switzerland). The resulting, grey suspension is stirred under reflux for 2 hours and then is allowed to cool back down to 65° C., after which a solution of 1.08 g (0.863 ml, d=1.258; 10 mmol) of R(+)-2-chloropropionic acid (Fluka, Buchs, Switzerland; puriss.) in absolute 1,4-dioxane is added dropwise within the space of approximately 8 min. The resulting brown suspension is diluted with dioxane so that, in the end, the reaction mixture contains 55 ml of dioxane, and this mixture is then heated for 3 hours under reflux and while stirring. The mixture is subsequently stirred at room temperature for a further 14 hours. The brown suspension which is thus obtained is now treated dropwise with 40 ml of water within the space of 2 min, and the resulting yellow solution is evaporated to dryness under HV. The residue is taken up in 200 ml of water, and the aqueous solution is extracted once, in each case, with 250 ml and with 150 ml of ethyl acetate. The organic phases are washed once with 100 ml of water. All the water phases are combined and then acidified (pH 1) with 4N hydrochloric acid. The solution thus obtained is saturated with sodium chloride and extracted twice with 300 ml of ethyl acetate on each occasion. The organic phases are washed three times with 150 ml of a saturated solution of sodium chloride on each occasion. Subsequently, all the ethyl acetate extracts are combined, dried over magnesium sulfate, filtered and evaporated to dryness under HV and at 30° C. The residue (yellow oil) is purified by kugelrohr distillation (b.p. approximately 160° C. at 0.8 mm Hg). The title compound is obtained as a colourless oil which, on standing, solidifies to give colourless crystals which melt between 33.7° and 67.6° C. and still contain 0.13 mol (1.30%) of water. [α]$_D^{20}$=−46.7°±1.0° (c=1.035; CHCl$_3$).

Example 38

5(S)-(Boc-Amino)-4(S)-hydroxy-6-phenyl-2(R)-[(p-benzyloxyphenyl)methyl]hexanoyl-(L)-Val-N-(2-methoxyethyl)amide In analogy with Example 1, the title compound is obtained by proceeding from 1.29 g (1.63 mmol) of 5(S)-(Boc-amino)-4(S)-(tert-butyldimethylsilyloxy)-6-phenyl-2(R)-[(p-benzyloxyphenyl)methyl]hexanoyl-(L)-Val-N-(2-methoxyethyl)amide and 1.03 g (3.26 mmol) of TBAF trihydrate. TLC R$_f$(M)=0.58; t$_{ret}$(I)=16.9 min.

The starting material is prepared as follows:

38a) 5(S)-(Boc-Amino)-4(S)-(tert-butyldimethylsilyloxy)-6-phenyl-2(R)-[(p-benzyloxyphenyl)methyl]hexanoyl-(L)-Val-N-(2-methoxyethyl)amide In analogy with Example 1c), the title compound is obtained as a colourless resin, after chromatographic purification on silica gel using hexane/ethyl acetate (1:1) as eluent, by proceeding from 1.14 g (1.8 mmol) of 5(S)-(Boc-amino)-4(S)-(tert-butyldimethylsilyloxy)-6-phenyl-2(R)-[(p-benzyloxyphenyl)methyl]hexanoic acid, 313 mg (1.8 mmol) of H-(L)-Val-N-(2-methoxyethyl)amide (preparation, Example 1b)) and 751 mg (1.98 mmol) of HBTU in 18 ml of a 0.25M solution of NMM in acetonitrile. TLC R$_f$(hexane/ethyl acetate (1:1))=0.19; t$_{ret}$(I)=23.3 min; FAB MS (M+H)$^+$=790.

38b) 5(S)-[1(S)-(Boc-Amino)-2-phenylethyl]-3(R)-[(p-benzyloxyphenyl)methyl]-dihydrofuran-2-(3H)-one In analogy with Example 1h), 1.13 g (3.70 mmol) of 5(S)-[1(S)-(Boc-amino)-2-phenylethyl]dihydrofuran-2-(3H)-one [Example 2b)], dissolved in 4.8 ml of THF and 0.75 ml of 1,3-dimethyl-3,4,5,6-tetrahydro-2(1H)-pyrimidinone, are deprotonated, at −75° C., with 7.25 ml of a 1M solution of lithium bis(trimethylsilyl)amide in THF, and alkylated (15 min) with 1.2 g (3.7 mmol) of p-benzyloxybenzyl iodide (Example 1d)) in 2 ml of THF. Column chromatography (SiO$_2$, hexane/ethyl acetate, 2:1) affords the pure title compound: TLC R$_f$(D)=0.30; t$_{Ret}$(I)=28.2 min; FAB-MS (M+H)$^+$=502.

38c) 5(S)-(Boc-Amino)-4(S)-hydroxy-6-phenyl-2(R)-[(p-benzyloxyphenyl)methyl]-hexanoic acid In analogy with Example 1i), 1.4 g (2.79 mmol) of 5(S)-[1(S)-(Boc-amino)-2-phenylethyl]-3(R)-[(p-benzyloxyphenyl)methyl]dihydrofuran-2-(3H)-one in 45 ml of dimethoxyethane and 23 ml of water are hydrolysed with 11 ml of a 1M lithium hydroxide solution. The reaction mixture, which has been partially evaporated, is poured onto a mixture of ice, 137 ml of sat. NH$_4$Cl solution, 11 ml of 10% citric acid solution and 56 ml of methylene chloride, and methanol is added until the precipitated solid dissolves. The aqueous phase is extracted with 2 portions of methylene chloride/methanol, approximately 10:1, and the organic phases are washed with saline, dried with Na$_2$SO$_4$ and evaporated: t$_{Ret}$(I)=24.0 min; FAB-MS (M+H)$^+$=520.

38d) 5(S)-(Boc-Amino)-4(S)-(tert-butyldimethylsilyloxy)-6-phenyl-2(R)-[(p-benzyloxylphenyl)methyl]hexanoic acid 1.4 g (2.69 mmol) of 5(S)-(Boc-amino)-4(S)-hydroxy-6-phenyl-2(R)-[(p-benzyloxyphenyl)methyl]-hexanoic acid in 2.9 ml of DMF are stirred, at RT for 18 h, together with 1.87 g (12.4 mmol) of tert-butyldimethylchlorosilane and 1.5 g (22 mmol) of imidazole. The reaction mixture is then poured onto ice water, and this mixture is extracted with 3 portions of ethyl acetate; the combined organic phases are washed with 10% citric acid solution, water and saline, dried with sodium sulfate and evaporated. An oil is obtained. This is followed by hydrolysis of the silyl ester function of the oil, at RT, using 2.2 g of potassium carbonate in 63 ml of methanol/water/THF, 3:1:1, and partial evaporation at RT. The aqueous residue is poured onto 10% citric acid solution and ice, and this mixture is extracted 3 times with ethyl acetate; the organic phases are washed twice with water and saline, dried with sodium sulfate and evaporated. Column chromatography (SiO$_2$, D) of the crude product yields the title compound: TLC R$_f$(D)=0.17; t$_{Ret}$(I)=33.7 min; FAB-NS (M+H)$^+$=634.

Example 39

5(S)-(Boc-Amino)-4(S)-hydroxy-6-1phenyl-2(R)-[(p-hydroxyphenyl)methyl]hexanoyl-(L)-Val-N-(2-methoxyethyl)amide A solution of 718 mg (1.06 mmol) of 5(S)-(Boc-amino)-4(S)-hydroxy-6-phenyl-2(R)-[(p-benzyloxyphenyl)methyl]

hexanoyl-(L)-Val-N-(2-methoxyethyl)amide from Example 38 in 50 ml of methanol is hydrogenated, at RT for 3 h, in the presence of 150 mg of 10% palladium on charcoal and under 1 atm hydrogen pressure. The title compound is obtained as an amorphous solid after the catalyst has been filtered off and the filtrate has been evaporated. TLC $R_f$(hexane/ethyl acetate (2:1))=0.29; $t_{ret}$(I)=12.8 min; FAB MS (M+H)$^+$=586.

Example 40

(S)-(Boc-Amino)-4(S)-hydroxy-6-phenyl-2(R)-[(p-isobutoxylphenyl)methyl]-hexanoyl-(L)-Val-N-(2-methoxyethyl)amide A suspension consisting of 585 mg (1 mmol) of 5(S)-(Boc-amino)-4(S)-hydroxy-6-phenyl-2(R)-[(p-hydroxyphenyl)methyl]hexanoyl-(L)-Val-N-(2-methoxyethyl)amide from Example 39 and 1.22 g of caesium carbonate in 50 ml of dioxane is stirred at RT for 16 h under a nitrogen atmosphere; it is then treated with 2.7 ml of isobutyl iodide (Fluka, Buchs, Switzerland) and heated at 80° C. for 3 h until TLC monitoring can no longer detect any starting materials. Finally, the mixture is diluted with methylene chloride and the precipitate is filtered off. The filtrate is evaporated and yields the title compound after chromatographic purification on silica gel using methylene chloride/methanol (95:5) as the eluent and crystallization from ethyl acetate/hexane. TLC $R_f$(L)=0.5; $t_{ret}$(I)=17.1 min; FAB MS (M+H)$^+$=642.

Example 41

5(S)-(Boc-Amino)-4(S)-hydroxy-6-phenyl-2(R)-[(p-(2-pyridylmethoxy)phenyl)methyl]hexanoyl-(L)-Val-N-(2-methoxyethyl)amide In analogy with Example 40, the title compound is obtained, after chromatographic purification on silica gel using methylene chloride/methanol (97:3) as eluent and crystallization from ethyl acetate, by proceeding from 65 mg of 5(S)-(Boc-amino)-4(S)-hydroxy-6-phenyl-2(R)-[(p-hydroxyphenyl)methyl]-hexanoyl-(L)-Val-N-(2-methoxyethyl)amide from Example 39, 137 mg of caesium carbonate and 3 ml of 2-picolyl chloride (liberated from the HCl salt (Fluka, Buchs, Switzerland) with NaHCO$_3$ solution). TLC $R_f$(L)=0.4; $t_{ret}$(I)=11.7 min; FAB MS (M+H)$^+$=677.

Example 42

5(S)-(Boc-Amino)-4(S)-hydroxy-6-phenyl-2(R)-[(p-(3-pyridylmethoxy)phenyl)methyl]hexanoyl-(L)-Val-N-(2-methoxyethyl)amide A suspension consisting of 585 mg (1 mmol) of 5(S)-(Boc-amino)-4(S)-hydroxy-6-phenyl-2(R)-[(p-hydroxyphenyl)methyl]hexanoyl-(L)-Val-N-(2-methoxyethyl)amide from Example 39 and 1.22 g caesium carbonate is stirred overnight, at RT and under a nitrogen atmosphere; it is then treated with 4.0 g of 3-picolyl chloride (librated from HCl salt (Fluka, Buchs, Switzerland) with NaHCO$_3$ solution) and heated at 85° C. for 6 h. After the addition of 100 mg of sodium iodide and 500 mg of caesium carbonate, it is heated for a further 18 h. For the working-up, the mixture is eluted with methylene chloride and the precipitate is filtered off. The filtrate is evaporated and yields the title compound, as an amorphous solid, after chromatographic purification using methylene chloride THF (2:1) and lyophilization from dioxane. TLC $R_f$(L)=0.5; $t_{ret}$(I)=11.5 min; FAB MS (M+H)$^+$=677.

Example 43

5(S)-(Boc-Amino)-4(S)-hydroxy-6-phenyl-2(R)-[(p-methoxyphenyl)methyl]hexanoyl-(L)-Val-N-(2-methoxyethyl)amide A solution of 90 mg (0.154 mmol) of 5(S)-(Boc-amino)-4(S)-hydroxy-6-phenyl-2(R)-[(p-hydroxyphenyl)methyl]hexanoyl-(L)-Val-N-(2-methoxyethyl)amide from Example 39 in 5 ml of dioxane/DMF (1:1) is treated, at 0° C., with 100 mg (0.31 mmol) of caesium carbonate and then with 0.01 ml (0.15 mmol) of methyl iodide. After having been stirred at RT for 14 h under a nitrogen atmosphere, the reaction mixture is poured onto ice-water, and this mixture is extracted with methylene chloride. The organic extacts are washed with sat. sodium bicarbonate solution and saline, filtered through wadding and evaporated. The title compound is obtained after chromatographic purification on silica gel using methylene chloride/methanol (19:1) and lyophilization from dioxane. TLC $R_f$(methylene chloride/methanol (19:1))=0.27; $t_{ret}$(I)=14.6 min; FAB MS (M+H)$^+$=600.

Example 44

5(S)-(Boc-Amino)-4(S)-hydroxy-6-phenyl-2(R)-[(3,4-methylenedioxyphenyl)methyl]hexanoyl-(L)-Val-N-(2-methoxyethyl)amide A solution of 165 mg of 5(S)-(Boc-amino)-4(S)-(tert-butyldimethylsilyloxy)-6-phenyl-2(R)-[(3,4-methylenedioxyphenyl)methyl]hexanoyl-(L)-Val-N-(2-methoxyethyl)amide in 4.04 ml of abs. DMF is treated with 127.4 mg of TBAF, and the reaction mixture is stirred at RT for 21 h. The slightly turbid, yellowish solution is poured onto 30 ml of water, and this mixture is extracted with ethyl acetate. The organic phase is washed, so that it becomes neutral, in succession, with sat. sodium bicarbonate solution and saline, and dried over sodium sulfate. The title compound is dissolved in methylene chloride and precipitated with hexane. TLC $R_f$(A)=0.42; FAB-MS (M+H)$^+$=614.

The starting material is prepared as follows:

44a) 3,4-Methylenedioxybenzyl chloride 15.04 ml of thionyl chloride are added dropwise, at 0° C., over the space of 25 min and under argon, to 10.82 g of 3,4-methylenedioxybenzyl alcohol (Fluka, Buchs, Switzerland) and 48 g of diisopropylaminomethylpolystyrene (polyhünig base: polystyrene crosslinked with 2% divinylbenzene, diisopropylaminomethylated; Fluka, Buchs, Switzerland) in 200 ml of abs. ether. After having been stirred at 0° C. for a further 1.5 h, the mixture is filtered with suction and the filtrate is concentrated on a RE and then under HV. The residue is purified by chromatography on silica gel (eluent: C), and the title compound thus obtained. TLC $R_f$(hexane:ethyl acetate, 4:1)=0.47; $^1$H-NMR (200 MHz, CDCl$_3$): 6.95–6.7(m, 3H), 5.97(s, 2H), 4.53(s, 2H).

44b) 3,4-Methylenedioxybenzyl iodide 11.65 g 3,4-methylenedioxybenzyl chloride in 128 ml of abs. acetone are treated with 49.7 g of sodium iodide, and this mixture is stirred at RT for 2.5 h under argon and while excluding light. The reaction mixture is diluted with 1.5 l of ether, and this mixture is washed with 10% sodium thiosulfate solution (600 ml) and saline. The title compound is obtained after drying over sodium sulfate and removing the solvent. It is recrystallized from ether/hexane. m.p.: 51° C.

TLC R_f(hexane:ethyl acetate, 4:1)=0.43. ¹H-NMR (360 MHz, CDCl₃): 6.93–6.77(m, 2H), 6.77–6.64(m,1H), 5.95(s, 2H), 4.44 (s,2H).

44c) 5(S)-[1(S)-(Boc-Amino)-2-phenylethyl]-3(R)-[(3,4-methylenedioxyphenyl)methyl]dihydrofuran-2-(3H)-one Under an N₂ atmosphere, a solution of 500 mg of 5(S)-[1(S)-(Boc-amino)-2-phenylethyl]-dihydrofuran-2-(3H)-one [Example 2b)] in 2 ml of abs. THF and 0.33 ml of 1,3-dimethyl-3,4,5,6-tetrahydro-2(1H)-pyrimidone (DMPU) is cooled down to −75° C. and treated, at an internal temperature of below −70° C., with 3.21 ml of a 1M solution of lithium bis(trimethylsilyl)amide in THF (Aldrich, Steinheim, FRG), and this mixture is then stirred at −75° C. for 20 min. 429 mg of 3,4-methylenedioxybenzyl iodide in 1 ml of abs. THF are added dropwise to the reaction solution within the space of 10 min using a syringe, during which period the internal temperature is not allowed to exceed −70° C., and this mixture is then thoroughly stirred at −75° C. for 1 h. 0.611 ml of propionic acid are then added to the clear solution, at from −75° C. to −70° C., using a syringe, and this is followed by 0.611 ml of water. During this procedure, the temperature rises to −30° C. After that, the reaction mixture is diluted with 35 ml of ethyl acetate, and the whole is stirred up with 10 ml of 10% citric acid solution for 5 min in the cold (ice/water cooling). The aqueous phase is separated off and the organic phase is washed, in succession, with saline, sat. sodium bicarbonate solution, and once again with saline. The combined aqueous phases are reextracted 2 times with ethyl acetate. The combined organic phases are dried over sodium sulfate and concentrated. The title compound is obtained as a brownish oil. Purification is effected by chromatography on silica gel (eluent D). TLC R_f(D)=0.38; FAB-MS (M+H)⁺=440.

44d) 5(S)-(Boc-Amino)-4(S)-hydroxy-6-phenyl-2(R)-[(3,4-methylenedioxyphenyl)methyl]hexanoic acid A solution of 278 mg of 5(S)-[1(S)-(Boc-amino)-2-phenylethyl]-3(R)-[(3,4-methylenedioxyphenyl)methyl]dihydrofuran-2-(3H)-one in 10.25 ml of ethylene glycol dimethyl ether and 5.15 ml of water is treated dropwise, at RT, with 2.53 ml of a 1M lithium hydroxide solution. After that, the reaction mixture is stirred at RT for 3 h, diluted with ethyl acetate and THF, and washed in a separating funnel until neutral with a mixture consisting of 31 ml of sat. ammonium chloride solution and 2.6 ml of 10% citric acid solution, followed by saline and water. The title compound, which is subjected to further processing without any further purification, is obtained after drying over sodium sulfate and removing the solvent. FAB-MS (M+H)⁺=458.

44e) 5(S)-(Boc-Amino)-4(S)-(tert-butyldimethylsilyloxy)-6-phenyl-2(R)-[(3,4-methylenedioxyphenyl)methyl] hexanoic acid A solution of 271 mg of 5(S)-(Boc-amino)-4(S)-hydroxy-6-phenyl-2(R)-[(3,4-methylenedioxyphenyl)methyl] hexanoic acid in 2.13 ml of DMF is treated, while being stirred, with 338 mg of imidazole and 415 mg of tert-butyldimethylchlorosilane. After having been stirred at RT for 20 h, the reaction solution is poured onto ice-water, and this mixture is extracted with ethyl acetate. The organic phase is washed with 10% citric acid solution and saline. A crude product is obtained which is dissolved in 7.13 ml of methanol and 2.75 ml of THF, with this solution then being treated, at RT, with a solution of 485 mg of potassium carbonate in 2.75 ml of water. The reaction mixture is stirred at RT for 2 h, concentrated down to approximately half its volume and poured onto 10% citric acid solution and ice; this mixture is then extracted with ethyl acetate. The organic phase is washed with (cold) saline. After drying over sodium sulfate, the solvent is evaporated and the residue is chromatographed on silica gel (eluent C), and the title compound is obtained. TLC R_f(C)=0.27. FAB-MS (M+H)⁺=572.

44f) 5(S)-(Boc-Amino)-4(S)-(tert-butyldimethylsilyloxy)-6-phenyl-2(R)-[(3,4-methylenedioxyphenyl)methyl] hexanoyl-(L)-Val-N-(2-methoxyethyl)amide A mixture of 120 mg of 5(S)-(Boc-amino)-4(S)-(tert-butyldimethylsilyloxy)-6-phenyl-2(R)-[(3,4-methylenedioxyphenyl)methyl]hexanoic acid, 87.6 mg of HBTU and 40.2 mg of H-(L)-Val-N-(2-methoxyethyl)amide [preparation, see Example 1b)] in 1.97 ml of a 0.25M solution of NMM in acetonitrile is stirred at RT for 19 h under argon. The solution is concentrated down to half its volume on a RE, diluted with cold ethyl acetate, and washed, in succession, with 10% citric acid, water, sat. sodium bicarbonate solution and saline. The title compound, which is subjected to further processing without being purified, is obtained after drying over sodium sulfate and removing the solvent. TLC R_f(D)=0.21. FAB-MS (M+H)⁺=728.

Example 45

5(S)-(Boc-Amino)-4(S)-hydroxy-6-phenyl-2(R)-[(3,4-dimethoxyphenyl)methyl]hexanoyl-(L)-Val-N-(2-methoxyethyl)amide In analogy with Example 44, 136 mg of 5(S)-(Boc-amino)-4(S)-(tert-butyldimethylsilyloxy)-6-phenyl-2(R)-[(3,4-dimethoxyphenyl)methyl]hexanoyl-(L)-Val-N-(2-methoxyethyl)amide in 3.38 ml of abs. DMF are desilylated with 113.6 mg of TBAF to give the title compound. Purification is effected by chromatographing twice on silica gel (eluent A, THF and methanol). The title compound is recrystallized from methylene chloride/hexane. TLC R_f(A)=0.37. FAB-MS (M+H)⁺=630.

45a) 3,4-Dimethoxybenzyl chloride

In analogy with Example 44a), the title compound is obtained from 10 g of 3,4-dimethoxybenzyl alcohol (Fluka, Buchs, Switzerland), 46.2 g of diisopropylaminomethylpolystyrene (polyhünig base) and 4.62 ml of thionyl chloride in 200 ml of abs. ether. TLC R_f(hexane:ethyl acetate 4:1)=0.31. ¹H-NMR (200 MHz, CDCl₃): 7.0–6.87 (m, 2H); 6.82 (d, 1H); 4.56 (s, 2H); 3.9 (s, 3H); 3.87 (s, 3H).

45b) 3,4-Dimethoxybenzyl iodide

In analogy with Example 44b), the title compound is obtained from 6.185 g of 3,4-dimethoxybenzyl chloride and 24.19 g of sodium iodide in 62 ml of abs. acetone. TLC R_f(hexane:ethyl acetate 4:1)=0.40. ¹H-NMR (200 MHz, CDCl₃): 6.95 (d×d, 1H); 6.88 (d, 1H); 6.75 (d, 1H); 4.47 (s, 2H); 3.87 (s, 3H); 3.86 (s, 3H).

45c) 5(S)-[1(S)-(Boc-Amino)-2-phenylethyl]-3(R)-[(3,4-dimethoxyphenyl)methyl]dihydrofuran-2-(3H)-one In analogy with Example 44c), 1 g of 5(S)-[1(S)-(Boc-amino)-2-phenylethyl]dihydrofuran-2-(3H)-one [Example 2b)] in 4 ml of abs. THF is deprotonated (−75° C.) with 6.42 ml of a 1M solution of lithium bis(trimethylsilyl)amide in THF, with the addition of 0.66 ml of DMPU, and alkylated with 911 mg of 3,4-dimethoxybenzyl iodide. Chromatography on silica gel (eluents D, C and J) gives the pure title compound. TLC R_f(C)=0.42. MS M⁺=455.

45d) 5(S)-(Boc-Amino)-4(S)-hydroxy-6-phenyl-2(R)-[(3,4-dimethoxyphenyl)methyl]hexanoic acid In analogy with Example 44d), 778 mg of 5(S)-[1(S)-(Boc-amino)-2-phenylethyl]-3(R)-[(3,4-dimethoxyphenyl)methyl]dihydrofuran-2-(3H)-one in 27.67 ml of dimethoxyethane and 13.91 ml of water are hydrolysed with 6.83 ml of 1M lithium hydroxide solution to give the title compound, which is subjected directly to further processing. TLC R_f(C)=0.07.

45e) 5(S)-(Boc-Amino)-4(S)-(tert-butyldimethylsilyloxy)-6-phenyl-2(R)-[(3,4-dimethoxyphenyl)methyl]hexanoic acid In analogy with Example 44e), 804 mg of 5(S)-(Boc-amino)-4(S)-hydroxy-6-phenyl-2(R)-[(3,4-dimethoxyphenyl)methyl]hexanoic acid in 5.94 ml of DMF are silylated with 1.162 g of tert-butyldimethylchlorosilane and 946.6 mg of imidazole. The silyl ester in the crude product is cleaved at RT in 2 h in a mixture consisting of 19.61 ml of methanol, 7.56 ml of THF, 7.56 ml of water and 1.334 g of potassium carbonate. The title compound is purified by being chromatographed twice on silica gel (eluents: D, C, J and B). TLC $R_f(C)$=0.27. MS $M^+$=557.

45f) 5(S)-(Boc-Amino)-4(S)-(tert-butyldimethylsilyloxy)-6-phenyl-2(R)-[(3,4-dimethoxyphenyl)methyl]hexanoyl-(L)-Val-N-(2-methoxyethyl)amide In analogy with Example 44f), 109.9 mg of 5(S)-(Boc-amino)-4(S)-(tert-butyldimethylsilyloxy)-6-phenyl-2(R)-[(3,4-dimethoxyphenyl)methyl]hexanoic acid, 78.1 mg of HBTU and 35.9 mg of H-(L)-Val-N-(2-methoxyethyl)amide [Example 1b)] in 1.75 ml of 0.25M NMM/CH$_3$CN are reacted to yield the title compound. TLC $R_f(A)$=0.39. FAB-MS $(M+H)^+$=744.

Example 46

5(S)-(Boc-Amino)-4(S)-hydroxy-6-phenyl-2(R)-[(3-methoxyphenyl)methyl]hexanoyl-(L)-Val-N-(2-methoxyethyl)amide In analogy with Example 44, 300 mg of 5(S)-(Boc-amino)-4(S)-(tert-butyldimethylsilyloxy)-6-phenyl-2(R)-[(3-methoxyphenyl)methyl]hexanoyl-(L)-Val-N-(2-methoxyethyl)amide in 6.63 ml of abs. DMF are desilylated with 217.7 mg of TBAF to give the title compound. Purification is effected by chromatography on silica gel (eluent A and methanol), or by precipitating the substance from cold ethyl acetate. TLC $R_f(A)$=0.32. FAB-MS $(M+H)^+$=600.

46a) 3-Methoxybenzyl iodide

In analogy with Example 44b), the title compound is obtained from 2 ml of 3-methoxybenzyl chloride (Fluka, Buchs, Switzerland) and 9.72 g of sodium iodide in 23 ml of abs. acetone. TLC $R_f$(hexane/ethyl acetate, 2.5:1)=0.71. $^1$H-NMR (200 MHz, CDCl$_3$): 7.20 (m, 1H); 7.0–6.87 (m, 2H); 6.78 (d×d, 1H); 4.42 (s, 2H); 3.8 (s, 3H).

46b) 5(S)-[1(S)-(Boc-Amino)-2-phenylethyl-3(R)-[(3-methoxyphenyl)methyl]dihydrofuran-2-(3H)-one In analogy with Example 44c), 1.5 g of 5(S)-[1(S)-(Boc-amino)-2-phenylethyl]-dihydrofuran-2-(3H)-one [Example 2b)] in 3 ml of abs. THF are deprotonated (–75° C.) with 9.62 ml of a 1M solution of lithium bis(trimethylsilyl)amide in THF, and with the addition of 0.998 ml of DMPU and alkylated with 1.22 g of 3-methoxybenzyl iodide. Chromatography on silica gel (eluent E) affords the pure title compound. TLC $R_f$(hexane/ethyl acetate, 2.5:1)=0.32. FAB-MS $(M+H)^+$=426.

46c) 5(S)-(Boc-Amino)-4(S)-hydroxy-6-1phenyl-2(R)-[(3-methoxyphenyl)methyl]hexanoic acid In analogy with Example 44d), 1.315 g of 5(S)-[1(S)-(Boc-amino)-2-phenylethyl]-3(R)-[(3-methoxyphenyl)methyl]dihydrofuran-2-(3H)-one in 49.9 ml of dimethoxyethane and 25.16 ml of water are hydrolysed with 12.36 ml of a 1M lithium hydroxide solution to give the title compound, which is directly subjected to further processing. TLC $R_f(C)$=0.09. FAB-MS $(M+H)^+$=444.

46d) 5(S)-(Boc-Amino)-4(S)-(tert-butyldimethylsilyloxy)-6-phenyl-2(R)-[(3-methoxyphenyl)methyl]hexanoic acid In analogy with Example 44e), 1.3 g of 5(S)-(Boc-amino)-4(S)-hydroxy-6-phenyl-2(R)-[(3-methoxyphenyl)methyl]hexanoic acid in 13 ml of DMF are silylated with 1.987 g of tert-butyldimethylchlorosilane and 1.646 g of imidazole. The silyl ester group in the crude product is detached at RT in 2 h in a mixture consisting of 38.94 ml of methanol, 13.34 ml of THF, 13.34 ml of water and 2.35 g of potassium carbonate. Chromatography on silica gel (eluents: E, D and C) yields the pure title compound. TLC $R_f(D)$=0.06. FAB-MS $(M+H)^+$=558.

46e) 5(S)-(Boc-Amino)-4(S)-(tert-butyldimethylsilyloxy)-6-phenyl-2(R)-[(3-methoxyphenyl)methyl]hexanoyl-(L)-Val-N-(2-methoxyethyl)amide In analogy with Example 44f), 200 mg of 5(S)-(Boc-amino)-4(S)-(tert-butyldimethylsilyloxy)-6-phenyl-2(R)-[(3-methoxyphenyl)methyl]hexanoic acid and 68.6 mg of H-(L)-Val-N-(2-methoxyethyl)amide [Example 1b)] in 3.36 ml of 0.25M NMM/CH$_3$CN are reacted with 149.4 mg of HBTU to give the title compound. TLC $R_f(C)$=0.20. FAB-MS $(M+H)^+$=714.

Example 47

5(S)-(Boc-Amino)-4(S)-hydroxy-6-phenyl-2(R)-[(2,3,4-trimethoxyphenyl)methyl]hexanoyl-(L)-Val-N-(2-methoxyethyl)amide

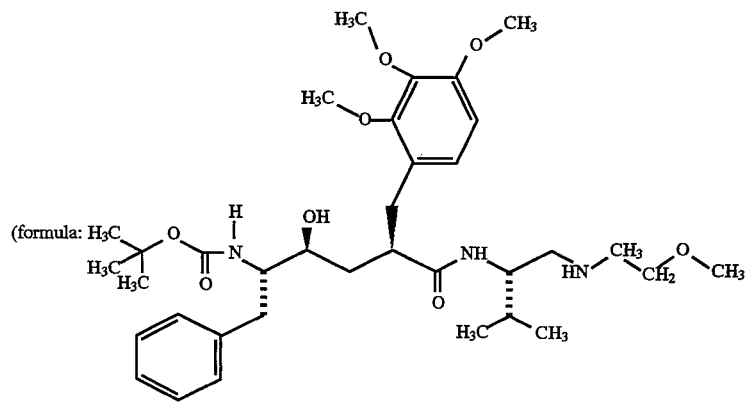

337 mg (0.379 mmol) of 5(S)-(Boc-amino)-4(S)-(tert-butyldimethylsilyloxy)-6-phenyl-2(R)-[(2,3,4-trimethoxyphenyl)methyl]hexanoyl-(L)-Val-N-(2-methoxyethyl)amide in 7.28 ml of abs. DMF are treated with 244 mg (0.758 mmol) of TBAF, and this mixture is stirred at RT for 20 h under argon. The reaction mixture is diluted with approximately 50 ml of ethyl acetate, and this mixture is washed, in succession, with water, sat. sodium bicarbonate solution and saline. The combined aqueous phases are reextracted with ethyl acetate. The combined organic phases are dried over sodium sulfate and concentrated at approximately 30° C. The residue is dissolved in a little ethyl acetate. Adding hexane results in the desired title compound being crystallized. Additional product is obtained by purifying the mother liquor on silica gel (eluent, ethyl acetate:methanol, 9:1). m.p.: 141°–143° C. TLC $R_f$ (ethyl acetate)=0.16. FAB-MS (M+H)$^+$=660. HPLC $t_{Ref}$=14.59 min (gradient II). IR (KBr)=inter alia, 1687, 1651, 1622, 1525, 1495 and 1172 cm$^{-1}$. $^1$H-NMR(CD$_3$OD)=inter alia, 7.30–7.10/m (5H); 6.78 and 6.63/each d (each 1H); 4.03/d (1H); 3.85, 3.81 and 3.80/each s (each 3H); 1.32 and 1.26/each s (in all, 9H from Boc); 0.82/pseudo t (6H).

The starting material is prepared as follows:

47a) 2,3,4-Trimethoxybenzyl chloride 5 g (24.47 mmol) of 2,3,4-trimethoxybenzyl alcohol (Aldrich, Steinheim, FRG) are dissolved, under argon, in 13.9 ml of abs. methylene chloride, and this solution is treated with 0.278 ml of pyridine. 3.05 ml of thionyl chloride in 6.94 ml of abs. methylene chloride are added dropwise to this solution, while cooling slightly (ice/water), within the period of 20 min. During this procedure, the internal temperature rises to approximately 18°–23° C. The mixture is left to react subsequently for 45 min and the slightly yellow solution is then poured onto ice/water. After the phases have been separated, the organic phase is washed once each with 1N sulfuric acid and water. After drying over Na$_2$SO$_4$, and removing the solvent, the oily residue is distilled under HV (b.p.: 93°–95° C./0.07 Torr), and the title compound is obtained. $^1$H-NMR (220 MHz, CDCl$_3$): 7.05 (d, 1H); 6.65 (d, $^1$H); 4.61 (s, 2H); 3.97 (s, 3H); 3.85 (s, 3H). HPLC: $t_{Ref}$=8.1 min (gradient II).

47b) 2,3,4-Trimethoxybenzyl iodide 46.64 g (215.2 mmol) of 2,3,4-trimethoxybenzyl chloride in 466 ml of abs. acetone are treated with 156.7 g (4.86 equivalents) of sodium iodide, and this mixture is stirred at RT for 2.75 h while excluding light. The reaction mixture is treated with approximately 3 l of (cold) ether, and the organic phase is washed once with 10 sodium thiophosphate solution and twice with saline (both kinds of solutions being cold). The combined aqueous phases are reextracted with ether. The combined organic phases are dried over Na$_2$SO$_4$ and evaporated on a RE at approximately 30° C. The residue, which is the desired title compound, is dried again under HV and subjected to further processing as a crude product. $^1$H-NMR (200 MHz, CDCl$_3$): 7.03 and 6.59 (each d; each 1H); 4.47 (s, 2H); 4.05, 3.85 and 3.84 (each s, each 3H).

47c) 5(S)-[1(S)-(Boc-Amino)-2-phenylethyl]-3(R)-[(2,3,4-trimethoxyphenyl)methyl]dihydrofuran-2-(3H)-one A solution of 1.368 g (4.48 mmol) of 5(S)-[1(S)-(Boc-amino)-2-phenylethyl]dihydrofuran-2-(3H)-one [Example 2b)] in 5 ml of abs. THF and 0.91 ml (1.67 equivalents) of DMPU is cooled down to −75° C., under argon, and treated dropwise, at an internal temperature of below −70° C. and over the period of approximately 20 min, with 8.78 ml of a 1M solution of lithium bis(trimethylsilyl)amide in THF (Aldrich). After a further 15 min, a solution of 1.38 g (1 equivalent) of 2,3,4-trimethoxybenzyl iodide in 2.5 ml of abs. THF is added dropwise to this mixture, within the period of approximately 15 min, and the mixture is allowed to react at −75° C. for a further 2.25 h. For the working-up, the reaction mixture is treated with 1.67 ml of propionic acid and 1.67 ml of water, and the temperature is allowed to rise to 0° C. The mixture is poured onto 20 ml of (cold) 10% citric add, and approximately 50 ml of (cold) ethyl acetate is added to this mixture. After stirring for a further 5 min, the phases are separated. The organic phase is washed, in succession, with saline, sat. sodium bicarbonate solution and saline once again. The combined aqueous phases are reextracted twice with ethyl acetate. The combined organic phases are dried over Na$_2$SO$_4$ and concentrated. The residue which remains after removing the solvent is chromatographed on silica gel (hexane:ethyl acetate, 3:1), and the title compound thereby obtained. HPLC $t_{Ref}$=16.49 min (gradient II). FAB-MS (M+H)$^+$=486 and M$^+$=485. IR(KBr)=inter alia, 3312, 1759, 1686, 1603, 1537, 1165 and 1104 cm$^{-1}$. $^1$H-NMR(CD$_3$OD)=inter alia, 7.30–7.10 (m, 5H); 6.84 and 6.66 (each d, each 1H); 3.85, 3.82 and 3.87 (each s, each 3H); 1.30 (s, 9H).

47d) 5(S)-(Boc-Amino)-4(S)-hydroxy-6-phenyl-2(R)-[(2,3,4-trimethoxophenyl)methyl]hexanoic acid A solution of 1.354 g (2.685 mmol) of 5(S)-[1(S)-(Boc-amino)-2-phenylethyl]-3(R)-[(2,3,4-trimethoxyphenyl)methyl]dihydrofuran-2-(3H)-one in 43.36 ml of dimethoxyethane and 21.86 ml of water is treated, at RT, with 10.74 ml of a 1M solution of lithium hydroxide in water, and this reaction mixture is stirred for 2 h. It is then transferred to a separating funnel, diluted with 132 ml of sat. ammonium chloride solution and 11 ml of a 10% citric acid solution (both cold), and this mixture is then extracted with ethyl acetate and a little THF. The title compound, which is dried under HV and subjected to further processing without being purified, is obtained after washing the organic phase with (cold) saline and drying it over sodium sulfate. TLC $R_f$(C)=0.03. MS (M-H$_2$O)$^+$=485.

47e) 5(S)-(Boc-Amino)-4(S)-(tert-butyldimethylsilyloxy)-6-phenyl-2(R)-[(2,3,4-trimethoxyphenyl)methyl]hexanoic acid A solution of 1.308 g (2.597 mmol) of 5(S)-(Boc-amino)-4(S)-hydroxy-6-phenyl-2(R)-[(2,3,4-trimethoxyphenyl)methyl]hexanoic acid, 1.443 g (20.776 mmol) of imidazole and 1.816 g (11.686 mmol) of tert-butyldimethylchlorosilane in 13 ml of abs. DMF is stirred at RT for 17 h under argon. After that, the reaction mixture is poured onto ice-water and this mixture is extracted with ethyl acetate. The organic phase is washed with cold 10% citric acid solution and saline. The combined aqueous phases are reextracted with ethyl acetate. The combined organic phases are dried over sodium sulfate and evaporated on a RE at approximately 30° C. The resulting product is dissolved in 34.51 ml of methanol and 11.82 ml of THF, and this solution is treated, at RT, with 2.08 g of potassium carbonate in 11.82 ml of water. After it has been stirred for 2.5 h, the reaction mixture is concentrated down, at approximately 30° C., to half its volume and treated with ethyl acetate and 10% citric acid solution (cold), and the phases are separated. The organic phase is washed a further two times with (cold) saline. The combined aqueous phases are reextracted with ethyl acetate. The combined organic phases are dried over Na$_2$SO$_4$ and concentrated. The residue is purified by chromatography on silica gel (hexane:ethyl acetate, 1:1, and then 1:1.5), and the title compound is obtained. TLC $R_f$(J)=0.02. FAB-MS (M+H)$^+$=618 IR(KBr) inter alia: 1712, 1495, 1366, 1101 and 836 cm$^{-1}$. $^1$H-NMR(CD$_3$OD) inter alia: 7.30–7.10 (m, 5H); 6.84 and 6.67 (each d, each $^1$H); 6.23 and 5.55 (each d, in all $^1$H from NH); 3.86, 3.81 and 3.80 (each s, each 3H); 1.31 and 1.20 (each s, in all 9H from Boc); 0.93 (s, 9H); 0.14 and 0.11 (each s, each 3H).

47f) 5(S)-(Boc-Amino)-4(S)-(tert-butyldimethylsilyloxy)-6-phenyl-2(R)-[(2,3,4-trimethoxy-phenyl)methyl]hexanoyl-(L)-Val-N-(2-methoxyethyl)amide A mixture of 250 mg (0.405 mmol) of 5(S)-(Boc-amino)-4(S)-(tert-butyldimethylsilyloxy)-6-phenyl-2(R)-[(2,3,4-trimethoxyphenyl)methyl]hexanoic acid, 168:8 mg (0.445 mmol) of HBTU and 77.55 mg (0.445 mmol) of H-(L)-Val-N-(2-methoxyethyl)amide [Example 1b)] in 3.8 ml of a 0.25M solution of NMM in acetonitrile (2.35 equivalents) is stirred for 21 h under argon and at RT. After that, the reaction mixture is concentrated on a RE at approximately 30° C., and the residue is taken up in ethyl acetate; this solution is washed, in succession, with 10% citric acid solution, water, sat. sodium bicarbonate solution and saline (all being cold). The combined aqueous phases are reextracted with ethyl acetate. The combined organic phases are dried over $Na_2SO_4$ and concentrated. The crude product (title compound) is subjected to further processing without purification. TLC $R_f(A)$=0.57. FAB-MS $(M+H)^+$=774. HPLC $t_{Ret}$=21.68 min (gradient II). IR(KBr)=inter alia 1711, 1653, 1495, 1468, 1100 and 836 cm$^{-1}$. $^1$H-NMR($CD_3OD$)=inter alia, 7.3–7.1 (m, 5H); 6.79 and 6.65 (each d, each 1H); 5.93 and 5.57 (each d, in all 1H from NH); 3.87, 3.83 and 3.80 (each s, each 3H); 3.35 (s, 2H); 1.30 and 1.20 (each s, in all 9H from Boc); 0.96 (s, 9H); 0.90 and 0.87 (each 3H); 0.18 and 0.16 (each s, each 3H).

Alternatively, the compound described in Example 47 can also be readily obtained in the following manner [see, in this context, J. Med. Chem. 37, 2991 (1994)]:

47g) 5(S)-(Boc-Amino)-4(S)-hydroxy-6-phenyl-2(R)-[(2,3,4-trimethoxyphenyl)methyl]hexanoyl-(L)-Val-N-(2-methoxyethyl)amide 1 g (2.06 mmol) of 5(S)-[1(S)-(Boc-amino)-2-phenylethyl]-3(R)-[(2,3,4-trimethoxyphenyl)methyl]dihydrofuran-2-(3H)-one [prepared in accordance with Example 47c)] and 2.51 g (7 equivalents) of H-(L)-Val-N-(2-methoxyethyl)amide [prepared in accordance with Example 1b)] are reacted, at 70° C. for 18 h, with 0.354 ml (3 equivalents) of acetic acid in a bomb tube. The mixture is allowed to cool down and the residue is taken up in ethyl acetate, and the organic phase is washed, in succession, with 1N hydrochloric acid, water and saline. After drying over sodium sulfate and removal of the solvent, the residue is recrystallized from ethanol/water. The resulting compound is identical to the title compound described in Example 47.

Another alternative method for preparing the title compound from Example 47:

47h) 5(S)-(Boc-Amino)-4(S)-hydroxy-6-phenyl-2(R)-[(2,3,4-trimethoxylphenyl)methyl]hexanoyl-(L)-Val-N-(2-methoxyethyl)amide 500 mg (1.03 mmol) of 5(S)-[1(S)-(Boc-amino)-2-phenylethyl]-3(R)-[(2,3,4-trimethoxyphenyl)methyl]dihydrofuran-2-(3H)-one [prepared in accordance with Example 47c)] and 538.5 mg (3 equivalents) of H-(L)-Val-N-(2-methoxyethyl)amide [prepared in accordance with Example 1b)] are reacted, at 90° C. for 40 h, with 101 mg (1 equivalent) of 2-hydroxypyridine in a bomb tube. The residue is taken up in 4 ml of ethanol and poured onto 50 ml of water, and this mixture is stirred for 2 h. The crystalline precipitate is filtered off with suction, washed with water and dried. The resulting compound is identical to the title compound described in Example 47.

Alternatively, and in a manner analogous to that indicated in Example 47c), the title compound described in that example can also be prepared using 2,3,4-trimethoxybenzyl bromide (instead of 2,3,4-trimethoxybenzyl iodide). The 2,3,4-trimethoxybenzyl bromide is prepared in the following manner:

47i) 2,3,4-Trimethoxybenzyl bromide 2.04 g (10 mmol) of 2,3,4-trimethoxybenzyl alcohol in 30 ml of abs. toluene are treated with 0.258 ml (0.32 equivalents) of pyridine, and the solution is cooled down to approximately 4° C. using ice-water. 0.951 ml of phosphorus tribromide in 5 ml of abs. toluene is added dropwise, at this temperature and over the period of 30 min, to this solution, which is left to stir at this temperature for a further 45 min. The reaction mixture is diluted with ether and the whole is poured onto ice-water, with this mixture then being stirred for 5 min. After the phases have been separated, the organic phase is washed, in succession, with water, saline, sat. sodium bicarbonate solution and once again with saline (all being cold). After the organic phase has been dried over sodium sulfate, it is concentrated, and residual solvents are removed from the residue under high vacuum for 1 h. The resulting title compound is subjected, without purification, to further processing. $^1$H-NMR (200 MHz; $CDCl_3$)=7.05/d (1H); 6.65/d (1H); 4.55/s (2H); 4.07, 3.88 and 3.85/each s (each 3H).

Example 48

5(S)-(Boc-Amino)-4(S)-hydroxy-6-phenyl-2(R)-[(3,4,5-trimethoxyphenyl)methyl]hexanoyl-(L)-Val-N-(2-methoxyethyl)amide In analogy with Example 44, 191 mg of 5(S)-(Boc-amino)-4(S)-(tert-butyldimethylsilyloxy)-6-phenyl-2(R)-[(3,4,5-trimethoxyphenyl)methyl]hexanoyl-(L)-Val-N-(2-methoxyethyl)amide in 4.6 ml of abs. DMF are desilylated with 159 mg of TBAF to give the title compound. The crude product is purified by chromatography on silica gel (eluent A), dissolved in dioxane and lyophilized. TLC $R_f(A)$=0,26. FAB-MS $(M+H)^+$=660.

The starting material is prepared as follows:

48a) 3,4,5-Trimethoxybenzyl iodode

In analogy with Example 44b), the title compound is obtained from 5 g of 3,4,5-trimethoxybenzyl chloride (Fluka, Buchs, Switzerland) and 16.89 g of sodium iodide in 40 ml of abs. acetone. TLC $R_f$(hexane:ethyl acetate, 4:1)= 0.27. $^1$H-NMR (360 MHz, $CDCl_3$): 6.60 (s, 2H); 4.44 (s, 2H); 3.86 (s, 6H); 3.83 (s, 3H).

48b) 5(S)-[1(S)-(Boc-Amino)-2-phenylethyl]-3(R)-[(3,4,5-trimethoxyphenyl)methyl]dihydrofuran-2-(3H)-one In analogy with Example 44c), 1 g of 5(S)-[1(S)-(Boc-amino)-2-phenylethyl]-dihydrofuran-2-(3H)-one [Example 2b)] in 4 ml of abs. THF is deprotonated (−75° C.) with 6.42 ml of a 1M solution of lithium bis(trimethylsilyl)amide in THF, and with the addition of 0.66 ml of DMPU and alkylated with 1.008 g 3,4,5-trimethoxybenzyl iodide. Chromatography on silica gel (eluent, hexane/acetone 3:1) affords the title compound. TLC $R_f$(hexane/acetone, 3:1)= 0.22. FAB-MS $M^+$=485.

48c) 5(S)-(Boc-Amino)-4(S)-hydroxy-6-phenyl-2(R)-[(3,4,5-trimethoxyphenyl)methyl]hexanoic acid In analogy with Example 44d), 1.097 g of 5(8)-[1(S)-(Boc-amino)-2-phenylethyl]-3(R)-[(3,4,5-trimethoxyphenyl)methyl]dihydrofuran-2-(3H)-one in 36.48 ml of dimethoxyethane and 18.39 ml of water are hydrolysed with 9.03 ml of 1M lithium hydroxide solution to give the title compound, which is subjected, without purification, to further processing.

48d) 5(S)-(Boc-Amino)-4(S)-(tert-butyldimethylsilyloxy)-6-phenyl-2(R)-[(3,4,5-trimethoxyphenyl)methyl]hexanoic acid In analogy with Example 44e), 1.526 g of 5(S)-(Boc-amino)-4(S)-hydroxy-6-phenyl-2(R)-[(3,4,5-trimethoxyphenyl)methyl]hexanoic acid in 15.16 ml of DMF are silylated with 2.11 g of tert-butyldimethylchlorosilane and 1.683 g of imidazole. The silyl ester group in the crude product is detached, at RT in 2.5 h, in a mixture consisting of 40.3 ml of methanol, 13.8 ml of THF, 13.8 ml of water and 2.42 g of potassium carbonate. The title compound is purified by being chromatographed twice on silica gel (solvents: hexane, C and J). TLC $R_f(A)$=0.39. FAB-MS $(M+H)^+$=618.

48e) 5(S)-(Boc-Amino)-4(S)-(tert-butyldimethylsilyloxy)-6-phenyl-2(R)-[(3,4,5-trimethoxyphenyl)methyl]hexanoyl-(L)-Val-N-(2-methoxyethyl)amide In analogy with Example 44f), 202 mg of 5(S)-(Boc-amino)-4(S)-(tert-butyldimethylsilyloxy)-6-phenyl-2(R)-[(3,4,5-trimethoxyphenyl)methyl]hexanoic acid and 62.6 mg of H-(L)-Val-N-(2-methoxyethyl)amide [prepared in accordance with Example 1b)] in 3.07 ml of 0.25M NMM/CH$_3$CN are reacted with 136.4 mg of HBTU, and with a further 24.8 mg of HBTU, to form the title compound, which is subjected, without purification, to further processing, after a reaction time of 20 h. TLC $R_f(A)$=0.32. FAB-MS $(M+H)^+$=774.

Example 49

5(S)-(Boc-Amino)-4(S)-hydroxy-6-phenyl-2(R)-[(2,4-dimethoxyphenyl)methyl]hexanoyl-(L)-Val-N-(2-methoxyethyl)amide 599 mg (0.805 mmol) of 5(S)-(Boc-amino)-4(S)-(tert-butyldimethylsilyloxy)-6-phenyl-2(R)-[(2,4-dimethoxyphenyl)methyl]hexanoyl-(L)-Val-N-(2-methoxyethyl)amide in 15.5 ml of abs. DMF are treated with 508 mg (1.6 mmol) of TBAF and the reaction mixture is stirred at RT for 20 h under argon. It is then diluted with approximately 80 ml of ethyl acetate, and the whole is washed, in succession, with water, sat. sodium bicarbonate solution and saline. The combined aqueous phases are reextracted with ethyl acetate. The combined organic phases are dried over Na$_2$SO$_4$ and concentrated down to approximately 30 ml on a RE. During this procedure, the title compound precipitates in pure form. The latter is filtered off with suction, washed with hexane and dried to constant weight. TLC $R_f(A)$=0.28. FAB-MS $(M+H)^+$=630. HPLC $t_{Ret}$=14.79 min (gradient II). IR(KBr)=inter alia 3463, 3340, 3305, 1685, 1648, 1620 und 1524 cm$^{-1}$. $^1$H-NMR(CD$_3$OD) =inter alia 7.29–7.09/m (5H); 6.90/d (1H); 6.46/d (1H); 6.35/dxd (1H); 4.01/d (1H); 3.80 and 3.75/each s (each 3H); 3.30/s (3H); 1.35/s (9H); 0.83/pseudo t (6H).

The starting material is prepared as follows:

49a) 2,4-Dimethoxybenzyl bromide 2 g (11.77 mmol) of 2,4-dimethoxybenzyl alcohol (Aldrich, Steinheim, FRG) are dissolved in 30 ml of abs. toluene, and this solution is untreated with 0.3 ml of pyridine. The clear solution is cooled down to approximately 4° C. and 1.12 ml (0.992 equivalents) of PBr$_3$ in 6 ml of abs. toluene are added dropwise to it over the space of 30 min. After a further 45 min, the reaction solution is poured onto ice-water and the whole is extracted with ether. The organic phase is washed, in succession, with water, sat. sodium bicarbonate solution and saline (all being cold). The combined aqueous phases are reextracted with ether. The combined organic phases are dried over Na$_2$SO$_4$ and the ether is removed on a RE at about 30° C. The toluene solution which remains, and which contains the title compound, is immediately subjected to further use. TLC (hexane:ethyl acetate, 1:1): decomposition.

49b) 5(S)-[1(S)-(Boc-Amino)-2-phenylethyl]-3(R)-[(2,4-dimethoxyphenyl)methyl]-dihydrofuran-2-(3H)-one A solution of 3.57 g (11.7 mmol) of 5(S)-[1(S)-(Boc-amino)-2-phenylethyl]dihydrofuran-2-(3H)-one [Example 2b)] in 12 ml of abs. THF and 2.35 ml of DMPU (1.65 equivalents) is cooled down to −75° C., under argon, and is treated dropwise, at an internal temperature of less than −70° C. and over a period of 30 min, with 22.9 ml (1.96 equivalents) of a 1M solution of lithium bis(trimethylsilyl) amide in THF (Aldrich, Steinheim, FRG). After a further 15 min, 25 ml of a toluene solution containing approximately 1 equivalent of 2,4-dimethoxybenzyl bromide is added dropwise to this mixture, over the space of 20 min, and this mixture is allowed to react at −70° C. for 2 h. 4.36 ml of propionic acid and 4.36 ml of water are then added to this solution and the temperature is allowed to rise to 0° C. The reaction mixture is diluted with 200 ml of (cold) ethyl acetate and stirred up for 5 min with 60 ml of (cold) 10% citric acid. After that, the phases are separated. The organic phase is washed, in succession, with saline, sat. sodium bicarbonate solution and with saline once again, dried over Na$_2$SO$_4$ and concentrated. The title compound is isolated by flash chromatography on silica gel (E). TLC $R_f$ (E)=0.24. FAB-MS $(M+H)^+$=455. HPLC $t_{Ret}$=16.85 min (gradient II). IR(CH$_2$Cl$_2$)=inter alia 3429, 1769, 1712, 1613 and 1506 cm$^{-1}$. $^1$H-NMR(CDCl$_3$)=inter alia 7.34–7.10/m (5H); 6.98/d (1H); 6.45–6.29/m (2H); 4.31/txd (1H); 3.78 and 3.71/each s (each 3H); 3.08 and 2.66/each dxd (each 1H); 1.35/s (9H).

49c) 5(S)-(Boc-Amino)-4(S)-hydroxy-6-phenyl-2(R)-[(2,4-dimethoxyphenyl)methyl]hexanoic acid A solution of 1.58 g (3.47 mmol) of 5(S)-[1(S)-(Boc-amino)-2-phenylethyl]-3(R)-[(2,4-dimethoxyphenyl)methyl]dihydrofuran-2-(3H)-one in 56 ml of ethylene glycol dimethyl ether and 28.2 ml of water is treated, at RT, with 13.87 ml of a 1M solution of LiOH in water, and this mixture is stirred for 1.75 h. After that, the reaction mixture is diluted with ethyl acetate and a little THF and the whole is washed firstly with a mixture consisting of 170.6 ml of sat. ammonium chloride solution and 14.25 ml of 10% citric acid solution (both being cold) and then with saline. The combined aqueous phases are reextracted with ethyl acetate. The combined organic phases are dried over Na$_2$SO$_4$ and evaporated on a RE at about 30° C. The residue, which is the title compound, is triturated with hexane and filtered off with suction. M.p.: 144°–145° C. TLC $R_f$ (D)=at the start. FAB-MS $(M+H)^+$=474. HPLC $T_{Ret}$=14.34 min (gradient II). IR(KBr)=u.a. 3420, 3350, 2818, 1686, 1518 and 1508 cm$^{-1}$. $^1$H-NMR(CD$_3$OD)=inter alia 7.30–7.09/m (5H); 6.94/d (1H); 6.47/d (1H); 6.37/dxd (1H); 3.78 and 3.75/each s (each 3H); 1.33/s (9H).

49d) 5(S)-(Boc-Amino)-4(S)-(tert-butyldimethylsilyloxy)-6-phenyl-2(R)-[(2,4-dimethoxylphenyl)methyl]hexanoic acid A solution of 1.5 g (3.17 mmol) of 5(S)-(Boc-amino)-4 (S)-hydroxy-6-phenyl-2(R)-[(2,4-dimethoxyphenyl)methyl] hexanoic acid, 1.76 g (25.36 mmol) of imidazole and 2.22 g (14.26 mmol) of tert-butyldimethylchlorosilane in 16 ml of abs. DMF is stirred at RT for 20 h under argon. After that, the reaction mixture is poured onto ice-water and the whole is extracted with ethyl acetate. The organic phase is washed with cold 10% citric acid solution and saline. The combined aqueous phases are reextracted with ethyl acetate. The combined organic phases are dried over Na$_2$SO$_4$, and the solvent is removed on a RE at about 30° C. An oil is obtained which is dissolved in 42.1 ml of methanol and 14.4 ml of THF, and this solution is then treated, at RT, with 2.5 g of potassium carbonate in 14.4 ml of water. After it has been stirred at RT for 2 h, the reaction mixture is concentrated down to half its volume at approximately 30° C. and the residue is diluted with ethyl acetate; the whole is then washed with 10% citric acid solution and with saline (both being cold). The combined aqueous phases are reextracted with ethyl acetate. The combined organic phases are dried over $Na_2SO_4$ and evaporated. Chromatography on silica gel (D) affords the pure title compound. TLC $R_f(C)$=0.34. FAB-MS $(M+H)^+$=588. HPLC $t_{Ref}$=20.24 min (gradient II). IR(KBr)=inter alia 1712, 1654, 1614, 1588 und 1507 cm$^{-1}$. $^1$H-NMR(CD$_3$OD)=inter alia 7.30–7.10/m (5H); 6.98/d (1H); 6.50/d (1H); 6.40//dxd (1H); 3.80 and 3.76/each s (each 3H); 1.31/s (9H); 0.93/s (9H); 0.14 and 0.11/each s (each 3H).

49e) 5(S)-(Boc-Amino)-4(S)-(tert-butyldimethylsilyloxy)-6phenyl-2(R)-[(2,4-dimethoxophenyl)methyl]hexanoyl-(L)-Val-N-(2-methoxyethyl)amide A mixture of 497 mg (0.845 mmol) of 5(S)-(Boc-amino)-4(S)-(tert-butyldimethylsilyloxy)-6-phenyl-2(R)-[(2,4-dimethoxyphenyl)methyl]hexanoic acid, 352 mg (0.929 mmol of HBTU and 162 mg (0.929 mmol) of H-(L)-Val-N-(2-methoxyethyl)amide [Example 1b)] in 7.94 ml of a 0.25M solution of NMM in acetonitrile (2.35 equivalents) is stirred at RT for 20 h under argon. After that, the reaction mixture is concentrated on a RE at about 30° C. and the residue is taken up in ethyl acetate, with this solution being washed with sat. sodium bicarbonate solution and saline. The combined aqueous phases are reextracted with ethyl acetate. The combined organic phases are dried over $Na_2SO_4$, and the solvent is removed on a RE. The residue consists of the title compound in virtually pure form. TLC $R_f(J)$=0.25. FAB-MS $(M+H)^+$=744. HPLC $t_{Ref}$=21.55 min (gradient II). IR(CH$_2$Cl$_2$)=inter alia 3434, 1703, 1667, 1506 and 838 cm$^{-1}$. $^1$H-NMR(CD$_3$OD)=inter alia 7.31–7.11/m (5H); 6.91/d (1H); 6.50/d (1H); 6.37/dxd (1H); 3.84 and 3.76/each s (each 3H); 3.31/s (3H); 1.30/s (9H); 0.94/s (9H); 0.85 and 0.83/each d (each 3H); 0.16 and 0.15/each s (each 3H).

Example 50

5(S)-(Boc-Amino)-4(S)-hydroxy-6-phenyl-2(R)-[(2-methoxyphenyl)methyl]hexanoyl-(L)-Val-N-(2-methoxyethyl)amide 311 mg (0.436 mmol) of 5(S)-(Boc-amino)-4(S)-(tert-butyldimethylsilyloxy)-6-phenyl-2(R)-[(2-methoxyphenyl)methyl]hexanoyl-(L)-Val-N-(2-methoxyethyl)amide in 8.4 ml of abs. DMF are treated with 275 mg (0.871 mmol) of TBAF, and this reaction mixture is stirred at RT for 21 h under argon. It is then diluted with approximately 60 ml of ethyl acetate, and the whole is washed, in succession, with water, sat. sodium bicarbonate solution and saline. The combined aqueous phases are reextracted with ethyl acetate. The combined organic phases are dried over $Na_2SO_4$ and concentrated down to 10 ml on a RE at approximately 30° C. During this procedure, the title compound is precipitated in pure form. It is filtered off with suction, washed with hexane and dried overnight under HV. TLC $R_f$(ethyl acetate) =0.38. FAB-MS $(M+H)^+$=600. HPLC $t_{Ref}$=14.78 min (gradient II). IR(KBr)=inter alia 3335, 1685, 1653, 1619, and 1526 cm$^{-1}$. $^1$H-NMR(CD$_3$OD)=inter alia 7.28–7.06/m (6H); 7.00/d (1H); 6.88/d (1H); 6.76/t (1H); 3.81/s (3H); 3.48/s (3H); 1.33/s (9H); 0.81/pseudo t (6H).

The starting material is prepared as follows:
50a) 2-Methoxybenzyl chloride 16.8 ml of thionyl chloride are added dropwise, over the space of approximately 30 min, to 10 ml of 2-methoxybenzyl alcohol (Fluka, Buchs, Switzerland) and 53.76 g of diisopropylaminomethylpolystyrene (polyhünig base, see Ex. 44a)) in 200 ml of abs. ether. After the mixture has been stirred at 0° C. for a further 1.5 h, it is filtered with suction and the filtrate is concentrated on a RE and under HV. The residue is purified by chromatography on silica gel (eluent: hexane/ethyl acetate, 6:1). TLC $R_f$(hexane:ethyl acetate=4:1)=0.5. $^1$H-NMR (200 MHz, CDCl$_3$): 7.42–7.24 (m, 2H); 7.0–6.84 (m, 2H); 4.68 (s, 2H); 3.9 (s, 3H).

50b) 2-Methoxybenzyl iodide 2 g of 2-methoxybenzyl chloride in 22 ml of abs. acetone are treated with 9.3 g of sodium iodide and the reaction mixture is stirred at RT overnight. It is then diluted with 250 ml of ether and the whole is washed with 10% sodium thiosulfate solution and saline. After drying over sodium sulfate, and removing the solvent, the title compound, which is subjected, without purification, to further processing, is obtained. TLC $R_f$(hexane:ethyl acetate=4:1)=0.46. $^1$H-NMR (200 MHz, CDCl$_3$): 7.36–7.2 (m, 2H); 6.92–6.8 (m, 2H); 4.48 (s, 2H); 3.91 (s, 3H).

50c) 5(S)-[1(S)-(Boc-Amino)-2-phenylethyl]-3(R)-[(2-methoxyphenyl)methyl]dihydrofuran-2-(3H)-one A solution of 1 g (3.275 mmol) of 5(S)-[1(S)-(Boc-amino)-2-phenylethyl]dihydrofuran-2-(3H)-one [Example 2b)] in 4 ml of abs. THF and 0.66 ml of DMPU (1.67 equivalents) is cooled down to −75° C., under argon, and treated dropwise, at an internal temperature of below −70° C. and over the space of 30 min, with 6.42 ml (1.96 equivalents) of a 1M solution of lithium bis(trimethylsilyl)amide in THF (Aldrich, Steinheim, FRG). After a further 15 min, 812 mg (3.275 mmol) of 2-methoxybenzyl iodide, dissolved in 2 ml of THF, are added dropwise to this mixture within the space of 10 min, and the whole is allowed to react at −70° C. for 2 h. 1.22 ml of propionic acid and 1.22 ml of water are subsequently added to this solution, and the temperature is allowed to rise to 0° C. The reaction mixture is diluted with 50 ml of (cold) ethyl acetate and stirred, for 5 min, with 20 ml of (cold) 10% citric acid, and, after that, the phases are separated. The organic phase is washed, in succession, with saline, sat. sodium bicarbonate solution and once again with saline, dried over $Na_2SO_4$ and concentrate. The title compound is isolated by means of flash chromatography on silica gel (hexane:ethyl acetate=3:1). TLC $R_f$ (hexane:ethyl acetate=3:1)=0.54. MS $M^+$=455. HPLC $t_{Ref}$=17.09 min (gradient II). IR(CH$_2$Cl$_2$)=inter alia 3429, 1769, 1712, and 1495 cm$^{-1}$. $^1$H-NMR(CDCl$_3$)=inter alia 7.38–7.13/m (5H); 7.20/d (1H); 7.08/d (1H); 6.87/t (1H); 6.81/d (1H); 3.74/s (3H); 1.34/s (9H).

50d) 5(S)-(Boc-Amino)-4(S)-hydroxy-6-phenyl-2(R)-[(2-methoxylphenyl)methyl]hexanoic acid A solution of 474 mg of 5(S)-[1(S)-(Boc-amino)-2-phenylethyl]-3(R)-[(2-methoxyphenyl)methyl]dihydrofuran-2-(3H)-one in 18 ml of dimethoxyethane and 9.07 ml of water is treated dropwise, at RT, with 4.45 ml of a 1M lithium hydroxide solution. After that, the reaction mixture is stirred at RT for 3 h and diluted with ethyl acetate and THF, and the whole is washed in a separating funnel until neutral with a mixture consisting of 54.78 ml of sat. ammonium chloride solution and 4.58 ml of 10% citric acid solution, followed by saline and water. The title compound, which is subjected to further processing without any further purification, is obtained after drying over sodium sulfate and removing the solvent. TLC $R_f$(hexane/ethyl acetate 2.5:1)= 0.15.

50e) 5(S)-(Boc-Amino)-4(S)-(tert-butyldimethylsilyloxy)-6-phenyl-2(R)-[(2-methoxyphenyl)methyl]hexanoic acid A solution of 500 mg of 5(S)-(Boc-amino)-4(S)-hydroxy-6-phenyl-2(R)-[(2-methoxyphenyl)methyl]hexanoic acid in 5 ml of DMF is treated, while being stirred, with 614 mg of imidazole and 796 mg of tert-butyldimethylchlorosilane. After it has been stirred at RT for 20 h, the reaction solution is poured onto ice-water and the whole is extracted with ethyl acetate. The organic phase is washed with 10% citric acid solution and saline. The silyl ester group in the crude product is detached, at RT in 2 h, in a mixture consisting of 13.29 ml of methanol, 5.13 ml of THF, 5.13 ml of water and 904 mg of potassium carbonate. The mixture is concentrated down to half its volume on a RE at approximately 30° C., and the residue is diluted with ethyl acetate, and the organic phase is washed with 10% citric acid and saline (all being cold). The combined aqueous phases are reextracted with ethyl acetate. The combined organic phases are dried over sodium sulfate and the residue is chromatographed on silica gel (eluent, hexane:ethyl acetate, 3:1 and 1:1), and the title compound is obtained. TLC $R_f$(hexane/ethyl acetate 2.5:1) =0.12. FAB-MS (M+H)$^+$=558.

50f) 5(S)-(Boc-Amino)-4(S)-(tert-butyldimethylsilyloxy)-6-1phenyl-2(R)-[(2-methoxyphenyl)methyl]hexanoyl-(L)-Val-N-(2-methoxyethyl)amide A mixture of 250 mg (0.448 mmol) of 5(S)-(Boc-amino)-4(S)-(tert-butyldimethylsilyloxy)-6-phenyl-2(R)-[(2-methoxyphenyl)methyl]hexanoic acid, 187 mg (0.493 mmol) of HBTU and 86 mg (0.493 mmol) of H-(L)-Val-N-(2-methoxyethyl)amide [Example 1b)] in 4.2 ml of a 0.25M solution of NMM in acetonitrile (2.35 equivalents) is stirred at RT for 20 h under argon. After that, the reaction mixture is concentrated on a RE at approximately 30° C. and residue is taken up in ethyl acetate, and the whole is washed, in succession, with 10% citric acid solution, sat. sodium bicarbonate solution and saline (all being cold). The combined aqueous phases are reextracted with ethyl acetate. The combined organic phases are dried over Na$_2$SO$_4$ and the solvent is removed on a RE. The residue consists of the title compound in virtually pure form. TLC $R_f$ (hexane:ethyl acetate 1:2)=0.29. FAB-MS (M+H)$^+$=714. HPLC $t_{Ref}$=21.66 min (gradient II). IR(CH$_2$Cl$_2$)=inter alia 3435, 1704, 1667, 1495 and 836 cm$^{-1}$. $^1$H-NMR(CD$_3$OD)=inter alia 7.29–7.10/m (6H); 7.02/d (1H); 6.91/d (1H); 6.80/t (1H); 3.86/s (3H); 3.30/s (3H); 1.31/s (9H); 0.93/s (9H); 0.85/d (6H); 0.16 and 0.15/each s (each 3H).

Example 51

5(S)-(Boc-Amino)-4(S)-hydroxy-6-phenyl-2(R)-[(2,3-dimethyl-4-methoxyphenyl)methyl]hexanoyl-(L)-Val-N-(2-methoxyethyl)amide 323.5 mg (0.436 mmol) of 5(S)-(Boc-amino)-4(S)-(tert-butyldimethylsilyloxy)-6-phenyl-2(R)-[(2,3-dimethyl-4-methoxyphenyl)methyl]hexanoyl-(L)-Val-N-(2-methoxyethyl)amide in 8.4 ml of abs. DMF are treated with 280.7 mg (0.872 mmol) of TBAF, and this reaction mixture is stirred at RT for 20 h under argon. It is then diluted with approximately 80 ml of ethyl acetate and the whole is washed, in succession, with water, sat. sodium carbonate solution and saline. The combined aqueous phases are reextracted with ethyl acetate. The combined organic phases are dried over sodium sulfate and concentrated. The resulting gel-like product is chromatographed on silica gel (hexane:ethyl acetate, 1:2). The product-containing fractions are pooled and concentrated. The residue is dissolved in dioxane and lyophilized, with the title compound being obtained. TLC $R_f$(hexane:ethyl acetate 1:2)=0.18. FAB-MS (M+H)$^+$=628. HPLC $t_{Ref}$=15.52 min (gradient II). IR(KBr) =inter alia 1688, 1650, 1619, 1519 and 1261 cm$^{-1}$. $^1$H-NMR (CD$_3$OD)=inter alia 7.31–7.10 (m, 5H); 6.87 and 6.63 (each d, each 1H); 4.03 (d, 1H); 3.75, 2.20 and 2.11 (each s, each 3H); 1.35 (s, 3H); 0.83 (pseudo t, 6H).

The starting material is prepared as follows:

51a) 2,3-Dimethyl-4-methoxybenzyl chloride 1 g (6.016 mmol) of 2,3-dimethyl-4-methoxybenzyl alcohol (Aldrich, Steinheim, FRG) and 4.8 g of diisopropylaminomethylpolystyrene (polyhünig base, see Ex. 44a) in 21 ml of abs. ether are treated dropwise, at from 0° C. to 5° C. and over the space of approximately 25 min, with 0.482 ml of thionyl chloride. After the reaction has ended, the mixture is filtered with suction and the solvent and the excess reagent are removed. The residue, which is the desired title compound, is subjected, without purification, to further processing. TLC $R_f$(hexane:ethyl acetate 4:1)=0.59. IR(CH$_2$Cl$_2$) inter alia: 1599, 1485, 1466 und 1107 cm$^{-1}$. $^1$H-NMR (200 MHz, CDCl$_3$): 7.14 (d, 1H); 6.69 (d, 1H); 4.64 (s, 2H); 3.82, 2.34 and 2.18 (each s, each 3H).

51b) 2,3-Dimethyl-4-methoxybenzyl iodide 838.6 mg (4.54 mmol) of 2,3-dimethyl-4-methoxybenzyl chloride in 8.5 ml abs. acetone are treated with 3.328 g (22.1 mmol) of sodium iodide, and this mixture is stirred at RT for 15 h while excluding light. A dark-brown suspension is obtained which is taken up, for working-up, in 100 ml of diethyl ether with this solution then being washed with 10% sodium thiosulfate solution. After drying with sodium sulfate and removing the solvent, the desired title compound is obtained as a yellowish solid which is subjected, without purification, to further processing. TLC $R_f$ (hexane:ethyl acetate 4:1)=0.63. IR (CH$_2$Cl$_2$) inter alia: 1610, 1495, 1120 and 820 cm$^{-1}$. $^1$H-NMR (200 MHz, CDCl$_3$): 7.17 and 6.65 (each d, each 1H); 4.52 (s, 2H); 3.82, 2.23 and 2.18 (each s, each 3H).

51c) 5(S)-[1(S)-(Boc-Amino)-2-phenylethyl]-3(R)-[(2,3-dimethyl-4-methoxyphenyl)methyl]dihydrofuran-2(3H)-one A solution of 1.248 g (4.087 mmol) of 5(S)-[1(S)-(Boc-amino)-2-phenylethyl]dihydrofuran-2-(3H)-one (Example 2b)) in 5 ml of abs. THF and 0.823 ml (6.825 mmol) of DMPU is cooled down to −75° C., under argon, and treated dropwise, at an internal temperature of below −70° C. and over the space of approximately 17 min, with 8 ml of a 1M solution of lithium bis(trimethylsilyl)amide in THF (Aldrich). After a further 15 min, a solution of 1.128 g (4.087 mmol) of 2,3-dimethyl-4-methoxybenzyl iodide in 3 ml of abs. THF is added dropwise to this mixture within the space of 10 min, and the whole is allowed to react at −75° C. for a further 2 h. For the working-up, the reaction mixture is treated with 1.5 ml of propionic acid and 1.5 ml of water and the temperature is allowed to rise to 0° C. The mixture is poured onto 35 ml of (cold) 10% citric acid solution, and approximately 70 ml of (cold) ethyl acetate is added to this mixture. After stirring for a further 5 min, the phases are separated. The organic phase is washed, in succession, with saline, sat. sodium bicarbonate solution and with saline once again, dried over Na$_2$SO$_4$ and concentrated. The residue which remains after removing the solvent is chromatographed on silica gel (hexane:ethyl acetate, 2:1). The title compound is obtained as a colourless foam. TLC $R_f$ (hexane:ethyl acetate 2:1)=0.37. HPLC $t_{Ref}$=17.83 min (gradient II). FAB-MS (M+H)$^+$_453. IR(CH$_2$Cl$_2$)=inter alia 3428, 1769, 1712 and 1495 cm$^{-1}$. $^1$H-NMR(CDCl$_3$)=inter alia 7.38–7.08 (m, 5H); 6.86 and 6.62 (each d, each 1H); 3.78 (3H); 3.21 and 2.16 (each d×d, each 1H); 2.19 and 2.13 (each s, each 3H); and 1.35 (s, 9H).

51d) 5(S)-(Boc-Amino)-4(S)-hydroxy-6-phenyl-2(R)-[(2,3-dimethyl-4-methoxyphenyl)-methyl]hexanoic acid A solution of 1.001 g (2.2 mmol) of 5(S)-[1(S)-(Boc-amino)-2-phenylethyl]-3(R)-[(2,3-dimethyl-4-methoxyphenyl)methyl]dihydrofuran-2-(3H)-one in 35.8 ml of dimethoxyethane and 18 ml of water is treated, at RT, with 8.8 ml of a 1M solution of lithium hydroxide in water, and this reaction mixture is stirred for 2.5 h. It is then transferred to a separating funnel and diluted with 108.5 ml of sat. ammonium chloride solution and 9 ml of a 10% citric acid solution (both being cold); the whole is then extracted with ethyl acetate and a little THF. The title compound, which is subjected to further processing without being purified, is obtained after washing the organic phase with (cold) saline and drying it over sodium sulfate. TLC $R_f$(hexane:ethyl acetate 1:1)=at the start. FAB-MS (M+H)$^+$=472; IR(KBr) inter alia: 1724, 1666, 1527 and 1169 cm$^{-1}$. $^1$H-NMR (CD$_3$OD) inter alia: 7.31–7.11 (m, 5H); 6.93 and 6.68 (each d, each 1H); 3.76 (s, 3H); 3.23 and 2.59 (each d×d, each 1H); 2.21 and 2.12 (each s, each 3H); 1.27 (s, 9H).

51e) 5(S)-(Boc-Amino)-4(S)-(tert-butyldimethylsilyloxy)-6-phenyl-2(R)-[(2,3-dimethyl-4-methoxyphenyl)methyl]hexanoic acid A solution of 1.153 g (2.445 mmol) of 5(S)-(Boc-amino)-4(S)-hydroxy-6-phenyl-2(R)-[(2,3-dimethyl-4-methoxyphenyl)methyl]hexanoic acid, 1.372 g (20.05 mmol) of imidazole and 1.709 g (11.0 mmol) of tert-butyldimethylchlorosilane in 8.7 ml of abs. DMF is stirred at RT for 18 h under argon. After that, the reaction mixture is poured onto ice-water and the whole is extracted with ethyl acetate. The organic phase is washed with cold 10% citric acid solution and saline. The combined aqueous phases are reextracted with ethyl acetate. The combined organic phases are dried over sodium sulfate and evaporated on a RE at approximately 30° C. The resulting product is dissolved in 28.8 ml of methanol and 11.2 ml of THF, and this solution is treated, at RT, with 1.962 g of potassium carbonate in 11.2 ml of water. After having been stirred for 2.25 h, the reaction mixture is concentrated down to half its volume at approximately 30° C. and the residue is treated with ethyl acetate and (cold) 10% citric acid solution, and the phases are separated. The organic phase is washed a further two times with saline. The combined aqueous phases are reextracted with ethyl acetate. The combined organic phases are dried over sodium sulfate and concentrated. The residue is purified by being chromatographed twice on silica gel (hexane:ethyl acetate, 1:1 and then 3:1), and the title compound is obtained. TLC $R_f$(hexane:ethyl acetate. 1:1)=0.42. FAB-MS (M+H)$^+$=586. IR (KBr) inter alia: 1711, 1485, 1260 and 1107 cm$^{-1}$. $^1$H-NMR (CD$_3$OD) inter alia: 7.30–7.06 (m, 5H); 6.91 and 6.65 (each d, each 1H); 6.00 and 5.41 (each d, in all 1H from NH); 3.75 (s, 3H); 2.21 and 2.12 (each s, each 3H); 1.31 and 1.21 (each s, in all 9H from Boc); 0.89 (s, 9H); 0.12 and 0.08 (each s, each 3H).

51f) 5(S)-(Boc-Amino)-4(S)-(tert-butyldimethylsilyloxy)-6-phenyl-2(R)-[(2,3-dimethyl-4-methoxyphenyl)methyl]hexanoyl-(L)-Val-N-(2-methoxyethyl)amide A mixture of 319.6 mg (0.546 mmol) of 5(S)-(Boc-amino)-4(S)-(tert-butyldimethylsilyloxy)-6-phenyl-2(R)-[(2,3-dimethyl-4-methoxyphenyl)methyl]hexanoic acid, 232.5 mg (0.613 mmol) of HBTU and 106.8 mg (0.613 mmol) of H-(L)-Val-N-(2-methoxyethyl)amide (preparation, see Example 1b)) in 5.3 ml of a 0.25M solution of NMM in acetonitrile (2.4 equivalents) is stirred at RT for 2.25 h under argon. After that, the reaction mixture is concentrated on a RE at approximately 30° C. and the residue is taken up in ethyl acetate; this solution is then washed, in succession, with 10% citric acid, sat. sodium bicarbonate solution and saline (all being cold). The combined aqueous phases are reextracted with ethyl acetate. The combined organic phases are dried over Na$_2$SO$_4$ and concentrated. The crude product is chromatographed twice on silica gel (hexane:ethyl acetate, 1:2 and 1:1), and the title compound is obtained. TLC $R_f$ (hexane:ethyl acetate, 1:1)=0.16. FAB-MS (M+H)$^+$=742. HPLC $t_{Ret}$=22.41 min (gradient II).

IR(CH$_2$Cl$_2$)=inter alia 3434, 1701, 1667, 1499 and 1165 cm$^{-1}$. $^1$H-NMR(CD$_3$OD)=inter alia 7.3–7.1 (m, 5H); 6.85 and 6.64 (each d, each 1H); 5.59 and 5.61 (each d, in all 1H from NH); 3.75 (s, 3H); 2.16 and 2.02 (each s, each 3H); 1.31 and 1.20 (each s, in all 9H from Boc); 0.95 (s, 9H); 0.68 and 0.66 (each d, each 3H); 0.17 and 0.16 (each s, each 3H).

Example 52

5(S)-(Boc-Amino)-4(S)-hydroxy-6-phenyl-2(R)-[(2,4,5-trimethoxyphenyl)methyl]hexanoyl-(L)-Val-N-(2-methoxyethyl)amide In analogy with Example 44, the title compound is obtained from 5(S)-(Boc-amino)-4(S)-(tert-butyldimethylsilyloxy)-6-phenyl-2(R)-[(2,4,5-trimethoxyphenyl)methyl]hexanoyl-(L)-Val-N-(2-methoxyethyl)amide in abs. DMF using TBAF. [The starting compound for the 2,4,5-trimethoxybenzyl substituent can be bought from Fluka, Buchs, Switzerland, as 2,4,5-trimethoxybenzaldehyde, from which the corresponding alcohol is obtained as an intermediate by reducing with sodium borohydride].

Example 53

5(S)-(Boc-Amino)-4(S)-hydroxy-6-phenyl-2(R)-[(2,4,6-trimethoxyphenyl)methyl]hexanoyl-(L)-Val-N-(2-methoxyethyl)amide In analogy with Example 44, the title compound is obtained from 5(S)-(Boc-amino)-4(S)-(tert-butyldimethylsilyloxy)-6-phenyl-2(R)-[(2,4,6-trimethoxyphenyl)methyl]hexanoyl-(L)-Val-N-(2-methoxyethyl)amide in abs. DMF using TBAF. [The starting compound for the 2,4,6-trimethoxybenzyl substituent can be bought from Fluka, Buchs, Switzerland, as 2,4,6-trimethoxybenzaldehyde, from which the corresponding alcohol is obtained as an intermediate by reducing with sodium borohydride].

Example 54

5(S)-(Boc-Amino)-4(S)-hydroxy-6-phenyl-2(R)-[(5,6,7,8-tetrahydro-1-naphthyl)methyl]hexanoyl-(L)-Val-N-(2-methoxyethyl)amide In analogy with Example 44, the title compound is obtained from 5(S)-(Boc-amino)-4(S)-(tert-butyldimethylsilyloxy)-6-phenyl-2(R)-[(5,6,7,8-tetrahydro-1-naphthyl)methyl]hexanoyl-(L)-Val-N-(2-methoxyethyl)amide in abs. DMF using TBAF. [The starting compound for preparing the tetrahydronaphthyl substituent is obtained from tetralin by chloromethylation, see also, J. Org. Chem. 43, 2167(1978) for the instructions].

Example 55

5(S)-(Boc-Amino)-4(S)-hydroxy-6-phenyl-2(R)-[(2,5-dimethoxyphenyl)methyl]hexanoyl-(L)-Val-N-(2-methoxyethyl)amide In analogy with Example 44, the title compound is obtained from 5(S)-(Boc-amino)-4(S)-(tert-butyldimethylsilyloxy)-6-phenyl-2(R)-[(2,5-dimethoxyphenyl)methyl]hexanoyl-(L)-Val-N-(2-methoxyethyl)amide in abs. DMF using TBAF. [The starting compound for the 2,5-dimethoxybenzyl substituent can be bought from Flaka, Buchs, Switzerland as 2,5-dimethoxybenzyl alcohol].

Example 56

5(S)-(Boc-Amino)-4(S)-hydroxy-6-phenyl-2(R)-[(2,6-dimethoxyphenyl)methyl]hexanoyl-(L)-Val-N-(2-methoxyethyl)amide In analogy with Example 44, the title compound is obtained from 5(S)-(Boc-amino)-4(S)-(tert-butyldimethylsilyloxy)-6-phenyl-2(R)-[(2,6-dimethoxyphenyl)methyl]hexanoyl-(L)-Val-N-(2-methoxyethyl)amide in abs. DMF using TBAF. [The starting compound for the 2,6-dimethoxybenzyl substituent, 2,6-dimethoxybenzyl alcohol, is prepared from methyl 2,6-dimethoxybenzoate by reduction with lithium aluminium hydride in abs. THF. Methyl 2,6-dimethoxybenzoate is obtained from 2,6-dimethoxybenzoic acid (Fluka, Buchs, Switzerland) by reaction with dimethyl sulfate in acetone and in the presence of potassium carbonate (see instructions in Chem. Letters, 1990, 389)].

Example 57

5(S)-(Boc-Amino)-4(S)-hydroxy-6-phenyl-2(R)-[(4-methoxy-1-naphthyl)methyl]hexanoyl-(L)-Val-N-(2-methoxyethyl)amide In analogy with Example 44, the title compound is obtained from 5(S)-(Boc-amino)-4(S)-(tert-butyldimethylsilyloxy)-6-phenyl-2(R)-[(4-methoxy-1-naphthyl)methyl]hexanoyl-(L)-Val-N-(2-methoxyethyl)amide in abs. DMF using TBAF. [The starting compound for preparing the naphthylmethyl substituent, 1-bromomethyl-4-methoxynaphthalene, is obtained from 1-methoxynaphthalene (Fluka, Buchs, Switzerland) by brominating with $I_2/Br_2$ in $CHCl_3$, reacting the resulting bromide by means of a Grignard reaction and working up with $CO_2$ to form the corresponding acid; reaction of the latter with lithium aluminium hydride to form 1-hydroxymethyl-4-methoxynaphthalene (reduction); and reaction of the latter with $PBr_3$, thereby yielding the desired starting material (see Can. J. Chem. 59, 2629 (1981))].

Example 58

5(S)-(Boc-Amino)-4(S)-hydroxy-6-phenyl-2(R)-[(4-cyano-1-naphthyl)methyl]hexanoyl-(L)-Val-N-(2-methoxyethyl)amide In analogy with Example 44, the title compound is obtained from 5(S)-(Boc-amino)-4(S)-(tert-butyldimethylsilyloxy)-6-phenyl-2(R)-[(4-cyano-1-naphthyl)methyl]hexanoyl-(L)-Val-N-(2-methoxyethyl)amide in abs. DMF using TBAF. [1-Bromomethyl-4-cyanonaphthalene, the starting compound for the 4-cyanonaphthylmethyl side chain, is obtained by Friedel-Crafts acylation of 1-bromonaphthalene (Fluka, Buchs, Switzerland), followed by hypochlorite oxidation of the resulting bromoacetophenone to give bromonaphthoic acid, whose reduction then leads to the carbinol, from which the corresponding cyano compound is prepared using copper(I) cyanide, with the 1-bromomethyl-4-cyanonaphthalene side chain precursor being obtained from this cyano compound in the usual manner using $PBr_3$ (see Can. J. Chem. 59, 2629 (1981))].

Example 59

5(S)-(Boc-Amino)-4(S)-hydroxy-6-1phenyl-2(R)-[(4-fluoro-1-naphthyl)methyl]hexanoyl-(L)-Val-N-(2-methoxyethyl)amide In analogy with Example 44, the title compound is obtained from 5(S)-(Boc-amino)-4(S)-(tert-butyldimethylsilyloxy)-6-phenyl-2(R)-[(4-fluoro-1-naphthyl)methyl]hexanoyl-(L)-Val-N-(2-methoxyethyl)amide in abs. DMF using TBAF. [The starting compound for preparing the 4-fluoronaphthylmethyl side chain, 1-bromomethyl-4-fluoronaphthalene, is prepared by reducing 4-fluoro-1-naphthoic acid (Aldrich, Steinheim, FRG) with lithium aluminium hydride followed by the reaction with $PBr_3$ (see Can. J. Chem. 59, 2629 (1981))].

Example 60

5(S)-(Boc-Amino)-4(S)-hydroxy-6-cyclohexyl-2(R)-[(2,3,4-trimethoxyphenyl)methyl]hexanoyl-(L)-Val-N-(2-methoxyethyl)amide A solution of 178 mg (0.204 mmol) of 5(S)-(Boc-amino)-4(S)-(tert-butyldimethylsilyloxy)-6-cyclohexyl-2(R)-[(2,3,4-trimethoxyphenyl)methyl]hexanoyl-(L)-Val-N-(2-methoxyethyl)amide in 4 ml of abs. DMF is treated with 131 mg (0.408 mmol) of TBAF, and the reaction mixture is stirred at RT for 21 h. For the working up, the solution is diluted with approximately 30 ml of ethyl acetate, and the whole is washed, in succession, with water, sat. sodium bicarbonate solution and saline. The combined aqueous phases are reextracted with ethyl acetate. The combined organic phases are dried with sodium sulfate and concentrated. The residue is chromatographed on silica gel (ethyl acetate). The product-containing fractions are combined, concentrated, dissolved once again in a little dioxane and lyophilized, with the title compound being obtained. IR($CH_2Cl_2$) inter alia: 3432, 1708, 1681, 1670, 1495, 1167 and 1099 $cm^{-1}$. FAB-MS $(M+H)^+$=666. HPLC $t_{Ref}$=16.49 min (gradient II). $^1$H-NMR ($CD_3OD$) inter alia: 6.80 and 6.63 (each d, each 1H); 4.09 (d, 1H); 3.86 (s, 3H); 3.80 (2xs, 6H); 3.31 (s, 3H); 1.42 (s, 9H); 0.90 (d, 6H).

The starting material is prepared as follows:

60a) 5(S)-[1(S)-(Boc-Amino)-2-cyclohexylethyl]dihydrofuran-2-(3H)-one 15 g (49.12 mmol) of 5(S)-[1(S)-(Boc-amino)-2-phenylethyl]dihydrofuran-2-(3H)-one [Example 2b)] are dissolved in 150 ml of methanol, and this solution is treated with 0.75 g of Nishimura catalyst and hydrogenated (RT, standard pressure) until there is no further uptake of hydrogen. The catalyst is filtered off, the solvent is removed, and the residue is chromatographed on silica gel (toluene/ethyl acetate, 5:1). The title compound is obtained as a thick, viscous oil. IR ($CH_2Cl_2$) inter alia: 3431, 1774, 1711, 1501 und 1170 $cm^{-1}$. FAB-MS $(M+1)^+$=312. $^1$H-NMR (DMSO-$d_6$) inter alia: 6.80 (d, 1H); 4.40 (m, 1H); 3.66 (m, 1H); 2.58–2.43 (m, 2H); 2.37 (dxq, 1H); 2.14 (m, 1H) and 1.39 (s, 9H).

60b) 5(S)-[1(S)-(Boc-Amino)-2-cyclohexylethyl]-3(R)-[(2,3,4-trimethoxyphenyl)methyl]dihydrofuran-2-(3H)-one A solution of 1.47 g (4.72 mmol) of 5(S)-[1(S)-(Boc-amino)-2-cyclohexylethyl]dihydrofuran-2-(3H)-one in 6 ml of abs. THF and 1 ml (1.65 equivalents) of DMPU is cooled down to −75° C., under argon, and treated dropwise, at an internal temperature of below −70° C. and over the space of approximately 20 min, with 9.44 ml of a 1M solution of lithium bis(trimethylsilyl)amide in THF (Aldrich). After a further 20 min at −75° C., a solution of 1.45 g (4.72 mmol) of 2,3,4-trimethoxybenzyl iodide [Example 47b)] in 3 ml of abs. THF is added dropwise to this mixture, within the space of approximately 10 min, and this mixture is allowed to react at −75° C. for a further 2.5 h. For the working up, the reaction mixture is treated with 1.76 ml of propionic acid, followed by 1.76 ml of water, and the temperature is allowed to rise to 0° C. The reaction mixture is diluted with approximately 70 ml of ethyl acetate and stirred up with 30 ml of (cold) 10% citric acid. The aqueous phase is separated off and the organic phase is washed, in succession, with saline, sat. sodium bicarbonate solution and with saline once again. The combined aqueous phases are reextracted twice with ethyl acetate. The combined organic phases are dried over sodium sulfate and concentrated. The residue which remains after removing the solvent is chromatographed on silica gel (toluene:ethyl acetate, 5:1). HPLC $t_{Ref}$=19.13 min (gradient II). FAB-MS (M+H)$^+$=491. IR(CH$_2$Cl$_2$)=inter alia 3429, 1766, 1711, 1602, 1495, 1165 und 1100 cm$^{-1}$. $^1$H-NMR (CD$_3$OD)=inter alia 6.86 (d, 1H); 6.70 (d, 1H); 4.37 (m, 1H); 3.87, 3.82 and 3.81 (each s, each 3H); 3.37 (m, 1H); 3.13 (dxd, 1H); 2.94 (m, 1H); 2.59 (dxd, 1H) and 1.40 (s, 9H).

60c) 5(S)-(Boc-Amino)-4(S)-hydroxy-6-cyclohexyl-2(R)-[(2,3,4-trimethoxyphenyl)methyl]hexanoic acid A solution of 600 mg (1.22 mmol) of 5(S)-[1(S)-(Boc-amino)-2-cyclohexylethyl]-3(R)-[(2,3,4-trimethoxyphenyl)methyl]dihydrofuran-2-(3H)-one in 20 ml of dimethoxyethane and 9.9 ml of water is treated, at RT, with 4.9 ml of a 1M solution of lithium hydroxide in water, and this reaction mixture is stirred for 2 h. It is then transferred to a separating funnel and diluted with 60 ml of sat. ammonium chloride solution and 5 ml of a 10% citric acid solution (both being cold); this mixture is then extracted with ethyl acetate and a little THF. The title compound, which is dried under HV and subjected to further processing without being purified, is obtained after washing the organic phase with (cold) saline and drying it over sodium sulfate. IR(CH$_2$Cl$_2$) inter alia: 3431, 1710, 1602, 1495, 1165 and 1100 cm$^{-1}$. FAB-MS (M+H)$^+$=510. HPLC $t_{Ref}$=16.13 min (gradient II).

60d) 5(S)-(Boc-Amino)-4(S)-(tert-butyldimethylsilyloxy)-6-cyclohexyl-2(R)-[(2,3,4-trimethoxyphenyl)methyl]hexanoic acid A solution of 598 mg (1.175 mmol) of 5(S)-(Boc-amino)-4(S)-hydroxy-6-cyclohexyl-2(R)-[(2,3,4-trimethoxyphenyl)methyl]hexanoic acid in 6 ml of DMF is treated, while being stirred, with 653 mg (9.4 mmol) of imidazole and 822 mg (5.287 mmol) of t-butyldimethylchlorosilane. After it has been stirred for 17 h at RT, and under argon, the reaction solution is poured onto ice-water and the whole is extracted with ethyl acetate. The organic phase is washed with 10% citric acid solution and saline (cold). The combined aqueous phases are reextracted with ethyl acetate. The combined organic phases are dried with Na$_2$SO$_4$ and evaporated. The crude product is dried under HV for approximately 2 h and, after that, is dissolved in 15.6 ml of methanol and 5.3 ml of THF, and this solution is treated with 941 mg of potassium carbonate in 5.3 ml of water. This reaction mixture is stirred at RT for approximately 3 h, then concentrated down, at approximately 30° C., to half the volume and diluted with ethyl acetate; the organic phase is washed with 10% citric acid and saline (both being cold). The combined aqueous phases are reextracted with ethyl acetate. The combined organic phases are dried over Na$_2$SO$_4$ and evaporated. The crude product is chromatographed on silica gel (hexane:ethyl acetate, 2:1), and the title compound is obtained. IR(CH$_2$Cl$_2$) inter alia: 3436, 1708, 1603, 1494, 1166, 1100 and 837 cm$^{-1}$. FAB-MS (M+H)$^+$=624. HPLC $t_{Ref}$=23.14 min (gradient II). $^1$H-NMR (CD$_3$OD) inter alia: 6.76 (d, 1H); 6.59 (d, 1H); 6.07 and 5.50 (each d, in all 1H, rotamers of NH), 3.86, 3.82 and 3.81 (each s, each 3H); 3.75–3.57 (m, 2H); 2.93–2.75 (m, 2H); 2.70 (m, 1H); 1.42 (s, 9H); 0.87 (s, 6H); 0.11 and 0.08 (each s, each 3H).

60e) 5(S)-(Boc-Amino)-4(S)-(tert-butyldimethylsilyloxy)-6-cyclohexyl-2(R)-[(2,3,4-trimethoxyphenyl)methyl]hexanoyl-(L)-Val-N-(2-methoxyethyl)amide A mixture of 135 mg (0.265 mmol) 5(S)-(Boc-amino)-4(S)-(tert-butyldimethylsilyloxy)-6-cyclohexyl-2(R)-[(2,3,4-trimethoxyphenyl)methyl]hexanoic acid, 100 mg (0.265 mmol) of HBTU and 51 mg (0.291 mmol) of H-(L)-Val-N-(2-methoxyethyl)amide [preparation, see Example 1b)] in 2.5 ml of a 0.25M solution of NMM in acetonitrile is stirred at RT for 21 h under argon. The solution is concentrated down to half the volume on a RE at approximately 30° C. and diluted with cold ethyl acetate; this solution is then washed, in succession with 10% citric acid, water, sat. sodium bicarbonate solution and saline. The title compound, which is subjected to further processing without being purified, is obtained after drying over sodium sulfate and removing the solvent. IR (CH$_2$Cl$_2$) inter alia: 3434, 1667, 1495, 1166, 1097 and 838 cm$^{-1}$. FAB-MS (M+H)$^+$=780. HPLC $t_{Ref}$=24.79 min (gradient II). $^1$H-NMR (CD$_3$OD) inter alia: 6.80 and 6.64 (each d, each 1H); 5.85 (d, 1H); 3.88, 3.83 and 3.81 (each s, each 3H); 3.32 (s, 3H); 1.43 (s, 9H); 0.90 (s, 9H); 0.13 (d, 6H).

Example 61

5(S)-(Boc-Amino)-4(S)-hydroxy-6-cyclohexyl-2(R)-[(p-methoxyphenyl)methyl]hexanoyl-(L)-Ala-N-(2-methoxyethyl)amide In analogy with Example 1), 115 mg (0.17 mmol) of 5(S)-(Boc-amino)-4(S)-(tert-butyldimethylsilyloxy)-6-cyclohexyl-2(R)-[(p-methoxyphenyl)methyl]hexanoyl-(L)-Ala-N-(2-methoxyethyl)amide in 5 ml of DMF are desilylated with 114 mg (0.36 mmol) of TBAF and worked up. Column chromatography (SiO$_2$, ethyl acetate/hexane, 2:1→3:1→100% ethyl acetate) affords the title compound: TLC R$_f$(A)=0.42; $t_{Ref}$(II)=15.4 min; FAB-MS (M+H)$^+$=578.

The starting material is prepared as follows:

61a) Z-(L)-Ala-N-(2-methoxyethyl)amide

Under protective gas, an ice-cold solution of 5.0 g (28.5 mmol) of Z-(L)-alanine in 125 ml of methylene chloride is activated with 6.48 g (31.4 mmol) of DCC and 4.24 g (31.4 mmol) of HOBT. 2.45 ml (28.5 mmol) of 2-methoxyethylamine (Fluka, Buchs, Switzerland) are subsequently added dropwise to the resulting suspension, and this reaction mixture is thoroughly stirred at RT for 60 h. It is then filtered and the filtrate is washed with sat. NaHCO$_3$ solution and saline, dried with Na$_2$SO$_4$ and evaporated. Digesting the crude product with DIPE and medium pressure chromatography [(®LiChroprep Si 60; silica gel for medium pressure chromatography; Merck, Darmstadt, FRG), loading as a solution in methylene chloride/methanol; eluting with methylene chloride→methylene chloride/methanol 19:1→92:8)] affords the title compound: TLC R$_f$(B)=0.56; $t_{Ref}$(II)=9.5 min.

61b) H-(L)-Ala-N-(2-methoxyethyl)amide

Hydrogenating 4.6 g (16.4 mmol) of Z-(L)-Ala-N-(2-methoxyethyl)amide in 100 ml of methanol, at RT under low pressure and in the presence of 1 g of 10% Pd/C, affords the title compound after filtering off the catalyst, evaporating the filtrate and filtering a solution of the crude product in methylene chloride through silica gel with 10% methanol in methylene chloride: FAB-MS (M+H)$^+$=147; $^1$H-NMR (200 MHz, CD$_3$OD): 1.25 (d, J=7 Hz, H$_3$C), 3.33 (s, H$_3$C—O), 3.3–3.5 (m, HC$^\alpha$, H$_2$C—CH$_2$).

61c) 5(S)-(Boc-Amino)-4(S)-(tert-butyldimethylsilyloxy)-6-cyclohexyl-2(R)-[(p-methyoxyphenyl)methyl]hexanoyl-(L)-Ala-N-(2-methoxyethyl)amide Under an N$_2$ atmosphere, 150 mg (0.27 mmol) of 5(S)-(Boc-amino)-4(S)-(tert-butyldimethylsilyloxy)-6-cyclohexyl-2(R)-[(p-methoxyphenyl)methyl]hexanoic acid (Example 12d)] and 42.8 mg (0.29 mmol) of H-(L)-Ala-N-(2-methoxyethyl)amide are dissolved in 2.6 ml of 0.25M NMM/CH$_3$CN, and this solution is treated with 111 mg (0.29 mmol) of HBTU. Since HPLC indicates that starting material is still present after 18 h at RT, a further 1.1 equivalents of HBTU are added. After a total of 48 h, the reaction mixture is evaporated and the residue is taken up in ethyl acetate; this solution is washed with water, 2 portions of 10% citric acid solution, water, 2 portions of sat. NaHCO$_3$ solution and, finally, saline. The inorganic phases are extracted a further 2× with ethyl acetate, and the organic phases are dried with Na$_2$SO$_4$ and evaporated. Column chromatography (SiO$_2$, hexane/ethyl acetate, 2:1→1:1) yields the title compound: TLC R$_f$(C)=0.14; t$_{Ref}$(II)=22.6 min.

Example 62

5(S)-(Boc-Amino)-4(S)-hydroxy-6-[p-(2-methoxyethoxy)phenyl]-2(R)-[(p-benzyloxyphenyl)methyl]hexanoyl-(L)-Val-N-(2-methoxyethyl)amide 1.21 g (1.41 mmol) of 5(S)-(Boc-amino)-4(S)-(tert-butyldimethylsilyloxy)-6-[p-(2-methoxyethoxy)phenyl]-2(R)-[(p-benzyloxyphenyl)methyl]hexanoyl-(L)-Val-N-(2-methoxyethyl)amide (Example 62f)) in 31 ml of DMF are desilylated with 890 mg (2.82 mmol) of TBAF under an N$_2$ atmosphere. After 18 h at RT, the mixture is poured onto 430 ml of water and the whole is extracted with 3 portions of ethyl acetate/methanol, ~10:1. The organic phases are washed 2 times with sat. NaHCO$_3$ solution and with saline, dried with Na$_2$SO$_4$ and evaporated to give the title compound: TLC R$_f$(F)=0.38; t$_{Ref}$(II)=16.4 min; FAB-MS (M+H)$^+$=750.

The starting material is prepared as follows:

62a) 5(S)-[1(S)-(Boc-Amino)-2-(p-hydroxyphenyl)ethyl]-dihydrofuran-2-(3H)-one

Hydrogenating 3.0 g (7.29 mmol) of 5(S)-[1(S)-(Boc-amino)-2-(p-benzyloxyphenyl)ethyl]dihydrofuran-2-(3H)-one [preparation, see Example 1g)] in 100 ml of methanol with 0.6 g of 10% Pd/C results in the title compound, after filtering off the catalyst and evaporating the filtrate: t$_{Ref}$(II) =10.6 min.

62b) 5(S)-[1(S)-(Boc-Amino)-2-[p-(2-methoxyethoxy)phenyl]ethyl]dihydrofuran-2-(3H)-one 3.17 g (9.86 mmol) of 5(S)-[1(S)-(Boc-amino)-2-(p-hydroxyphenyl)ethyl]dihydrofuran-2-(3H)-one in 190 ml of DMF/dioxane, 1:1, are treated, under an N$_2$ atmosphere, with 6.4 g (19.7 mmol) of Cs$_2$CO$_3$ and 2.0 g (9.86 mmol) of 2-methoxyethyl iodide. Since HPLC indicates that unreacted 5(S)-[1(S)-(Boc-amino)-2-(p-hydroxyphenyl)ethyl] dihydrofuran-2-(3H)-one is still present after 18 h at RT, a further 1.2 g of 2-methoxyethyl iodide are added in portions. As soon as HPLC indicates that the reaction is complete, the reaction mixture is poured onto 190 ml of ice-water, and the whole is extracted 3× with methylene chloride. The organic phases are washed with water and saline, dried with Na$_2$SO$_4$ and evaporated. Stirring up the residue with hexane in an ultrasonication bath affords the title compound: TLC R$_f$(D) =0.08; FAB-MS (M+H)$^+$=380.

62b') 2-Methoxyethyl iodide

A solution of 10 ml (109 mmol) of 2-chloroethyl methyl ether in 205 ml of acetone is treated in portions with 80.1 g (534 mmol) of NaI, and the mixture is boiled under reflux for 20 h. Partitioning the reaction mixture between 2 portions of ether and saline, drying the organic phases with Na$_2$SO$_4$ and evaporating them (RT, 300 mbar) affords the title compound: $^1$H-NMR (200 MHz, CDCl$_3$): 3.25 (t, J=7 Hz, 2H), 3.39 (s, 3H), 3.65 (t, J=7 Hz, 2H).

62c) 5(S)-[1(S)-(Boc-Amino)-2-[p-(2-methoxyethoxy) phenyl]ethyl]-3(R)-[(p-benzyloxyphenyl)methyl] dihydrofuran-2-(3H)-one Under an N$_2$ atmosphere, 3.6 g (9.48 mmol) of 5(S)-[1 (S)-(Boc-amino)-2-[p-(2-methoxyethoxy)phenyl]ethyl] dihydrofuran-2-(3H)-one, dissolved in 17.3 ml of THF and 1.9 ml of DMPU, are deprotonated, at −70° C., with 18.58 ml of a 1M solution of lithium bis(trimethylsilyl)amide in THF, and, after 15 min, alkylated with 3.07 g (9.48 mmol) of p-benzyloxybenzyl iodide (Example 1d)) in 6 ml of THF. After 30 min at −75° C., the mixture is protonated with 3.53 ml (47.4 mmol) of propionic acid and 3.53 ml of water and warmed to 0° C. The reaction mixture is diluted with 95 ml of ethyl acetate and the whole is washed with 10% citric acid solution, sat. NaHCO$_3$ solution and saline. The aqueous phases are extracted with 2 portions of ethyl acetate. The organic phases are dried with Na$_2$SO$_4$ and evaporated. Column chromatography (SiO$_2$, hexane/ethyl acetate, 1:1) and crystallization from ethyl acetate/hexane yields the pure title compound: TLC R$_f$(C)=0.38; t$_{Ref}$(II)=18.0 min; FAB-MS (M+H)$^+$=576.

62d) 5(S)-(Boc-Amino)-4(S)-hydroxy-6-[p-(2-methoxyethoxy)phenyl]-2(R)-[(p-benzyloxyphenyl)methyl] hexanoic acid 3.85 g (6.68 mmol) of 5(S)-[1(S)-(Boc-amino)-2-[p-(2-methoxyethoxy)phenyl]ethyl]-3(R)-[(p-benzyloxyphenyl) methyl]dihydrofuran-2-(3H)-one in 107 ml of dimethoxyethane and 54 ml of water are hydrolysed, under a protective gas, with 26.5 ml of a 1M lithium hydroxide solution. After 17 h at RT, the reaction mixture is treated with an ice-cold mixture of 324 ml of sat. NH$_4$Cl solution, 27 ml of 10% citric acid solution and 134 ml of methylene chloride. Methanol is added in order to dissolve the product completely. The aqueous phase is separated off and extracted 2× with methylene chloride. The organic phases are washed with saline, dried with Na$_2$SO$_4$ and evaporated: t$_{Ref}$(II)=15.8 min; FAB-MS (M+H)$^+$=594.

62e) 5(S)-(Boc-Amino)-4(S)-(tert-butyldimethylsilyloxy)-6-[D-(2-methoxyethoxy)phenyl-2(R)-[(p-benzyloxyphenyl) methyl]hexanoic acid 3.85 g (6.48 mmol) of 5(S)-(Boc-amino)-4(S)-hydroxy-6-[p-(2-methoxyethoxy)phenyl]-2(R)-[(p-benzyloxyphenyl) methyl]hexanoic acid in 11 ml of DMF are silylated, at RT for 16 h and under a protective gas, with 4.49 g (29.8 mmol) of tert-butyldimethylchlorosilane and 3.6 g (53.1 mmol) of imidazole. The reaction mixture is poured onto ice-water and the whole is extracted 3 times with ethyl acetate. The organic phases are washed with 10% citric acid solution, 2 times with water and with saline, dried with Na$_2$SO$_4$ and evaporated. The residue is dissolved in 79 ml of methanol and 30 ml of THF, and this solution is treated with 5.37 g of potassium carbonate and 30 ml of water and stirred at RT for 3 h. The reaction mixture is subsequently poured onto an ice-cold 10% citric acid solution, and this mixture is extracted 3 times with ethyl acetate. The organic phases are washed with 2 portions of H$_2$O and saline, dried with Na$_2$SO$_4$ and evaporated. Column chromatography (SiO$_2$, hexane/ethyl acetate, 1:1) affords the title compound: TLC R$_f$(C)=0.28; t$_{Ref}$(II)=20.9 min.

62f) 5(S)-(Boc-Amino)-4(S)-(tert-butyldimethylsilyloxy)-6-[p-(2-methoxyethoxy]phenyl]-2(R)-[(p-benzyloxyphenyl) methyl]hexanoyl-(L)-Val-N-(2-methoxyethyl)amide 1.00 g (1.41 mmol) of 5(S)-(Boc-amino)-4(S)-(tert-butyldimethylsilyloxy)-6-[p-(2-methoxyethoxy)phenyl]-2 (R)-[(p-benzyloxyphenyl)methyl]hexanoic acid and 270 mg (1.55 mmol) of H-(L)-Val-N-(2-methoxyethyl)amide (Example 1b)) in 13.5 ml of 0.25M NMM/CH$_3$CN are reacted, under a protective gas, with 588 mg (1.55 mmol) of HBTU. After 18 h at RT, the mixture is finally evaporated. The residue is taken up in ethyl acetate, and the solution is washed with water, 2× with 10% citric acid solution, water, 2× with sat. NaHCO$_3$ solution, 1× with water and 1× with saline. The aqueous phases are extracted a further 2× with ethyl acetate, and the organic phases are dried with sodium sulfate and evaporated. The title compound is obtained: t$_{Ref}$(II)=22.7 min; FAB-MS (M+H)$^+$=864.

Example 63

5(S)-(Boc-Amino)-4(S)-hydroxy-6-[p-(2-methoxyethoxy)phenyl]-2(R)-[(p-hydroxyphenyl)methyl]hexanoyl-(L)-Val-N-(2-methoxyethyl)amide Hydrogenating a solution of 600 mg (0.80 mmol) of 5(S)-(Boc-amino)-4(S)-hydroxy-6-[p-(2-methoxyethoxy)phenyl]-2(R)-[(p-benzyloxyphenyl)methyl]hexanoyl-(L)-Val-N-(2-methoxyethyl)amide (Example 62) in 20 ml of methanol in the presence of 200 mg of 10% Pd/C, filtering the mixture and evaporating it, results in the title compound: TLC R$_f$(F)=0,19; t$_{Ref}$(II)=12.3 min; FAB-MS (M+H)$^+$=660.

Example 64

5(S)-(BoC-Amino)-4(S)-hydroxy-6-[p-(2-methoxyethoxy)phenyl]-2(R)-[(p-methoxyphenyl)methyl]hexanoyl-(L)-Val-N-(2-methoxyethyl)amide Under an N$_2$ atmosphere, 100 mg (0.152 mmol) of 5(S)-(Boc-amino)-4(S)-hydroxy-6-[p-(2-methoxyethoxy)phenyl]-2(R)-[(p-hydroxyphenyl)methyl]hexanoyl-(L)-Val-N-(2-methoxyethyl)amide (Example 63) in 3 ml of DMF/dioxane, 1:1, are treated, at 0° C., with 98.7 mg (0.303 mmol) of Cs$_2$CO$_3$ and 9.4 μl (0.152 mmol) of methyl iodide, and the mixture is stirred at RT for 24 h. Since HPLC indicates that the starting material is still present, a further 6 μl of methyl iodide are added. After a further 20 h at RT, the reaction mixture is poured onto water and the whole is extracted with 3 portions of methylene chloride. The organic phases are washed with water and saline, dried with Na$_2$SO$_4$ and evaporated. Recrystallizing from methylene chloride, a little methanol and DIPE yields the title compound: TLC R$_f$(H)=0.47; t$_{Ref}$(II)=14.0 min; FAB-MS (M+H)$^+$=674.

Example 65

5(S)-(Boc-Amino)-4(S)-hydroxy-6-[p-(2-methoxyethoxy)phenyl]-2(R)-{[p-(2-methoxyethoxy)phenyl]methyl}-hexanoyl-(L)-Val-N-(2methoxyethyl)amide Under an N$_2$ atmosphere, 100 mg (0.152 mmol) of 5(S)-(Boc-amino)-4(S)-hydroxy-6-[p-(2-methoxyethoxy)phenyl]-2(R)-[(p-hydroxyphenyl)methyl]hexanoyl-(L)-Val-N-(2-methoxyethyl)amide (Example 63) in 3 ml of DMF/dioxane, 1:1, are treated, at 0°C., with 98.7 mg (0.303 mmol) of Cs$_2$CO$_3$ and 40 mg (0.152 mmol) of 2-methoxyethyl iodide (Example 62b'), and the mixture is stirred at RT for 24 h. Since HPLC indicates that starting material is still present, a further 60 mg of 2-methoxyethyl iodide are added in 3 portions, with the mixture being stirred at RT for a few hours on each occasion. Precipitating out of the reaction mixture with 4 ml of ice-water, filtering, column chromatography (SiO$_2$, methylene chloride THF, 3:1), and digesting in hexane, yields the pure title compound: TLC R$_f$(H)=0.59; t$_{Ref}$(II)=13.9 min; FAB-MS (M+H)$^+$=718.

Example 66

5(S)-(Boc-Amino)-4(S)-hydroxy-6-cyclohexyl-2(R)-[4-{2-(methoxy)ethoxy}phenylmethyl]hexanoyl-(L)-Val-N-(2-methoxyethyl)amide In analogy with Example 1, 3.7 g (4.84 mmol) of 5(S)-(Boc-amino)-4(S)-(tert-butyldimethylsilyloxy)-6-cyclohexyl-2(R)-[4-{2-(methoxy)ethoxy}phenylmethyl]hexanoyl-(L)-Val-N-(2-methoxyethyl)amide (Example 66f)) in 15 ml of DMF are reacted with 3.09 g (9.78 mmol) of TBAF trihydrate to give the title compound. The reaction mixture is poured onto water and the whole is extracted with 4 portions of ethyl acetate. The organic phases are washed with sat. NaHCO$_3$ solution, water and saline, dried with Na$_2$SO$_4$ and evaporated. The pure title compound is finally obtained after stirring up with diethyl ether and filtering. TLC R$_f$ (A)=0.4; t$_{Ref}$(II)=15.97 min; FAB-MS (M+H$^+$)= 650.

The starting compound is prepared in the following manner:

66a) 3(R)-[(4-Benzyloxyphenyl)methyl]-5(S)-[1(S)-(Boc-amino)-2-cyclohexylethyl]dihydrofuran-2-one In analogy with Example 1h), 5.2 g (16.7 mmol) of 5(S)-[1(S)-(Boc-amino)-2-cyclohexylethyl]dihydrofuran-2-one (Example 12a)), dissolved in 50 ml of THF, are deprotonated, at −70° C., with 33.4 ml of a 1M solution of lithium bis(trimethylsilyl)amide in THF, and alkylated (at −75° C. for 1 h) with 5.2 g (16.07 mmol) of p-benzyloxybenzyl iodide [preparation, see Example 1d)] in 15 ml of THF. Adding 6.2 ml (83.02 mmol) of propionic acid and water at −75° C., and further working up, affords the title compound after column chromatography (SiO$_2$, hexane/ethyl acetate: 4:1). TLC R$_f$(hexane/ethyl acetate: 4:1)=0.27; t$_{Ref}$(II)=20.41 min.

66b) 5(S)-(Boc-Amino)=4(S)-hydroxy-6-cyclohexyl-2(R)-[(4-benzyloxyphenyl)methyl]hexanoic acid 2.4 g (4.728 mmol) of 3(R)-[(4-benzyloxyphenyl)methyl]-5(S)-[1(S)-(Boc-amino)-2-cyclohexylethyl]dihydrofuran-2-one in 10 ml of dimethoxyethane are hydrolysed, under a protective gas, with 9.45 ml of a 1M lithium hydroxide solution. After 17 h at RT, the reaction mixture is aerated with an ice-cold mixture of 324 ml of sat. NH$_4$Cl solution, 27 ml of 10% citric acid solution and 134 ml of methylene chloride. Methanol is added to dissolve the product completely. The aqueous phase is separated off and extracted 2× with methylene chloride. The organic phases are washed with saline, dried with Na$_2$SO$_4$ and evaporated. The crude product is purified by column chromatography (SiO$_2$, eluent C), with the title compound being obtained. TLC R$_f$ (C)=0.35; t$_{Ref}$(II)=17.88 min FAB-MS (M+H$^+$)= 526.

66c) 5(S)-(Boc-Amino)-4(S)-(tert-butyldimethylsilyloxy)-6-cyclohexyl-2(R)-[(4-benzyloxyphenyl)methyl]hexanoic acid In analogy with Example 1 j), 28.8 g (54.8 mmol) of 5(S)-(Boc-amino)-4(S)-hydroxy-6-cyclohexyl-2(R)-[(4-benzyloxyphenyl)methyl]hexanoic acid in 288 ml of DMF, are converted into the title compound with 35.8 g (237.6 mmol) of tert-butyldimethylchlorosilane and 30 g (440 mmol) of imidazole. The title compound is purified by column chromatography (SiO$_2$, hexane/ethyl acetate: 4:1 1:1); TLC R$_f$(E)=0.34; t$_{Ref}$(gradient from 75 to 100% (a) in (b) over 20 min)=25.06 min; FAB-MS (M+H$^+$)=526.

66d) 5(S)-(Boc-Amino)-4(S)-(tert-butyldimethylsilyloxy)-6-cyclohexyl-2(R)-[(4-benzyloxyphenyl)methyl]hexanoyl-(L)-Val-N-(2-methoxyethyl)amide A solution of 3 g (18.7 mmol) of H-(L)-Val-N-(2-methoxy-ethyl)amide and 10 g (15.6 mmol) of 5(S)-(Boc-amino)-4(S)-(tert-butyldimethylsilyloxy)-6-cyclohexyl-2 (R)-[(4-benzyloxyphenyl)methyl]hexanoic acid in 50 ml of DMF is cooled down to 5° C. in an ice bath and treated with 2.9 ml (17.2 ml) of diethyl cyanophosphonate (Aldrich, Milwaukee, U.S.A.) and, after that, with 5.5 ml of triethylamine. After the mixture has been stirred at RT, it is poured onto water and the whole is extracted 3 times with ethyl acetate. The combined organic phases are washed with water, saturated sodium bicarbonate solution (twice) and saline, and, after having been dried over sodium sulfate, concentrated under reduced pressure. The title compound is purified by column chromatography (SiO$_2$, eluent C); TLC R$_f$ (A)=0.56; t$_{Ref}$(B)=24.82 min. FAB-MS (M+H$^+$)=796.

66e) 5(S)-(Boc-Amino)-4(S)-(tert-butyldimethylsilyloxy)-6-cyclohexyl-2(R)-[(4-hydroxyphenyl)methyl]hexanoyl-(L)-Val-N-(2-methoxyethyl)amide 0.64 g (0.804 mmol) of 5(S)-(Boc-amino)-4(S)-(tert-butyldimethylsilyloxy)-6-cyclohexyl-2(R)-[(4-benzyloxyphenyl)methyl]hexanoyl-(L)-Val-N-(2-methoxyethyl)amide in 20 ml of methanol is hydrogenated in the presence of 0.32 g of 10% Pd/C. The title compound, which is obtained after filtering off the catalyst and evaporating the filtrate, is subjected to further reaction without any additional purification; TLC R$_f$ (C)= 0.18; t$_{Ref}$(II)=21.81 min; FAB-MS (M+H$^+$)=706.

66f) 5(S)-(Boc-Amino)-4(S)-(tert-butyldimethylsilyloxy)-6-cyclohexyl-2(R)-[(4-{2-(methoxy)ethoxy}phenyl) methyl]hexanoyl-(L)-Val-N-(2-methoxyethyl)amide A solution of 0.75 g (1.06 mmol) of 5(S)-(Boc-amino)-4(S)-(tert-butyldimethylsilyloxy)-6-cyclohexyl-2(R)-[(4-hydroxyphenyl)methyl]hexanoyl-(L)-Val-N-(2-methoxyethyl)amide in 10 ml of dioxane is treated with 1.384 g (4.25 mmol) of caesium carbonate and, after 4 h, with 0.79 g (4.25 mmol) of 2-methoxyethyl iodide (Example 62b')). After having been stirred at 80° C. for 24 h, the reaction mixture is poured onto water and ethyl acetate. After the organic phase has been separated off, the aqueous solution is washed a further 3 times with ethyl acetate. The combined extracts are washed, in succession, with water, saturated aqueous sodium bicarbonate solution and saline. After drying over sodium sulfate and evaporating under reduced pressure, the resulting residue is stirred up with hexane and filtered off. Column chromatography (SiO$_2$, hexane/acetone: 2:1) yields the pure title compound. TLC R$_f$ (C)=0.2; t$_{Ref}$(II)=21.9 min; FAB-MS (M+H$^+$)=764.

Example 67

5(S)-(2,2,2-Trifluoroethoxycarbonylamino)-4(S)-hydroxy-6-cyclohexyl-2(R)-[(4-{2-(methoxy) ethoxy}phenyl)methyl]hexanoyl-(L)-Val-N-(2-methoxyethyl)amide 500 mg (0.909 mmol) of 5(S)-amino-4(S)-hydroxy-6-cyclohexyl-2(R)-[(4-{2-(methoxy)ethoxy}-phenyl)methyl] hexanoyl-(L)-Val-N-(2-methoxyethyl)amide in 5 ml of DMF are treated, at 0° C. and in succession, with 0.51 ml (3.65 mmol) of triethylamine and 0.34 g (2.09 mmol) of trifluoroethyl chloroformate (U.S. Pat. No. 3,852,464). After having been stirred for 10 min, the reaction mixture is poured onto water and the whole is extracted 3× with ethyl acetate. The combined extracts are washed, in succession, with aqueous, saturated sodium bicarbonate solution and saline, and, after having been dried over sodium sulfate, concentrated under reduced pressure. The title compound is obtained from the residue by treating it with ethyl acetate. TLC R$_f$ (B)=0.77; t$_{Ref}$(II)=15.26 min; FAB-MS (M+H$^+$)= 676.

The starting compound is prepared in the following manner:

67a) 5(S)-Amino-4(S)-hydroxy-6-cyclohexyl-2(R)-[(4-{2-(methoxy)ethoxy}phenyl)-methyl]hexanoyl-(L)-Val-N-(2-methoxyethyl)amide 2.3 g (3.54 mmol) of 5(S)-(Boc-amino)-4(S)-hydroxy-6-cyclohexyl-2(R)-[(4-{2-(methoxy)ethoxy}phenyl)methyl] hexanoyl-(L)-Val-N-(2-methoxyethyl)amide (Example 66) in 25 ml of methylene chloride are treated, at 0° C., with 25 ml of trifluoroacetic acid. After having been stirred at RT for 2 h, the reaction mixture is evaporated and the residue is partitioned between saturated, aqueous sodium bicarbonate solution and ethyl acetate. The organic phase is washed once again with saturated, aqueous sodium bicarbonate solution and saline, and evaporated to dryness. The dry residue is digested in 100 ml of diethyl ether in an ultrasonication bath, after which it is filtered off with suction and washed. The title compound is obtained by drying the filter residue at RT under high vacuum: TLC R$_f$ (B)=0.4; t$_{Ref}$(II)=10.2 min; FAB-MS (M+H$^+$)=550.

Example 68

5(S)-(Boc-Amino)-4(S)-hydroxy-6-cyclohexyl-2(R)-[(3,4-methylenedioxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(3,4-methylenedioxyphenyl)methyl]hexanoyl-(L)-Val-N-(2-methoxyethyl)amide using TBAF in abs. DMF.

Example 69

5(S)-(Boc-Amino)-4(S)-hydroxy-6-cyclohexyl-2(R)-[(3,4-dimethoxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(3,4-dimethoxyphenyl)methyl]hexanoyl-(L)-Val-N-(2-methoxyethyl)amide using TBAF in abs. DMF.

Example 70

5(S)-(Boc-Amino)-4(S)-hydroxy-6-cyclohexyl-2(R)-[(3-methoxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(3-methoxyphenyl)methyl]hexanoyl-(L)-Val-N-(2-methoxyethyl)amide using TBAF in abs. DMF.

Example 71

5(S)-(Boc-Amino)-4(S)-hydroxy-6-cyclohexyl-2(R)-[(3,4,5-trimethoxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(3,4,5-trimethoxyphenyl)methyl]hexanoyl-(L)-Val-N-(2-methoxyethyl)amide using TBAF in abs. DMF.

Example 72

5(S)-(Boc-Amino)-4(S)-hydroxy-6-cyclohexyl-21R)-r(2,4-dimethoxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(2,4-dimethoxyphenyl)methyl]hexanoyl-(L)-Val-N-(2-methoxyethyl)amide using TBAF in abs. DMF.

Example 73

5(S)-(Boc-Amino)-4(S)-hydroxy-6-cyclohexyl-2(R)-[(2-methoxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(2-methoxyphenyl)methyl]hexanoyl-(L)-Val-N-(2-methoxyethyl)amide using TBAF in abs. THF.

Example 74

5(S)-(Boc-Amino)-4(S)-hydroxy-6-cyclohexyl-2(R)-[(23-dimethyl-4-methoxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(2,3-dimethyl-4-methoxyphenyl)methyl]hexanoyl-(L)-Val-N-(2-methoxyethyl)amide using TBAF in abs. DMF.

Example 75

5(S)-(Boc-Amino)-4(S)-hydroxy-6-cyclohexyl-2(R)-[(2,4,5-trimethoxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(2,4,5-trimethoxyphenyl)methyl]hexanoyl-(L)-Val-N-(2-methoxyethyl)amide using TBAF in abs. THF.

Example 76

5(S)-(Boc-Amino)-4(S)-hydroxy-6-cyclohexyl-2(R)-[(2,4,6-trimethoxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(2,4,6-trimethoxyphenyl)methyl]hexanoyl-(L)-Val-N-(2-methoxyethyl)amide using TBAF in abs. DMF.

Example 77

5(S)-(Boc-Amino)-4(S)-hydroxy-6-cyclohexyl-2(R)-[(5,6,7,8-tetrahydro-1-methyl)naphthyl]hexanoyl-(L)-Val-N-(2-methoxyethyl)amide In analogy with Example 60, the title compound is obtained from 5(S)-(Boc-amino)-4(S)-(tert-butyldimethylsilyoxy)-6-cyclohexyl-2(R)-[(5,6,7,8-tatrahydro-1-methyl)naphthyl]hexanoyl-(L)-Val-N-(2-methoxyethyl)amide using TBAF in abs. DMF.

Example 78

5(S)-(Boc-Amino)-4(S)-hydroxy-6-cyclohexyl-2(R)-[(2,5-dimethoxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyoxy)-6-cyclohexyl-2(R)-[(2,5-dimethoxyphenyl)methyl]hexanoyl-(L)-Val-N-(2-methoxyethyl)amide using TBAF in abs. DMF.

Example 79

5(S)-(Boc-Amino)-4(S)-hydroxy-6-cyclohexyl-2(R)-[(2,6-dimethoxyphenyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(2,6-dimethoxyphenyl)methyl]hexanoyl-(L)-Val-N-(2-methoxyethyl)amide using TBAF in abs. DMF.

Example 80

5(S)-(Boc-Amino)-4(S)-hydroxy-6-cyclohexyl-2(R)-[(4-methoxy-1-naphthyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(4-methoxy-1-naphthyl)methyl]hexanoyl-(L)-Val-N-(2-methoxyethyl)amide using TBAF in abs. DMF.

Example 81

5(S)-(BoC-Amino)-4(S)-hydroxy-6-cyclohexyl-2(R)-[(4-cyano-1-naphthyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(4-cyano-1-naphthyl)methyl]hexanoyl-(L)-Val-N-(2-methoxyethyl)amide using TBAF in abs. DMF.

Example 82

5(S)-(Boc-Amino)-4(S)-hydroxy-6-cyclohexyl-2(R)-[(4-fluoro-1-naphthyl)methyl]hexanoyl-(L)-Val-N-(2-methoxyethyl)amide In analogy with Example 60, the title compound is obtained from 5(S)-(Boc-amino)-4(S)-(tert-butyldimethylsilyloxy)-6-cyclohexyl-2(R)-[(4-fluoro-naphthyl)methyl]hexanoyl-(L)-Val-N-(2-methoxyethyl)amide using TBAF in abs. DMF.

Example 83

5(S)-(3-Hydroxy-2-methylphenylcarbonylamino)-4(S)-hydroxy-6-phenyl-2(R)-[(2,3,4-trimethoxyphenyl)methyl]hexanoyl-(L)-Val-N-(2-methoxyethyl)amide 150 mg (0.251 mmol) of 5(S)-amino-4(S)-hydroxy-6-phenyl-2(R)-[(2,3,4-trimethoxyphenyl)methyl]hexanoyl-(L)-Val-N-(2-methoxyethyl)amide (hydrochloride salt) are dissolved in dichloromethane, and the organic phase is washed with sat. sodium bicarbonate solution, dried over sodium sulfate and concentrated. The amine which has been liberated is stirred, at RT for 16 h, in 2.36 ml of a (0.25M) solution of NMM in acetonitrile together with 105 mg of HBTU (1.1 equivalents) and 42 mg (1.1 equivalents) of 3-hydroxy-2-methylbenzoic acid [prepared in accordance with F. Fringuelli, V. Mancini and A. Taticchi, Tetrahedron 25, 4249 (1969)]. The reaction mixture is taken up in a cold ethyl acetate/THF mixture, and the whole is washed, in succession, with 10% citric acid, water, sat. sodium bicarbonate solution and saline. After the mixture has been dried over sodium sulfate, the solvent is removed and the residue is digested twice with diethyl ether. The solid precipitate is filtered off with suction, washed with diethyl ether and dried, resulting in the title compound: FAB-MS (M+H)$^+$=694; $t_{Ref}$(II)=9.08 min.

The starting material is prepared as follows:
83a) 5(S)-Amino-4(S)-hydroxy-6-phenyl-2(R)-[(2,3,4-trimethoxyphenyl)methyl]hexanoyl-(L)-Val-N-(2-methoxyethyl)amide (hydrochloride salt)

1.5 g (2.27 mmol) of 5(S)-(Boc-amino)-4(S)-hydroxy-6-phenyl-2(R)-[(2,3,4-trimethoxyphenyl)methyl]hexanoyl-(L)-Val-N-(2-methoxyethyl)amide (Ex. 47) is added, under argon and in portions, to 10 ml of ice-cooled 4N hydrogen chloride in dioxane, and the mixture is stirred for 3.5 h while being cooled with ice. The reaction solution is briefly evacuated in order to remove the excess hydrogen chloride and then frozen and lyophilized. The lyophilisate is stirred up for a further 1 h in acetone and then filtered off with suction, washed with hexane and dried, thereby yielding the title compound: FAB-MS (M+H)$^+$=560; $t_{Ref}$(II)=7.30 min.

Example 84

5(S)-(2-Methoxy-1(R,S)-methylethoxycarbonylamino)-4(S)-hydroxy-6-cyclohexyl-2(R)-[(p-methoxyphenyl)methyl]hexanoyl-(L)-Val-N-(2-methoxyethyl)amide 1 g (1.84 mmol) of 5(S)-amino-4(S)-hydroxy-6-cyclohexyl-2(R)-[(p-methoxyphenyl)methyl]hexanoyl-(L)-Val-N-(2-methoxyethyl)amide [prepared in accordance with Example 22a)] in 30 ml of THF is cooled down to approximately 7° C. using ice-water, and treated with 0.909 ml (3.5 equivalents) of triethylamine followed by 563 mg (2 equivalents) of 2-methoxy-1(R,S)-methylethyl chloroformate. The cooling bath is removed and the mixture is subsequently stirred at RT for a further 1 h. The reaction mixture is poured onto water and the whole is extracted with ethyl acetate. The organic phase is washed, in succession, with water, sat. sodium bicarbonate solution, water and saline. After drying over sodium sulfate, and removing the solvent, the residue is digested with ether, the precipitate is filtered off and dried and the title compound thus obtained: FAB-MS (M+H)$^+$=622; $t_{Ref}$(I)-, 14.55 and 14.70 min (diastereomeric mixture).

The starting material is prepared in the following manner:
84a) 2-Methoxy-1(R,S)-methylethyl chloroformate 1 ml (10.2 mmol) of 1-methoxy-2-propanol (Fluka, Buchs, Switzerland) is injected slowly into an ice-cold solution of 916 mg (1.1 equivalent) of bis(trichloromethyl) carbonate (triphosgene; Fluka, Buchs, Switzerland) in 35 ml of ether using a syringe. At the same time, 1 ml (1.2 equivalents) of pyridine in 5 ml of ether is added dropwise from a dropping funnel. After the addition has ended, the mixture is left to stir at RT for a further 60 min. The reaction mixture is filtered through wadding and the solvent is carefully evaporated off (35° C. waterbath). The oily residue (title compound) is subjected to further processing without any purification. $^1$H-NMR (200 MHz; CDCl$_3$)=inter alia 5.05/m (1H); 3.30/s (3H); 1.27/d (3H).

Example 85

5(S)-(Boc-Amino)-4(S)-hydroxy-6-cyclohexyl-2(R)-[(D-methoxyphenyl)methyl]hexanoyl-(L)-[(cyclohexyl)Gly]-N-(2-methoxyethyl)amide In analogy with Example 12, the title compound is obtained from 5(S)-(Boc-amino)-4(S)-(tert-butyldimethylsilyloxy)-6-cyclohexyl-2(R)-[(p-methoxyphenyl)methyl]hexanoyl-(L)-[(cyclohexyl)Gly]-N-(2-methoxyethyl)amide using TBAF in DMF.

FAB-MS (M+H)$^+$=646; $t_{Ref}$(I)=17.46 min.

The starting material is prepared as follows:
85a) 5(S)-(Boc-Amino)-4(S)-(tert-butyldimethylsilyloxy)-6-cyclohexyl-2(R)-[(p-methoxyphenyl)methyl]hexanoyl-(L)-[(cyclohexyl)Gly]-N-(2-methoxyethyl)amide In analogy with Example 12e), the title compound is obtained from 1.128 g (2 mmol) of 5(S)-(Boc-amino)-4(S)-(tert-butyldimethylsilyloxy)-6-cyclohexyl-2(R)-[(p-methoxyphenyl)methyl]hexanoic acid [prepared in accordance with Example 12d)], 472 mg (1.1 equivalents) of H-(L)-[(cyclohexyl)Gly]-N-(2-methoxyethyl)amide [prepared in accordance with Example 20c)], 0.36 ml (1.1 equivalents) of diethyl cyanophosphonate (Aldrich, Milwaukee/U.S.A.) and 0.7 ml (2.5 equivalents) of triethylamine in 10 ml of DMF. FAB-MS (M+H)$^+$=760; $t_{Ref}$(I)=24.73 min.

Example 86

5(S)-(Ethoxycarbonyl-(L)-Val-amino)-4(S)-hydroxy-6-cyclohexyl-2(R)-[(p-methoxyphenyl)methyl]hexanoyl-(L)-Val-N-(2-methoxyethyl)amide In analogy with Example 27, the title compound is obtained as a colourless solid, after digesting with ether, by proceeding from 1 g (1.844 mmol) of 5(S)-amino-4(S)-hydroxy-6-cyclohexyl-2(R)-[(p-methoxyphenyl)methyl]hexanoyl-(L)-Val-N-(2-methoxyethyl)amide [prepared in accordance with Example 22a)], 500 mg (1.4 equivalents) of ethoxycarbonyl-(L)-valine, 0.43 ml (1.5 equivalents) of diethyl cyanophosphonate and 1.34 ml (9.61 mmol) of triethylamine in 40 ml of DMF. FAB-MS (M+H)$^+$=677; $t_{Ref}$(I)=14.68 min.

The starting material is prepared in the following manner:
86a) N-(Ethoxycarbonyl)-(L)-valine The title compound is prepared, in analogy with Example 30a), from L-valine in 2N NaOH and dioxane using ethyl chloroformate (Fluka, Buchs, Switzerland), and subjected to further processing without purification.

Example 87

5(S)-(1,1-Dimethyl-2-methoxyethoxycarbonylamino)-4(S)-hydroxy-6-cyclohexyl-2(R)-[(p-methoxyphenyl)methyl]hexanoyl-(L)-Val-N-(2-methoxyethyl)amide In analogy with Example 26, the title compound is obtained from 813 mg (1.5 mmol) of 5(S)-amino-4(S)-hydroxy-6-cyclohexyl-2(R)-[(p-methoxyphenyl)methyl]hexanoyl-(L)-Val-N-(2-methoxyethyl)amide [prepared in accordance with Example 22a)], 490 mg (2 equivalents) of (1,1-dimethyl-2-methoxy)ethyl chloroformate and 0.6 ml (2.9 equivalents) of triethylamine. Purification is effected by chromatography on silica gel (eluent:hexane/acetone, 2:1). FAB-MS (M+H)$^+$=636; $t_{Ref}$(I)=15.45 min.

The starting material is prepared as follows:
87a) 1-Methoxy-2-methyl-2-propanol 10.8 g (0.1 mol) of 1-chloro-2-methyl-2-propanol (Lancaster Synthesis, Bischheim, France) in 30 ml of methanol is treated, under argon, with 20.4 ml of a solution of sodium methoxide (110 mmol; 1.1 equivalents) in methanol, and the mixture is boiled under reflux for 2.5 h. After the reaction has ended, the precipitate is filtered off and the solvent is distilled off via a Vigreux column, and the residue is distilled at standard pressure, yielding the title compound: 1-H-NMR (200 MHz; CDCl₃)=3.33/s (3H); 3.15/s (2H); 1.13/s (6H). FAB-MS (M+H)⁺=105. [see, also Amer., Soc. 75, 155 (1953)].

87b) (1,1-Dimethyl-2-methoxy)ethyl chloroformate 770 mg (2.59 mmol) of bis(trichloromethyl) carbonate (triphosgene; Fluka, Buchs, Switzerland) is dissolved, at RT, in 25 ml of ether, and this solution is treated with 737 mg (7.07 mmol) of 1-methoxy-2-methyl-2-propanol dissolved in a little ether. The solution is cooled in an ice bath and slowly treated with 0.67 ml (8.48 mmol) of pyridine in 3 ml of ether. After the addition has ended, the ice bath is removed and the mixture is subsequently stirred at RT for 1 h. The reaction mixture is filtered through wadding and the solvent is distilled off at RT. The crude product (title compound) is subjected to further processing without purification. IR (CH₂Cl₂): inter alia: 1780, 1210, 1198, 1145 and 1120 cm⁻¹.

Example 88

5(S)-(Boc-Amino)-4(S)-hydroxy-6-phenyl-2(R)-[(4-biphenylyl)methyl]hexanoyl-(L)-Val-N-(2-methoxyethyl)amide 0.21 g (0.276 mmol) of 5(S)-(Boc-amino)-4(S)-(tert-butyldimethylsilyloxy)-6-phenyl-2(R)-[(4-biphenylyl)methyl]hexanoyl-(L)-Val-N-(2-methoxyethyl)amide in 4 ml of DMF is desilylated, under an N₂ atmosphere, with 0.174 g (0.55 mmol) of TBAF. After 18 h at RT, the reaction mixture is poured onto water and the whole is extracted with 3 portions of ethyl acetate. The organic phases are washed with sat. NaHCO₃ solution and saline, dried with Na₂SO₄ and evaporated. Stirring up in DIPE affords the title compound: TLC $R_f(B)$=0.55; $t_{Ret}(II)$=16.5 min; FAB-MS (M+H) +=646.

The starting material is prepared in the following manner:

88a) 5(S)-[1(S)-(Boc-Amino)-2-phenylethyl]-3(R)-[(4-biphenyl)methyl]dihydrofuran-2-(3H)-one In analogy with Example 5d), 5.0 g (16.37 mmol) of 5(S)-[1(S)-(Boc-amino)-2-phenylethyl]dihydrofuran-2-(3H)-one dissolved in 24 ml of THF and 2.8 ml of DMPU are deprotonated, at −70° C., with 32.7 ml of a 1M solution of lithium bis(trimethylsilyl)amide in THF, and alkylated (from −75° C. to −50° C.) with 6.07 g (24.6 mmol) of 4-biphenylylmethyl bromide (Salor;, Milwaukee/U.S.A.) in 20 ml of THF. Protonating with 6.1 ml (81.9 mmol) of propionic acid and 6.1 ml of water, at −75° C., extracting and medium pressure chromatography (gradient: 0–1% ethyl acetate in toluene) affords the title compound: TLC $R_f(D)$=0.57; $t_{Ret}(II)$=18.8 min.

88b) 5(S)-(Boc-Amino)-4(S)-hydroxy-6-phenyl-2(R)-[(4-biphenylyl)methyl]hexanoic acid 1.3 g (2.76 mmol) of 5(S)-[1(S)-(Boc-amino)-2-phenylethyl]-3(R)-[(4-biphenylyl)methyl]dihydrofuran-2-(3H)-one are hydrolysed, in 28 ml of dimethoxyethane, with 11 ml of a 1M solution of lithium hydroxide in water. After 16 h at PT, the dimethoxyethane is evaporated off on a RE and the residue is treated with an ice-cold mixture of 15 ml of sat. NH₄Cl solution, 80 ml of 10% citric acid solution and methylene chloride. The aqueous phase is separated off and extracted 2× with methylene chloride. The organic phases are washed with saline, dried with Na₂SO₄ and evaporated to give the title compound: TLC $R_f(B)$=0.4; $t_{Ret}(II)$=16.4 min.

88c) 5(S)-(Boc-Amino-4(S)-(tert-butyldimethylsilyloxy)-6-phenyl-2(R)-[(4-biphenylyl)methyl]hexanoic acid Under a protective gas, 1.23 g (2.51 mmol) of 5(S)-(Boc-amino)-4(S)-hydroxy-6-phenyl-2(R)-[(4-biphenylyl)methyl]hexanoic acid in 25 ml of DMF are silylated, at RT and for 20 h, with 1.74 g (11.5 mmol) of tert-butyldimethylchlorosilane and 1.40 g (20.6 mmol) of imidazole. The reaction mixture is evaporated and the residue is taken up in ethyl acetate, with this solution being washed with sat. NaHCO₃ solution, water and saline. The aqueous phases are extracted 2× with ethyl acetate and the organic phases are dried with Na₂SO₄ and evaporated. The residue is dissolved in 30 ml of methanol and 7 ml of THF, and this solution is treated with 2.0 g of potassium carbonate and 7 ml of water and stirred at RT for 1 h. The reaction mixture is then partially evaporated and the residue is diluted with ice-cold 10% citric acid solution and the whole extracted 3× with ethyl acetate. The organic phases are washed with 2 portions of water and saline, dried with Na₂SO₄ and evaporated. Medium pressure chromatography (gradient: 0–50% ethyl acetate in hexane) results in the title compound: TLC $R_f(C)$=0.56; $t_{Ret}(II)$=22.1 min.

88d) 5(S)-(Boc-Amino)-4(S)-(tert-butyldimethylsilyloxy)-6-phenyl-2(R)-[(4-biphenylyl)methyl]hexanoyl-(L)-Val-N-(2-methoxyethyl)amide 280 mg (0.46 mmol) of 5(S)-(Boc-amino)-4(S)-(tert-butyldimethylsilyloxy)-6-phenyl-2(R)-[(4-biphenylyl)methyl]hexanoic acid in 4.44 ml of 0.25M NMM/CH₃CN are activated, under an N₂ atmosphere, with 193 mg (0.51 mmol) of HBTU. After 5 min. 90 mg (0.51 mmol) of H-(L)-Val-N-(2-methoxyethyl)amide (Example 1b)) are added and the mixture is thoroughly stirred at RT for 20 h. Working up in an analogy with Example 1c), and digestion of the crude product in hexane, results in the title compound: TLC $R_f(D)$=0.2; $t_{Ret}(II)$=22.7 min.

Example 89

5(S)-(Boc-Amino)-4(S)-hydroxy-6-(p-benzyloxyphenyl)-2(R)-[(4-biphenylyl)methyl]hexanoyl-(L)-Val-N-(2-methoxyethyl)amide Under a protective gas, 1.4 g (1.6 mmol) of 5(S)-(Boc-amino)-4(S)-(tert-butyldimethylsilyloxy)-6-(p-benzyloxyphenyl)-2(R)-[(4-biphenylyl)methyl]hexanoyl(L)-Val-N-(2-methoxyethyl)amide in 30 ml of DMF are desilylated with 1.0 g (3.2 mmol) of TBAF and, after 20 h, are worked up in analogy with Example 88. Column chromatography (silica gel, methylene chloride→methylene chloride/methanol 9:1) and stirring up in DIPE affords the title compound: $t_{Ret}(II)$=18.0 min; FAB-MS (M+H)⁺=752.

The starting material is prepared in the following manner:

89a) 5(S)-[1(S)-(Boc-Amino)-2-(p-benzyloxyphenyl)-ethyl]-3(R)-[(4-biphenylyl)methyl]dihydrofuran-2-(3H)-one In analogy with Example 5d), 5.55 g (13.5 mmol) of 5(S)-[1(S)-0Boc-amino)-2-(p-benzyloxyphenyl)ethyl]dihydrofuran-2-(3H)-one [preparation, see Example 1g)], dissolved in 20 ml of THF and 23 ml of DMPU, are deprotonated, at −70° C., with 27 ml of a 1M solution of lithium bis(trimethylsilyl)amide in THF, and alkylated (1 h) with 5.0 g (20.2 mmol) of 4-biphenylylmethyl bromide (Salor, Milwaukee, U.S.A.) in 16 ml of THF. Protonating with 5 ml (67.4 mmol) of propionic acid and 5 ml of water, at −75° C., extracting and medium pressure chromatography (gradient: 30–50% ethyl acetate in toluene) results in the title compound: TLC $R_f(Q)$=0.15; $t_{Ret}(II)$=20.0 min.

89b) 5(S)-(Boc-Amino)-4(S)-hydroxy-6-(p-benzyloxyphenyl)-2(R)-[(4-biphenylylmethyl]hexanoic acid 4.56 g (7.9 mmol) of 5(S)-[1(S)-(Boc-amino)-2-(p-benzyloxyphenyl)ethyl]-3(R)-[(4-biphenylyl)methyl]

dihydrofuran-2-(3H)-one are hydrolysed, in 80 ml of dimethoxyethane, with 31.6 ml of a 1M solution of lithium hydroxide in water. After 18 h at RT, the dimethoxyethane is evaporated off on a RE and the residue is treated with an ice-cold mixture of 43 ml of sat. NH$_4$Cl solution, 229 ml of 10% citric acid solution and methylene chloride. The aqueous phase is separated off and extracted 2× with methylene chloride. The organic phases are washed with saline, dried with Na$_2$SO$_4$ and evaporated. Crystallization from DIPE yields the title compound: t$_{Ref}$(II)=17.9 min.

89c) 5(S)-(Boc-Amino)-4(S)-(tert-butyldimethylsilyloxy)-6-(p-benzyloxyphenyl)-2(R)-[(4-biphenylyl)methyl] hexanoic acid 3.19 g (5.4 mmol) of 5(S)-(Boc-amino)-4(S)-hydroxy-6-(p-benzyloxyphenyl)-2(R)-[(4-biphenylyl)methyl]hexanoic acid in 55 ml of DMF are silylated, at RT for 20 h and under a protective gas, with 3.71 g (24.6 mmol) of tert-butyldimethylchlorosilane and 3.0 g (44 mmol) of imidazole. The reaction mixture is evaporated and the residue is taken up in ethyl acetate; this solution is then washed with sat. NaHCO$_3$ solution, water and saline. The aqueous phases are extracted 2× with ethyl acetate and the organic phases are dried with Na$_2$SO$_4$ and evaporated. The residue is dissolved in 64 ml of methanol and 15 ml of THF, and this solution is treated with 4.5 g of potassium carbonate and 15 ml of water and stirred at RT for 1 h. Working up in analogy with Example 88c), and medium pressure chromatography (gradient: 0–10% methanol in methylene chloride), results in the title compound: TLC R$_f$(B)=0.7; t$_{Ref}$(II)=22.7 min.

89d) 5(S)-(Boc-Amino)-4(S)-(tert-butyldimethylsilyloxy)-6-(p-benzyloxyphenyl)-2(R)-[(4-biphenylyl)methyl] hexanoyl-(L)-Val-N-(2-methoxyethyl)amide 1000 mg (1.44 mmol) of 5(S)-(Boc-amino)-4(S)-(tert-butyldimethylsilyloxy)-6-(p-benzyloxyphenyl)-2(R)-[(4-biphenylyl)methyl]hexanoic acid in 13.8 ml of 0.25M NMM/CH$_3$CN are activated, under an N$_2$ atmosphere, with 601 mg (1.58 mmol) of HBTU. After 5 min, a quantity of 276 mg (1.58 mmol) of H-(L)-Val-N-(2-methoxyethyl) amide (Example 1b) is added and the mixture is thoroughly stirred at RT for 20 h. Working up in analogy with Example 1c), and medium pressure chromatography (gradient: 40–60% ethyl acetate in hexane), results in the title compound: TLC R$_f$(C)=0.33; t$_{Ref}$(II)=23.5 min.

Example 90

5(S)-(Boc-Amino)-4(S)-hydroxy-6-(p-hydroxyphenyl)-2(R)-[(4-biphenylyl)methyl] hexanoyl-(L)-Val-N-(2-methoxyethyl)amide Hydrogenating 200 mg (0.265 mmol) of 5(S)-(Boc-amino)-4(S)-hydroxy-6-(p-benzyloxyphenyl)-2(R)-[(4-biphenylyl)methyl]hexanoyl-(L)-Val-N-(2-methoxy-ethyl) amide (Example 89) in 20 ml of methanol/methylene chloride, 1:1, in the presence of 0.1 g of 10% Pd/C, filtering off the catalyst and evaporating, affords the title compound: t$_{Ref}$(II)=14.5 min; FAB-MS (M+H)$^+$=662.

Example 91

5(S)-(Boc-Amino)-4(S)-hydroxy-6-(p-methoxyphenyl)-2(R)-[(4-biphenylyl)methyl] hexanoyl-(L)-Val-N-(2-methoxyethyl)amide A solution of 173 mg (0.26 mmol) of 5(S)-(Boc-amino)-4(S)-hydroxy-6-(p-hydroxyphenyl)-2(R)-[(4-biphenylyl) methyl]hexanoyl-(L)-Val-N-(2-methoxyethyl)amide (Example 90) in 5 ml of DMF/dioxane, 1:1, is treated, under an N$_2$ atmosphere and while cooling with ice, with 170 mg (0.52 mmol) of Cs$_2$CO$_3$ and 16 µl (0.26 mmol) of methyl iodide. After the mixture has been stirred at RT for 20 h, 4.5 ml of ice-water are added and the mixture is finally diluted with water and methylene chloride. The aqueous phase is separated off and extracted 2× with methylene chloride. The organic phases are washed with water and saline, dried with Na$_2$SO$_4$ and evaporated. Stirring up the residue in hexane affords the title compound: t$_{Ref}$(II)=16.2 min; FAB-MS (M+H)$^+$=676.

Example 92

5(S)-(Boc-Amino)-4(S)-hydroxy-6-(p-benzyloxyphenyl)-2(R)-[({2'-cyanobiphenyl}-4-yl) methyl]hexanoyl-(L)-Val-N-(2-methoxyethyl)amide Under an N$_2$ atmosphere, 2.11 g (2.36 mmol) of 5(S)-(Boc-amino)-4(S)-(tert-butyldimethylsilyloxy)-6-(p-benzyloxyphenyl)-2(R)-[({2'-cyanobiphenyl}-4-yl)methyl] hexanoyl-(L)-Val-N-(2-methoxyethyl)amide in 49 ml of DMF are desilylated with 1.49 g (4.7 mmol) of TBAF and, after 20 h, worked up in analogy with Example 88). Stirring up in hexane affords the title compound: t$_{Ref}$(II)=17.4 min; FAB-MS (M+H)$^+$=777.

The starting material is prepared in the following manner:

92a) 5(S)-[1(S)-(Boc-Amino)-2-(p-benzyloxyphenyl)ethyl]-3(R)-[({2'-cyanobiphenyl}-4-yl)methyl]dihydrofuran-2-(3H)-one In analogy with Example 5d), 5.00 g (12.1 mmol) of 5(S)-[1(S)-(Boc-amino)-2-(p-benzyloxyphenyl)ethyl] dihydrofuran-2-(3H)-one [preparation, see Example 1g)], dissolved in 22 ml of THF and 2.4 ml of DMPU, are deprotonated, at −70° C., with 23.5 ml of a 1M solution of lithium bis(trimethylsilyl)amide in THF, and alkylated (2 h) with 3.43 g (12.1 mmol) of 4-(bromomethyl)-2'-cyanobiphenyl [96%; for preparation, see for example: J. Med. Chem. 34, 2525 (1991)]. Protonating with 4.5 ml of propionic acid and 4.5 ml of water, at −75° C., extracting, column chromatography (silica gel, hexane/ethyl acetate, 2:1) and recrystallization from hot ethyl acetate/hexane, results in the title compound: TLC R$_f$(D)=0.3; t$_{Ref}$(II)=19.0 min; FAB-MS (M+H)$^+$=603.

92b) 5(S)-(Boc-Amino)-4(S)-hydroxy-6-(p-benzyloxyphenyl)-2(R)-[({2'-cyanobiphenyl}-4-yl)methyl] hexanoic acid (lithium salt)

4.59 g (7.6 mmol) of 5(S)-[1(S)-(Boc-amino)-2-(p-benzyloxyphenyl)ethyl]-3(R)-[({2'-cyanobiphenyl}-4-yl) methyl]dihydrofuran-2-(3H)-one in 120 ml of dimethoxyethane and 61 ml of water are stirred together with 30 ml of a 1M solution of lithium hydroxide in water, with a white suspension being formed. After 16 h at RT, the crystals are filtered off with suction and washed with dimethoxethane (→lithium salt of the title compound): anal. calc. for C$_{38}$H$_{39}$N$_2$O$_6$Li×2H$_2$O: C 68.87%, H 6.54%, N 4.23%, H$_2$O 5.44; found: C 68.4%, H 6.5%, N 4.2%, H$_2$O 5.23; t$_{Ref}$(II) =17.2 min; FAB-MS (M+H)$^+$=627. The mother liquor is partially evaporated and the residue is treated with an ice-cold mixture of 340 ml of sat. NH$_4$Cl solution, 30 ml of 10% citric acid solution and methylene chloride. The aqueous phase is separated off and extracted 2× with methylene chloride. Washing the organic phases with saline, drying them with Na$_2$SO$_4$ and evaporating them yields the title compound as a free acid.

92c) 5(S)-(Boc-Amino)-4(S)-(tert-butyldimethylsilyloxy)-6-(p-benzyloxyphenyl)-2(R)-[({2'-cyanobiphenyl}-4-yl) methylhexanoic acid 4.7 g (7.5 mmol) of 5(S)-(Boc-amino)-4(S)-hydroxy-6-(p-benzyloxyphenyl)-2(R)-[({2'-cyanobiphenyl}-4-yl)

methyl]hexanoic acid (lithium salt) in 8.1 ml of DMF is stirred, at RT for 20 h, together with 5.2 g (34.6 mmol) of tert-butyldimethylchlorosilane and 4.18 g (61.4 mmol) of imidazole while excluding moisture. Since HPLC indicates that starting material is still present, a further 1.02 g of imidazole and 1.13 g of tert-butyldimethylchlorosilane are added. After 2 days, the reaction mixture is poured onto ice-water and the whole is extracted 3× with ethyl acetate. The organic phases are washed with 10% citric acid solution, water and saline, dried with $Na_2SO_4$ and evaporated. The residue is taken up in 91 ml of methanol and 34 ml of THF, and this solution is treated with 6.2 g of potassium carbonate and 34 ml of water, and stirred at RT for 1.5 h. The reaction mixture is subsequently partially evaporated and the residue is diluted with ice-cold 10% citric acid solution with the whole then being extracted with 3× ethyl acetate. The organic phases are washed with 2 portions of water and saline, dried with $Na_2SO_4$ and evaporated. Column chromatography (silica gel, hexane/ethyl acetate, 1:1) results in the title compound: TLC $R_f(C)$=0.21; $t_{Ret}(II)$=22.0 min.

92d) 5(S)-(Boc-Amino)-4(S)-(tert-butyldimethylsilyloxy)-6-(p-benzyloxyphenyl)-2(R)-[({2'-cyanobiphenyl}-4-yl)methyl]hexano yl-(L)-Val-N-(2-methoxyethyl)amide 2.00 g (2.72 mmol) of 5(S)-(Boc-amino)-4(S)-(tert-butyldimethylsilyloxy)-6-(p-benzyloxyphenyl)-2(R)-[({2'-cyanobiphenyl}-4-yl)methyl]hexanoic acid, 652 mg (4.83 mmol) of HOBT, 1.54 g (8.05 mmol) of EDC and 1.17 ml (8.37 mmol) of triethylamine are initially introduced in 24 ml of DMF under an $N_2$ atmosphere. 674 mg (3.87 mmol) of H-(L)-Val-N-(2-methoxyethyl)amide (Example 1b) are added to this mixture, and the whole is thoroughly stirred at RT overnight. The reaction mixture is evaporated under HV. The residue is partitioned between 3 portions of methylene chloride, 10% citric acid solution, sat. $NaHCO_3$ solution and saline. Drying the organic phases with $Na_2SO_4$, evaporating them, and recrystallizing the residue from hot ethyl acetate/hexane, affords the title compound: $t_{Ret}(II)$=22.7 min; FAB-MS $(M+H)^+$=891.

Example 93

5(S)-(Boc-Amino)-4(S)-hydroxy-6-(p-hydroxyphenyl)-2(R)-[({2'-cyanobiphenyl}-4-yl)methyl]hexanoyl-(L)-Val-N-(2-methoxyethyl)amide Hydrating 1.20 g (1.54 mmol) of 5(S)-(Boc-amino)-4(S)-hydroxy-6-(p-benzyloxyphenyl)-2(R)-[({2'-cyanobiphenyl}-4-yl)methyl]hexanoyl-(L)-Val-N-(2-methoxyethyl)amide (Example 92) in 40 ml of methanol and 15 ml of THF in the presence of 0.24 g of 10% Pd/C, filtering off the catalyst, evaporating, and precipitating with DIPE from a concentrated solution in methanol, affords the title compound: $t_{Ret}(II)$=13.7 min; FAB-MS $(M+H)^+$=687.

Example 94

5(S)-(Boc-Amino)-4(S)-hydroxy-6-(p-methoxyphenyl)-2(R)-[({2'-cyanobiphenyl}-4-yl)methyl]hexanoyl-(L)-Val-N-(2-methoxyethyl)amide A solution of 100 mg (0.145 mmol) of 5(S)-(Boc-amino)-4(S)-hydroxy-6-(p-hydroxyphenyl)-2(R)-[({2'-cyanobiphenyl}-4-yl)methyl]hexanoyl-(L)-Val-N-(2-methoxyethyl)amide (Example 93) in 3 ml of DMF/dioxane, 1:1 is treated, under an $N_2$ atmosphere and while being cooled with ice, with 94.6 mg (0.29 mmol) of $Cs_2CO_3$ and 9 µl (0.145 mmol) of methyl iodide. After the mixture has been stirred at RT for 20 h, HPLC indicates that starting material is still present; the same quantities of $Cs_2CO_3$ and methyl iodide are therefore added once again and the mixture is stirred over a further night 2.5 ml of ice-water are added to the reaction mixture and the suspension is diluted with water and methylene chloride. The aqueous phase is separated off and extracted 2× with methylene chloride. The organic phases are washed with water and saline, dried with $Na_2SO_4$ and evaporated. Column chromatography (silica gel, methylene chloride/THF 15:1→4:1) and stirring up the residue in hexane affords the title compound: TLC $R_f(R)$=0.1; $t_{Ret}(II)$=15.5 min; FAB-MS $(M+H)^+$=701.

Example 95

5(S)-(BoC-Amino)-4(S)-hydroxy-6-phenyl-2(R)-[(2,3,4-trimethoxyphenyl)methyl]hexanoyl-(L)-Val-N-(2-ethoxyethyl)amide 1120 mg (1.42 mmol) of 5(S)-(Boc-amino);4(S)-(tert-butyldimethylsilyloxy)-6-phenyl-2(R)-[(2,3,4-trimethoxyphenyl)methyl]hexanoyl-(L)-Val-N-(2-ethoxyethyl)amide in 14 ml of abs. DMF are treated with 920 mg (2.84 mmol) of TBAF, and the reaction mixture is stirred at RT for 21 h under argon. It is then poured onto cold saline and the solid is filtered. This solid is dissolved in ethyl acetate and the solution is washed, in succession, with water, sat. sodium bicarbonate solution and saline. The combined aqueous phases are reextracted with ethyl acetate. The combined organic phases are dried over sodium sulfate and concentrated at approximately 30° C. The residue is digested in diisopropyl ether and filtered off. After having been filtered off, the title compound is washed with hexane and subsequently dried under reduced pressure. m.p.: 117° C. TLC $R_f(A)$=0.28. FAB-MS $(M+H)^+$=674. HPLC $t_{Ret}$=15.19 min (gradient II); IR (methylene chloride)=inter alia 3431, 2967, 1680, 1494, 1467, 1367, 1275 and 1166 $cm^{-1}$; $^1$H-NMR ($CD_3OD$)=inter alia 7.30–7.10/m (5H); 6.78 and 6.61/each d (each 1H); 4.03/d (1H); 3.85, 3.81 and 3.80/each s (each 3H); 3.46/q (2H), 1.32 and 1.26/each s (in all 9H from Boc), 1.15/t (3H); 0.82/pseudo t (6H).

The starting material is prepared in the following manner:
95a) 5(S)-(Boc-Amino)-4(S)-(tert-butyldimethylsilyloxy)-6-phenyl-2(R)-[(2,3,4-trimethoxylphenyl]methyl)hexanoyl-(L)-Val-N-(2-ethoxyethyl)amide In analogy with Example 1c), 1.27 g (2.05 mmol) of 5(S)-(Boc-amino)-4(S)-(tert-butyldimethylsilyloxy)-6-phenyl-2(R)-[(2,3,4-trimethoxyphenyl)methyl]hexanoic acid (Example 47e)) and 460 mg of H-(L)-Val-N-(2-ethoxyethyl)amide in 19.2 ml of 0.25M $NMM/CH_3CN$ are reacted with 860 mg of HBTU, within a reaction time of 20 h, to form the title compound. The latter is dissolved in ethyl acetate and this solution is washed, in succession, with 10% cold citric acid, water, saturated sodium bicarbonate solution and saline (2×). After the organic phase has been dried over sodium sulfate, it is filtered and concentrated under reduced pressure. The title compound is purified by medium pressure column chromatography (8 bar, methylene chloride/methanol). TLC $R_f(A)$=0.5; FAB-MS $(M+H)^+$=788; IR (methylene chloride)=inter alia 3436, 2932, 1666, 1602, 1495, 1467, 1367, 1249 and 1164 $cm^{-1}$.

95b) H-(L)-Val-N-(2-ethoxyethyl)amide

In analogy with Example 1b), the pure title compound is obtained as an oil, after filtering off the catalyst and evaporating the filtrate, by hydrogenating 6.12 g (19.59 mmol) of Z-(L)-Val-N-(2-ethoxyethyl)amide in 120 ml of methanol at RT, under low pressure and in the presence of 0.61 g of 10% Pd/C: $^1$H-NMR (200 MHz, $CDCl_3$): 0.80 and 0.95 (2d, 6H), 1.2 (t, 3H), 1.35 (b, 2H), 2.25 (m, 1H), 3.2 (d, 1H), 3.45 (t, 2H), 3.47 (m, 4H), 7.5 (b, 1H).

95c) Z-(L)-Val-N-(2-ethoxyethyl)amide 5.025 g (20 mmol) of Z-(L)-valine are dissolved in 20 ml of methylene chloride and this solution is treated, at from −10° to −15° C., with 2.68 ml (20.4 mmol) of isobutyl chloroformate (Fluka, Buchs, Switzerland) and 22.2 ml (20 mmol) of NMM. After the mixture has been stirred for 15 minutes, 2.064 g (23.2 mmol) of 2-ethoxyethylamine (Pfaltz & Bauer, Waterbury, U.S.A.) are added under a protective gas. The beige suspension is warmed to RT and treated with 100 ml of ethyl acetate and 40 ml of water. After the organic phase has been separated off, it is washed with 40 ml of 1N sodium hydroxide solution and with saline (3×). The solution is dried over sodium sulfate and subsequently evaporated under HV. The residue is digested in hexane and filtered off with suction. The title compound, which has thus been obtained, is subjected to further reaction without any additional purification. TLC $R_f(A)$=0.4; $^1$H-NMR (200 MHz, CDCl$_3$): 0.95 (2d, 6H), 1.2 (t, 3H), 2.1 (m, 1H), 3.4–3.55 (m, 6H), 3.97 (dd, 1H), 5.2 (s, 2H), 5.4 (b, 1H), 6.2(b, 1H), 7.35 (s, 5H).

Example 96

5(S)-(Boc-Amino)-4(S)-hydroxy-6-phenyl-2(R)-[(2,3,4-trimethoxyphenyl)methyl]hexanoyl-(L)-Val-N-(3-methoxypropyl)amide 1.19 g (1.51 mmol) of 5(S)-(Boc-amino)-4(S)-(tert-butyldimethylsilyloxy-6-phenyl-2(R)-[(2,3,4-trimethoxyphenyl)methyl]-hexanoyl-(L)-Val-N-(3-methoxypropyl)amide in 14.5 ml of abs. DMF are treated with 980 mg (3.02 mmol) of TBAF, and the reaction mixture is stirred at RT for 22 h under argon. It is then poured onto cold saline and the solid is filtered off. This solid is dissolved in ethyl acetate and the solution is washed, in succession, with water, sat. sodium bicarbonate solution and saline. The combined aqueous phases are reextracted with ethyl acetate. The combined organic phases are dried over sodium sulfate and concentrated at approximately 30° C. The residue is digested in diisopropyl ether and filtered off. After having been filtered off, the title compound is dried under reduced pressure. m.p.: 131°–132° C.; TLC $R_f$ (A)=0.23; FAB-MS (M+H)$^+$=674. HPLC $t_{Ref}$=14.88 min (gradient II). IR (methylene chloride)=inter alia 3430, 2966, 1665, 1494, 1467, 1367, 1275 and 1167 cm$^{-1}$; $^1$H-NMR (CD$_3$OD)=inter alia 7.30–7.20/m (5H); 6.78 and 6.61/each d (each 1H); 4.03/d (1H); 3.85, 3.81 and 3.80/each s (each 3H); 3.7 (m, 1H), 3.53 (m, 1H), 3.39 (t, 2H), 3.29 (s, 3H), 1.32 and 1.26/each s (in all 9H from Boc), 0.85/pseudo t (6H). The starting material is prepared in the following manner:

96a) 5(S)-(Boc-Amino)-4(S)-(tert-butyldimethylsilyloxy)-6-phenyl-2(R)-[(2,3,4-trimethoxyphenyl)methyl]hexanoyl-(L)-Val-N-(3-methoxypropyl)amide In analogy with Example 1c), 2.47 g (4 mmol) of 5(S)-(Boc-amino)-4(S)-(tert-butyl-dimethylsilyloxy)-6-phenyl-2(R)-[(2,3,4-trimethoxyphenyl)methyl]hexanoic acid (Example 47e)) and 830 mg (4.4 mmol) of H-(L)-Val-N-(3-methoxypropyl)amide in 37.6 ml of 0.25M NMM/CH$_3$CN are reacted with 1.67 g HBTU, within a reaction time of 22 h, to form the title compound. The latter is dissolved in ethyl acetate and this solution is washed, in succession, with 10 cold citric acid, water, saturated sodium bicarbonate solution and saline (2×). After the organic phase has been dried over sodium sulfate, it is filtered and concentrated under reduced pressure. The title compound is purified by medium pressure column chromatography (8 bar, methylene chloride/methanol). TLC $R_f(A)$=0.35; FAB-MS (M+H)$^+$=788; IR (methylene chloride)=inter alia 3436, 2932, 1665, 1602, 1494, 1468, 1390, 1367, 1250 and 1165 cm$^{-1}$.

96b) H-(L)-Val-N-(3-methoxypropyl)amide

In analogy with Example 1b), the pure title compound is obtained as an off, after filtering off the catalyst and evaporating the filtrate, by hydrogenating 22.26 g (69.044 mmol) of Z-(L)-Val-N-(3-methoxypropyl)amide in 463.3 ml of methanol at RT, under low pressure and in the presence of 2.226 g of 10% Pd/C: FAB-MS (M+H)$^+$=189; $^1$H-NMR (360 MHz, DMSO-D$_6$): 0.76 and 0.87 (2d, 6H), 1.6 (b, 2H), 1.63 (m, 2H), 1.84 (m, 1H), 3.1 (m, 2H), 3.22 (s, 3H), 3.31 (m, 2H), 7.82 (b, 1H).

96c) Z-(L)-Val-N-(3-methoxypropyl)amide

In analogy with Example 1a), 20 g (79.6 mmol) of Z-(L)-valine in 250 ml of CH$_3$CN and 20.5 ml of 95% NMM (175.1 mmol) are treated with 9 ml (87.55 mmol) of 3-methoxypropylamine (Fluka, Buchs, Switzerland). 33.2 g (87.55 mmol) of HBTU are added to the thick suspension and the whole is thoroughly stirred at RT for 22 h. The reaction mixture is evaporated under HV and the residue is taken up in ethyl acetate, with this solution being extracted with water, 2× 10% citric acid solution, water, 2× sat. NaHCO$_3$ solution and saline. The aqueous phases are extracted a further 2× with ethyl acetate and the organic phases are dried with Na$_2$SO$_4$ and evaporated. Crystallization from ethyl acetate/hexane results in the title compound: TLC $R_f(G)$=0.41; $t_{Ref}$(II)=11.86 min; FAB-MS (M+H)$^+$= 323.

Example 97

5(S)-(Boc-Amino)-4(S)-hydroxy-6-phenyl-2(R)-[(2,3,4-trimethoxyphenyl)methyl]hexanoyl-(L)-Val-N-(3-ethoxypropyl)amide 0.97 g (1.57 mmol) of 5(S)-(Boc-amino)-4(S)-(tert-butyldimethylsilyloxy)-6-phenyl-2(R)-[(2,3,4-trimethoxyphenyl)methyl]hexanoyl-(L)-Val-N-(3-ethoxypropyl)amide in 11 ml of abs. DMF is treated with 814 mg of TBAF and the reaction mixture is stirred at RT for 18 h under argon. It is then dissolved in ethyl acetate and this solution is washed, in succession, with water, sat. sodium bicarbonate solution and saline. The combined aqueous phases are reextracted with ethyl acetate. The combined organic phases are dried over sodium sulfate and concentrated at approximately 30° C. The residue is purified by column chromatography (silica gel, C). TLC $R_f$ (A)=0.44; FAB-MS (M+H)$^+$=688;HPLC $t_{Ref}$=15.43 min (gradient II); $^1$H-NMR (CD$_3$OD)=inter alia 7.30–7.10/m (5H); 6.78 and 6.61/each d (each 1H); 4.0 (d, 1H); 3.85, 3.81 and 3.80/each s (each 3H); 3.7 (m, 1H), 3.53 (m, 1H), 3.45 (q, 2H) and (m, 2H), 3.17 (m, 2H), 2.85–2.7 (2m, 5H), 1.93–1.6 (m, 5H), 1.32 and 1.26/each s (in all 9H from Boc), 0.85/pseudo-t (6H).

The starting material is prepared in the following manner:
97a) 5(S)-(Boc-Amino)-4(S)-(tert-butyldimethylsilyloxy)-6-phenyl-2(R)-[(2,3,4-trimethoxyphenyl)methyl]hexanoyl-(L)-Val-N-(3-ethoxypropyl)amide In analogy with Example 1c), 1.235 g (2 mmol) of 5(S)-(Boc-amino)-4(S)-(tert-butyldimethylsilyloxy)-6-phenyl-2(R)-[(2,3,4-trimethoxyphenyl)methyl]hexanoic acid (Example 47e)) and 445 mg (2.2 mmol) of H-(L)-Val-N-(3-ethoxypropyl)amide in 18.8 ml of 0.25M NMM/CH$_3$CN are reacted with 0.835 g of HBTU, within a reaction time of 22 h to form the title compound. After the suspension has been concentrated, it is dissolved in ethyl acetate and this solution is washed, in succession, with 10% cold citric acid, water, saturated sodium bicarbonate solution and saline (2×). After the organic phase has been dried over sodium sulfate, it is filtered and concentrated under reduced pressure. The title compound is purified by column chromatography (silica gel, methylene chloride/methanol: 99/1). TLC $R_f(C)=0.32$; $t_{Ret}(II)=22.58$ min; FAB-MS $(M+H)^+=802$.

97b) H-(L)-Val-N-(3-ethoxypropyl)amide

In analogy with example 1b), the pure title compound is obtained as an oil, after filtering off the catalyst and evaporating the filtrate, by hydrogenating 6.2 g (18.4 mmol) of Z-(L)-Val-N-(3-ethoxypropyl)amide in 120 ml of methanol at RT, under low pressure and in the presence of 0.62 g of 10 Pc/C: $^1$H-NMR (200 MHz, CDCl$_3$): 0.8 and 0.97 (2d, 6H), 1.2 (t, 3H), 1.3 (b, 2H), 1.8 (m, 2H), 2.25 (m, 1H), 3.2 (d, 1H), 3.38 (m, 2H), 3.45 (m, 4H), 7.55 (b, 1H).

97c) Z-(L)-Val-N-(3-ethoxypropyl)amide 5.025 g (20 mmol) of Z-(L)-valine are dissolved in 20 ml of methylene chloride and this solution is treated, at from −10° to −15° C., with 2.68 ml (20.4 mmol) of isobutyl chloroformate and 2.2 ml (20 mmol) of NMM. After the mixture has been stirred for 15 minutes, 2.78 ml (23.2 mmol) of 3-ethoxypropylamine are added under a protective gas. The beige suspension is warmed to RT and treated with 100 ml of ethyl acetate and 40 ml of water. After the organic phase has been separated off, it is washed with 40 ml of 1N sodium hydroxide solution and with saline (3×). The solution is dried over sodium sulfate and then evaporated under HV. The residue is digested in hexane and filtered off with suction. The title compound which is thus obtained is subjected to further reaction without any additional purification. TLC $R_f(C)=0.35$; $^1$H-NMR (200 MHz, CDCl$_3$): 0.95 (2d, 6H), 1.2 (t, 3H), 1.75 (m, 2H), 2.1 (m, 1H), 3.3–3.55 (m, 7H), 3.93 (dd, 1H), 5.1 (s, 2H), 5.4 (b, 1H), 6.55 (b, 1H); 7.35 (s, 5H).

Example 98

5(S)-(Boc-Amino)-4(S)-hydroxy-6-phenyl-2(R)-[(2, 3,4-trimethoxyphenyl)methyl]hexanoyl-(L)-Val-N-(3-(n-propyloxy)propyl)amide 1.4 g (1.71 mmol) of 5(S)-(Boc-amino)-4(S)-(tert-butyldimethylsilyloxy)-6-phenyl-2(R)-[(2,3,4-trimethoxyphenyl)methyl]hexanoyl-(L)-Val-N-(3-(n-propyloxy)propyl)amide in 16 ml of abs. DMF are treated with 1.17 g of TBAF and the reaction mixture is stirred at RT for 18 h under argon. It is then poured onto saline/ice, and insoluble material is filtered off. The residue is dissolved in ethyl acetate and this solution is washed, in succession, with water, sat. sodium bicarbonate solution and saline. The combined aqueous phases are reextracted with ethyl acetate. The combined organic phases are dried over sodium sulfate and concentrated at approximately 30° C. The residue is crystallized from diisopropyl ether, a little ethyl acetate and hexane. TLC $R_f$ (A)=0.53; FAB-MS $(M+H)^+=702$; HPLC $T_{Ref}=16.31$ min (gradient II); $^1$H-NMR (CD$_3$OD)=inter alia 7.30–7.10/(m, 5H); 6.78 and 6.61/each d (each 1H); 4.0 (d, 1H); 3.85, 3.81 and 3.80 (each s, each 3H); 3.7 (m, 1H), 3.54 (m, 1H), 3.43 (t, 2H) 3.37 (t, 2H), 3.15 (m, 2H), 2.9–2.63 (2m, 5H), 1.93 (m, 1H), 1.82–1.5 (m, 6H), 1.32 and 1.26/ each s (in all 9H from Boc), 0.85/pseudo t (6H).

The starting material is prepared in the following manner:
98a) 5(S)-(Boc-Amino)-4(S)-(tert-butyldimethylsilyloxy)-6-phenyl-2(R)-[(2,3,4-trimethoxphenyl)methyl]hexanoyl-(L)-Val-N-(3-(n-propyloxy)propyl)amide In analogy with Example 1c), 1.235 g (2 mmol) of 5(S)-(Boc-amino)-4(S)-(tert-butyldimethylsilyloxy)-6-phenyl-2(R)-[(2,3,4-trimethoxyphenyl)methyl]hexanoic acid (Example 47e)) and 497 mg (2.3 mmol) of H-(L)-Val-N-(3-(n-propyloxy)propyl)amide in 18.8 ml of 0.25M NMM/CH$_3$CN are reacted with 0.835 g of HBTU, within a reaction time of 22 h, to form the title compound. After the suspension has been concentrated, it is dissolved in cold ethyl acetate and this solution is washed, in succession, with 10% cold citric acid, water, saturated sodium bicarbonate solution and saline (2×). After the organic phase has been dried over sodium sulfate, it is filtered and concentrated under reduced pressure. The title compound is purified by column chromatography (silica gel, methylene chloride/methanol: 99/1). TLC $R_f(C)=0.27$; $t_{Ref}(II)=23.09$ min; FAB-MS $(M+H)^+=816$.

98b) H-(L)-Val-N-(3-(n-propyloxy)propyl)amide

In analogy with Example 1b), the pure title compound is obtained as an oil, after filtering off the catalyst and evaporating the filtrate, by hydrogenating 6.3 g (17.48 mmol) of Z-(L)-Val-N-(3-(n-propyloxy)propyl)amide in 120 ml of methanol at RT, under low pressure and in the presence of 0.63 g of 10% Pd/C: $^1$H-NMR (200 MHz, CDCl$_3$): 0.8 (d, 3H), 0.9 and 0.97 (2d, 6H), 1.25 (b, 2H), 1.4 (m, 2H), 1.78 (m, 2H), 2.25 (m, 1H), 3.2 (d, 1H), 3.38 (m, 4H), 3.5 (m, 2H), 7.5 (b, 1H).

98c) Z-(L)-Val-N-(3-(n-propyloxy)propyl)amide 5.025 g (20 mmol) of Z-(L)-valine are dissolved in 20 ml of methylene chloride and this solution is treated, at from −10° to −15° C., with 2.68 ml (20.4 mmol) of isobutyl chloroformate and 2.2 ml (20 mmol) of NMM. After the mixture has been stirred for 15 min, 2.72 ml (23.2 mmol) of 3-(n-propyloxy)propylamine (Tokyo Kasei Organic Chemicals, Tokyo, Japan) are added under a protective gas. The beige suspension is warmed to RT and treated with 100 ml of ethyl acetate and 40 ml of water. After the organic phase has been separated off, it is washed with 40 ml of 1N sodium hydroxide solution and with saline (3×). The solution is dried over sodium sulfate and then evaporated under HV. The residue is digested in hexane and filtered off with suction. The title compound which is thereby obtained is subjected to further reaction without any additional purification. TLC $R_f(C)=0.6$; $^1$H-NMR (200 MHz, CDCl$_3$): 0.92 (m, 9H), 1.6 (m, 2H), 1.75 (m, 2H), 2.1 (m, 1H), 3.35 (m, 4H), 3.5 (m, 2H), 3.93 (dd, 1H), 5.1 (s, 2H), 5.4 (b, 1H), 6.5 (b, 1H), 7.35 (s, 5H).

Example 99

5(S)-(3-Hydroxy-2-methylphenylcarboxylamino)-4 (S)-hydroxy-6-(p-methoxyphenyl)-2(R)-[({2'-cyanobiphenyl}-4-yl)methyl]hexanoyl-(L)-Val-N-(2-methoxyethyl)amide The title compound is prepared in analogy with one of the methods described in the abovementioned examples.

Example 100

5(S)-(Boc-Amino)-4(S)-hydroxy-6-phenyl-2(R)-[({2'-cyanobiphenyl}-4-yl)methyl]hexanoyl-(L)-Val-N-(2-methoxyethyl)amide The title compound is prepared in analogy with one of the methods described in the abovementioned examples.

Example 101

5(S)-(Boc-Amino)-4(S)-hydroxy-6-cyclohexyl-2(R)-[({2'-cyanobiphenyl}-4-yl)methyl]hexanoyl-(L)-Val-N-(2-methoxyethyl)amide The title compound is prepared in analogy with one of the methods described in the abovementioned examples.

Example 102

5(S)-(p-Nitrobenzenesulfonylamino)-4(S)-hydroxy-6-phenyl-2(R)-[(2,3,4-trimethoxophenyl)methyl] hexanoyl-(L)-Val-N-(2-methoxyethyl)amide 1.00 g (1.67 mmol) of 5(S)-amino-4(S)-hydroxy-6-phenyl-2(R)-[(2,3,4-trimethoxyphenyl)methyl]hexanoyl- (L)-Val-N-(2-methoxyethyl)amide (hydrochloride salt) (Example 83a)) is dissolved in dichloromethane, and the organic phase is washed with sat. sodium bicarbonate solution, dried over sodium sulfate and concentrated. The liberated amine is stirred, at 0° C. for 17 h, in 25 ml of pyridine together with 475 mg (1.25 equivalents) of 4-nitrobenzenesulfonyl chloride (Fluka, Buchs, Switzerland). After a further 285 mg (0.75 equivalents) of 4-nitrobenzenesulfonyl chloride have been added, the mixture is allowed to continue reacting at RT for a further 3 h. The reaction mixture is concentrated. The oily residue is taken up in cold ethyl acetate and this solution is washed, in succession, with 10% citric acid solution, saline, sat. sodium bicarbonate solution and saline. After drying over sodium sulfate, the solvent is removed. The resulting crystalline, residue is crystallized from ethyl acetate/hexane, filtered off with suction, washed with hexane and dried, with the title compound being obtained: FAB-MS (M+H)$^+$=745; m.p.: 195°–198° C.; $t_{Ref}$(II)=10.45 min.

Example 103

5(S)-(p-Aminobenzenesulfonylamino)-4(S)-hydroxy-6-phenyl-2(R)-[(2,3,4-trimethoxyphenylmethyl]hexanoyl-(L)-Val-N-(2-methoxyethyl)amide 200 mg (0.268 mmol) of 5(S)-(p-nitrobenzenesulfonylamino)-4(S)-hydroxy-6-phenyl-2(R)-[(2,3,4-trimethoxyphenyl)methyl]hexanoyl-(L)-Val-N-(2-methoxyethyl)amide (Example 102) are dissolved in 6 ml of methanol and 1 equivalent of acetic acid. After the addition of 50 mg of Raney nickel (in ethanol), the mixture is hydrogenated at RT and under standard pressure. After hydrogenation is complete, the reaction solution is separated off through ®Hyflo Super Cel (filtering aid based on kieselguhr (diatomaceous earth); Fluka, Buchs, Switzerland). The solution is concentrated. The resulting crystalline residue is recrystallized from methanol/hexane. The title compound is obtained after filtering off the residue and washing it with hexane: FAB-MS (M+H)$^+$=715; m.p.: 200°–206° C.; $t_{Ref}$(II)=9.14 min.

Example 104

5(S)-[(o-Methyl-p-nitrobenzenesulfonyl)amino]-4(S)-hydroxy-6-phenyl-2(R)-[(2,3,4-trimethoxyphenyl)methyl]hexanoyl-(L)-Val-N-(2-methoxyethyl)amide The title compound is prepared in analogy with one of the methods described in the abovementioned examples.

Example 105

5(S)-[(o-Methyl-p-aminobenzenesulfonyl)amino]-4(S)-hydroxy-6-phenyl-2(R)-](2,3,4-trimethoxyphenyl)methyl]hexanoyl-(L)-Val-N-(2-methoxyethyl)amide The title compound is prepared in analogy with one of the methods described in the abovementioned examples.

Example 106

Capsules (I)

Crystalline 5(S)-(Boc-amino)-4(S)-hydroxy-6-phenyl-2(R)-(2,3,4-trimethoxyphenylmethyl)-hexanoyl-(L)-Val-N-(2-methoxy-ethyl)amide (active substance) is micronized (particle size, from approximately 1 to 100 μm) with a customary knife mixer (for example Turmix). ®Pluronic F 68 (block polymer consisting of polyethylene and polypropylene glycol; Wyandotte Chem. Corp., Michigan, U.S.A.; also obtainable from Emkalyx, France; BASF trademark) is likewise micronized with a customary mixer, and the fine fraction is separated by screening using a sieve (0.5 mm) and subjected to further use as described below. 16.00 g of sesame oil are initially introduced in a beaker, and 1.20 g of the micronized active substance, 1.20 g of the fine fraction of ®Pluronic F 68 and 1.20 g of hydroxypropyl methyl cellulose (HP-M-603 cellulose from Shin-Etsu Chemicals Ltd., Tokyo, Japan) are added while stirring with an agitator (IKA-Werk, FRG) which is combined with a cogged stirrer (diameter: 46 mm) (stirring speed: 2000 rpm). 20 min of stirring at the given stirring speed produces a suspension of a pasty consistency which is used to fill hard gelatin capsules (20×40 mm; R. P. Scherer AG, Eberbach, FRG).

Example 107

Capsules (II):

The following constituents are processed as follows in order to prepare 10,000 capsules containing 100 mg of active compound (for example 5(S)-(Boc-amino)-4(S)-hydroxy-6-phenyl-2(R)-(2,3,4-trimethoxyphenylmethyl)-hexanoyl-(L)-Val-N-(2-methoxyethyl)amide) per capsule:

| Active compound | 1000 g |
|---|---|
| ®Pluronic F 68 | 1000 g |
| Hydroxypropyl methyl cellulose | 1000 g |
| Sesame oil | 1000 g |

(origin of the constituents: see Example 106)

The sesame oil is initially introduced in a heatable vessel (Fryma), and the Pluronic F 68 is sprinkled in. The vessel is heated to 60° C. and the Pluronic F 68 is distributed by stirring the mixture (duration approximately 2 h). The mixture is cooled down to approximately 30° C. while being stirred and homogenized. The hydroxypropyl methyl cellulose and the active compound are sprinkled in and distributed in the oily mass while stirring and homogenizing (approximately 1 h). The suspension, which is of a pasty consistency, is used to fill hard gelatin capsules (size 0; obtainable, for example, from Elanco or Parke-Davies (Caprogel)) or soft gelatin capsules (20 mm oblong; R. P. Scherer AG, Eberbach, FRG) with the aid of the customary equipment.

Example 108

Gelatin solution:

An aqueous solution, which has been sterilized by filtration and which contains, as active compound, one of the compounds of the formula I mentioned in the preceding examples, together with 20% cyclodextrins as solubilizers, is mixed, under aseptic conditions and while heating, with a sterile gelatin solution, which contains phenol as preservative, such that 1.0 ml of solution has the following composition:

| Active compound | 3 mg |
|---|---|
| Gelatin | 150.0 mg |
| Phenol | 4.7 mg |
| Dist. water containing 20% cyclodextrins as solubilizers | 1.0 ml |

Example 108

Sterile dry substance for injection:

5 mg of one of the compounds of the formula I mentioned in the preceding examples, as active compound, are dissolved in 1 ml of an aqueous solution containing 20 mg of mannitol and 20% cyclodextrins as solubilizers. The solution is sterilized by filtration and used, under aseptic conditions, to fill a 2 ml ampoule, after which it is frozen and lyophilized. Before use, the lyophilisate is dissolved in 1 ml of distilled water or 1 ml of physiological sodium chloride solution. The solution is used for intramuscular or intravenous administration. This formulation can also be used to fill double-chambered disposable syringes.

Example 109

Nasal spray:

500 mg of a finely ground (<5.0 μm) powder of one of the compounds of the formula I mentioned in the preceding examples, as active compound, are suspended in a mixture of 3.5 ml of Myglyol 812® and 0.08 g of benzyl alcohol. This suspension is introduced into a container possessing a dosing valve. 5.0 g of Freon 12®, which is under pressure due to the valve, are introduced into the container. The "Freon" is dissolved in the Myglyol/benzyl alcohol mixture by shaking. This spray container contains approximately 100 individual doses which can be administered individually.

Example 110

Lacquered tablets

The following constituents are processed for preparing 10,000 tablets each containing 100 mg of active compound:

| | |
|---|---|
| Active compound | 1000 g |
| Corn starch | 680 g |
| Colloidal silicic acid | 200 g |
| Magnesium stearate | 20 g |
| Stearic acid | 50 g |
| Sodium carboxymethyl starch | 250 g |
| Water | quantum satis |

A mixture of one of the compounds of the formula I mentioned in the preceding examples, as active compound, 50 g of corn starch and the colloidal silicic acid is processed together with starch paste consisting of 250 g of corn starch and 2.2 kg of demineralized water to form a moist mass. This is forced through a sieve of 3 mm mesh size and dried in a fluidized-bed dryer at 45° for 30 min. The dried granulate is pressed through a sieve of 1 mm mesh size, mixed with a previously screened mixture (1 mm sieve) of 330 g of corn starch, the magnesium stearate, the stearic acid and the sodium carboxymethyl starch, and pressed into slightly domed tablets.

Example 111

Pharmacokinetics in the dog
Formulation: Capsules from Example 106

Conduct of the experiment: 2 female beagle breeding dogs (Ciba Geigy, Sisseln) are used. During the experiment, the bitches have free access to water and are given their last meal approximately 16 h before the beginning of the experiment. Feed is proffered once again at 8 h after the beginning of the experiment. Each bitch is given 2 capsules of the specified formulation, which capsules together contain 1.2 g of 5(S)-(Boc-amino)-4(S)-hydroxy-6-phenyl-2(R)-(2,3,4-trimethoxyphenylmethyl)hexanoyl-(L)-Val-N-(2-methoxyethyl)amide (active substance), corresponding to an average dose of approximately 100 mg/kg of body weight. Blood from the saphenous vein is collected in heparinized tubes at different times after the administration.

In order to analyses the plasma concentration, the heparinized blood is centrifuged (4000×g, 20 min) and the plasma is removed and mixed with an equal volume of acetonitrile. The mixture is kept on ice for 30 min. The protein precipitate is removed by centrifugation (10,000×g, 5 min) and the supernatant is centrifuged once again. The concentration of the active substance in the final supernatant which is obtained is determined by means of reversed-phase HPLC: the HPLC analysis is carried out on an analytical 125×4.6 mm Nucleosil C18 (5 μm) column (Macherey & Nagel, Düren, FRG), which is equilibrated with a mobile phase of 50% acetonitrile and 0.1% trifluoroacetic acid in water. The flow rate is 1 ml/min. Under these conditions, the detection limit is 0.1 μM. The active substance is detected by UV absorption at 215 nm. The concentrations are determined by the external standard method; the heights of the peaks are used to determine the concentrations by comparison with standard curves. The standard curves am obtained by HPLC analysis of dog plasmas containing known added concentrations of the active substance, which plasmas are themselves worked up in a manner analogous to that for the active samples, by means of the abovementioned steps.

Results:

| Table of values | The values are given in ng/ml | |
|---|---|---|
| Time (h) | Bitch 1 | Bitch 2 |
| 2 | 7592 | 13947 |
| 4 | 4688 | 4570 |
| 6 | 616 | 192 |
| 8 | 44 | 18 |
| 12 | 11 | <0.1 |
| 24 | 14 | <0.1 |
| Area under the curve (AUC) for the period from 0 to 24 h (ng × h/ml) | 26101 | 37473 |

Example 112

Synergistic effect produced by combining 5(S)-(Boc-amino)-4(S)-hydroxy-6-phenyl-2(R)-[(2,3,4-trimethoxyphenyl)methyl]hexanoyl-(L)-Val-N-(2-methoxyethyl)amide (compound from Example 47) with indinavir or saquinavir in the experiment using cell lines The activities of the individual compounds, and the combinations, mentioned in the title, in the coculture of the CEM-SS cell line and the permanently infected cell line H9/HIV-1/IIIB are determined using the method described above in association with the description of the pharmacological properties. The measurement result is expressed as % reduction of the reverse transcriptase (RT) activity. The results are presented in the following table; measurement results which confirm the occurrence of synergism are emphasized by underlining:

a) Combination with saquinavir:

| Concentration of the active compound | | % Inhibition of the RT activity by | | |
|---|---|---|---|---|
| Example 47 title compound (nM) | Saquinavir (nM) | Example 47 title compound alone | Saquinavir alone | Combination of Example 47 and Saquinavir |
| 3.125 | 0.78 | 2.7% | 6.6% | 24.2% |
|  | 1.56 | — | 14.7% | 23.7% |
|  | 3.125 | — | 39.3% | 83.7% |
| 6.25 | 1.56 | 1.3% | 14.7% | 58.0% |
|  | 3.125 | — | 39.3% | 90.5% |
|  | 6.26 | — | 93.8% | 96.6% | b) Combination with indinavir:

| Concentration of the active compound | | % Inhibition of the RT activity by | | |
|---|---|---|---|---|
| Example 47 title compound (nM) | Indinavir (nM) | Example 47 title compound alone | Indinavir alone | Combination of Example 47 and Indinavir |
| 6.25 | 12.5 | 1.3% | 3.2% | 39.1% |
| 12.5 | 12.5 | 52.0% | 3.2% | 76.6% |
|  | 25 | — | 59.7% | 90.7% |

Consequently, an additive to synergistic effect can be seen in coculture.

Example 113

Synergistic effect produced by combining 5(S)-(Boc-amino)-4(S)-hydroxy-6-phenyl-2(R)-[(2,3,4-trimethoxyphenyl)methyl]hexanoyl-(L)-Val-N-(2-methoxyethyl)amide (compound from Example 47) with indinavir or saquinavir in the experiment using peripheral mononuclear blood cells The activities of the individual compounds, and the combinations, specified in the title, in the peripheral mononuclear blood cell culture are determined using the method described above in association with the description of the pharmacological properties. The measurement result is expressed as the cumulative activity of the reverse transcriptase (RT), in cpm/1.25 µl (number of measured $^{32}P$ disintegrations per 1.25 µl of test mixture and minute) on day 17 after the infection. The results are presented in the following table; measurement results which confirm the occurrence of synergism are emphasized by underlining. The test compound(s) is/are re-added in associated with each change of the medium (on days 0, 3, 6, 10 and 13):

| Cumulative RT activity (cpm/µl) on day 17 after the infection | | | | | | |
|---|---|---|---|---|---|---|
| Concentration of the title compound | Concentration of saquinavir (nM) | | | | | |
| from Example 47 | 0 | 7.5 | 15 | 30 | 60 | 120 |
| 0 | 7505 | 9411 | 10299 | 111 | 64 | 47 |
| 7.5 | 7909 | 8724 | 541 | 57 | 64 | 57 |
| 15 | 9132 | 5381 | 120 | 61 | 58 | 50 |
| 30 | 8457 | 255 | 63 | 51 | 59 | 53 |
| 60 | 1823 | 91 | 59 | 45 | 57 | 43 |
| 120 | 49 | 60 | 50 | 70 | 63 | 63 |

Consequently, a synergistic effect can also be detected in the experiment using human peripheral mononuclear blood cells.

What is claimed is:

1. A compound of the formula 1

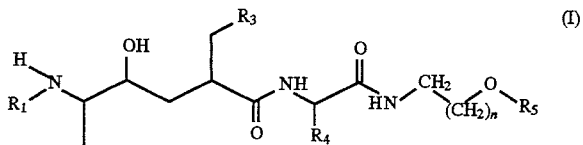

wherein $R_1$ is lower alkoxycarbonyl, $R_2$ is phenyl, $R_3$ is phenyl that is substituted by one or more lower alkoxy moieties, $R_4$ is lower alkyl, $R_5$ is lower alkyl, and n is 1 or 2, or a salt thereof, provided at least one salt-forming group is present.

2. A compound of the formula I according to claim 1, wherein $R_3$ is 2,3,4-tri-lower-alkoxyphenyl.

3. A compound of the formula I according to claim 1, wherein $R_1$ is ethoxycarbonyl or tert-butoxycarbonyl, $R_3$ is trimethoxyphenyl, $R_4$ is isopropyl, and $R_5$ is ethyl or methyl.

4. A compound of the formula I according to claim 1, wherein $R_1$ is lower-alkoxycarbonyl, $R_3$ is 2,3,4-tri-lower-alkoxyphenyl, $R_4$ is isopropyl, $R_5$ is methyl, and n is 1.

5. A compound according to claim 1 of the formula I'

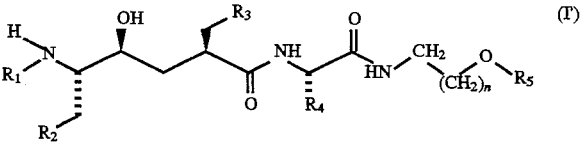

wherein the substituents are as defined.

6. A compound of the formula I' according to claim 5, wherein $R_3$ is 2,3,4-tri-lower-alkoxyphenyl, $R_4$ is isopropyl, $R_5$ is methyl, and n is 1.

7. A compound of the formula I according to claim 1 which is 5(S)-(Boc-amino)-4(S)-hydroxy-6-phenyl-2(R)-[(2,3,4-trimethoxyphenyl)methyl]-hexanoyl-(L)-Val-N-(2-methoxyethyl)amide.

8. A compound of the formula I according to claim 1 which is selected from the group consisting of 5(S)-(Boc-amino)-4(S)-hydroxy-6-phenyl-2(R)-[p-methoxyphenylmethyl]-hexanoyl-(L)-Val-N-(2-methoxyethyl)amide, 5(S)-(Boc-amino)-4(S)-hydroxy-6-phenyl-2(R)-[(2,3,4-trimethoxyphenyl)methyl]-hexanoyl-(L)-Val-N-(2-ethoxyethyl)amide, 5(S)-(Boc-amino)-4(S)-hydroxy-6-phenyl-2(R)-[(2,3,4-trimethoxyphenyl)methyl]-hexanoyl-(L)-Val-N-(3-methoxypropyl)amide, 5(S)-(Boc-amino)-4(S)-hydroxy-6-phenyl-2(R)-[(2,3,4-trimethoxyphenyl)methyl]-hexanoyl-(L)-Val-N-(3-ethoxypropyl)amide, and 5(S)-(Boc-amino)-4(S)-hydroxy-6-phenyl-2(R)-[(2,3,4-trimethoxyphenyl)methyl]-hexanoyl-(L)-Val-N-(3-(n-propyloxy)propyl)amide.

9. A compound of the formula I according to claim 1 which is selected from the group consisting of 5(S)-(Boc-amino)-4(S)-hydroxy-6-phenyl-2(R)-[(3-methoxyphenyl)methyl]-hexanoyl-(L)-Val-(2-methoxyethyl)amide, 5(S)-(Boc-amino)-4(S)-hydroxy-6-phenyl-2(R)-[(3,4,5-trimethoxyphenyl-methyl]hexanoyl-(L)-N-(2-methoxyethyl)amide, 5(S)-(Boc-amino)-4(S)-hydroxy-6-phenyl-2(R)-[(2,4-dimethoxyphenyl)-methyl]hexanoyl-(L)-N-(2-methoxyethyl)amide, 5(S)-(Boc-amino)-4(S)-hydroxy-6-phenyl-2(R)-[(2-methoxyphenyl)methyl]-hexanoyl-(L)-Val-N-(2-methoxyethyl)amide, 5(S)-(Boc-amino)-4(S)-hydroxy-6-phenyl-2(R)-[(2,4,5-trimethoxyphenyl)methyl]hexanoyl-(L)-Val-N-(2-methoxyethyl)amide, 5(S)-(Boc-amino)-4(S)-hydroxy-6-phenyl-2(R)-[(2,4,6-trimethoxyphenyl)methyl]hexanoyl-(L)-Val-N-(2-methoxyethyl)amide, 5(S)-(Boc-amino)-4(S)-hydroxy-6-phenyl-2(R)-[(2,5-dimethoxyphenyl)methyl]hexanoyl-(L)-Val-N-(2-methoxyethyl)amide and 5(S)-(Boc-amino)-4(S)-hydroxy-6-phenyl-2(R)-[(2,6-dimethoxyphenyl)methyl]-hexanoyl-(L)-Val-N-(2-methoxyethyl)amide.

10. A pharmaceutical preparation which is appropriate for the treatment of a disease that is caused by a retrovirus, said preparation comprising an amount of a compound of formula I according to claim 1 that is active against a retroviral disease, or a pharmaceutically acceptable salt thereof, and at least one pharmaceutically acceptable carrier material.

11. A method for treating diseases caused by retroviruses, where a combination, which is therapeutically effective against retroviral diseases, of a) a novel compound of the formula I according to claim 1 and b) a further compound, or two or more thereof, which is effective against retroviruses is administered to a mammal in a quantity which is therapeutically effective against retroviral diseases in order to treat a retroviral disease.

* * * * *